(12) United States Patent
Gurney

(10) Patent No.: US 9,499,630 B2
(45) Date of Patent: Nov. 22, 2016

(54) FRIZZLED-BINDING AGENTS AND USES THEREOF

(71) Applicant: OncoMed Pharmaceuticals, Inc., Redwood City, CA (US)

(72) Inventor: Austin L. Gurney, San Francisco, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 195 days.

(21) Appl. No.: 13/974,792

(22) Filed: Aug. 23, 2013

(65) Prior Publication Data

US 2014/0105917 A1    Apr. 17, 2014

Related U.S. Application Data

(62) Division of application No. 13/078,728, filed on Apr. 1, 2011, now Pat. No. 8,551,789.

(60) Provisional application No. 61/320,175, filed on Apr. 1, 2010.

(51) Int. Cl.
| | |
|---|---|
| C07K 7/08 | (2006.01) |
| C07K 7/64 | (2006.01) |
| C07K 14/00 | (2006.01) |
| A61K 38/08 | (2006.01) |
| A61K 38/12 | (2006.01) |
| A61K 38/16 | (2006.01) |
| C07K 16/30 | (2006.01) |
| C07K 14/47 | (2006.01) |

(Continued)

(52) U.S. Cl.
CPC .......... *C07K 16/30* (2013.01); *C07K 14/4702* (2013.01); *C07K 14/71* (2013.01); *C07K 16/28* (2013.01); *C07K 2317/34* (2013.01); *C07K 2317/55* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,109,496 A | 8/1978 | Allemann et al. |
| 4,323,546 A | 4/1982 | Crockford et al. |

(Continued)

FOREIGN PATENT DOCUMENTS

| | | |
|---|---|---|
| EP | 0662827 A1 | 7/1995 |
| EP | 0 861 894 A1 | 9/1998 |

(Continued)

OTHER PUBLICATIONS

Accession No. GSP: ARJ99386, EBI database, First entry on May 15, 2008, accessed on Jul. 18, 2013, 1 page.

(Continued)

*Primary Examiner* — Claire Kaufman
(74) *Attorney, Agent, or Firm* — Sterne, Kessler, Goldstein & Fox PLLC

(57) ABSTRACT

Novel anti-cancer agents, including, but not limited to, antibodies and other polypeptides, that bind to human frizzled receptors are provided. Novel epitopes within the human frizzled receptors which are suitable as targets for anti-cancer agents are also identified. Methods of using the agents or antibodies, such as methods of using the agents or antibodies to inhibit Wnt signaling and/or inhibit tumor growth are further provided. Screening methods are also provided.

15 Claims, 65 Drawing Sheets

Figure 1:
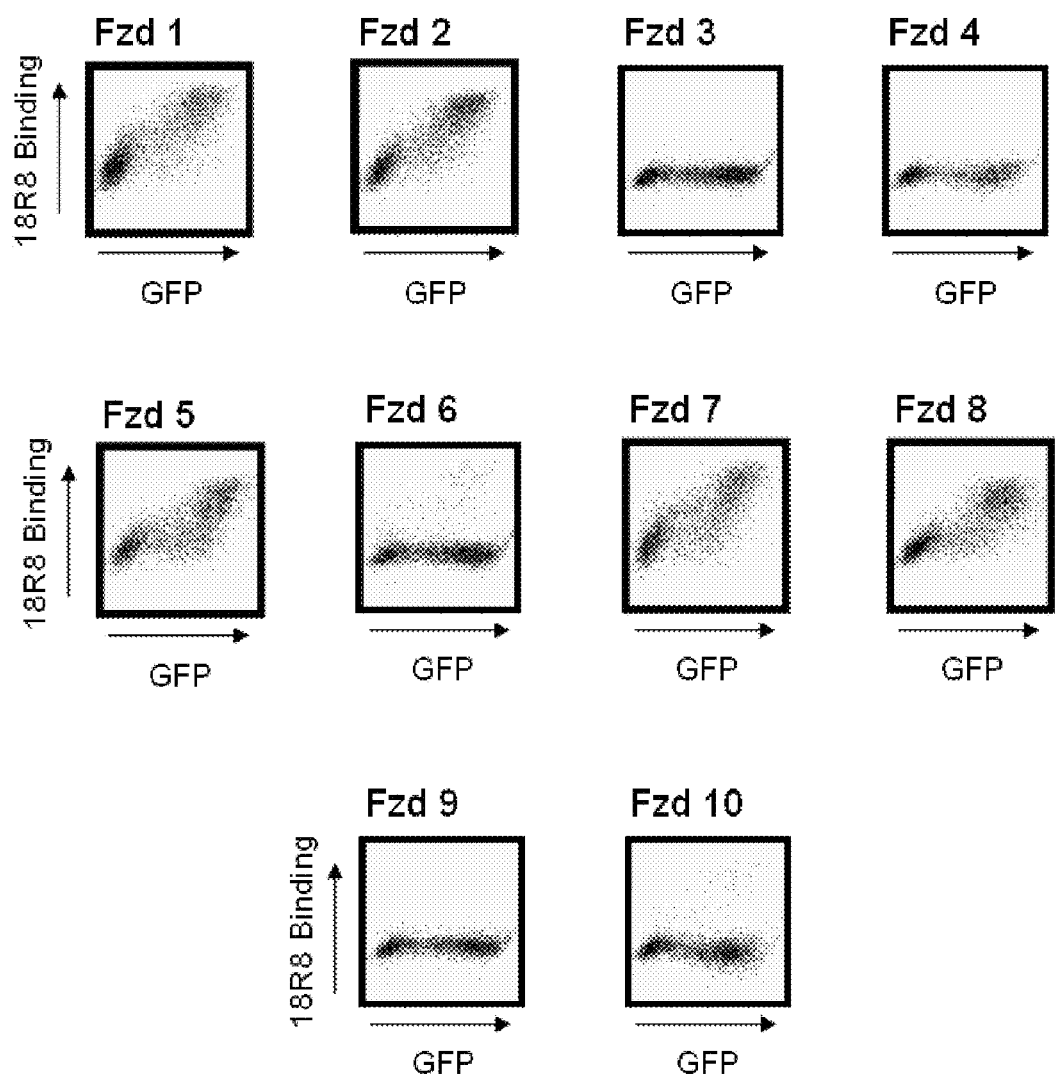

(51) Int. Cl.
  *C07K 14/71* (2006.01)
  *C07K 16/28* (2006.01)

(56) References Cited

U.S. PATENT DOCUMENTS

| | | |
|---|---|---|
| 4,411,990 A | 10/1983 | Salmon et al. |
| 4,612,282 A | 9/1986 | Schlom et al. |
| 4,670,393 A | 6/1987 | Seeburg |
| 4,873,191 A | 10/1989 | Wagner et al. |
| 4,968,103 A | 11/1990 | McNab et al. |
| 4,981,785 A | 1/1991 | Nayak |
| 5,019,497 A | 5/1991 | Olsson |
| 5,034,506 A | 7/1991 | Summerton et al. |
| 5,061,620 A | 10/1991 | Tsukamoto et al. |
| 5,087,570 A | 2/1992 | Weissman et al. |
| 5,223,409 A | 6/1993 | Ladner et al. |
| 5,225,539 A | 7/1993 | Winter |
| 5,283,317 A | 2/1994 | Saifer et al. |
| 5,358,691 A | 10/1994 | Clark et al. |
| 5,489,677 A | 2/1996 | Sanghvi et al. |
| 5,534,617 A | 7/1996 | Cunningham et al. |
| 5,538,848 A | 7/1996 | Livak et al. |
| 5,539,082 A | 7/1996 | Nielsen et al. |
| 5,565,332 A | 10/1996 | Hoogenboom et al. |
| 5,585,089 A | 12/1996 | Queen et al. |
| 5,589,376 A | 12/1996 | Anderson et al. |
| 5,599,677 A | 2/1997 | Dowell et al. |
| 5,602,240 A | 2/1997 | De Mesmaeker et al. |
| 5,614,396 A | 3/1997 | Bradley et al. |
| 5,631,169 A | 5/1997 | Lakowicz et al. |
| 5,639,606 A | 6/1997 | Willey |
| 5,643,741 A | 7/1997 | Tsukamoto et al. |
| 5,643,765 A | 7/1997 | Willey |
| 5,648,464 A | 7/1997 | Artavanis-Tsakonas et al. |
| 5,650,317 A | 7/1997 | Chang et al. |
| 5,654,183 A | 8/1997 | Anderson et al. |
| 5,672,499 A | 9/1997 | Anderson et al. |
| 5,674,739 A | 10/1997 | Shyjan |
| 5,688,666 A | 11/1997 | Bass et al. |
| 5,693,482 A | 12/1997 | Anderson et al. |
| 5,705,188 A | 1/1998 | Junichi et al. |
| 5,714,331 A | 2/1998 | Buchardt et al. |
| 5,719,262 A | 2/1998 | Buchardt et al. |
| 5,739,277 A | 4/1998 | Presta et al. |
| 5,750,373 A | 5/1998 | Garrard et al. |
| 5,750,376 A | 5/1998 | Weiss et al. |
| 5,753,229 A | 5/1998 | Mordoh et al. |
| 5,753,506 A | 5/1998 | Johe |
| 5,780,300 A | 7/1998 | Artavanis-Tsakonas et al. |
| 5,786,158 A | 7/1998 | Artavanis-Tsakonas et al. |
| 5,789,195 A | 8/1998 | Artavanis-Tsakonas et al. |
| 5,814,511 A | 9/1998 | Chang et al. |
| 5,821,108 A | 10/1998 | Akashi et al. |
| 5,824,489 A | 10/1998 | Anderson et al. |
| 5,824,544 A | 10/1998 | Armentano et al. |
| 5,830,730 A | 11/1998 | German et al. |
| 5,834,598 A | 11/1998 | Lowman et al. |
| 5,849,535 A | 12/1998 | Cunningham et al. |
| 5,849,553 A | 12/1998 | Anderson et al. |
| 5,849,869 A | 12/1998 | Artavanis-Tsakonas et al. |
| 5,854,026 A | 12/1998 | Cunningham et al. |
| 5,856,441 A | 1/1999 | Artavanis-Tsakonas et al. |
| 5,859,535 A | 1/1999 | Liu |
| 5,861,832 A | 1/1999 | Nagaraj |
| 5,869,282 A | 2/1999 | Ish-Horowicz et al. |
| 5,872,154 A | 2/1999 | Wilson et al. |
| 5,876,978 A | 3/1999 | Willey et al. |
| 5,885,530 A | 3/1999 | Babson et al. |
| 5,885,808 A | 3/1999 | Spooner et al. |
| 5,914,108 A | 6/1999 | Tsukamoto et al. |
| 5,935,792 A | 8/1999 | Rubin et al. |
| 5,942,225 A | 8/1999 | Bruder et al. |
| 5,981,225 A | 11/1999 | Kochanek et al. |
| 5,986,170 A | 11/1999 | Subjeck |
| 5,994,106 A | 11/1999 | Kovesdi et al. |
| 5,994,128 A | 11/1999 | Fallaux et al. |
| 5,994,132 A | 11/1999 | Chamberlain et al. |
| 5,994,617 A | 11/1999 | Dick et al. |
| 6,001,557 A | 12/1999 | Wilson et al. |
| 6,004,528 A | 12/1999 | Bergstein |
| 6,004,924 A | 12/1999 | Ish-Horowicz et al. |
| 6,019,978 A | 2/2000 | Ertl et al. |
| 6,022,711 A | 2/2000 | Cunningham et al. |
| 6,033,908 A | 3/2000 | Bout et al. |
| 6,054,297 A | 4/2000 | Carter et al. |
| 6,080,912 A | 6/2000 | Bremel et al. |
| 6,083,904 A | 7/2000 | Artavanis-Tsakonas |
| 6,090,922 A | 7/2000 | Artavanis-Tsakonas et al. |
| 6,117,985 A | 9/2000 | Thomas et al. |
| 6,121,045 A | 9/2000 | McCarthy et al. |
| 6,127,526 A | 10/2000 | Blank |
| 6,135,653 A | 10/2000 | Aichi |
| 6,136,952 A | 10/2000 | Li et al. |
| 6,143,523 A | 11/2000 | Cunningham et al. |
| 6,149,902 A | 11/2000 | Artavanis-Tsakonas et al. |
| 6,156,305 A | 12/2000 | Brauker et al. |
| 6,159,750 A | 12/2000 | Edmonds |
| 6,180,370 B1 | 1/2001 | Queen et al. |
| 6,190,876 B1 | 2/2001 | Rubin et al. |
| 6,197,523 B1 | 3/2001 | Rimm et al. |
| 6,198,107 B1 | 3/2001 | Seville |
| 6,207,147 B1 | 3/2001 | Hiserodt et al. |
| 6,218,166 B1 | 4/2001 | Ravindranath et al. |
| 6,252,050 B1 | 6/2001 | Ashkenazi et al. |
| 6,262,025 B1 | 7/2001 | Ish-Horowicz et al. |
| 6,353,150 B1 | 3/2002 | Dick et al. |
| 6,379,925 B1 | 4/2002 | Kitajewski et al. |
| 6,380,362 B1 | 4/2002 | Watson et al. |
| 6,429,186 B1 | 8/2002 | Fuh et al. |
| 6,433,138 B1 | 8/2002 | Zimrin et al. |
| 6,433,155 B1 | 8/2002 | Umansky et al. |
| 6,448,229 B2 | 9/2002 | Teall |
| 6,506,559 B1 | 1/2003 | Fire et al. |
| 6,537,775 B1 | 3/2003 | Tournier-Lasserve et al. |
| 6,551,795 B1 | 4/2003 | Rubenfield et al. |
| 6,583,115 B1 | 6/2003 | Kopchick et al. |
| 6,632,620 B1 | 10/2003 | Makarovskiy |
| 6,660,843 B1 | 12/2003 | Feige et al. |
| 6,664,098 B1 | 12/2003 | Sakano |
| 6,683,091 B2 | 1/2004 | Asberom et al. |
| 6,689,744 B2 | 2/2004 | Gao et al. |
| 6,703,221 B1 | 3/2004 | Chan et al. |
| 6,703,489 B1 | 3/2004 | Ish-Horowicz et al. |
| 6,713,206 B2 | 3/2004 | Markoski et al. |
| 6,716,974 B1 | 4/2004 | Maciag et al. |
| 6,756,511 B2 | 6/2004 | Castro Pineiro et al. |
| 6,894,522 B2 | 5/2005 | Averill et al. |
| 6,984,522 B2 | 1/2006 | Clarke et al. |
| 7,091,321 B2 | 8/2006 | Gillies et al. |
| 7,091,323 B2 | 8/2006 | Pan et al. |
| 7,115,360 B2 | 10/2006 | Clarke et al. |
| 7,115,653 B2 | 10/2006 | Baxter et al. |
| 7,118,853 B2 | 10/2006 | Botstein et al. |
| 7,138,370 B2 | 11/2006 | Oliner et al. |
| 7,211,404 B2 | 5/2007 | Lagasse et al. |
| 7,361,336 B1 | 4/2008 | Bergstein |
| 7,381,408 B2 | 6/2008 | Mezo et al. |
| 7,404,956 B2 | 7/2008 | Peters et al. |
| 7,413,873 B2 | 8/2008 | Waterman et al. |
| 7,442,778 B2 | 10/2008 | Gegg et al. |
| 7,507,406 B2 | 3/2009 | Gillies et al. |
| 7,608,453 B2 | 10/2009 | Cattaneo et al. |
| 7,635,530 B2 | 12/2009 | Kenis et al. |
| 7,659,116 B2 | 2/2010 | Buehring et al. |
| 7,662,931 B2 | 2/2010 | Gegg et al. |
| 7,682,607 B2 | 3/2010 | Rhee et al. |
| 7,713,526 B2 | 5/2010 | Rhee et al. |
| 7,723,477 B2 | 5/2010 | Gurney et al. |
| 7,803,370 B2 | 9/2010 | Nakamura et al. |
| 7,803,783 B2 | 9/2010 | Lee et al. |
| 7,803,913 B2 | 9/2010 | Dimitrov et al. |
| 7,867,705 B2 | 1/2011 | Wands et al. |
| 7,879,322 B2 | 2/2011 | Kneissel et al. |
| 7,947,277 B2 | 5/2011 | Ernst et al. |

(56) References Cited

U.S. PATENT DOCUMENTS

| | | |
|---|---|---|
| 7,982,013 B2 | 7/2011 | Gurney et al. |
| 8,017,559 B2 | 9/2011 | Etzerodt et al. |
| 8,158,761 B2 | 4/2012 | Wands et al. |
| 8,410,061 B2 | 4/2013 | Williams et al. |
| 8,431,532 B2 | 4/2013 | Brennan et al. |
| 8,507,442 B2 | 8/2013 | Gurney et al. |
| 8,551,789 B2 | 10/2013 | Gurney |
| 8,809,287 B2 | 8/2014 | Bafico et al. |
| 9,157,904 B2 | 10/2015 | Satyal et al. |
| 2002/0119565 A1 | 8/2002 | Clarke et al. |
| 2002/0137129 A1 | 9/2002 | Barnes et al. |
| 2002/0151487 A1 | 10/2002 | Nickoloff et al. |
| 2002/0169300 A1 | 11/2002 | Waterman et al. |
| 2002/0187502 A1 | 12/2002 | Waterman et al. |
| 2003/0032184 A1 | 2/2003 | Lagasse et al. |
| 2003/0044409 A1 | 3/2003 | Carson et al. |
| 2003/0064384 A1 | 4/2003 | Hung et al. |
| 2003/0086934 A1 | 5/2003 | Botstein et al. |
| 2003/0114387 A1 | 6/2003 | Castro Pineiro et al. |
| 2003/0119029 A1 | 6/2003 | Glick et al. |
| 2003/0135044 A1 | 7/2003 | Asberom et al. |
| 2003/0139457 A1 | 7/2003 | Baxter et al. |
| 2003/0162709 A1 | 8/2003 | Rossi et al. |
| 2003/0165500 A1 | 9/2003 | Rhee et al. |
| 2003/0166543 A1 | 9/2003 | Williams et al. |
| 2003/0175877 A1 | 9/2003 | Baker et al. |
| 2003/0180784 A1 | 9/2003 | McCarthy et al. |
| 2003/0185829 A1 | 10/2003 | Koller et al. |
| 2003/0229023 A1 | 12/2003 | Oliner et al. |
| 2004/0023244 A1 | 2/2004 | Griffin et al. |
| 2004/0037815 A1 | 2/2004 | Clarke et al. |
| 2004/0038876 A1 | 2/2004 | Pepinsky et al. |
| 2004/0048249 A1 | 3/2004 | Tang et al. |
| 2004/0058217 A1 | 3/2004 | Ohlsen et al. |
| 2004/0058443 A1 | 3/2004 | Artavanis-Tsakonas et al. |
| 2004/0105862 A1 | 6/2004 | Pan et al. |
| 2004/0127474 A1 | 7/2004 | Dudek et al. |
| 2004/0171559 A1 | 9/2004 | Weissman et al. |
| 2004/0203003 A1 | 10/2004 | Rhee et al. |
| 2004/0214186 A1 | 10/2004 | Engelberg et al. |
| 2004/0219579 A1 | 11/2004 | Aziz et al. |
| 2004/0247593 A1 | 12/2004 | He et al. |
| 2005/0123900 A1 | 6/2005 | Dimitrov et al. |
| 2005/0130199 A1 | 6/2005 | Carson et al. |
| 2005/0272063 A1 | 12/2005 | Nakamura et al. |
| 2005/0288864 A1 | 12/2005 | Cattaneo et al. |
| 2006/0019256 A1 | 1/2006 | Clarke et al. |
| 2006/0019320 A1 | 1/2006 | Civenni et al. |
| 2006/0040883 A1 | 2/2006 | You et al. |
| 2006/0210867 A1 | 9/2006 | Kenis et al. |
| 2007/0014776 A1 | 1/2007 | Gimeno et al. |
| 2007/0072238 A1 | 3/2007 | Bhat |
| 2007/0116701 A1 | 5/2007 | Gurney et al. |
| 2007/0117751 A1 | 5/2007 | Gurney et al. |
| 2007/0237770 A1 | 10/2007 | Lai et al. |
| 2007/0238658 A1 | 10/2007 | Levin et al. |
| 2008/0038272 A1 | 2/2008 | Buehring et al. |
| 2008/0044423 A1 | 2/2008 | Cochrane et al. |
| 2008/0075714 A1 | 3/2008 | Lee et al. |
| 2008/0118432 A1 | 5/2008 | Bergstein et al. |
| 2008/0171319 A1 | 7/2008 | Urdea et al. |
| 2008/0194457 A1 | 8/2008 | Wands et al. |
| 2008/0299136 A1 | 12/2008 | Ernst et al. |
| 2009/0023905 A1 | 1/2009 | Askew et al. |
| 2009/0074777 A1 | 3/2009 | Wands et al. |
| 2009/0130113 A1 | 5/2009 | Kneissel et al. |
| 2009/0163407 A1 | 6/2009 | Bafico et al. |
| 2009/0186010 A1 | 7/2009 | Li et al. |
| 2009/0234104 A1 | 9/2009 | Gegg et al. |
| 2009/0263400 A1 | 10/2009 | Urdea et al. |
| 2009/0304695 A1 | 12/2009 | He et al. |
| 2010/0104574 A1 | 4/2010 | Gurney et al. |
| 2010/0169025 A1 | 7/2010 | Arthur et al. |
| 2011/0020368 A1 | 1/2011 | Hynes |
| 2011/0224243 A1 | 9/2011 | Rethore |
| 2011/0237514 A1 | 9/2011 | Kakitani et al. |
| 2011/0318341 A1 | 12/2011 | Gurney et al. |
| 2012/0003222 A1 | 1/2012 | Brennan et al. |
| 2012/0023600 A1 | 1/2012 | Shulok et al. |
| 2012/0027778 A1 | 2/2012 | Gurney |
| 2012/0141481 A1 | 6/2012 | Ernst et al. |
| 2013/0209475 A1 | 8/2013 | Richards et al. |
| 2013/0252326 A1 | 9/2013 | Gurney et al. |
| 2013/0295105 A1 | 11/2013 | Gurney et al. |
| 2013/0295106 A1 | 11/2013 | Gurney et al. |
| 2014/0105917 A1 | 4/2014 | Gurney |
| 2014/0134159 A1 | 5/2014 | Stagg et al. |

FOREIGN PATENT DOCUMENTS

| | | |
|---|---|---|
| EP | 1 004 669 A1 | 5/2000 |
| EP | 1 576 119 | 9/2005 |
| EP | 1 805 519 | 7/2007 |
| WO | WO 90/08832 A1 | 8/1990 |
| WO | WO 92/19734 A1 | 11/1992 |
| WO | WO 94/07474 A1 | 4/1994 |
| WO | WO 94/10300 A1 | 5/1994 |
| WO | WO 97/01571 A1 | 1/1997 |
| WO | WO 97/30731 A2 | 8/1997 |
| WO | WO 97/37004 A1 | 10/1997 |
| WO | WO 98/05775 A1 | 2/1998 |
| WO | WO 98/45434 A1 | 10/1998 |
| WO | WO 98/51799 A1 | 11/1998 |
| WO | WO 98/57621 A1 | 12/1998 |
| WO | WO 99/02685 A1 | 1/1999 |
| WO | WO 00/06726 A2 | 2/2000 |
| WO | WO 00/09675 A1 | 2/2000 |
| WO | WO 00/12738 A1 | 3/2000 |
| WO | WO 00/52143 A2 | 9/2000 |
| WO | WO-0102568 A2 | 1/2001 |
| WO | WO 01/26643 A1 | 4/2001 |
| WO | WO-0122920 A2 | 4/2001 |
| WO | WO 01/98354 A2 | 12/2001 |
| WO | WO 01/98537 A2 | 12/2001 |
| WO | WO 02/00576 A1 | 1/2002 |
| WO | WO 02/88081 A2 | 1/2002 |
| WO | WO 02/12447 A2 | 2/2002 |
| WO | WO 02/18544 A2 | 3/2002 |
| WO | 0 662 827 | 4/2002 |
| WO | WO 02/78703 A1 | 10/2002 |
| WO | WO 02/092635 A2 | 11/2002 |
| WO | WO 02/102978 A2 | 12/2002 |
| WO | WO 03/000893 A2 | 1/2003 |
| WO | WO 03/004045 A2 | 1/2003 |
| WO | WO 03/042246 A2 | 5/2003 |
| WO | WO 03/047316 A1 | 6/2003 |
| WO | WO 03/050502 A2 | 6/2003 |
| WO | WO 03/062273 A2 | 7/2003 |
| WO | WO-03053921 A2 | 7/2003 |
| WO | WO 03/088964 A1 | 10/2003 |
| WO | WO-03080672 A1 | 10/2003 |
| WO | WO 2004/001004 A2 | 12/2003 |
| WO | WO 2004/020668 A2 | 3/2004 |
| WO | WO 2004/032838 A2 | 4/2004 |
| WO | WO 2004/042028 A2 | 5/2004 |
| WO | WO 2004/053069 A2 | 6/2004 |
| WO | WO 2004/065545 A2 | 8/2004 |
| WO | WO 2004/073657 A2 | 9/2004 |
| WO | WO 2004/101739 A2 | 11/2004 |
| WO | WO 2005/001025 A2 | 1/2005 |
| WO | WO 2005/004912 A1 | 1/2005 |
| WO | WO 2005/005601 A2 | 1/2005 |
| WO | WO 2006/034328 A2 | 3/2006 |
| WO | 1 805 221 | 4/2006 |
| WO | WO 2006/036173 A2 | 4/2006 |
| WO | WO 2006/036175 A2 | 4/2006 |
| WO | WO 2006/040163 A1 | 4/2006 |
| WO | WO 2006/055635 A2 | 5/2006 |
| WO | WO 2006/056340 A2 | 6/2006 |
| WO | WO 2006/130076 A1 | 12/2006 |
| WO | WO 2007/053577 A2 | 5/2007 |
| WO | WO-2007070538 A2 | 6/2007 |
| WO | WO 2007/096149 A1 | 8/2007 |
| WO | WO 2007/134876 A2 | 11/2007 |

(56) References Cited

FOREIGN PATENT DOCUMENTS

| WO | WO-2007133250 A2 | 11/2007 |
|---|---|---|
| WO | WO 2007/142711 A2 | 12/2007 |
| WO | WO 2007/148417 A1 | 12/2007 |
| WO | WO 2008/031009 A2 | 3/2008 |
| WO | WO-2008039071 A2 | 4/2008 |
| WO | WO 2008/057459 A2 | 5/2008 |
| WO | WO 2008/061020 A2 | 5/2008 |
| WO | WO 2009/042971 A2 | 4/2009 |
| WO | WO 2009/118300 A1 | 10/2009 |
| WO | WO-2009124535 A1 | 10/2009 |
| WO | WO 2010/031979 A1 | 3/2010 |
| WO | WO-2010037041 A2 | 4/2010 |
| WO | WO 2010/038756 A1 | 8/2010 |
| WO | WO-2011088123 A2 | 7/2011 |
| WO | WO-2011101409 A1 | 8/2011 |
| WO | WO-2011112678 A1 | 9/2011 |
| WO | WO 2011/123785 A2 | 10/2011 |
| WO | WO-2011123785 A3 | 12/2011 |
| WO | WO-2012003189 A1 | 1/2012 |
| WO | WO-2012006027 A1 | 1/2012 |
| WO | WO-2012058393 A2 | 5/2012 |
| WO | WO-2014121196 A1 | 8/2014 |

OTHER PUBLICATIONS

Accession No. UNITPROT: A6CA06, EBI database (Jul. 24, 2007), accessed on Jul. 8, 2013, 2 pages.

Al-Hajj, M., et al., "Prospective Identification of Tumorigenic Breast Cancer Cells," Proceedings of the National Academy of Sciences 100(7):3983-3988, The National Academy of Sciences United States (2003).

Bourhis, E., et al., "Reconstitution of a Frizzled8.Wnt3a.LRP6 Signaling Complex Reveals Multiple Wnt andDkk1 Binding Sites on LRP6," The Journal of Biological Chemistry 285(12):9172-9179, American Society for Biochemistry and Molecular Biology, United States (2010).

Caricasole, A., et al., "Functional Characterization of WNT7A Signaling in PC12 Cells," The Journal of Biological Chemistry 278(39):37024-37031, The American Society for Biochemistry and Molecular Biology, United States (2003).

Cong, F., et al., "Wnt Signals across the Plasma Membrane to Activate the Beta-catenin Pathway by Forming Oligomers Containing its Receptors, Frizzled and LRP," Development 131(20):5103-5115, Company of Biologists, England (2004).

"Frizzled Antibody (H-300): sc-9169" accessed at http://scbt.corn/datasheet-9169-frizzled-h-300-antibody.html, accessed on Mar. 20, 2015, 6 pages, (2015).

Gaudio, A., et al , "Increased Sclerostin Serum Levels Associated with Bone Formation and Resorption Markers in Patients with Immobilization-Induced Bone Loss," The Journal of Clinical Endocrinology and Metabolism 95(5):2248-2253, The Endocrine Society, United States (2010).

Gore, L., et al., "Safety, pharmacokinetics, and pharmacodynamics results from a phase I trial of BAY 86/9766 (RDEA119), a MEK inhibitor, in patients with advanced cancer," J Clin Oncol 29:2 pages, presented at the 2011 ASCO Annual Meeting, American Society of Clinical Oncology, United States (2011) (Abstract 3007).

International Search Report for International Application No. PCT/US14/68097, United States Patent and Trademark Office, United States, mailed on Apr. 30, 2015, 10 page.

International Search Report for International Application No. PCT/US2012/068351, US Patent Office, Virginia, mailed on May 24, 2013, 7 pages.

International Search Report for International Application No. PCT/US2014/014443, United States Patent and Trademark Office, United States, mailed on Apr. 15, 2014, 4 pages.

International Search Report of the International Searching Authority for International Application No. PCT/US13/66087 mailed on Jan. 16, 2014, United States Patent and Trademark Office, United States, 5 pages.

Jimeno, A., et al., "A first-in-human phase 1 study of anticancer stem cell agent OMP-54F28 219 (FZD-Fc), decoy receptor for WNT ligands, in patient with advanced solid tumors," 2014 ASCO Annual Meeting, Abstract 2505, 2 pages (2014).

Kabacik, S., et al., "Gene Expression Following Ionising Radiation: Identification of Biomarkers for Dose Estimation and Prediction of Individual Response," International Journal of Radiation Biology 67(2):115-129, Informa Healthcare, England (2011).

Lo, P.K., et al., "Epigenetic Suppression of Secreted Frizzled Related Protein 1 (SFRP1) Expression in Human Breast Cancer," Cancer Biology & Therapy 5(3):e1-e6, Landes Bioscience, Austin, United States (2006).

Miele, L. and Osborne, B., "Arbiter of Differentiation and Death: Notch Signaling Meets Apoptosis," Journal of Cellular Physiology 181(3):393-409, Wiley-Liss, Inc., United States (1999).

Office Action mailed Apr. 18, 2013, in U.S. Appl. No. 13/078,728, Gurney, A.L., et al., filed Apr. 1, 2011.

Office Action mailed Nov. 16, 2012, in U.S. Appl. No. 13/078,728, Gurney, A.L., filed Apr. 1, 2011.

OncoMed Pharmaceuticals Press Release, "OncoMed Announces Abstracts Accepted at the 2014 ASCO Annual Meeting," Apr. 23, 2014, 2 pages.

OncoMed Pharmaceuticals Press Release, "OncoMed Pharmaceuticals Announces FDA Clearance to Commence Phase 1 Testing of Anti-Cancer Stem Cell Therapeutic OMP-18R5," Apr. 28, 2011, 2 pages.

OncoMed Pharmaceuticals Press Release, "OncoMed Pharmaceuticals Commences Third Phase 1b Clinical Trial for OMP-54F28 (Fzd8-Fc) With Carboplatin and Paclitaxel in Ovarian Cancer," Feb. 20, 2014, 3 pages.

OncoMed Pharmaceuticals Press Release, "OncoMed Pharmaceuticals Initiates First Phase 1b Clinical Trial of First-in-Class WNT-Pathway-Targeting Antibody Vantictumab (OMP-18R5) With Paclitaxel in Breast Cancer," Oct. 29, 2013, 3 pages.

OncoMed Pharmaceuticals Press Release, "OncoMed Pharmaceuticals Initiates First Phase 1b Clinical Trial of OMP-54F28 (Fzd8-Fc) With Nab-Paclitaxel (Abraxane(R)) and Gemcitabine in Pancreatic Cancer," Jan. 13, 2014, 3 pages.

OncoMed Pharmaceuticals Press Release, "OncoMed Pharmaceuticals Initiates Phase I Clinical Trial of Anti-Cancer Stem Cell Therapeutic OMP-54F28 (Fzd8-Fc)," Jul. 12, 2012, 2 pages.

OncoMed Pharmaceuticals Press Release. "OncoMed Pharmaceuticals Initiates Second Phase 1b Clinical Trial for OMP-54F28 (Fzd8-Fc) With Sorafenib (Nexavar(R)) in Hepatocellular Cancer," Feb. 18, 2014, 3 pages.

OncoMed Pharmaceuticals Press Release, "OncoMed Pharmaceuticals Initiates Second Phase 1b Clinical Trial of First-in-Class WNTPathway-Targeting Antibody Vantictumab (OMP-18R5) With Docetaxel in Non-Small Cell Lung Cancer (NSCLC)," Nov. 15, 2013, 3 pages.

OncoMed Pharmaceuticals Press Release, "OncoMed Pharmaceuticals Initiates Third Phase 1b Clinical trial of First-in-Class WNTPathway-Targeting Antibody Vantictumab (OMP-18R5) With Nab-Paclitaxel (Abraxane®) and Gemcitabine in Stage IV Pancreatic Cancer," Dec. 4, 2013, 3 pages.

OncoMed Pharmaceuticals Press Release, "OncoMed Pharmaceuticals Presents Data From Clinical Trials for Four Novel Anti-Cancer Stem Cell (Anti-CSC) Therepeutics at the AACR-NCI-EORTC International Conference on Molecular Targets and Cancer Therapeutics in Boston, Oct. 19-23, 2013," Oct. 21, 2013, 4 pages.

OncoMed Pharmaceuticals Press Release, "OncoMed Pharmaceuticals Presents Phase 1 Data in Solid Tumor Patients for the First-in-Class Wnt Pathway Targeting Antibody Vantictumab (OMP-18R5) at ASCO," Jun. 3, 2013, 2 pages.

OncoMed Pharmaceuticals Press Release, "OncoMed Pharmaceuticals Presents Updated Phase 1a Data in Advanced Solid Tumor Patients for the First-in-Class WNT-Pathway-Targeting Antibody Vantictumab (OMP-18R5) at the European Cancer Congress 2013," Sep. 29, 2013, 3 pages.

OncoMed Pharmaceuticals Press Release, "OncoMed Pharmaceuticals Recaps New Data Presented at AACR," Apr. 3, 2012, 2 pages.

(56) References Cited

OTHER PUBLICATIONS

OncoMed Pharmaceutics Press, "OncoMed Pharmaceuticals to Present Data From Clinical Trials of Four Novel Anti-Cancer Stem Cell (Anti-CSC) Therapeutics in Five Posters at the AACR-NCI-EORTC International Conference on Molecular Targets and Cancer Therapeutics in Boston, Oct. 19-23, 2013," Oct. 14, 2013, 4 pages.
OncoMed Pharmaceuticals Press Release, "OncoMed Pharmaceuticals to Present Phase 1a Data Advanced Solid Tumor Patients for the First-in-Class WNT-Pathway-Targeting Antibody Vantictumab (OMP-18R5) at the European Cancer Congress 2013 (ECC 2013)," Sep. 23, 2013, 2 pages.
OncoMed Pharmaceuticals, Press Release, "OncoMed Present Data on Multiple Anti-Cancer Stem Cell Programs at American Association for Cancer Research Annual Meeting," Apr. 8, 2014, 4 pages.
OncoMed Pharmaceuticals Press Release, "OncoMed Presents New Data in Six Anti-Cancer Stem Cell Programs at AACR," Apr. 9, 2013, 3 pages.
OncoMed Pharmaceuticals Press Release, "OncoMed Provides Update on FZD8-Fc (OMP-54F28) Phase I Clinical Trials," Jun. 18, 2014, 2 pages.
OncoMed Pharmaceuticals Press Release, "OncoMed to Present Data From Three Clinical Studies at the 2014 ASCO Annual Meeting," May 14, 2014, 4 pages.
OncoMed Pharmaceuticals Press Release, "OncoMed to Present New Data in Six Anti-Cancer Stem Cell Programs at AACR," Apr. 2, 2013, 2 pages.
OncoMed Pharmaceuticals Press Release, "PNAS Published OncoMed Data Demonstrating Potent Anti-Cancer Activity for Novel Wnt Pathway Antibody OMP-18R5," Jul. 3, 2012, 2 pages.
Smith, D.C., of al., "A first-in-human Phase 1 study of anti-cancer stem cell (CSC) agent OMP-54F28 (FZD8-Fc) targeting the WNT pathway in patients with advanced solid tumors," AACR-NCI-EORTC International Conference on Molecular Targets and Cancer Therapeutics, Oct. 19-23, 2013, Abstract B79, 1 page (2013).
Smith, D.C., et al., "Biomarker analysis in the first-in-human Phase 1a study for vantictumab (OMP-18R5; anti-Frizzled) demonstrates pharmacodynamics (PD) modulation of the Wnt pathway in patients with advanced solid tumors," AACR-NCI-EORTC International Conference on Molecular Targets and Cancer Therapeutics in Boston, Oct. 19-23, 2013, Poster 823, 1 page (2013).
Wheater, G., et al., "The clinical utility of bone marker measurements in osteoporosis," Journal of Translational Medicine 11(201):11 pages, BioMed Central Ltd, England (2013).
Written Opinion for International Application No. PCT/US14/68097, United States Patent and Trademark Office, United States, mailed on Apr. 30, 2015, 25 pages.
Written Opinion for the Internatonal Searching Authority for International Application No. PCT/US13/66087 mailed on Jan. 16, 2014 The International Bureau of WIPO, Switzerland, 5 pages.
Yen, W-C., et al., "Enhanced anti-tumor effect of WNT pathway antagonists in combination with 251 taxanes " AACR Annual Meeting 2014, Apr. 5-9, Abstract 4547, 1 page (2014).
Yeung, P. at al "Wnt pathway antagonist OMP-54F28 (FZD8-Fc) inhibits tumor growth and reduces tumor-initiating cell frequency in patient-derived hepatocellular carcinoma and ovarian cancer xenograft models," AACR Annual Meeting 2014, Apr. 5-9, Abstract 1907, 1 page (2014).
Zhang, C., et al., "Predictive biomarker identification for response to vantictumab (OMP-18R5; anti-Frizzled) by mining gene expression data of human breast cancer xeongrafts," AACR Annual Meeting, Apr. 5-9, Abstract 2830, 1 page (2014).
US 5,962,233, 10/1999, Livak et al. (withdrawn).
Austin, T,W., et al., "A Role for the *Wnt* Gene Family in Hematopoiesis: Expansion of Multilineage Progenitor Cells," *Blood* 89:3624-3635, The American Society of Hematology, Untied States (1997).
Ayyanan, A., et al., "Increased Wnt signaling triggers oncogenic conversion of human breast epithelial cells by a Notch-dependent mechanism," *Proc. Natl. Acad. Sci.* 103:3799-3804, The National Academy of Sciences, United States (2006).
Bafico, A. et al., "An autocrine mechanism for constitutive Wnt pathway activation in human cancer cells," *Cancer Cell* 6:497-506, Cell Press, United States (2004).
Bafico, A., et al., "Interaction of Frizzled Related Protein (FRP) with Wnt Ligands and the Frizzled Receptor Suggests Alternative Mechanisms for FRP Inhibition of Wnt Signaling," *J. Biol. Chem.* 274:16180-16187, The American Society for Biochemistry and Molecular Biology, Inc., United States (1999).
Barker, N. and Clevers, H., "Mining the Wnt pathway for cancer therapeutics," *Nat. Rev. Drug Discov.* 5:997-1014, Nature Publishing Group, England (2006).
Battula, V.L., et al., "Prospective isolation and characterization of mesenchymal stem cells from human placenta using a frizzled-9-specific monoclonal antibody," *Differentiation* 76:326-336, International Society of Differentiation, England (2008).
Benhamouche, S., et al., "*Apc* Tumor Suppressor Gene is the "Zonation-Keeper" of Mouse Liver," *Dev. Cell* 10:759-770, Elsevier Inc., United States (2006).
Bhanot, P., et al., "A new member of the *frizzled* family from *Drosophila* functions as a Wingless receptor," *Nature* 382:225-230, Nathre Publishing Group, England (1996).
Bienz, M., β-Catenin: A Pivot between Cell Adhesion and Tent Signalling, *Current Biology* 15;R64-R67, Cell Press, England (2004).
Booy, E.P., or al., "Monoclonal and bispecific antibodies as novel therapeutics," *Arch. Immunol. Ther. Exp.* 54:85-101, Birkhauser publications, Switzerland (2006).
Brabletz, T., et al., "Variable β-catenin expression in colorectal cancers indicates tumor progression driven by the tumor environment," *Proc. Natl. Acad. Sci.* 98: 10356-10361, National Academy of Sciences, United States (2001).
Brennan, K.R. and Brown, A.M.C,, "Wnt Proteins in Mammary Development and Cancer," *J. Mammary Gland Biol. Neoplasia* 9:119-131, Kluwer Academic/Plenum Publishers, United States (2004).
Burgess, W.H., et al., "Possible Dissociation of the Heparin binding and Mitogenic Activities of Heparin-binding (Acidic Fibroblast) Growth Factor-1 from Its Receptor-binding Activities by Site-directed Mutagenesis of a Single Lysine Residue," *J. Cell Bio.* 111:2129-2138, the Rockefeller University Press, United States (1990).
Cadigan, K.M., and Nusse, R., "Wnt signaling: a common theme in animal development," *Genes & Dev.* 11:3286-3305, Cold Spring Harbor Laboratory Press United States (1997).
Caldwell, G.M., et al.,"The Wnt Antagonist *s-FRP1* in Colorectal Tumorigertesis," *Cancer Res* 64:883-888, the American Association for Cancer Research, United States (2004).
Chan, E.F., et al., "A common human skin tumour is caused by activating mutations in β-catenin," Nature Genetics 21: 410-413, Nature Publishing Company, United States (1999).
Chen, Y., et al., "Selection and Analysis of an Optimized Anti-VEGF Antibody: Crystal Structure of an Affinity-matured Fab in Complex with Antigen," *J. Mol. Biol.* 293:865-881, Academic Press, England (1999).
Clevers, H., "Axirt and hepatocellular carcinomas," *Nature Genetics* 24:206-208, Nature America Inc., United States (2000).
Daniel, C., et al., "Mapping of Linear Antigenic Sites on the S Glycoprotein of a Neurotropic Murine Coronavirus with Synthetic Peptides: A Combination of Nine Prediction Algorithms Fails to Identify Relevant Epitopes and Peptide Immunogenicity Is Drastically Influenced by the Nature of the Protein Carrier," *Virology* 202:540-549, Academic Press, Inc., United States (1994).
Dann, C.E., et al., "Insight into Wnt binding and signaling from the structures of two Frizzled cysteine-rich domains," *Nature* 412:86-90, Macmillan Magazine Ltd., England (2001).
Datta, D.V., "Viral Hepatitis," *Jr. Asso. Phys. Ind.* 25:325-330, Association of Physicians of India, India (1977).

(56) References Cited

OTHER PUBLICATIONS

Davidson, G., et al., "Casein kinase 1γ couples Wnt receptor activation to cytoplasmic signal transduction," *Nature* 438:867-872, Nature Publishing Group, England (2005).

De Lau, W, and Clevers, H., "LEF1 turns over a new leaf," *Nature Genetics* 28:3-4, Nature Publishing Group, United States (2001).

De Pascalis, R., etas., "Grafting of "Abbreviated" Complementarity-Determining Regions Containing Specificity-Determining Residues Essential for Ligand Contact to Engineer a Less Immunogenic Humanized Monoclonal Antibody," *J. Immunol.* 169:3076-3084, The American Association of Immunologists, United States (2002).

Dealmeida, V.I., et al., "The Soluble Wnt Receptor Frizzled8CRD-hFc Inhibits the Growth of Teratocarcirtornas In vivo," *Cancer Res* 67:5371-5379, American Association for Cancer Research, United States (2007).

Dorvillius, M., et al., "Targeting of Human Breast Cancer by a Bispecific Antibody Directed against Two Tumour-Associated Antigens: ErbB-2 and Carcinoembryonic Antigen", *Tumor. Biol.* 23:337-347, S. Karger Medical and Scientific Publishers, Netherlands (2002).

Fillmore, C.M. and Kuperwasser, C., "Human breast cancer cell lines contain stem-like cells that self-renew, give rise to phenotypically diverse progeny and survive chemotherapy," *Breast Cancer Res.* 10:R25-R37, BioMed Central Ltd., England (2008).

Finch, P.W., at al., "Purification and molecular cloning of a secreted, Frizzled-related antagonist of Wnt action," *Proc. Natl. Acad. Sci.* 94:6770-6775, The National Academy of Sciences, United States (1997).

Fogel, M. et al., "L1 expression as a predictor of progression and survival in patients with uterine and ovarian carcinomas," *Lancet*362: 869-875, Lancet Publishing Group, England (2003).

Furukawa, C., et al., "Radioimmunotherapy of human synovial sarcoma using a monoclonal antibody against FZD10," *Cancer Sci,* 99:432-440, Japanese Cancer Association, England (2008).

Gavert, N. et cal.. "L1, a novel target β-catenin signaling, transforms cells and is expressed at the invasive front of colon cancers," *J. Cell Biol.* 168:633-642, The Rockefeller University Press, United States (2005).

Gazit A. et al., "Human frizzled 1 interacts with transforming Wnts to transduce a TCF dependent transcriptional response," *Oncogene* 18;5959-5966, Stockton Press, England (1999).

Golan, T., et al., "The Human Frizzled 6 (HFz6) Acts as a Negative Regulator of the Canonical Wnt.β-Catenin Signaling Cascade," *J. Biol. Chem.* 279:14879-14888, The American Society for Biochemistry and Molecular Biology, United States (2004).

Greenspan, N.S. and Di Cera, E., "Defining epitopes: It's not as easy as it seems," *Nature Biotechnology* 17:936-937, Nature American Publishing, United States (1999).

Gregorieff., et al., "Expression Pattern of Wnt Signaling Components in the Adult Indestine," *Gastroenterology* 129:626-638, the American Gastroenterological Association, United States (2005).

Greiner, D.E., et at., "SCID Mouse Models of Human Stem Cell Engraftment." *Stem Cells* 16:166-177, AlphaMed Press, United States (1998).

Guo, H.H. et al., "Protein tolerance to random ammo acid change," *Proc. Natl. Acad. Sci.* 101:9205-9210, The National Academy of Sciences, United States (2004).

Harada, N., et al., "Intestinal polyposis in mice with a dominant stable mutation of the β-catenin gene," *EMBO J.* 18:5931-5942, European Molecular Biology Organization, England (1999).

He, X. and Axelrod, J.D., "A WNTer wonderland in Snowbird," *Developement* 133:2597-2603, The Company of Biologists, England (2006).

Hering, H. and Sheng, M., "Direct interaction of Frizzled-1, -2, -4, and -7 with PD1 domains of PSD-95," *FEBS Lett.* 521:185-189, Elsevier Science, B.V., Netherlands (2002).

Hicks, C., et al., "Fringe differentially modulates Jagged1 and Delta1 signalling through Notch1 and Notch2," *Nat. Cell Biol.* 2:515-520, Macmillan Magazines, Ltd., England (2000).

Hill, R.P., "Identifying Cancer Stem Cells in Solid Tumors: Case Not Proven," *Cancer Res.* 66:1891-1896, American Association for Cancer Research, United States (2006).

Holcombe, R.F., et ai., "Expression of Wnt ligands and Frizzled receptors in colonic mucosa and in colon carcinoma," *J. Clin. Pathol: Mol. Pathol.* 55:220-226, BMJ Publishing Group, England (2002).

Holmes, E.H., "PSMA specific antibodies and their diagnostic and therapeutic use," *Exp. Opin. Invest. Drugs* 10:511-519, Ashley Publications Ltd England (2001).

Hsieh, A.C. and Moasser, M.M., "Targeting HER proteins in cancer therapy and the role of the non-target HER3," *Br. J. Cancer* 97:453-457, Cancer Research UK, England (2007).

Hsieh, J.-C., et al., "Biochemical characterization of Wnt-Frizzled interactions using a soluble, biologically active vertebrate Wnt protein," *Proc. Natl. Acad. Sci.* 96:3546-3551, The National Academy of Sciences, United States (1999).

Huang, H-C. and Klein, P.S., "The Frizzled family: receptors for multiple signal transduction pathways," *Genome Biol.* 5:234.1-234.7, BioMed Central Ltd., England (2004).

Ilyas, M., "Wnt Signaling and the mechanistic basis of tumor development," *J. Pathol.* 205:130-144, John Wiley and Sons, England (2005).

Ishikawa, T., et al., "Mouse Wnt receptor gene *Fzd5* is essential for yolk sac and placental angiogenesis," *Development* 128:25-33, The Company of Biologists Limited, England (2001).

Ishitani, T., et al., "The TAK1-NLK Mitogen-Activated Protein Kinase Cascade Functions in the Wnt-5a/$Ca^{2+}$ Pathway to Antagonize Wnt/β-Catertin Signaling," *Mol. Cell. Biol.* 23:131-139, American Society for Microbiology, United States (2003).

Jamieson, C.H.M., et al., "Granulocyte-Macrophage Progenitors as Candidate Leukemic Stem Cells in Blast-Crisis CML," *N. Engl. J. Med.* 351:657-667, Massachusetts Medical Society, United States (2004).

Janssens, N., et al,, "Alteration of Frizzled Expression in Renal Cell Carcinoma," *Tumor Biol.*, 25:161-171, S. Barger AG, Netherlands (2004).

Jiang, B., et al., "A Novel Peptide Isolated from a Phage Display Peptide Library with Trastuzamab Can Mimic Antigen Epitope of HER-2," *J. Biol. Chem.* 280:4656-4662, The American Society for Biochemistry and Molecular Biology, Inc., United States (2005).

Joesting, M.S., et al.,"Identification of SFRP1 as a Candidate Mediator of Stromal-to-Epithelial Signaling in Prostate Cancer," *Cancer Res.* 65:10423-10430, the American Association for Cancer Research, United States (2005).

Johnson, M.L., et al., "LRP5 and Wnt Signaling: A Union Made for Bone," *J. Bone Miner. Res.* 19:1749-1757, American Society for Bone and Mineral Research, United. States (2004).

Jones, D.T., "Critically assessing the state-of-the-art in protein structure prediction," *Pharmacogenomics J.* 1:126-134, Nature Publishing Group, United States (2001).

Jönnson, M., et al., "Involvement of adenomatous polyposis coli (APC)/beta-catenin signaling in human breast cancer." *Eur. J. Cancer* 36:242-248, Elsevier Science Ltd., England (2000).

Katch, M, and Katoh, M., "WNT Signaling Pathway and Stem Cell Signaling Network," *Clin. Cancer Res.* 13:4042-4045, American Association for Cancer Research, United States (2007).

Katoh, M., and Katoh, M., "STAT3-induced WNT5A signaling loop in embryonic stem cells, adult normal tissues, chronic persistent inflamation, rheumatoid arthritis and cancer (Review)," *Int. J. Mol. Med.* 19:273-278, D.A. Spandidos, Greece (2007).

Kawakami, Y,, et al., "Involvement of Frizzled-10 in Wnt-7a signaling during chick limb development," *Develop. Growth Differ.* 42:561-569, Blackwell Publishing, Japan (2000).

Kawano, Y. and Kypta, R., "Secreted antagonists of the Wnt signalling pathway," *J Cell Sci.* 116:2627-2634, The Company of Biologists Ltd, England (2003).

Kirikoshi, H., et al,. "Expression of Wnt10A in human cancer," *Int. J. Oncol.* 19:997-1001. D.A. Spandidos, Greece (2001).

Kirikoshi, H., et al., "Molecular Cloning and Characterization of human *Frizzled*-4 on Chromosome 11q14-q21," *Biochem. Biophys. Res. Commun.* 264:955-961, Academic Press, United States (1999).

(56) References Cited

OTHER PUBLICATIONS

Kirikoshi, H., et al., "Up-regulation of *Frizzled-7* (*FZD7*) in human gastric cancer," *Int. J. Oncol.* 19:111-115, D.A. Spandidos, Greece (2001).

Kirkina A.F., et al., "Melanoma-associated antigens recognized by cytotoxic T lymphocytes," *APMIS* 106:665-679, Murtksgaard, Denmark (1998).

Klaus, A. and Birchmeier, W., "Wnt signalling and its impact on development and cancer." *Nat. Rev. Can.* 8:387-398, Nature Publishing Group, England (2008).

Kobielak, A. and Fuchs, E., "α-Catenin: At the Junction of Intercellular Adhesion and Actin Dynamics," *Nat. Rev. Mol. Cell Biol.* 5;614-25, Nature Pub. Group, England (2004).

Koike, J., et al.,"Molecular Cloning of *Frizzled-10*, a Novel Member of the *Frizzled* Gene Family," *Biochem. Biophys. Res. Commun.* 262:39-43, Academic Press, United States (1999).

Korinek, V., et al., Two Members of the Tcf Family Implicated in Wnt/α- Catenin Signaling during Embryogenesis in the Mouse, *Mol. Cell. Biol.* 18:1248-1256, American Society for Microbiology, United States (1998).

Kuhnert, F., et al., "Essential requirement for Wnt signaling in proliferation of adult small intestine and colon revealed by adenoviral expression of Dickkopf-1," *Proc. Natl. Acad. Sci,* 101:266-271, The National Academy of Sciences, United States (2004).

Lazar, E., et al., "Transforming Growth Factor α: Mutation of Aspartic Acid 47 and Leucine 48 Results in Different Biological Activities," *Mol. Cell. Bio.* 8:1247-1252, American Society for Microbiology, United States (1988).

Lee, H.X., et al., "Embryonic Dorsal-Ventral Signaling: Secreted Frizzled-Related Proteins as Inhibitors of Tolloid Proteinases," *Cell* 124:147-159, Elsevier Inc., United States (2006).

Li, Y., et al., "LRP6 expression promotes cancer cell proliferation and tumorigenesis by altering β-catenin subcellular distribution," *Oncogene* 23:9129-9135, Nature Publishing Group, England (2004).

Li, Y., et al,, "The Gene for Autosomal Dominant Familial Exudative Vitreoretinopathy (Criswick-Schepens) on the Long Arm of Chromosome 11," *Am. J. Opthamol.* 113:712-714, Elsevier Science, United States (1992).

Li, Y., et al., "Evidence that transgenes encoding components of the Wnt signaling pathway preferentially induce mammary cancers trout progenitor cells," *Proc. Natl. Acad. Sci.* 100:15853-15858, The National Academy of Sciences, United States (2003).

Lin, S.-Y., et al., "β-Catenin, a novel prognostic marker for breast cancer: Its roles in cyclin D1 expression and cancer progression," *Proc. Natl. Acad. Sci.* 97:4262-4266, The National Academy of Sciences, United States (2000).

Liu, S., et at, "Interaction of hedgehog and notch pathways, and Bmi-1 in the regulation of human breast stern cell self-renewal," *Proc Amer Associ Cancer Res* 46 (2005).

Lo, P.-K., et al., "Epigenetic Suppression of Secreted Frizzled Related Protein 1 (SFRP1) Expression in Human Breast Cancer," *Cancer Biol. Ther.* 5:e1-e6, Landes Bioscience, United States (2006).

Lodygin, D., et al., "Functional Epigenomics Identifies Genes Frequently Silenced in Prostate Cancer," *Cancer Res.* 65:4218-4227, American Association for Cancer Research, United States (2005).

Lu, D., et al., "Repression of β-catenin function in malignant cells by nonsteroidal antiinflammatory drugs," *Proc. Natl. Acad. Sci.* 102:18567-18571, the National Academy of Sciences, United States (2005).

Mazieres, J., et al., "Wnt signaling in lung cancer," *Cancer Lett,* 222:1-10, Elsevier Ireland Ltd., Ireland (2005).

Miller, J.R., et al., "Mechanism and function of signal transduction by the Wnt/β-catenin and Wnt/$Ca^{2+}$ pathways," *Oncogene* 18:7860-7872, Stockton Press, England (1999).

Milovanovic, T., at al., "Expression of Wnt genes and frizzled 1 and 2 receptors in normal breast epithelium and infiltrating breast carcinoma," *Int J. Oncol.* 25:1337-1342, D.A. Spandidos, Greece (2004).

Moon, R.T., "Wnt/β-Catenin Pathway," *Sci. STKE* 271:1-3, American Association for the Advancement of Science, United States (2005).

Morrell, N.T ., et al., "Liposomal Packaging Generates Wnt protein with In Vivo Biological Activity," *PLoS One* 3:e2930, Public Library of Science, United States (2008).

Murdoch, B., et al., "Wnt-5A augments repopulating capacity and primitive hematopoietic development of human blood stern cells in vivo," *Proc. Natl. Acad. Sci.* 100:3422-3427, The National Academy of Sciences, United States (2003).

Nagayama, S., et al., "Therapeutic potential of antibodies against FZD10, a cell-surface protein, for synovial sarcomas," *Oncogene* 24:6201-6212, Nature Publishing Group, England (2005).

Nunnally, A.P. and Parr, B.A., "Analysis of *Fz10* expression in mouse embryos," *Dev. Genes Evol.* 214:144-148, Springer-Verlag, Germany (2004).

Nusse, R., et al., "A New Nomenclature for *int*-1 and Related Genes:The *Wnt* Gene Family," *Cell* 64:231-232, Cell Press, United States (1991).

Nusse, R., "The Wnt gene family in tumorigenesis and in normal development," *J Steroid Biochem. Mol. Biol.* 43:9-12, Pergamon Press, England (1992).

Olson, D.J. and Gibo, D.M., "Antisense *wnt*-5a Mimics *wnt*-1-Mediated C57MG Mammary Epithelial Cell Transformation," *Exp. Cell Res.* 241:134-141, Academic Press, United States (1998).

Oshima, H., et al., Morphological and Molecular Processes of Polyp Formation in $Apc^{\Delta716}$ Knockout Mice, *Cancer Res.* 57;1644-1649, The American Association for Cancer Research, United States (1997).

Patel, S., et al., "Glycogen synthase kinase-3 in insulin and Wnt signalling: a double-edged sword?," *Biochemical Society Transactions* 32:803-808, Portland Press Ltd., England (2004).

Pinto, D. and Clevers, H., "Wnt control of stem cells and differentiation in the intestinal epithelium," *Exp. Cell Res* 306:357-363, Elsevier Inc,, United States (2005).

Polakis, P., "Wnt signaling and cancer," *Genes Dev* 14:1837-1851, Cold Spring Harbor Laboratory Press, United States (2000).

Radtke, F. and Clevers, H., "Self-Renewal and Cancer of the Gut: Two Sides of a Coin," *Science* 307:1904-1909, American Association for the Advancement of Science, United States (2005).

Reya., T., et al.. "Wnt Signaling Regulates B Lymphocyte Proliferation through a LEF-1 Dependent Mechanism," *Immunity* 13:15-24, Cell Press, United States (2000).

Reya, T., et al., "Stem cells, cancer, and cancer stem cells" *Nature* 414:105-111, Nature Publish Group, England (2001).

Reya, T. and Clevers, H., "Wnt Signalling in stem cells and cancer," *Nature* 434:843-850, Nature Publishing Group, England (2005).

Reya, T., et al., "A role for Wnt signalling in self-renewal of haeatopoietic stem cells," *Nature* 423:409-41:4, Nature Publishing Group, England (2003).

Rhee, C.-S., et al., "Wnt and frizzled receptors as potential targets for immunotherapy in head and neck squamous cell carcinomas," *Oncogene* 21:6598-6605, Nature Publishing Group, England (2002).

Sagara. N., et al., "Molecular Cloning, Differential Expression, and Chromosomal Localization of Human *Frizzled-1, Frizzled-2,* and *Frizzled-7,"* *Biochem. Biophys. Res. Commun.* 252:117-122, Academic Press, United States (1998).

Saitoh, T., et al., "Frequent up-regulation of WNT5A mRNA in primary gastric cancer," *Int. J. Mol. Med.* 9:515-519, D.A. Spandidos, Greece (2002).

Saitoh, T., et al., "Molecular cloning and characterization of human *Frizzled-8* gene on chromosome 10p11.2," *Int. J. Oncol.* 18:991-996, D.A. Spandidos, Greece (2001).

Saitoh, T., et al., "Up-regulation of *Frizzled-10* (*FZD10*) by β-estradiol in MCF-7 cells and by retinoic acid in NT2 cells," *Int. J. Oncol.* 20:117-120, D.A. Spandidos, Greece (2002).

(56) References Cited

OTHER PUBLICATIONS

Sala, C.F., et al., "Identification, Gene Structure, and Expression of Human Frizzled-3 (*FZD3*)," *Biochem. Biophys. Res. Commun.* 273:27-34, Academic Press, United States (2000).

Saneyosiii, T., et al., "The Wnt/calcium pathway activates NF-AT and promotes ventral cell fate in *Xenopus* embryos," *Nature* 417:295-299, Macmillan Magazines Ltd., England (2002).

Schweizer, L. and Varmus, H., "Wnt/Wingless signaling through β-catenin requires the function of both LRP/Arrow and frizzled classes of receptors," *BMC Cell Biology* 4:4-14, Bio-Med Central Ltd., England (2003).

Semënov, M., et al., "SOST is a Ligand for LRP5/LRP6 and a Wnt Signaling Inhibitor," *J. Biol. Chem.* 280:26770-26775, The Ameriecan Society for Biochemistry and Molecular Biology, United States (2005).

Sen, M., et al., "Blockade of Wnt-5A/Frizzled 5 Signaling Inhibits Rheumatoid Synoviocyte Activation," *Arthritis Rheum.* 44:772-781, American College of Rheumatology, United States (2001).

Shalaby, M.R., et al., "Bispecific *HER2* x CD3 Antibodies Enhance T-Cell Cytotoxicity in Vitro and Localize *HER2*-Overexpressing Xenografts in Nude Mice," *Clin. Immunol. and Immunopathol,* 74:185-192, Academic Press, United States (1995).

Skolnick, J. and Fetrow, J.S., "From genes to protein structure and function: novel applications of computational approaches in the genomic era," *Trends Biotechnol.* 18:34-39, Elsevier Science Publishers, England (2000).

Suresh, M.R. et al.," Advantages of bispecific hybridomas in one-step immunocytochemistry and immunoassays," *Proc. Natl. Acad. Sci.* 83:7989-7993, The National Academy of Sciences, United States (1986).

Suzuki, H., et al., "A genomic screen for genes upregulated by demethylation and histone deacetylase inhibition in human colorectal cancer," *Nature Generics* 31:141-149, Nature Publishing Group, United States (2002).

Suzuki, H., et al., "Epigenetic inactivation *SFRP* genes allows constitutive WNT signaling in colorectal cancer," *Nature Genetics* 36:417-422, Nature Publishing Group, United States (2004).

Suzuki, H., et al., "Frequent epigenetic inactivation of Wnt antagonist genes in breast cancer," *Br. J. Cancer* 98:1147-1156, Cancer Research UK, England (2008).

Tanaka, S., at al., "A novel frizzled gene identified in human esophageal carcinoma mediates APC/β-catenin signals," *Proc. Natl. Acad. Sci. USA* 95:10164-10169, National Academy of Sciences, United States (1998).

Terasaki, H., et al., "*Frizzled-10*, up-regulated in primary colorectal cancer, is a positive regulator of the WNT—β-catenin—TCF signaling pathway", *Int. J. Mol. Med.* 9:107-112, D.A. Spandidos, Greece (2002).

Tokuhara, M., et al., "Molecular Cloning of Human *Frizzled-6,"* *Biochem Biophys. Res. Commun.* 243:622-627, Academic Press, United States (1998).

Topol, L., et at., "Wnt-521 inhibits the canonical Wnt pathway by promoting GSK-3-independent β-catenin degradation." *J. Cell Biol.* 162:899-908, The Rockefeller University Press, United States (2003).

Tosatto, S.C.E. and Toppo, S., "Large-Scale Prediction of Protein Structure and Function from Sequence," *Curr. Pharm. Des.* 12:2067-2086, Bentham Science Publishers, Netherlands (2006).

Townsend, A. and Trowsdale, J., "The transporters associated with antigen presentation," *Semin. Cell Biol.* 4:53-61, Academic Press, England (1993).

Toyofuku, T., et al., "Wnt/frizzled-2 Signaling induces Aggregation and Adhesion among Cardiac Myocytes by Increased Cadherio-β-Catenin Complex," *J. Cell. Biol.* 150:225-241, The Rockefeller University Press, United States (2000).

Umbhauer, M., et al., "The C-terminal cytoplasmic Lys-Thr-X-X-X-Trp motif in frizzled receptors mediates Wnt/β-catenin signalling," *EMBO J.* 19;4944-4954, Oxford University Press, England (2000).

Unkeless, J.C., "Characterization of a Monoclonal Antibody Directed Against Mouse Macrophage and Lymphocyte Fc Receptors," *J. Exp. Med.* 150:580-596, The Rockefeller University Press, United States (1979).

Unknown Author., "Purified Rat Anti-Mouse CD16/CD32 (Mouse BD Fc BlockTM)," Technical Data Sheet 553142 Rev. 16, 2 pages, BD Biosciences (copyright date 2006), URL:http://www.bdbiosciences.com/external_files/pm/doc/tds/mouse/live/web_enabled/01241D_553142.pdf.

Üren, A., et al., "Secreted Frizzled-related Protein-1 Binds Directly to Wingless and Is a Biphasic Modulator of Wnt Signaling," *J. Biol. Chem.* 275:4374-4382, American Society for Biochemistry and Molecular Biology, United States (2000).

Uyttendaele, H., et al., "Notch4 and Wnt-1 proteins function to regulate branching morphogenesis o fmammary epithelial cells in an opposing fashion," *Dev. Biol.* 196:204-217, Elsevier, United States (1998).

Van De Vijver, M.J., et al., "A Gene-Expression Signature As a Predictor of Survival in Breast Cancer," *N Eng. J. Med.* 347:1999-2009, Boston Massachusetts Medical Society, United States (2002).

Van De Wetering, M. et al., "The β-Catenin/TCF-4 Complex Imposes a Crypt Progenitor Phenotype on Colorectal Cancer Cells," *Cell* 111:241-250, Cell Press, United States (2002).

Van Den Berg, D.J., et al.,"Role of Members of the *Wnt* Gene Family in Human Hematopoiesis," *Blood* 92:3189-3202, The American Society of Hematology, United States (1998).

Van Es, J. H. and Cliver H., "Notch and Wnt: inhibitors as potential new drugs for intestinal neoplasia disease," *Trends Mol. Med.* 11:496-502, Elsevier Science Ltd., England (2005).

Van 'T Veer, L.J., et al., "Gene expression profiling predicts clinical outcome of breast cancer," *Nature* 415:530-536, Macmillan Magazines Ltd., England (2002).

Veeman, M.T., et al., "A Second Canon: Functions and Mechanisms of β-Catenin-Independent Wnt Signaling," *Dev. Cell* 5:367-377, Cell Press, United States (2003).

Vincan, E., et al., "Frizzled-7 receptor ectodomain expression in a colon cancer cell line induces morphological change and attenuates tumor growth," *Differentiation* 73:142-153, International Society of Differentiation, England (2005).

Voronkov, A.E., et al., "Molecular model of the Wnt protein binding site on the surface of dimeric CRD domain of the hFzd8 receptor," *Dokl. Bioehem. Biophys.* 419:75-78, International Academic Pub. Co., Russia (2008).

Wang, Y., et al., "A Large Family of Putative Transmembrane Receptors Homologous to the Product of the *Drosophila* Tissue Polarity Gene *frizzled,"* *J. Biol. Chem.* 271:4468-4476, American Society for Biochemistry and Molecular Biology, United States (1996).

Wang, Y-K., et al., "Characterization and Expression Pattern of the *frizzied* Gene *Fzd9*, the Mouse Homolog of *FZD9* Which Is Deleted in Williams-Beuren Syndrome," *Genomics* 57:235-248, Academic Press, United States (1999).

Wang, Z., et al., "Wnt7b Activates Canonical Signaling in Epithelial and Vascular Smooth Muscle Cells through Interactions with Fzdl, Fzd10, and LRP5," *Mol. Cell. Biol.* 25:5022-5030, American Society for Microbiology, United States (2005).

Webb, T., "Work on breast cancer stein cells raises questions about treatment strategies," *J. Natl Cancer Inst.* 95: 774-775, Oxford University Press, United States (2003).

Weeraratna, A.T., et al., "Wnt5a signaling directly affects cell motility and invasion of metastatic melanoma," *Cancer Cell* 1:279-288, Cell Press, United States (2002).

Willert, K. and Jones, K.A., "Wnt signaling: is the party in the nucleus?," *Genes Dev.* 20:1394-1404, Cold Spring Harbor Laboratory Press, United States (2006).

Willert, K., et al., "Wnt proteins are lipid-modified and can act as stem cell growth factors," *Nature* 423:448-452, Nature Publishing Group, England (2003).

WNT-3A COPE, (Online 2010), accessed on Oct. 1, 2010, accessed from http://www.copewithcytokines.de/cope.cgi?key=Wnt-3a.paras 2 and 5.

(56) References Cited

OTHER PUBLICATIONS

Wong, N.A.C.S., and Pignatelli, M., "β-Catenin—A Linchpin in Colorectal Carcinogenesis?," *Am. J. Pathol.* 160:389-401, American Society for Investigative Pathology, United States (2002).
Wong, S,C., et al., Expression of frizzled-related protein and Wnt-signalling molecules in invasive human breast tumours. *J. Pathol.* 196:145153, John Wiley and Sons. England (2002).
Woodward, W.A., et al., "WNT/β-catenin mediates radiation resistance of mouse mammary progenitor cells," *Proc. Natl. Acad. Sci.* 104:618-623, The National Aeademy, of Sciences, United States (2007).
Wu, C.-H. and Inusse, R., "Ligand Receptor Interactions in the Wnt Signaling Pathway in *Drosophila*," *J. Biol. Chem.* 277:41762-41769, The American Society for Biochemistry and Molecular Biology, Inc., United States (2002).
Yamashita, J.K., et al., Prospective identification of cardiac progenitors by a novel single cell-based cardiomyocyte induction, *FASEB J.* 19, FASEB, (2005), 29 pages.
Yang, P., et at "Study design considerations in clinical outcome research of lung cancer using microarray analysis," *Lung Cancer* 46:215-226, Elsevier Scientific Publishers, Ireland (2004).
Yang-Snyder, J., et al.,"A *frizzled* homolog functions in a vertebrate *Wnt* signaling pathway," *Curr. Biol.* 6:1302-1306, Cell Press, England (1996).
Zeng, X., et al., "A dual kinase mechanism for Wnt co-receptor phosphorylation and activation," *Nature* 438:873-877, Nature Publishing Group, England (2005).
Zhao, Z., "A :Human Homologue of the *Drosophila* Polarity Gene frizzled Has Been Identified and Mapped to 17q21.1," *Genomics* 27:370-373, Academic Press, Inc., United States (1995).
Zhu, A.J. and Watt, F.M., "β-catenin signalling modulates proliferative potential of human epidermal keratinocytes independently of intercellular adhesion," *Development* 126:2285-2298, The Company of Biologists Limited, England (1999).
English language Abstract of German Patent Publication No. WO 02/00576 A1, European Patent Office, espacenet database (2002).
Sperger, J, M., et al., "Gene expression patterns in human embryonic stern cells and human pluripotent germ cell tumors," *Proc. Natl. Acad. Sci.* 100:46681-13355, National Academy of Sciences, United States (2003).
International Search Report for International Patent Application No. PCT/US11/30950, ISA/US, Alexandria, Virginia 22313-1450, mailed on Oct. 18, 2011.
Kirikosiii, H., et al., "Expression profiles of 10 members of *Frizzled* gene family in human gastric cancer," *Int. J. Oncol.* 19:767-771, D.A. Spandidos, Greece (2001).
Katoh, M., "Molecular Cloning and Characterization of *MFRP*, a Novel Gene Encoding a Membrane-Type Frizzled-Related Protein," *Biochem. Biophys Res. Commun.* 282:116-123 Academic Press, United States (2001).
Kirikoshi, H., et al., "Molecular Cloning and Genomic Structure of human *Frizzled-3* at Chromosome 8p21," *Biochem. Biophys. Res. Commun.* 271:8-14, Academic Press, United States (2000).
Saldanha, J., et al., "Identification of a Frizzled-like cysteine rich domain in the extracellular region of developmental receptor tyrosine kinases," *Protein Sci.* 7:1632-1635, The Protein Society, United States (1998).
Lyons, J.P., et al., "Wnt-4 activates the canonical β-cateran-mediated Wnt pathway and binds Frizzled-6 CRD: functional implications of Wnt/β-catenin activity in kidney epithelial cells," *Exp. Cell Res.* 298:369-387, Elsevier Inc., United States (2004).
Sagara, et al., "FZD4S, a Splicing Variant of *Frizzled-4*, Encodes a Soluble-Type Positive Regulator of the WNT Signaling Pathway," *Biochem. Biophys, Res. Commun.* 282:750-756, Academic Press, United States (2001).
Guyre, P.M. et al., "Increased potency of Fc-receptor-targeted antigens," *Cancer Immunol. Immunother.* 45:146-148, 1997.
Lepourcelet, M., et al., "Small-molecule antagonists ofthe oncogenic Tcf/β-catenin protein complex," *Cancer Cell* 5:91-102, Cell Press, U.S.A. (2004).

Lu, C., et al., "The Binding Sites for Competitive Antagortistic Allosteric Antagonistic, and Agonistic Antibodies to the I Domain of Intcgrin LFA-1," *J. Immunol.* 173:3972-3978 American Society of Immunologists, Inc., United States (2004).
Polakis, P., "Evidence for Wnt Signaling in Cancers lacking Genetic Defects," PowerPoint NYAS Presentation and transcript, presented on Oct. 25, 2005, 71 pages.
Wood, V., et at., "The genome sequence of *Schizosaccharomyces pombe*," *Nature* 415:871-880, Nature Publishing Group, United Kingdom (2002).
Decypher ClustalW Multiple Alignment, Stanford University (online, Sep. 2006), accessed on Sep. 30, 2010, accessed from http://web.archive.org/web/20060912071608/http://www2.stanford.edu/~musse/genealigns/inhifzalign.html>.
European Search Report for Application No. 07752161.5, dated Oct. 15, 2009, European Patent Office, Netherlands, 12 pages.
International Search Report of the International Searching Authority for International Application No. PCT/US07/005443, mailed on Oct. 30, 2008, United States Patent and Trademark Office, United States, 4 pages.
International Search Report fix International Application No. PCT/US09/58635, ISA/US, Alexandria, VA, mailed on Nov. 19, 2010.
Written Opinion for the International Searching Authority for International Application No. PCT/US07/05443, mailed on Oct. 30, 2008, The International Bureau of WIPO, Switzerland, 4 pages.
Written Opinion for International Application No. PCT/US09/58635, ISA/US, Alexandria, VA, mailed on Nov. 19, 2010.
Fredriksson et al. "The G-Protein-Coupled Receptors in the Human Genome Form Five Main Families. Phylogenetic Analysis, Paralogon Groups, and Fingerprints" *Mol. Pharmacol.* 63:1256-1272, The American Society for Pharmacology and Experimental Therapeutics, United States (2003).
De Gruijl, T. and Curiel, D.T., "Cancer vaccine strategies get bigger and better," *Nat. Med.* 5(10):1124-1125, Nature Publishing Company, United States (1999).
Vajdos, F.F., et at., "Comprehensive functional maps of the antigen binding site of an anti-ErbB2 antibody obtained with shotgun scanning mutagenesis," *J. Mol. Biol.* 320:415-428, Elsevier, England (2002).
Lee, K-H., et al., "Increased vaccine specific T Cell frequency after peptide based vaccination correlates with increased susceptibility to in vitro stimulation but does not lead to tumor regression," *J. Immunol.* 163(11):6292-300, Williams & Wilkins, United States (1999).
Bodey, B., et at., "Failure of cancer vaccines: the significant limitations of this approach to immununotherapy," *Anticancer Res.* 200:2665-2676, International Institute of Anticancer Research, Greece (2000).
MacCallum, RM et al. "Antibody antigen interactions: contact analysis and binding site topography," *J. Mol. Biol.* 262(5):732-745, Elsevier, England (1996).
Casset, F., et al., "A peptide mimetic of an anti-CD4 monoclonal antibody by rational design," *Biochem. Biophys. Res. Comm.* 37: 198-205, Academic Press, United States (2003).
Holm, P., et al., "Functional mapping and single chain construction of the anti-cytokeratin 8 monoclonal antibody TS1," *Mol. Immunol.* 44:1075-1084, Pergamon Press, England (2007).
Donnelly, J., "Cancer vaccine targets leukemia," *Nat. Med.* 9(11):1354-6, Nature Publishing Company, United States (2003).
Wu, H., et al., "Humanization of a murine monoclonal antibody by simultaneous optimization of framework and CDR residues," *J. Mol. Biol.* 294:151462, Elsevier, England (1999).
Ezzel, C. "Cancer 'Vaccines': An Idea Whose Time Has Come?" *Journal of NIH Research* 7:46-49, National Institutes of Health, United States (1995).
Forni, G. et al., "Immunopreventon of Cancer: Is the Time Ripe?" *Cancer Res* 60(10):2571-2575, American Association for Cancer Research, United States (2000).
Chatterjee, M.B, et al., "Idiotypic antibody immunotherapy of cancer," *Cancer Immunol. Immunother.* 38(2):75-82, Springer International, Germany (1994).

(56) References Cited

OTHER PUBLICATIONS

Rudikoff, S., et al., "Single amino acid substitution altering antigen binding specificity," *Proc. Natl. Acad. Sci.* 79(6):1979-83, National Academy of Sciences, United States (1982).
International Search Report of the International Searching Authority for International Application No. PCT/US11/20994, mailed on Aug. 15, 2011, United States Patent and Trademark Office, United States, 4 pages.
Written Opinion for the International Searching Authority for International Application No. PCT/US11/20994, mailed on Aug. 15, 2011, International Searching Authority, United States, 6 pages.
Unknown Author, "Biotinylated Anti-mouse Fzd-2 Antibody", 1 page, R&D Systems, dated Feb. 11, 2004, URL:http://www.rndsystems.com/pdf/baf1307.pdf, downloaded Sep. 27, 2012.
Aruffo, A., et al., "CD44 is the principal cell surface receptor for hyaluronate," *Cell* 610:1303-13, Cell Press, United States (1990).
"Frizzled 8 precursor (Frizled 8) (Fz-8) (hFz8)." [online], Sep. 2005, Accession Q9H461, Retrieved on Feb. 1, 2013 from http://www.ncbi.nlm.nih.gov/protein/17433053?sat=34&satkey-5096022.
"Frizzled 4 precursor (Frizled-4) (Fz-4) (Fz-4) (hFzE4)." [online], Sep. 2005, Accession Q9ULV1, Retrieved on Feb. 11, 2013 from http://www.ncbi/nlm.nih.gov/protein/62298045?sat=348zsatkey=4861841.
MacLeod, R.J., et al., "Wnt5a secretion stimulated by extracellular calcium-sensing receptor inhibits defective Wnt signaling in colon cancer cells," *Am. Physiol. Gastrointest. Liver. Physiol.* 293(1):G403-G411, American Physiological Society, United States (2007).
Khan. N.I., et al., "Activation of Wnt/beta-catenin pathway mediates growth and survival in B-cell progenitor acute lymphoblastic leukaemia," *Br. J. Haematol.* 1380:338-348, Wiley-Blackwell, England (2007).
You, L., et al., "Wnt-1 signal as a potential cancer therapeutic target," *Drug News Perspect.* 19(1):27-31, Thomson Reuters, United States (2006).
Katoh, Y. and Katoh, M., "Comparative genomics on Fzd8 orthologs," *Oncol. Rep.* 13(15):993-997, D.A. Spandidos, Greece (2005).
Merle, P., et al., "Functional consequences of frizzled-7 receptor overexpression in human hepatocellular carcinoma," *Gastroenterology* 127(4):1110-1122, W.B. Saunders, United States (2004)
Gurney, A., et al., "Wnt pathway inhibition via the targeting of Frizzled receptors results in decreased gtowth and tumorigenicity of human tumors," *Proc. Natl. Acad. Sci. USA* 109(29):11717-22, National Academy of Sciences, United States (2012).
Schulte. G. et al., "The Frizzled family of unconventional G-protein-coupled receptors," *TRENDS in Pharmacological Science* 28: 518-525 (2007).
Luu, H, et al., "Wnt/β-Catenin Signaling Pathway as Novel Cancer Drug Targets," *Current Cancer Drugs* 4: 653-671 (2004).
Ueno, K, et al., "Frizzled homolog proteins, microRNAs and Wnt Signaling in cancer," *International Journal of Cancer* 132: 1731-1740 (2013).
Accession No. GSP: AVA85292, EBI database, First entry on Apr. 2, 2009, accessed on Jul. 18, 2013, 1 page.
Albers, J., et al., "Control of Bone Formation by the Serpentine Receptor Frizzled-9," *The Journal of Cellular Biology* 192(6):1057-1072, Rockefeller University Press, United States (2011).
Cao, Y., et al., "Nuclear-Cytoplasmic Shuttling of Menin Regulates Nuclear Translocation of {beta}-Catenin," *Molecular and Cellular Biology* 29(20):5477-5487, American Society for Microbiology, United States (2009).
GenBank, "Alkaline phosphatase [Pseudotermotoga lettingae TMO]," Accession No. ABV34137, Accessed at http://www.ncbi.nlm.nih.gov/protein/ABV34137, Accessed on May 13, 2015, 2 pages.
GenBank, "Hypothetical protein BarnMEX5DRAFT_6767 [Burkholderia ambifaria MEX-5]," Accession No. EDT37460, Accessed at http://www.ncbi.nlm.nih.gov/protein/EDT37460, Accessed on May 13, 2015, 1 page.
GenBank, "Hypothetical protein, conserved, partial [Trypanosoma cruzl]," Accession No. EAN81721, Accessed at http://www.ncbi.nlm/nih/gov/protein/EAN81721, Accessed on May 13, 2015, 2 pages.
He, X., et al., "LDL Receptor-related Proteins 5 and 6 in WNT/beta-catenin Signaling: Arrows Point the Way," *Development* 131(8):1663-1677, Company of Biologists Limited, England (2004).
Hoppler, S., et al., "Expression of a Dominant-Negative Wnt Blocks Induction of MyoD in Xenopus Embryos," *Genes and Development* 10(21):2805-2817, Cold Spring Harbor Laboratory Press, United States (1996).
Hu, T. and Li, C., "Convergence between Wnt-beta-catenin and EGFR signaling in cancer," *Molecular Cancer* 9:236-242, BioMed Central Ltd., United Sates (2010).
Iverson, C., et al., "RDEA119/BAY 869766: A Potent, Selective, Allosteric Inhibitor of MEK1/2 for the Treatment of Cancer," *Cancer Research* 69:6839-6847, American Association for Cancer Research, United States (2009).
Kim, D., et al., "A Hidden Oncogenic Positive Feedback Loop Caused by Crosstalk between Wnt and ERK Pathways," *Oncogene* 26:4571-4579, Nature Publishing Group, England (2007).
Krishnan, V., et al., "Regulation of Bone Mass by Wnt Signaling," *The Journal of Clinical Investigation* 116(5):1202-1209, American Society for Clinical Investigation, United States (2006).
Le, P.N., et al., "Targeting the Wnt pathway in human cancers: Therapeutic targeting with a focus on OMP-54F28," *Pharmacology & Therapeutics* 146:1-11, Elsevier Inc., United States (2015).
O'Connell, M.P. and Weeraratna, A.T., "Hear the Wnt Ror: how melanoma cells adjust to changes in Wnt," *Pigment Cell & Melanoma Research* 22:724-739, Blackwell Munksgaard, England (2009).
OncoMed Pharmaceuticals Press Release, "OncoMed Presents Data on Clinical and Preclinical Anti-Cancer Stem Cell Programs at American Association for Cancer Research Annual Meeting," Apr. 21, 2015, 3 pages.
OncoMed Pharmaceuticals Press Release, "OncoMed to Present Data on Multiple Anti-Cancer Stem Cell Candidates at the American Association of Cancer Research Meeting," Mar. 19, 2015, 2 pages.
Schulte, G., "Frizzleds and Wnt/beta-catenin Signaling—The Black Box of Ligand-receptor Selectivity, Complex Stoichiometry and Activation Kinetics," *European Journal of Pharmacology*, epub:1-5, Elsevier B.V., Netherlands (2015).
Semba, S., et al., "Nuclear Accumulation of B-Catenin in Human Endocrine Tumors: Association with Ki-67 (MIB-1) Proliferative Activity," *Endocrine Pathology* 11(3):243-250, Humana Press, United States (2000).
Tamura, M., et al., "Structural Correlates of an Anticarcinoma Antibody: Identification of Specificity-Determining Residues (SDRs) and Development of a Minimally Immunogenic Antibody Variant by Retention of SDRs Only," *The Journal of Immunology* 164(3):1432-1441, American Association of Immunologists, United States (2000).
UniProtKB Database, "Submitted name: Putative uncharacterized protein," Accession No. B7AJZ5, Accessed on May 13, 2014, 5 pages, 2009.
UniProtKB Database, "Submitted name: Helix-turn-helix protein," Accession No. A2W361, Accessed on May 13, 2015, 5 pages, 2007.
Written Opinion for the International Searching Authority for International Application No. PCT/US2014/014443, mailed on Apr. 15, 2014, International Searching Authority, United States, 17 pages.
Extended European Search Report for EP Application No. 11763516, European Patent Office, Germany, mailed on Aug. 5, 2013, 9 pages.

FIGURE 13

18R5/18R8 heavy chain variable region (VH) amino acid sequence (SEQ ID NO:10):
EVQLVESGGGLVQPGGSLRLSCAASGFTFSHYTLSWVRQAPGKGLEWVSVISGDGSYTYYADSV
KGRFTISSDNSKNTLYLQMNSLRAEDTAVYYCARNFIKYVFANWGQGTLVTVSS Full-length 18R5/18R8 heavy chain (IgG2) amino acid sequence (SEQ ID NO:11; underlining indicates VH):
MKHLWFFLLLVAAPRWVLSEVQLVESGGGLVQPGGSLRLSCAASGFTFSHYTLSWVRQAPGKGL
EWVSVISGDGSYTYYADSVKGRFTISSDNSKNTLYLQMNSLRAEDTAVYYCARNFIKYVFANWG
QGTLVTVSSASTKGPSVFPLAPCSRSTSESTAALGCLVKDYFPEPVTVSWNSGALTSGVHTFPA
VLQSSGLYSLSSVVTVPSSNFGTQTYTCNVDHKPSNTKVDKTVERKCCVECPPCPAPPVAGPSV
FLFPPKPKDTLMISRTPEVTCVVVDVSHEDPEVQFNWYVDGVEVHNAKTKPREEQFNSTFRVVS
VLTVVHQDWLNGKEYKCKVSNKGLPAPIEKTISKTKGQPREPQVYTLPPSREEMTKNQVSLTCL
VKGFYPSDIAVEWESNGQPENNYKTTPPMLDSDGSFFLYSKLTVDKSRWQQGNVFSCSVMHEAL
HNHYTQKSLSLSPGK 18R8 light chain variable region (VL) amino acid sequence (SEQ ID NO:12):
DIELTQPPSVSVAPGQTARISCSGDKLGKKYASWYQQKPGQAPVLVIYEKDNRPSGIPERFSGS
NSGNTATLTISGTQAEDEADYYCSSFAGNSLEVFGGGTKLTVLG Full-length 18R8 light chain (lambda) amino acid sequence (SEQ ID NO:13; underlining indicates VL):
MAWALLLLTLLTQGTGSWADIELTQPPSVSVAPGQTARISCSGDKLGKKYASWYQQKPGQAPVL
VIYEKDNRPSGIPERFSGSNSGNTATLTISGTQAEDEADYYCSSFAGNSLEVFGGGTKLTVLGQ
PKAAPSVTLFPPSSEELQANKATLVCLISDFYPGAVTVAWKADSSPVKAGVETTTPSKQSNNKY
AASSYLSLTPEQWKSHRSYSCQVTHEGSTVEKTVAPTECS 18R5 light chain variable region (VL) amino acid sequence (SEQ ID NO:14):
DIELTQPPSVSVAPGQTARISCSGDNIGSFYVHWYQQKPGQAPVLVIYDKSNRPSGIPERFSGS
NSGNTATLTISGTQAEDEADYYCQSYANTLSLVFGGGTKLTVLG Full-length 18R5 light chain (lambda) amino acid sequence (SEQ ID NO:15; underlining indicates VL):
MAWALLLLTLLTQGTGSWADIELTQPPSVSVAPGQTARISCSGDNIGSFYVHWYQQKPGQAPVL
VIYDKSNRPSGIPERFSGSNSGNTATLTISGTQAEDEADYYCQSYANTLSLVFGGGTKLTVLGQ
PKAAPSVTLFPPSSEELQANKATLVCLISDFYPGAVTVAWKADSSPVKAGVETTTPSKQSNNKY
AASSYLSLTPEQWKSHRSYSCQVTHEGSTVEKTVAPTECS

FIGURE 14

Nucleotide sequence encoding 18R5/18R8 heavy chain variable region (VH) (SEQ ID NO:17):
GAAGTGCAACTGGTGGAAAGCGGCGGCGGCCTGGTGCAACCTGGCGGCAGCCTGAGACTGAGC
TGCGCTGCCTCCGGATTTACCTTTTCTCATTATACTCTGTCTTGGGTGCGCCAAGCCCCT
GGGAAGGGTCTCGAGTGGGTGAGCGTTATCTCTGGTGATGGTAGCTATACCTATTATGCT
GATAGCGTGAAAGGCAGATTTACCATTTCAAGTGATAATTCCAAAAACACCCTGTATCTG
CAAATGAACAGCCTGAGAGCTGAAGATACAGCCGTGTATTATTGCGCTAGAAATTTTATT
AAGTATGTTTTTGCTAATTGGGGCCAAGGCACCCTGGTGACAGTTAGCTCA Nucleotide sequence encoding full-length 18R5/18R8 heavy chain (IgG2) (SEQ ID NO:18; underlining indicates nt sequence encoding VH):
ATGAAACACCTGTGGTTCTTCCTCCTGCTGGTGGCAGCTCCCAGATGGGTCCTGTCCGAA
GTGCAACTGGTGGAAAGCGGCGGCGGCCTGGTGCAACCTGGCGGCAGCCTGAGACTGAGC
TGCGCTGCCTCCGGATTTACCTTTTCTCATTATACTCTGTCTTGGGTGCGCCAAGCCCCT
GGGAAGGGTCTCGAGTGGGTGAGCGTTATCTCTGGTGATGGTAGCTATACCTATTATGCT
GATAGCGTGAAAGGCAGATTTACCATTTCAAGTGATAATTCCAAAAACACCCTGTATCTG
CAAATGAACAGCCTGAGAGCTGAAGATACAGCCGTGTATTATTGCGCTAGAAATTTTATT
AAGTATGTTTTTGCTAATTGGGGCCAAGGCACCCTGGTGACAGTTAGCTCAGCCAGCACA
AAGGGCCCTAGCGTCTTCCCTCTGGCTCCCTGCAGCAGGAGCACCAGCGAGAGCACAGCC
GCCCTGGGCTGCCTGGTCAAGGACTACTTCCCCGAACCGGTGACGGTGTCGTGGAACTCA
GGCGCTCTGACCAGCGGCGTGCACACCTTCCCAGCTGTCCTACAGTCCTCAGGACTCTAC
TCCCTCAGCAGCGTGGTGACCGTGCCCTCCAGCAACTTCGGCACCCAGACCTACACCTGC
AACGTAGATCACAAGCCCAGCAACACCAAGGTGGACAAGACAGTTGAGCGCAAATGTTGT
GTCGAGTGCCCACCGTGCCCAGCACCACCTGTGGCAGGACCGTCAGTCTTCCTCTTCCCC
CCAAAACCCAAGGACACCCTCATGATCTCCCGGACCCCTGAGGTCACGTGCGTGGTGGTG
GACGTGAGCCACGAAGACCCCGAGGTCCAGTTCAACTGGTACGTGGACGGCGTGGAGGTG
CATAATGCCAAGACAAAGCCACGGGAGGAGCAGTTCAACAGCACGTTCCGTGTGGTCAGC
GTCCTCACCGTTGTGCACCAGGACTGGCTGAACGGCAAGGAGTACAAGTGCAAGGTCTCC
AACAAAGGCCTCCCAGCCCCCATCGAGAAAACCATCTCCAAAACCAAAGGGCAGCCCCGA
GAACCACAGGTGTACACCCTGCCCCCATCCCGGGAGGAGATGACCAAGAACCAGGTCAGC
CTGACCTGCCTGGTCAAAGGCTTCTACCCCAGCGACATCGCCGTGGAGTGGGAGAGCAAT
GGGCAGCCGGAGAACAACTACAAGACCACACCTCCCATGCTGGACTCCGACGGCTCCTTC
TTCCTCTACAGCAAGCTCACCGTGGACAAGAGCAGGTGGCAGCAGGGGAACGTCTTCTCA
TGCTCCGTGATGCATGAGGCTCTGCACAACCACTACACGCAGAAGAGCCTCTCCCTGTCT
CCGGGTAAA

FIGURE 15

Nucleotide sequence encoding 18R8 light chain variable region (VL) (SEQ ID NO:19):
GATATCGAACTGACCCAGCCTCCTTCAGTGAGCGTTGCACCAGGTCAGACCGCTAGAATCTCT
TGTAGCGGCGATAAGCTGGGTAAGAAGTATGCTTCTTGGTACCAGCAGAAACCCGGGCAG
GCTCCAGTTCTGGTGATTTATGAGAAGGATAATAGACCCTCAGGCATCCCTGAACGCTTT
AGCGGATCCAACAGCGGCAACACCGCTACCCTGACCATTAGCGGCACTCAGGCTGAAGAC
GAAGCCGATTATTATTGCTCTTCTTTTGCTGGTAATTCTCTGGAGGTGTTTGGCGGCGGC
ACCAAGTTAACCGTCCTGGGT Nucleotide sequence encoding full-length 18R8 light chain (lambda) (SEQ ID NO:20; underlining indicates nt sequence encoding VL):
ATGGCCTGGCTCTGCTGCTCCTCACCCTCCTCACTCAGGGCACAGGATCCTGGGCTGAT
ATCGAACTGACCCAGCCTCCTTCAGTGAGCGTTGCACCAGGTCAGACCGCTAGAATCTCT
TGTAGCGGCGATAAGCTGGGTAAGAAGTATGCTTCTTGGTACCAGCAGAAACCCGGGCAG
GCTCCAGTTCTGGTGATTTATGAGAAGGATAATAGACCCTCAGGCATCCCTGAACGCTTT
AGCGGATCCAACAGCGGCAACACCGCTACCCTGACCATTAGCGGCACTCAGGCTGAAGAC
GAAGCCGATTATTATTGCTCTTCTTTTGCTGGTAATTCTCTGGAGGTGTTTGGCGGCGGC
ACCAAGTTAACCGTCCTGGGTCAGCCCAAGGCTGCCCCAGCGTCACTCTGTTCCCTCCC
TCCTCTGAGGAGCTGCAAGCCAACAAGGCCACACTGGTGTGTCTCATAAGTGACTTCTAC
CCTGGAGCCGTGACAGTGGCCTGGAAGGCAGATAGCAGCCCCGTCAAGGCTGGAGTGGAG
ACCACCACACCCTCCAAACAAAGCAACAACAAGTACGCTGCCAGCAGCTATCTGAGCCTG
ACACCTGAGCAGTGGAAGTCCCACAGAAGCTACAGCTGCCAGGTCACACATGAAGGGAGC
ACCGTGGAGAAGACAGTGGCCCCTACAGAATGTTCA Nucleotide sequence encoding 18R5 light chain variable region (VL) (SEQ ID NO:21):
GATATCGAGCTGACTCAGCCTCCATCCGTGAGTGTGGCCCCTGGTCAGACAGCACGCATCAGC
TGCTCCGGGACAATATCGGATCTTTCTACGTGCACTGGTATCAGCAGAAGCCTGGTCAG
GCTCCAGTTCTCGTTATCTATGATAAGAGTAATCGCCCTCTGGGATTCCAGAGCGCTTC
AGCGGAAGCAACAGCGGAAATACTGCAACTCTCACAATTTCCGGTACTCAGGCTGAGGAC
GAAGCCGACTATTACTGCCAAAGCTACGCAAACACCCTGTCCCTCGTCTTCGGAGGCGGA
ACCAAGTTAACCGTCCTGGGT Nucleotide sequence encoding full-length 18R5 light chain (lambda) (SEQ ID NO:22; underlining nt sequence encoding VL):
ATGGCATGGGCACTGCTGCTGCTCACTCTGCTGACACAAGGTACTGGCTCTTGGGCCGAT
ATCGAGCTGACTCAGCCTCCATCCGTGAGTGTGGCCCCTGGTCAGACAGCACGCATCAGC
TGCTCCGGGACAATATCGGATCTTTCTACGTGCACTGGTATCAGCAGAAGCCTGGTCAG
GCTCCAGTTCTCGTTATCTATGATAAGAGTAATCGCCCTCTGGGATTCCAGAGCGCTTC
AGCGGAAGCAACAGCGGAAATACTGCAACTCTCACAATTTCCGGTACTCAGGCTGAGGAC
GAAGCCGACTATTACTGCCAAAGCTACGCAAACACCCTGTCCCTCGTCTTCGGAGGCGGA
ACCAAGTTAACCGTCCTGGGTCAGCCCAAGGCTGCCCCAGCGTCACTCTGTTCCCTCCC
TCCTCTGAGGAGCTGCAAGCCAACAAGGCCACACTGGTGTGTCTCATAAGTGACTTCTAC
CCTGGAGCCGTGACAGTGGCCTGGAAGGCAGATAGCAGCCCCGTCAAGGCTGGAGTGGAG
ACCACCACACCCTCCAAACAAAGCAACAACAAGTACGCTGCCAGCAGCTATCTGAGCCTG
ACACCTGAGCAGTGGAAGTCCCACAGAAGCTACAGCTGCCAGGTCACACATGAAGGGAGC
ACCGTGGAGAAGACAGTGGCCCCTACAGAATGTTCA

FIGURE 16

Fzd7 ECD Fc fusion protein amino acid sequence (SEQ ID NO:16):
MRDPGAAAPLSSLGLCALVLALLGALSAGAGAQPYHGEKGISVPDHGFCQPISIPLCTDIAYNQ
TILPNLLGHTNQEDAGLEVHQFYPLVKVQCSPELRFFLCSMYAPVCTVLDQAIPPCRSLCERAR
QGCEALMNKFGFQWPERLRCENFPVHGAGEICVGQNTSDGSGGPGGGPTAYPTAPYLPDLPFTA
LPPGASDGRGRPAFPFSCPRQLKVPPYLGYRFLGERDCGAPCEPGRANGLMYFKEEERRFARLG
RADKTHTCPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSKL
TVDKSRWQQGNVFSCSVMHEALHNHYTQKSLSLSPGK Nucleotide sequence encoding Fzd7 ECD Fc fusion protein (SEQ ID NO:23):
ATGCGGGACCCCGGCGCGGCCGCTCCGCTTTCGTCCCTGGGCCTCTGTGCCCTGGTGCTG
GCGCTGCTGGGCGCACTGTCCGCGGGCGCCGGGGCGCAGCCGTACCACGGAGAGAAGGGC
ATCTCCGTGCCGGACCACGGCTTCTGCCAGCCCATCTCCATCCCGCTGTGCACGGACATC
GCCTACAACCAGACCATCCTGCCCAACCTGCTGGGCCACACGAACCAAGAGGACGCGGGC
CTCGAGGTGCACCAGTTCTACCCGCTGGTGAAGGTGCAGTGTTCTCCGAACTCCGCTTT
TTCTTATGCTCCATGTATGCGCCCGTGTGCACCGTGCTCGATCAGGCCATCCCGCCGTGT
CGTTCTCTGTGCGAGCGCGCCCGCCAGGGCTGCGAGGCGCTCATGAACAAGTTCGGCTTC
CAGTGGCCCGAGCGGCTGCGCTGCGAGAACTTCCCGGTGCACGGTGCGGGCGAGATCTGC
GTGGGCCAGAACACGTCGGACGGCTCCGGGGGCCCAGGCGGCGGCCCCACTGCCTACCCT
ACCGCGCCCTACCTGCCGGACCTGCCCTTCACCGCGCTGCCCCGGGGGCCTCAGATGGC
AGGGGGCGTCCCGCCTTCCCCTTCTCATGCCCCGTCAGCTCAAGGTGCCCCCGTACCTG
GGCTACCGCTTCCTGGGTGAGCGCGATTGTGGCGCCCCGTGCGAACCGGGCCGTGCCAAC
GGCCTGATGTACTTTAAGGAGGAGGAGAGGCGCTTCGCCCGCCTCGGGCGCGCCGACAAA
ACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTG
GTGGTGGACGTGAGCCACGAAGACCCTGAGGTCAAGTTCAACTGGTACGTGGACGGCGTG
GAGGTGCATAATGCCAAGACAAAGCCGCGGGAGGAGCAGTACAACAGCACGTACCGTGTG
GTCAGCGTCCTCACCGTCCTGCACCAGGACTGGCTGAATGGCAAGGAGTACAAGTGCAAG
GTCTCCAACAAAGCCCTCCCAGCCCCCATCGAGAAAACCATCTCCAAAGCCAAAGGGCAG
CCCCGAGAACCACAGGTGTACACCCTGCCCCCATCCCGGGATGAGCTGACCAAGAACCAG
GTCAGCCTGACCTGCCTGGTCAAAGGCTTCTATCCCAGCGACATCGCCGTGGAGTGGGAG
AGCAATGGGCAGCCGGAGAACAACTACAAGACCACGCCTCCCGTGCTGGACTCCGACGGC
TCCTTCTTCCTCTACAGCAAGCTCACCGTGGACAAGAGCAGGTGGCAGCAGGGGAACGTC
TTCTCATGCTCCGTGATGCATGAGGCTCTGCACAACCACTACACACAGAAGAGCCTCTCC
CTGTCTCCGGGTAAA

FIGURE 17

Human FZD1 full length amino acid sequence (SEQ ID NO:26; underlining indicates ECD):
MAEEEAPKKSRAAGGGASWELCAGALSARLAEEGSGDAGGRRRPPVDPRRLARQLLLLW
LLEAPLLLGVRAQAAGQGPGQGPGPGQQPPPPPQQQQSGQQYNGERGISVPDHGYCQPIS
IPLCTDIAYNQTIMPNLLGHTNQEDAGLEVHQFYPLVKVQCSAELKFFLCSMYAPVCTVL
EQALPPCRSLCERARQGCEALMNKFGFQWPDTLKCEKFPVHGAGELCVGQNTSDKGTPTP
SLLPEFWTSNPQHGGGGHRGGFPGGAGASERGKFSCPRALKVPSYLNYHFLGEKDCGAPC
EPTKVYGLMYFGPEELRFSRTWIGIWSVLCCASTLFTVLTYLVDMRRFSYPERPIIFLSG
CYTAVAVAYIAGFLLEDRVVCNDKFAEDGARTVAQGTKKEGCTILFMMLYFFSMASSIWW
VILSLTWFLAAGMKWGHEAIEANSQYFHLAAWAVPAIKTITILALGQVDGDVLSGVCFVG
LNNVDALRGFVLAPLFVYLFIGTSFLLAGFVSLFRIRTIMKHDGTKTEKLEKLMVRIGVF
SVLYTVPATIVIACYFYEQAFRDQWERSWVAQSCKSYAIPCPHLQAGGGAPPHPPMSPDF
TVFMIKYLMTLIVGITSGFWIWSGKTLNSWRKFYTRLTNSKQGETTV Human FZD1 Fri domain amino acid sequence (SEQ ID NO:28; amino acids 87-237 of SEQ ID NO:26):
QQPPPPPQQQQSGQQYNGERGISVPDHGYCQPISIPLCTDIAYNQTIMPNLLGHTNQEDA
GLEVHQFYPLVKVQCSAELKFFLCSMYAPVCTVLEQALPPCRSLCERARQGCEALMNKFG
FQWPDTLKCEKFPVHGAGELCVGQNTSDKGT

FIGURE 18

Human FZD2 full length amino acid sequence (SEQ ID NO: 30; underlining indicates ECD):
MRPRSALPRLLLPLLLLPAAGPAQFHGEKGISIPDHGFCQPISIPLCTDIAYNQTIMPNL
LGHTNQEDAGLEVHQFYPLVKVQCSPELRFFLCSMYAPVCTVLEQAIPPCRSICERARQG
CEALMNKFGFQWPERLRCEHFPRHGAEQICVGQNHSEDGAPALLTTAPPPGLQPGAGGTP
GGPGGGGAPPRYATLEHPFHCPRVLKVPSYLSYKFLGERDCAAPCEPARPDGSMFFSQEE
TRFARLWILTWSVLCCASTFFTVTTYLVDMQRFRYPERPIIFLSGCYTMVSVAYIAGFVL
QERVVCNERFSEDGYRTVVQGTKKEGCTILFMMLYFFSMASSIWWVILSLTWFLAAGMKW
GHEAIEANSQYFHLAAWAVPAVKTITILAMGQIDGDLLSGVCFVGLNSLDPLRGFVLAPL
FVYLFIGTSFLLAGFVSLFRIRTIMKHDGTKTEKLERLMVRIGVFSVLYTVPATIVIACY
FYEQAFREHWERSWVSQHCKSLAIPCPAHYTPRMSPDFTVYMIKYLMTLIVGITSGFWIW
SGKTLHSWRKFYTRLTNSRHGETTV Human FZD2 Fri domain amino acid sequence (SEQ ID NO:32; amino acids 24-159 of SEQ ID NO:30):
QFHGEKGISIPDHGFCQPISIPLCTDIAYNQTIMPNLLGHTNQEDAGLEVHQFYPLVKVQ
CSPELRFFLCSMYAPVCTVLEQAIPPCRSICERARQGCEALMNKFGFQWPERLRCEHFPR
HGAEQICVGQNHSEDG

FIGURE 19

Human FZD1 full length DNA sequence (SEQ ID NO:29):
ATGGCTGAGGAGGAGGCGCCTAAGAAGTCCCGGGCCGCCGGCGGTGGCGCGAGCTGGGAA
CTTTGTGCCGGGGCGCTCTCGGCCCGGCTGGCGGAGGAGGGCAGCGGGGACGCCGGTGGC
CGCCGCCGCCCGCCAGTTGACCCCCGGCGATTGGCGCGCCAGCTGCTGCTGCTGCTTTGG
CTGCTGGAGGCTCCGCTGCTGCTGGGGGTCCGGGCCCAGGCGGCGGGCCAGGGGCCAGGC
CAGGGGCCCGGGCCGGGGCAGCAACCGCCGCCGCCGCCTCAGCAGCAACAGAGCGGGCAG
CAGTACAACGGCGAGCGGGGCATCTCCGTCCCGGACCACGGCTATTGCCAGCCCATCTCC
ATCCCGCTGTGCACGGACATCGCGTACAACCAGACCATCATGCCCAACCTGCTGGGCCAC
ACGAACCAGGAGGACGCGGGCCTGGAGGTGCACCAGTTCTACCCTCTAGTGAAAGTGCAG
TGTTCCGCTGAGCTCAAGTTCTTCCTGTGCTCCATGTACGCGCCCGTGTGCACCGTGCTA
GAGCAGGCGCTGCCGCCCTGCCGCTCCCTGTGCGAGCGCGCGCGCCAGGGCTGCGAGGCG
CTCATGAACAAGTTCGGCTTCCAGTGGCCAGACACGCTCAAGTGTGAGAAGTTCCCGGTG
CACGGCGCCGGCGAGCTGTGCGTGGGCCAGAACACGTCCGACAAGGGCACCCCGACGCCC
TCGCTGCTTCCAGAGTTCTGGACCAGCAACCCTCAGCACGGCGGCGGAGGGCACCGTGGC
GGCTTCCCGGGGGGCGCCGGCGCGTCGGAGCGAGGCAAGTTCTCCTGCCCGCGCGCCCTC
AAGGTGCCCTCCTACCTCAACTACCACTTCCTGGGGGAGAAGGACTGCGGCGCACCTTGT
GAGCCGACCAAGGTGTATGGGCTCATGTACTTCGGCCCGAGGAGCTGCGCTTCTCGCGC
ACCTGGATTGGCATTTGGTCAGTGCTGTGCTGCGCCTCCACGCTCTTCACGGTGCTTACG
TACCTGGTGGACATGCGGCGCTTCAGCTACCCGGAGCGGCCCATCATCTTCTTGTCCGGC
TGTTACACGGCCGTGGCCGTGGCCTACATCGCCGGCTTCCTCCTGGAAGACCGAGTGGTG
TGTAATGACAAGTTCGCCGAGGACGGGGCACGCACTGTGGCGCAGGGCACCAAGAAGGAG
GGCTGCACCATCCTCTTCATGATGCTCTACTTCTTCAGCATGGCCAGCTCCATCTGGTGG
GTGATCCTGTCGCTCACCTGGTTCCTGGCGGCTGGCATGAAGTGGGGCCACGAGGCCATC
GAAGCCAACTCACAGTATTTCACCTGGCCGCCTGGGCTGTGCCGGCCATCAAGACCATC
ACCATCCTGGCGCTGGGCCAGGTGGACGGCGATGTGCTGAGCGGAGTGTGCTTCGTGGGG
CTTAACAACGTGGACGCGCTGCGTGGCTTCGTGCTGGCGCCCTCTTCGTGTACCTGTTT
ATCGGCACGTCCTTTCTGCTGGCCGGCTTTGTGTCGCTCTTCCGCATCCGCACCATCATG
AAGCACGATGGCACCAAGACCGAGAAGCTGGAGAAGCTCATGGTGCGCATTGGCGTCTTC
AGCGTGCTGTACACTGTGCCAGCCACCATCGTCATCGCCTGCTACTTCTACGAGCAGGCC
TTCCGGGACCAGTGGGAACGCAGCTGGGTGGCCCAGAGCTGCAAGAGCTACGCTATCCCC
TGCCCTCACCTCCAGGCGGGCGGAGGCGCCCCGCCGCACCCGCCCATGAGCCCGGACTTC
ACGGTCTTCATGATTAAGTACCTTATGACGCTGATCGTGGGCATCACGTCGGGCTTCTGG
ATCTGGTCCGGCAAGACCCTCAACTCCTGGAGGAAGTTCTACACGAGGCTCACCAACAGC
AAACAAGGGGAGACTACAGTCTGA

FIGURE 20

Human FZD2 full length DNA sequence (SEQ ID NO: 33):
ATGCGGCCCCGCAGCGCCCTGCCCCGCCTGCTGCTGCCGCTGCTGCTGCTGCCCGCCGCC
GGGCCGGCCCAGTTCCACGGGGAGAAGGGCATCTCCATCCCGGACCACGGCTTCTGCCAG
CCCATCTCCATCCCGCTGTGCACGGACATCGCCTACAACCAGACCATCATGCCCAACCTT
CTGGGCCACACGAACCAGGAGGACGCAGGCCTAGAGGTGCACCAGTTCTATCCGCTGGTG
AAGGTGCAGTGCTCGCCCGAACTGCGCTTCTTCCTGTGCTCCATGTACGCACCCGTGTGC
ACCGTGCTGGAACAGGCCATCCCGCCGTGCCGCTCTATCTGTGAGCGCGCGCGCCAGGGC
TGCGAAGCCCTCATGAACAAGTTCGGTTTTCAGTGGCCCGAGCGCCTGCGCTGCGAGCAC
TTCCCGCGCCACGGCGCCGAGCAGATCTGCGTCGGCCAGAACCACTCCGAGGACGGAGCT
CCCGCGCTACTCACCACCGCGCCGCCGCCGGGACTGCAGCCGGGTGCCGGGGGCACCCCG
GGTGGCCCGGCGGCGGCGGCGCTCCCCGCGCTACGCCACGCTGGAGCACCCCTTCCAC
TGCCCGCGCGTCCTCAAGGTGCCATCCTATCTCAGCTACAAGTTTCTGGGCGAGCGTGAT
TGTGCTGCGCCCTGCGAACCTGCGCGGCCCGATGGTTCCATGTTCTTCTCACAGGAGGAG
ACGCGTTTCGCGCGCCTCTGGATCCTCACCTGGTCGGTGCTGTGCTGCGCTTCCACCTTC
TTCACTGTCACCACGTACTTGGTAGACATGCAGCGCTTCCGCTACCCAGAGCGGCCTATC
ATTTTTCTGTCGGGCTGCTACACCATGGTGTCGGTGGCCTACATCGCGGGCTTCGTGCTC
CAGGAGCGCGTGGTGTGCAACGAGCGCTTCTCCGAGGACGGTTACCGCACGGTGGTGCAG
GGCACCAAGAAGGAGGGCTGCACCATCCTCTTCATGATGCTCTACTTCTTCAGCATGGCC
AGCTCCATCTGGTGGGTCATCCTGTCGCTCACCTGGTTCCTGGCAGCCGGCATGAAGTGG
GGCCACGAGGCCATCGAGGCCAACTCTCAGTACTTCCACCTGGCCGCCTGGGCCGTGCCG
GCCGTCAAGACCATCACCATCCTGGCCATGGGCCAGATCGACGGCGACCTGCTGAGCGGC
GTGTGCTTCGTAGGCCTCAACAGCCTGGACCCGCTGCGGGCTTCGTGCTAGCGCCGCTC
TTCGTGTACCTGTTCATCGGCACGTCCTTCCTCCTGGCCGGCTTCGTGTCGCTCTTCCGC
ATCCGCACCATCATGAAGCACGACGGCACCAAGACCGAAAAGCTGGAGCGGCTCATGGTG
CGCATCGGCGTCTTCTCCGTGCTCTACACAGTGCCCGCCACCATCGTCATCGCTTGCTAC
TTCTACGAGCAGGCCTTCCGCGAGCACTGGGAGCGCTCGTGGGTGAGCCAGCACTGCAAG
AGCCTGGCCATCCCGTGCCCGGCGCACTACACGCCGCGCATGTCGCCCGACTTCACGGTC
TACATGATCAAATACCTCATGACGCTCATCGTGGGCATCACGTCGGGCTTCTGGATCTGG
TCGGGCAAGACGCTGCACTCGTGGAGGAAGTTCTACACTCGCCTCACCAACAGCCGACAC
GGTGAGACCACCGTGTGA

FIGURE 21

Human FZD3 full length amino acid sequence (SEQ ID NO:34):
MAMTWIVFSLWPLTVFMGHIGGHSLFSCEPITLRMCQDLPYNTTFMPNLLNHYDQQTAAL
AMEPFHPMVNLDCSRDFRPFLCALYAPICMEYGRVTLPCRRLCQRAYSECSKLMEMFGVP
WPEDMECSRFPDCDEPYPRLVDLNLAGEPTEGAPVAVQRDYGFWCPRELKIDPDLGYSFL
HVRDCSPPCPNMYFRREELSFARYFIGLISIICLSATLFTFLTFLIDVTRFRYPERPIIF
YAVCYMMVSLIFFIGFLLEDRVACNASIPAQYKASTVTQGSHNKACTMLFMILYFFTMAG
SVWWVILTITWFLAAVPKWGSEAIEKKALLFHASAWGIPGTLTIILLAMNKIEGDNISGV
CFVGLYDVDALRYFVLAPLCLYVVVGVSLLLAGIISLNRVRIEIPLEKENQDKLVKFMIR
IGVFSILYLVPLLVVIGCYFYEQAYRGIWETTWIQERCREYHIPCPYQVTQMSRPDLILF
LMKYLMALIVGIPSVFWVGSKKTCFEWASFFHGRRKKEIVNESRQVLQEPDFAQSLLRDP
NTPIIRKSRGTSTQGTSTHASSTQLAMVDDQRSKAGSIHSKVSSYHGSLHRSRDGRYTPC
SYRGMEERLPHGSMSRLTDHSRHSSSHRLNEQSRHSSIRDLSNNPMTHITHGTSMNRVIE
EDGTSA Human FZD3 Fri domain amino acid sequence (SEQ ID NO:36; amino acids 18-143 of SEQ ID NO:34):
GHIGGHSLFSCEPITLRMCQDLPYNTTFMPNLLNHYDQQTAALAMEPFHPMVNLDCSRDF
RPFLCALYAPICMEYGRVTLPCRRLCQRAYSECSKLMEMFGVPWPEDMECSRFPDCDEPY
PRLVDL

FIGURE 22

Human FZD4 full length amino acid sequence (SEQ ID NO:38):
MLAMAWRGAGPSVPGAPGGVGLSLGLLLQLLLLLGPARGFGDEEERRCDPIRISMCQNLG
YNVTKMPNLVGHELQTDAELQLTTFTPLIQYGCSSQLQFFLCSVYVPMCTEKINIPIGPC
GGMCLSVKRRCEPVLKEFGFAWPESLNCSKFPPQNDHNHMCMEGPGDEEVPLPHKTPIQP
GEECHSVGTNSDQYIWVKRSLNCVLKCGYDAGLYSRSAKEFTDIWMAVWASLCFISTAFT
VLTFLIDSSRFSYPERPIIFLSMCYNIYSIAYIVRLTVGRERISCDFEEAAEPVLIQEGL
KNTGCAIIFLLMYFFGMASSIWWVILTLTWFLAAGLKWGHEAIEMHSSYFHIAAWAIPAV
KTIVILIMRLVDADELTGLCYVGNQNLDALTGFVVAPLFTYLVIGTLFIAAGLVALFKIR
SNLQKDGTKTDKLERLMVKIGVFSVLYTVPATCVIACYFYEISNWALFRYSADDSNMAVE
MLKIFMSLLVGITSGMWIWSAKTLHTWQKCSNRLVNSGKVKREKRGNGWVKPGKGSETVV Human FZD4 Fri domain amino acid sequence (SEQ ID NO:40; amino acids 40-170 of SEQ ID NO:38):
FGDEEERRCDPIRISMCQNLGYNVTKMPNLVGHELQTDAELQLTTFTPLIQYGCSSQLQF
FLCSVYVPMCTEKINIPIGPCGGMCLSVKRRCEPVLKEFGFAWPESLNCSKFPPQNDHNH
MCMEGPGDEEV

FIGURE 23

Human FZD3 full length DNA sequence (SEQ ID NO:37):
ATGGCTATGACTTGGATTGTCTTCTCTCTTTGGCCCTTGACTGTGTTCATGGGGCATATA
GGTGGGCACAGTTTGTTTCTTGTGAACCTATTACCTTGAGGATGTGCCAAGATTTGCCT
TATAATACTACCTTCATGCCTAATCTTCTGAATCATTATGACCAACAGACAGCAGCTTTG
GCAATGGAGCCATTCCACCCTATGGTGAATCTGGATTGTTCTCGGGATTTCCGGCCTTTT
CTTTGTGCACTCTACGCTCCTATTTGTATGGAATATGGACGTGTCACACTTCCCTGTCGT
AGGCTGTGTCAGCGGGCTTACAGTGAGTGTTCGAAGCTCATGGAGATGTTTGGTGTTCCT
TGGCCTGAAGATATGGAATGCAGTAGGTTCCCAGATTGTGATGAGCCATATCCTCGACTT
GTGGATCTGAATTTAGCTGGAGAACCAACTGAAGGAGCCCCAGTGGCAGTGCAGAGAGAC
TATGGTTTTTGGTGTCCCCGAGAGTTAAAAATTGATCCTGATCTGGGTTATTCTTTTCTG
CATGTGCGTGATTGTTCACCTCCTTGTCCAAATATGTACTTCAGAAGAGAAGAACTGTCA
TTTGCTCGCTATTCATAGGATTGATTTCAATCATTTGCCTCTCGGCCACATTGTTTACT
TTTTTAACTTTTTTGATTGATGTCACAAGATTCCGTTATCCTGAAAGGCCTATTATATTT
TATGCAGTCTGCTACATGATGGTATCCTTAATTTTCTTCATTGGATTTTTGCTTGAAGAT
CGAGTAGCCTGCAATGCATCCATCCCTGCACAATATAAGGCTTCCACAGTGACACAAGGA
TCTCATAATAAAGCCTGTACCATGCTTTTTATGATACTCTATTTTTTTACTATGGCTGGC
AGTGTATGGTGGGTAATTCTTACCATCACATGGTTTTTAGCAGCTGTGCCAAAGTGGGGT
AGTGAAGCTATTGAGAAGAAAGCATTGCTGTTTCACGCCAGTGCATGGGGCATCCCCGGA
ACTCTAACCATCATCCTTTTAGCGATGAATAAAATTGAAGGTGACAATATTAGTGGCGTG
TGTTTTGTTGGCCTCTACGATGTTGATGCATTGAGATATTTTGTTCTTGCTCCCCTCTGC
CTGTATGTGGTAGTTGGGGTTTCTCTCCTCTTAGCTGGCATTATATCCCTAAACAGAGTT
CGAATTGAGATTCCATTAGAAAAGGAGAACCAAGATAAATTAGTGAAGTTTATGATCCGG
ATCGGTGTTTTCAGCATTCTTTATCTCGTACCACTCTTGGTTGTAATTGGATGCTACTTT
TATGAGCAAGCTTACCGGGGCATCTGGGAAACAACGTGGATACAAGAACGCTGCAGAGAA
TATCACATTCCATGTCCATATCAGGTTACTCAAATGAGTCGTCCAGACTTGATTCTCTTT
CTGATGAAATACCTGATGGCTCTCATAGTTGGCATTCCCTCTGTATTTTGGGTTGGAAGC
AAAAAGACATGCTTTGAATGGGCCAGTTTTTTTCATGGTCGTAGGAAAAAGAGATAGTG
AATGAGAGCCGACAGGTACTCCAGGAACCTGATTTTGCTCAGTCTCTCCTGAGGGATCCA
AATACTCCTATCATAAGAAAGTCAAGGGGAACTTCCACTCAAGGAACATCCACCCATGCT
TCTTCAACTCAGCTGGCTATGGTGGATGATCAAAGAAGCAAAGCAGGAAGCATCCACAGC
AAAGTGAGCAGCTACCACGGCAGCCTCCACAGATCACGTGATGGCAGGTACACGCCCTGC
AGTTACAGAGGAATGGAGGAGAGACTACCTCATGGCAGCATGTCACGACTAACAGATCAC
TCCAGGCATAGTAGTTCTCATCGGCTCAATGAACAGTCACGACATAGCAGCATCAGAGAT
CTCAGTAATAATCCCATGACTCATATCACACATGGCACCAGCATGAATCGGGTTATTGAA
GAAGATGGAACCAGTGCTTAA

FIGURE 24

Human FZD4 full length DNA sequence (SEQ ID NO:41):
ATGCTGGCCATGGCCTGGCGGGGCGCAGGGCCGAGCGTCCCGGGGGCGCCCGGGGGCGTC
GGTCTCAGTCTGGGGTTGCTCCTGCAGTTGCTGCTGCTCCTGGGGCCGGCGCGGGGCTTC
GGGGACGAGGAAGAGCGGCGCTGCGACCCCATCCGCATCTCCATGTGCCAGAACCTCGGC
TACAACGTGACCAAGATGCCCAACCTGGTTGGGCACGAGCTGCAGACGGACGCCGAGCTG
CAGCTGACAACTTTCACACCGCTCATCCAGTACGGCTGCTCCAGCCAGCTGCAGTTCTTC
CTTTGTTCTGTTTATGTGCCAATGTGCACAGAGAAGATCAACATCCCCATTGGCCCATGC
GGCGGCATGTGTCTTTCAGTCAAGAGACGCTGTGAACCCGTCCTGAAGGAATTTGGATTT
GCCTGGCCAGAGAGTCTGAACTGCAGCAAATTCCCACCACAGAACGACCACAACCACATG
TGCATGGAAGGGCCAGGTGATGAAGAGGTGCCCTTACCTCACAAAACCCCCATCCAGCCT
GGGGAAGAGTGTCACTCTGTGGGAACCAATTCTGATCAGTACATCTGGGTGAAAAGGAGC
CTGAACTGTGTGCTCAAGTGTGGCTATGATGCTGGCTTATACAGCCGCTCAGCCAAGGAG
TTCACTGATATCTGGATGGCTGTGTGGGCCAGCCTGTGTTTCATCTCCACTGCCTTCACA
GTACTGACCTTCCTGATCGATTCTTCTAGGTTTTCCTACCCTGAGCGCCCCATCATATTT
CTCAGTATGTGCTATAATATTTATAGCATTGCTTATATTGTCAGGCTGACTGTAGGCCGG
GAAAGGATATCCTGTGATTTTGAAGAGGCAGCAGAACCTGTTCTCATCCAAGAAGGACTT
AAGAACACAGGATGTGCAATAATTTTCTTGCTGATGTACTTTTTTGGAATGGCCAGCTCC
ATTTGGTGGGTTATTCTGACACTCACTTGGTTTTTGGCAGCAGGACTCAAATGGGGTCAT
GAAGCCATTGAAATGCACAGCTCTTATTTCCACATTGCAGCCTGGGCCATCCCCGCAGTG
AAAACCATTGTCATCTTGATTATGAGACTGGTGGATGCAGATGAACTGACTGGCTTGTGC
TATGTTGGAAACCAAAATCTCGATGCCCTCACCGGGTTCGTGGTGGCTCCCCTCTTTACT
TATTTGGTCATTGGAACTTTGTTCATTGCTGCAGGTTTGGTGGCCTTGTTCAAAATTCGG
TCAAATCTTCAAAAGGATGGGACAAAGACAGACAAGTTAGAAAGACTGATGGTCAAGATT
GGGGTGTTCTCAGTACTGTACACAGTTCCTGCAACGTGTGTGATTGCCTGTTATTTTTAT
GAAATCTCCAACTGGGCACTTTTTCGGTATTCTGCAGATGATTCCAACATGGCTGTTGAA
ATGTTGAAAATTTTTATGTCTTTGTTGGTGGGCATCACTTCAGGCATGTGGATTTGGTCT
GCCAAAACTCTTCACACGTGGCAGAAGTGTTCCAACAGATTGGTGAATTCTGGAAAGGTA
AAGAGAGAGAAGAGAGGAAATGGTTGGGTGAAGCCTGGAAAAGGCAGTGAGACTGTGGTA
TAA

FIGURE 25

Human FZD5 full length amino acid sequence (SEQ ID NO:42; underlining indicates ECD):
<u>MARPDPSAPPSLLLLLLAQLVGRAAAASKAPVCQEITVPMCRGIGYNLTHMPNQFNHDTQ</u>
<u>DEAGLEVHQFWPLVEIQCSPDLRFFLCSMYTPICLPDYHKPLPPCRSVCERAKAGCSPLM</u>
<u>RQYGFAWPERMSCDRLPVLGRDAEVLCMDYNRSEATTAPPRPFPAKPTLPGPPGAPASGG</u>
<u>ECPAGGPFVCKCREPFVPILKESHPLYNKVRTGQVPNCAVPCYQPSFSADERTFATFWIG</u>
LWSVLCFISTSTTVATFLIDMERFRYPERPIIFLSACYLCVSLGFLVRLVVGHASVACSR
EHNHIHYETTGPALCTIVFLLVYFFGMASSIWWVILSLTWFLAAGMKWGNEAIAGYAQYF
HLAAWLIPSVKSITALALSSVDGDPVAGICYVGNQNLNSLRGFVLGPLVLYLLVGTLFLL
AGFVSLFRIRSVIKQGGTKTDKLEKLMIRIGIFTLLYTVPASIVVACYLYEQHYRESWEA
ALTCACPGHDTGQPRAKPEYWVLMLKYFMCLVVGITSGVWIWSGKTVESWRRFTSRCCCR
PRRGHKSGGAMAAGDYPEASAALTGRTGPPGPAATYHKQVSLSHV Human FZD5 Fri domain amino acid sequence (SEQ ID NO:44; amino acids 27-157 of SEQ ID NO:42):
ASKAPVCQEITVPMCRGIGYNLTHMPNQFNHDTQDEAGLEVHQFWPLVEIQCSPDLRFFL
CSMYTPICLPDYHKPLPPCRSVCERAKAGCSPLMRQYGFAWPERMSCDRLPVLGRDAEVL
CMDYNRSEATT

FIGURE 26

Human FZD6 full length amino acid sequence (SEQ ID NO:46; underlining indicates ECD):
MEMFTFLLTCIFLPLLRG<u>HSLFTCEPITVPRCMKMAYNMTFFPNLMGHYDQSIAAVEMEH</u>
<u>FLPLANLECSPNIETFLCKAFVPTCIEQIHVVPPCRKLCEKVYSDCKKLIDTFGIRWPEE</u>
<u>LECDRLQYCDETVPVTFDPHTEFLG</u>PQKKTEQVQRDIGFWCPRHLKTSGGQGYKFLGIDQ
CAPPCPNMYFKSDELEFAKSFIGTVSIFCLCATLFTFLTFLIDVRRFRYPERPIIYYSVC
YSIVSLMYFIGFLLGDSTACNKADEKLELGDTVVLGSQNKACTVLFMLLYFFTMAGTVWW
VILTITWFLAAGRKWSCEAIEQKAVWFHAVAWGTPGFLTVMLLAMNKVEGDNISGVCFVG
LYDLDASRYFVLLPLCLCVFVGLSLLLAGIISLNHVRQVIQHDGRNQEKLKKFMIRIGVF
SGLYLVPLVTLLGCYVYEQVNRTTWEITWVSDHCRQYHIPCPYQAKAKARPELALFMIKY
LMTLIVGISAVFWVGSKKTCTEWAGFFKRNRKRDPISESRRVLQESCEFFLKHNSKVKHK
KKHYKPSSHKLKVISKSMGTSTGATANHGTSAVAITSHDYLGQETLTEIQTSPETSMREV
KADGASTPRLREQDCGEPASPAASISRLSGEQVDGKGQAGSVSESARSEGRISPKSDITD
TGLAQSNNLQVPSSSEPSSLKGSTSLLVHPVSGVRKEQGGGCHSDT Human FZD6 Fri domain amino acid sequence (SEQ ID NO:48; amino acids 19-146 of SEQ ID NO:46):
HSLFTCEPITVPRCMKMAYNMTFFPNLMGHYDQSIAAVEMEHFLPLANLECSPNIETFLC
KAFVPTCIEQIHVVPPCRKLCEKVYSDCKKLIDTFGIRWPEELECDRLQYCDETVPVTFD
PHTEFLG

FIGURE 27

Human FZD5 full length DNA sequence (SEQ ID NO:45):
ATGGCTCGGCCTGACCCATCCGCGCCGCCCTCGCTGTTGCTGCTGCTCCTGGCGCAGCTG
GTGGGCCGGGCGGCCGCCGCGTCCAAGGCCCCGGTGTGCCAGGAAATCACGGTGCCCATG
TGCCGCGGCATCGGCTACAACCTGACGCACATGCCCAACCAGTTCAACCACGACACGCAG
GACGAGGCGGGCCTGGAGGTGCACCAGTTCTGGCCGCTGGTGGAGATCCAATGCTCGCCG
GACCTGCGCTTCTTCCTATGCTCTATGTACACGCCCATCTGTCTGCCCGACTACCACAAG
CCGCTGCCGCCCTGCCGCTCGGTGTGCGAGCGCGCCAAGGCCGGCTGCTCGCCGCTGATG
CGCCAGTACGGCTTCGCCTGGCCCGAGCGCATGAGCTGCGACCGCCTCCCGGTGCTGGGC
CGCGACGCCGAGGTCCTCTGCATGGATTACAACCGCAGCGAGGCCACCACGGCGCCCCCC
AGGCCTTTCCCAGCCAAGCCCACCCTTCCAGGCCCGCCAGGGGCGCCGGCCTCGGGGGGC
GAATGCCCCGCTGGGGCCCGTTCGTGTGCAAGTGTCGCGAGCCCTTCGTGCCCATTCTG
AAGGAGTCACACCCGCTCTACAACAAGGTGCGGACGGGCCAGGTGCCCAACTGCGCGGTA
CCCTGCTACCAGCCGTCCTTCAGTGCCGACGAGCGCACGTTCGCCACCTTCTGGATAGGC
CTGTGGTCGGTGCTGTGCTTCATCTCCACGTCCACCACAGTGGCCACCTTCCTCATCGAC
ATGGAACGCTTCCGCTATCCTGAGCGCCCCATCATCTTCCTGTCAGCCTGCTACCTGTGC
GTGTCGCTGGGCTTCCTGGTGCGTCTGGTCGTGGGCCATGCCAGCGTGGCCTGCAGCCGC
GAGCACAACCACATCCACTACGAGACCACGGGCCCTGCACTGTGCACCATCGTCTTCCTC
CTGGTCTACTTCTTCGGCATGGCCAGCTCCATCTGGTGGGTCATCCTGTCGCTCACCTGG
TTCCTGGCCGCCGGCATGAAGTGGGGCAACGAGGCCATCGCGGGCTACGCGCAGTACTTC
CACCTGGCTGCGTGGCTCATCCCCAGCGTCAAGTCCATCACGGCACTGGCGCTGAGCTCC
GTGGACGGGGACCCAGTGGCCGGCATCTGCTACGTGGGCAACCAGAACCTGAACTCGCTG
CGCGGCTTCGTGCTGGGCCCGCTGGTGCTCTACCTGCTGGTGGGCACGCTCTTCCTGCTG
GCGGGCTTCGTGTCGCTCTTCCGCATCCGCAGCGTCATCAAGCAGGGCGGCACCAAGACG
GACAAGCTGGAGAAGCTCATGATCCGCATCGGCATCTTCACGCTGCTCTACACGGTCCCC
GCCAGCATTGTGGTGGCCTGCTACCTGTACGAGCAGCACTACCGCGAGAGCTGGGAGGCG
GCGCTCACCTGCGCCTGCCCGGGCCACGACACCGGCCAGCCGCGCGCCAAGCCCGAGTAC
TGGGTGCTCATGCTCAAGTACTTCATGTGCCTGGTGGTGGGCATCACGTCGGGCGTCTGG
ATCTGGTCGGGCAAGACGGTGGAGTCGTGGCGGCGTTTCACCAGCCGCTGCTGCTGCCGC
CCGCGGCGCGGCCACAAGAGCGGGGGCGCCATGGCCGCAGGGGACTACCCCGAGGCGAGC
GCCGCGCTCACAGGCAGGACCGGGCCGCCGGGCCCCGCCGCCACCTACCACAAGCAGGTG
TCCCTGTCGCACGTGTAG

FIGURE 28

Human FZD6 full length DNA sequence (SEQ ID NO:49):
ATGGAAATGTTTACATTTTTGTTGACGTGTATTTTCTACCCCTCCTAAGAGGGCACAGT
CTCTTCACCTGTGAACCAATTACTGTTCCCAGATGTATGAAAATGGCCTACAACATGACG
TTTTTCCCTAATCTGATGGGTCATTATGACCAGAGTATTGCCGCGGTGGAAATGGAGCAT
TTTCTTCCTCTCGCAAATCTGGAATGTTCACCAAACATTGAAACTTTCCTCTGCAAAGCA
TTTGTACCAACCTGCATAGAACAAATTCATGTGGTTCCACCTTGTCGTAAACTTTGTGAG
AAAGTATATTCTGATTGCAAAAAATTAATTGACACTTTTGGGATCCGATGGCCTGAGGAG
CTTGAATGTGACAGATTACAATACTGTGATGAGACTGTTCCTGTAACTTTTGATCCACAC
ACAGAATTTCTTGGTCCTCAGAAGAAAACAGAACAAGTCCAAAGAGACATTGGATTTTGG
TGTCCAAGGCATCTTAAGACTTCTGGGGGACAAGGATATAAGTTTCTGGGAATTGACCAG
TGTGCGCCTCCATGCCCCAACATGTATTTAAAAGTGATGAGCTAGAGTTTGCAAAAAGT
TTTATTGGAACAGTTTCAATATTTTGTCTTTGTGCAACTCTGTTCACATTCCTTACTTTT
TTAATTGATGTTAGAAGATTCAGATACCCAGAGAGACCAATTATATATTACTCTGTCTGT
TACAGCATTGTATCTCTTATGTACTTCATTGGATTTTTGCTAGGCGATAGCACAGCCTGC
AATAAGGCAGATGAGAAGCTAGAACTTGGTGACACTGTTGTCCTAGGCTCTCAAAATAAG
GCTTGCACCGTTTTGTTCATGCTTTTGTATTTTTTCACAATGGCTGGCACTGTGTGGTGG
GTGATTCTTACCATTACTTGGTTCTTAGCTGCAGGAAGAAAATGGAGTTGTGAAGCCATC
GAGCAAAAAGCAGTGTGGTTTCATGCTGTTGCATGGGGAACACCAGGTTTCCTGACTGTT
ATGCTTCTTGCTATGAACAAAGTTGAAGGAGACAACATTAGTGGAGTTTGCTTTGTTGGC
CTTTATGACCTGGATGCTTCTCGCTACTTTGTACTCTTGCCACTGTGCCTTTGTGTGTTT
GTTGGGCTCTCTCTTCTTTTAGCTGGCATTATTTCCTTAAATCATGTTCGACAAGTCATA
CAACATGATGGCCGGAACCAAGAAAAACTAAAGAAATTTATGATTCGAATTGGAGTCTTC
AGCGGCTTGTATCTTGTGCCATTAGTGACACTTCTCGGATGTTACGTCTATGAGCAAGTG
AACAGGATTACCTGGGAGATAACTTGGGTCTCTGATCATTGTCGTCAGTACCATATCCCA
TGTCCTTATCAGGCAAAAGCAAAAGCTCGACCAGAATTGGCTTTATTTATGATAAAATAC
CTGATGACATTAATTGTTGGCATCTCTGCTGTCTTCTGGGTTGGAAGCAAAAAGACATGC
ACAGAATGGGCTGGGTTTTTAAACGAAATCGCAAGAGAGATCCAATCAGTGAAAGTCGA
AGAGTACTACAGGAATCATGTGAGTTTTTCTTAAAGCACAATTCTAAAGTTAAACACAAA
AAGAAGCACTATAAACCAAGTTCACACAAGCTGAAGGTCATTTCCAAATCCATGGGAACC
AGCACAGGAGCTACAGCAAATCATGGCACTTCTGCAGTAGCAATTACTAGCCATGATTAC
CTAGGACAAGAAACTTTGACAGAAATCCAAACCTCACCAGAAACATCAATGAGAGAGGTG
AAAGCGGACGGAGCTAGCACCCCCAGGTTAAGAGAACAGGACTGTGGTGAACCTGCCTCG
CCAGCAGCATCCATCTCCAGACTCTCTGGGGAACAGGTCGACGGGAAGGGCCAGGCAGGC
AGTGTATCTGAAAGTGCGCGGAGTGAAGGAAGGATTAGTCCAAAGAGTGATATTACTGAC
ACTGGCCTGGCACAGAGCAACAATTTGCAGGTCCCCAGTTCTTCAGAACCAAGCAGCCTC
AAAGGTTCCACATCTCTGCTTGTTCACCCGGTTTCAGGAGTGAGAAAAGAGCAGGGAGGT
GGTTGTCATTCAGATACTTGA

FIGURE 29

Human FZD7 full length amino acid sequence (SEQ ID NO:50; ECD is underlined):
MRDPGAAAPLSSLGLCALVLALLGALSAGAGAQPYHGEKGISVPDHGFCQPISIPLCTDI
AYNQTILPNLLGHTNQEDAGLEVHQFYPLVKVQCSPELRFFLCSMYAPVCTVLDQAIPPC
RSLCERARQGCEALMNKFGFQWPERLRCENFPVHGAGEICVGQNTSDGSGGPGGGPTAYP
TAPYLPDLPFTALPPGASDGRGRPAFPFSCPRQLKVPPYLGYRFLGERDCGAPCEPGRAN
GLMYFKEEERRFARLWVGVWSVLCCASTLFTVLTYLVDMRRFSYPERPIIFLSGCYFMVA
VAHVAGFLLEDRAVCVERFSDDGYRTVAQGTKKEGCTILFMVLYFFGMASSIWWVILSLT
WFLAAGMKWGHEAIEANSQYFHLAAWAVPAVKTITILAMGQVDGDLLSGVCYVGLSSVDA
LRGFVLAPLFVYLFIGTSFLLAGFVSLFRIRTIMKHDGTKTEKLEKLMVRIGVFSVLYTV
PATIVLACYFYEQAFREHWERTWLLQTCKSYAVPCPPGHFPPMSPDFTVFMIKYLMTMIV
GITTGFWIWSGKTLQSWRRFYHRLSHSSKGETAV Human FZD7 Fri domain amino acid sequence (SEQ ID NO:52; amino acids 32-170 of SEQ ID NO:50):
AQPYHGEKGISVPDHGFCQPISIPLCTDIAYNQTILPNLLGHTNQEDAGLEVHQFYPLVK
VQCSPELRFFLCSMYAPVCTVLDQAIPPCRSLCERARQGCEALMNKFGFQWPERLRCENF
PVHGAGEICVGQNTSDGSG

FIGURE 30

Human FZD8 full length amino acid sequence (SEQ ID NO:54; ECD is underlined):
MEWGYLLEVTSLLAALALLQRSSGAAAASAKELACQEITVPLCKGIGYNYTYMPNQFNHD
TQDEAGLEVHQFWPLVEIQCSPDLKFFLCSMYTPICLEDYKKPLPPCRSVCERAKAGCAP
LMRQYGFAWPDRMRCDRLPEQGNPDTLCMDYNRTDLTTAAPSPPRRLPPPPPGEQPPSGS
GHGRPPGARPPHRGGRGGGGDAAAPPARGGGGGGKARPPGGGAAPCEPGCQCRAPMVS
VSSERHPLYNRVKTGQIANCALPCHNPFFSQDERAFTVFWIGLWSVLCFVSTFATVSTFL
IDMERFKYPERPIIFLSACYLFVSVGYLVRLVAGHEKVACSGGAPGAGGAGGAGGAAAGA
GAAGAGAGGPGGRGEYEELGAVEQHVRYETTGPALCTVVFLLVYFFGMASSIWWVILSLT
WFLAAGMKWGNEAIAGYSQYFHLAAWLVPSVKSIAVLALSSVDGDPVAGICYVGNQSLDN
LRGFVLAPLVIYLFIGTMFLLAGFVSLFRIRSVIKQQDGPTKTHKLEKLMIRLGLFTVLY
TVPAAVVVACLFYEQHNRPRWEATHNCPCLRDLQPDQARRPDYAVFMLKYFMCLVVGITS
GVWVWSGKTLESWRSLCTRCCWASKGAAVGGGAGATAAGGGGGPGGGGGGGPGGGGPGG
GGGSLYSDVSTGLTWRSGTASSVSYPKQMPLSQV Human FZD8 Fri domain amino acid sequence (SEQ ID NO:56; amino acids 28-158 of SEQ ID NO:54):
ASAKELACQEITVPLCKGIGYNYTYMPNQFNHDTQDEAGLEVHQFWPLVEIQCSPDLKFF
LCSMYTPICLEDYKKPLPPCRSVCERAKAGCAPLMRQYGFAWPDRMRCDRLPEQGNPDTL
CMDYNRTDLTT

FIGURE 31

Human FZD7 full length DNA sequence (SEQ ID NO:53):
ATGCGGGACCCCGGCGCGGCCGCTCCGCTTTCGTCCCTGGGCCTCTGTGCCCTGGTGCTG
GCGCTGCTGGGCGCACTGTCCGCGGGCGCCGGGGCGCAGCCGTACCACGGAGAGAAGGGC
ATCTCCGTGCCGGACCACGGCTTCTGCCAGCCCATCTCCATCCCGCTGTGCACGGACATC
GCCTACAACCAGACCATCCTGCCCAACCTGCTGGGCCACACGAACCAAGAGGACGCGGGC
CTCGAGGTGCACCAGTTCTACCCGCTGGTGAAGGTGCAGTGTTCTCCCGAACTCCGCTTT
TTCTTATGCTCCATGTATGCGCCCGTGTGCACCGTGCTCGATCAGGCCATCCCGCCGTGT
CGTTCTCTGTGCGAGCGCGCCCGCCAGGGCTGCGAGGCGCTCATGAACAAGTTCGGCTTC
CAGTGGCCCGAGCGGCTGCGCTGCGAGAACTTCCCGGTGCACGGTGCGGGCGAGATCTGC
GTGGGCCAGAACACGTCGGACGGCTCCGGGGGCCCAGGCGGCGGCCCCACTGCCTACCCT
ACCGCGCCCTACCTGCCGGACCTGCCCTTCACCGCGCTGCCCCCGGGGGCCTCAGATGGC
AGGGGGCGTCCCGCCTTCCCCTTCTCATGCCCCCGTCAGCTCAAGGTGCCCCCGTACCTG
GGCTACCGCTTCCTGGGTGAGCGCGATTGTGGCGCCCCGTGCGAACCGGGCCGTGCCAAC
GGCCTGATGTACTTTAAGGAGGAGGAGAGGCGCTTCGCCCGCCTCTGGGTGGGCGTGTGG
TCCGTGCTGTGCTGCGCCTCGACGCTCTTTACCGTTCTCACCTACCTGGTGGACATGCGG
CGCTTCAGCTACCCAGAGCGGCCCATCATCTTCCTGTCGGCTGCTACTTCATGGTGGCC
GTGGCGCACGTGGCCGGCTTCCTTCTAGAGGACCGCGCCGTGTGCGTGGAGCGCTTCTCG
GACGATGGCTACCGCACGGTGGCGCAGGGCACCAAGAAGGAGGGCTGCACCATCCTCTTC
ATGGTGCTCTACTTCTTCGGCATGGCCAGCTCCATCTGGTGGGTCATTCTGTCTCTCACT
TGGTTCCTGGCGGCCGGCATGAAGTGGGGCCACGAGGCCATCGAGGCCAACTCGCAGTAC
TTCCACCTGGCCGCGTGGGCCGTGCCCGCCGTCAAGACCATCACTATCCTGGCCATGGGC
CAGGTAGACGGGGACCTGCTGAGCGGGGTGTGCTACGTTGGCCTCTCCAGTGTGGACGCG
CTGCGGGGCTTCGTGCTGGCGCCTCTGTTCGTCTACCTCTTCATAGGCACGTCCTTCTTG
CTGGCCGGCTTCGTGTCCCTCTTCCGTATCCGCACCATCATGAAACACGACGGCACCAAG
ACCGAGAAGCTGGAGAAGCTCATGGTGCGCATCGGCGTCTTCAGCGTGCTCTACACAGTG
CCCGCCACCATCGTCCTGGCCTGCTACTTCTACGAGCAGGCCTTCCGCGAGCACTGGGAG
CGCACCTGGCTCCTGCAGACGTGCAAGAGCTATGCCGTGCCCTGCCCGCCCGGCCACTTC
CCGCCCATGAGCCCCGACTTCACCGTCTTCATGATCAAGTACCTGATGACCATGATCGTC
GGCATCACCACTGGCTTCTGGATCTGGTCGGGCAAGACCCTGCAGTCGTGGCGCCGCTTC
TACCACAGACTTAGCCACAGCAGCAAGGGGGAGACTGCGGTATGA

FIGURE 32

Human FZD8 full length DNA sequence (SEQ ID NO:57):
ATGGAGTGGGGTTACCTGTTGGAAGTGACCTCGCTGCTGGCCGCCTTGGCGCTGCTGCAG
CGCTCTAGCGGCGCTGCGGCCGCCTCGGCCAAGGAGCTGGCATGCCAAGAGATCACCGTG
CCGCTGTGTAAGGGCATCGGCTACAACTACACCTACATGCCCAATCAGTTCAACCACGAC
ACGCAAGACGAGGCGGGCCTGGAGGTGCACCAGTTCTGGCCGCTGGTGGAGATCCAGTGC
TCGCCCGATCTCAAGTTCTTCCTGTGCAGCATGTACACGCCCATCTGCCTAGAGGACTAC
AAGAAGCCGCTGCCGCCCTGCCGCTCGGTGTGCGAGCGCGCCAAGGCCGGCTGCGCGCCG
CTCATGCGCCAGTACGGCTTCGCCTGGCCCGACCGCATGCGCTGCGACCGGCTGCCCGAG
CAAGGCAACCCTGACACGCTGTGCATGGACTACAACCGCACCGACCTAACCACCGCCGCG
CCCAGCCCGCCGCGCCGCCTGCCGCCGCCGCCGCCCGGCGAGCAGCCGCCTTCGGGCAGC
GGCCACGGCCGCCCGCCGGGGGCCAGGCCCCGCACCGCGGAGGCGGCAGGGGCGGTGGC
GGCGGGGACGCGGCGGCGCCCCAGCTCGCGGCGGCGGCGGTGGCGGGAAGGCGCGGCCC
CCTGGCGGCGGCGCGGCTCCCTGCGAGCCCGGGTGCCAGTGCCGCGCGCCTATGGTGAGC
GTGTCCAGCGAGCGCCACCCGCTCTACAACCGCGTCAAGACAGGCCAGATCGCTAACTGC
GCGCTGCCCTGCCACAACCCCTTTTTCAGCCAGGACGAGCGCGCCTTCACCGTCTTCTGG
ATCGGCCTGTGGTCGGTGCTCTGCTTCGTGTCCACCTTCGCCACCGTCTCCACCTTCCTT
ATCGACATGGAGCGCTTCAAGTACCCGGAGCGGCCCATTATCTTCCTCTCGGCCTGCTAC
CTCTTCGTGTCGGTGGGCTACCTAGTGCGCCTGGTGGCGGGCCACGAGAAGGTGGCGTGC
AGCGGTGGCGCGCCGGGCGCGGGGGGCGCTGGGGGCGCGGGCGGCGCGGCGGCGGGCGCG
GGCGCGGCGGGCGCGGGCGCGGGCGGCCCGGGCGGGCGCGGCGAGTACGAGGAGCTGGGC
GCGGTGGAGCAGCACGTGCGCTACGAGACCACCGGCCCCGCGCTGTGCACCGTGGTCTTC
TTGCTGGTCTACTTCTTCGGCATGGCCAGCTCCATCTGGTGGGTGATCTTGTCGCTCACA
TGGTTCCTGGCGGCCGGTATGAAGTGGGGCAACGAAGCCATCGCCGGCTACTCGCAGTAC
TTCCACCTGGCCGCGTGGCTTGTGCCCAGCGTCAAGTCCATCGCGGTGCTGGCGCTCAGC
TCGGTGGACGGCGACCCGGTGGCGGGCATCTGCTACGTGGGCAACCAGAGCCTGGACAAC
CTGCGCGGCTTCGTGCTGGCGCCGCTGGTCATCTACCTCTTCATCGGCACCATGTTCCTG
CTGGCCGGCTTCGTGTCCCTGTTCCGCATCCGCTCGGTCATCAAGCAACAGGACGGCCCC
ACCAAGACGCACAAGCTGGAGAAGCTGATGATCCGCCTGGGCCTGTTCACCGTGCTCTAC
ACCGTGCCCGCCGCGGTGGTGGTCGCCTGCCTCTTCTACGAGCAGCACAACCGCCCGCGC
TGGGAGGCCACGCACAACTGCCCGTGCCTGCGGGACCTGCAGCCCGACCAGGCACGCAGG
CCCGACTACGCCGTCTTCATGCTCAAGTACTTCATGTGCCTAGTGGTGGGCATCACCTCG
GGCGTGTGGGTCTGGTCCGGCAAGACGCTGGAGTCCTGGCGCTCCCTGTGCACCCGCTGC
TGCTGGGCCAGCAAGGGCGCCGCGGTGGGCGGGGCGCGGGCGCCACGGCCGCGGGGGGT
GGCGGCGGGCCGGGGGGCGGCGGCGGCGGGGGACCCGGCGGCGGCGGGGGCCGGGCGGC
GGCGGGGGCTCCCTCTACAGCGACGTCAGCACTGGCCTGACGTGGCGGTCGGGCACGGCG
AGCTCCGTGTCTTATCCAAAGCAGATGCCATTGTCCCAGGTCTGA

FIGURE 33

Human FZD9 full length amino acid sequence (SEQ ID NO:58):
MAVAPLRGALLLWQLLAAGGAALEIGRFDPERGRGAAPCQAVEIPMCRGIGYNLTRMPNL
LGHTSQGEAAAELAEFAPLVQYGCHSHLRFFLCSLYAPMCTDQVSTPIPACRPMCEQARL
RCAPIMEQFNFGWPDSLDCARLPTRNDPHALCMEAPENATAGPAEPHKGLGMLPVAPRPA
RPPGDLGPGAGGSGTCENPEKFQYVEKSRSCAPRCGPGVEVFWSRRDKDFALVWMAVWSA
LCFFSTAFTVLTFLLEPHRFQYPERPIIFLSMCYNVYSLAFLIRAVAGAQSVACDQEAGA
LYVIQEGLENTGCTLVFLLLYYFGMASSLWWVVLTLTWFLAAGKKWGHEAIEAHGSYFHM
AAWGLPALKTIVILTLRKVAGDELTGLCYVASTDAAALTGFVLVPLSGYLVLGSSFLLTG
FVALFHIRKIMKTGGTNTEKLEKLMVKIGVFSILYTVPATCVIVCYVYERLNMDFWRLRA
TEQPCAAAAGPGGRRDCSLPGGSVPTVAVFMLKIFMSLVVGITSGVWVWSSKTFQTWQSL
CYRKIAAGRARAKACRAPGSYGRGTHCHYKAPTVVLHMTKTDPSLENPTHL Human FZD9 fri domain amino acid sequence (SEQ ID NO:60; amino
acids 23-159 of SEQ ID NO:58):
LEIGRFDPERGRGAAPCQAVEIPMCRGIGYNLTRMPNLLGHTSQGEAAAELAEFAPLVQY
GCHSHLRFFLCSLYAPMCTDQVSTPIPACRPMCEQARLRCAPIMEQFNFGWPDSLDCARL
PTRNDPHALCMEAPENA

FIGURE 34

Human FZD10 full length amino acid sequence (SEQ ID NO:62; ECD
is underlined):
MQRPGPRLWLVLQVMGSCAAISSMDMERPGDGKCQPIEIPMCKDIGYNMTRMPNLMGHEN
QREAAIQLHEFAPLVEYGCHGHLRFFLCSLYAPMCTEQVSTPIPACRVMCEQARLKCSPI
MEQFNFKWPDSLDCRKLPNKNDPNYLCMEAPNNGSDEPTRGSGLFPPLFRPQRPHSAQEH
PLKDGGPGRGGCDNPGKFHHVEKSASCAPLCTPGVDVYWSREDKRFAVVWLAIWAVLCFF
SSAFTVLTFLIDPARFRYPERPIIFLSMCYCVYSVGYLIRLFAGAESIACDRDSGQLYVI
QEGLESTGCTLVFLVLYYFGMASSLWWVVLTLTWFLAAGKKWGHEAIEANSSYFHLAAWA
IPAVKTILILVMRRVAGDELTGVCYVGSMDVNALTGFVLIPLACYLVIGTSFILSGFVAL
FHIRRVMKTGGENTDKLEKLMVRIGLFSVLYTVPATCVIACYFYERLNMDYWKILAAQHK
CKMNNQTKTLDCLMAASIPAVEIFMVKIFMLLVVGITSGMWIWTSKTLQSWQQVCSRRLK
KKSRRKPASVITSGGIYKKAQHPQKTHHGKYEIPAQSPTCV Human FZD10 fri domain amino acid sequence (SEQ ID NO:64; amino
acids 21-154 of SEQ ID NO:62):
ISSMDMERPGDGKCQPIEIPMCKDIGYNMTRMPNLMGHENQREAAIQLHEFAPLVEYGCH
GHLRFFLCSLYAPMCTEQVSTPIPACRVMCEQARLKCSPIMEQFNFKWPDSLDCRKLPNK
NDPNYLCMEAPNNG

FIGURE 35

Human FZD9 full length DNA sequence (SEQ ID NO:61):
ATGGCCGTGGCGCCTCTGCGGGGGGCGCTGCTGCTGTGGCAGCTGCTGGCGGCGGGCGGC
GCGGCACTGGAGATCGGCCGCTTCGACCCGGAGCGCGGGCGCGGGGCTGCGCCGTGCCAG
GCGGTGGAGATCCCCATGTGCCGCGGCATCGGCTACAACCTGACCCGCATGCCCAACCTG
CTGGGCCACACGTCGCAGGGCGAGGCGGCTGCCGAGCTAGCGGAGTTCGCGCCGCTGGTG
CAGTACGGCTGCCACAGCCACCTGCGCTTCTTCCTGTGCTCGCTCTACGCGCCCATGTGC
ACCGACCAGGTCTCGACGCCCATTCCCGCCTGCCGGCCCATGTGCGAGCAGGCGCGCCTG
CGCTGCGCGCCCATCATGGAGCAGTTCAACTTCGGCTGGCCGGACTCGCTCGACTGCGCC
CGGCTGCCCACGCGCAACGACCCGCACGCGCTGTGCATGGAGGCGCCCGAGAACGCCACG
GCCGGCCCCGCGGAGCCCCACAAGGGCCTGGGCATGCTGCCCGTGGCGCCGCGGCCCGCG
CGCCCTCCCGGAGACCTGGGCCCGGGCGCGGGCGGCAGTGGCACCTGCGAGAACCCCGAG
AAGTTCCAGTACGTGGAGAAGAGCCGCTCGTGCGCACCGCGCTGCGGGCCCGGCGTCGAG
GTGTTCTGGTCCCGGCGCGACAAGGACTTCGCGCTGGTCTGGATGGCCGTGTGGTCGGCG
CTGTGCTTCTTCTCCACCGCCTTCACTGTGCTCACCTTCTTGCTGGAGCCCCACCGCTTC
CAGTACCCCGAGCGCCCCATCATCTTCCTCTCCATGTGCTACAACGTCTACTCGCTGGCC
TTCCTGATCCGTGCGGTGGCCGGAGCGCAGAGCGTGGCCTGTGACCAGGAGGCGGGCGCG
CTCTACGTGATCCAGGAGGGCCTGGAGAACACGGGCTGCACGCTGGTCTTCCTACTGCTC
TACTACTTCGGCATGGCCAGCTCGCTCTGGTGGGTGGTCCTGACGCTCACCTGGTTCCTG
GCTGCCGGGAAGAAATGGGGCCACGAGGCCATCGAGGCCCACGGCAGCTATTTCCACATG
GCTGCCTGGGGCCTGCCCGCGCTCAAGACCATCGTCATCCTGACCCTGCGCAAGGTGGCG
GGTGATGAGCTGACTGGGCTTTGCTACGTGGCCAGCACGGATGCAGCAGCGCTCACGGGC
TTCGTGCTGGTGCCCCTCTCTGGCTACCTGGTGCTGGGCAGTAGTTTCCTCCTGACCGGC
TTCGTGGCCCTCTTCCACATCCGCAAGATCATGAAGACGGGCGGCACCAACACAGAGAAG
CTGGAGAAGCTCATGGTCAAGATCGGGGTCTTCTCCATCCTCTACACGGTGCCCGCCACC
TGCGTCATCGTTTGCTATGTCTACGAACGCCTCAACATGGACTTCTGGCGCCTTCGGGCC
ACAGAGCAGCCATGCGCAGCGGCCGCGGGGCCCGGAGGCCGGAGGGACTGCTCGCTGCCA
GGGGGCTCGGTGCCCACCGTGGCGGTCTTCATGCTCAAAATTTTCATGTCACTGGTGGTG
GGGATCACCAGCGGCGTCTGGGTGTGGAGCTCCAAGACTTTCCAGACCTGGCAGAGCCTG
TGCTACCGCAAGATAGCAGCTGGCCGGGCCCGGGCCAAGGCCTGCCGCGCCCCCGGGAGC
TACGGACGTGGCACGCACTGCCACTATAAGGCTCCACCGTGGTCTTGCACATGACTAAG
ACGGACCCCTCTTTGGAGAACCCCACACACCTCTAG

FIGURE 36

Human FZD10 full length DNA sequence (SEQ ID NO:65):
ATGCAGCGCCCGGGCCCCCGCCTGTGGCTGGTCCTGCAGGTGATGGGCTCGTGCGCCGCC
ATCAGCTCCATGGACATGGAGCGCCCGGGCGACGGCAAATGCCAGCCCATCGAGATCCCG
ATGTGCAAGGACATCGGCTACAACATGACTCGTATGCCCAACCTGATGGGCCACGAGAAC
CAGCGCGAGGCAGCCATCCAGTTGCACGAGTTCGCGCCGCTGGTGGAGTACGGCTGCCAC
GGCCACCTCCGCTTCTTCCTGTGCTCGCTGTACGCGCCGATGTGCACCGAGCAGGTCTCT
ACCCCCATCCCCGCCTGCCGGGTCATGTGCGAGCAGGCCCGGCTCAAGTGCTCCCCGATT
ATGGAGCAGTTCAACTTCAAGTGGCCCGACTCCCTGGACTGCCGGAAACTCCCCAACAAG
AACGACCCCAACTACCTGTGCATGGAGGCGCCCAACAACGGCTCGGACGAGCCCACCCGG
GGCTCGGGCCTGTTCCCGCCGCTGTTCCGGCCGCAGCGGCCCCACAGCGCGCAGGAGCAC
CCGCTGAAGGACGGGGGCCCCGGGCGCGGCGGCTGCGACAACCCGGGCAAGTTCCACCAC
GTGGAGAAGAGCGCGTCGTGCGCGCCGCTCTGCACGCCCGGCGTGGACGTGTACTGGAGC
CGCGAGGACAAGCGCTTCGCAGTGGTCTGGCTGGCCATCTGGGCGGTGCTGTGCTTCTTC
TCCAGCGCCTTCACCGTGCTCACCTTCCTCATCGACCCGGCCCGCTTCCGCTACCCCGAG
CGCCCCATCATCTTCCTCTCCATGTGCTACTGCGTCTACTCCGTGGGCTACCTCATCCGC
CTCTTCGCCGGCGCCGAGAGCATCGCCTGCGACCGGGACAGCGGCCAGCTCTATGTCATC
CAGGAGGGACTGGAGAGCACCGGCTGCACGCTGGTCTTCCTGGTCCTCTACTACTTCGGC
ATGGCCAGCTCGCTGTGGTGGGTGGTCCTCACGCTCACCTGGTTCCTGGCCGCCGGCAAG
AAGTGGGGCCACGAGGCCATCGAAGCCAACAGCAGCTACTTCCACCTGGCAGCCTGGGCC
ATCCCGGCGGTGAAGACCATCCTGATCCTGGTCATGCGCAGGGTGGCGGGGGACGAGCTC
ACCGGGGTCTGCTACGTGGGCAGCATGGACGTCAACGCGCTCACCGGCTTCGTGCTCATT
CCCCTGGCCTGCTACCTGGTCATCGGCACGTCCTTCATCCTCTCGGGCTTCGTGGCCCTG
TTCCACATCCGGAGGGTGATGAAGACGGGCGGCGAGAACACGGACAAGCTGGAGAAGCTC
ATGGTGCGTATCGGGCTCTTCTCTGTGCTGTACACCGTGCCGGCCACCTGTGTGATCGCC
TGCTACTTTTACGAACGCCTCAACATGGATTACTGGAAGATCCTGGCGGCGCAGCACAAG
TGCAAAATGAACAACCAGACTAAAACGCTGGACTGCCTGATGGCCGCCTCCATCCCCGCC
GTGGAGATCTTCATGGTGAAGATCTTTATGCTGCTGGTGGTGGGGATCACCAGCGGGATG
TGGATTTGGACCTCCAAGACTCTGCAGTCCTGGCAGCAGGTGTGCAGCCGTAGGTTAAAG
AAGAAGAGCCGGAGAAAACCGGCCAGCGTGATCACCAGCGGTGGATTTACAAAAAAGCC
CAGCATCCCCAGAAAACTCACCACGGGAAATATGAGATCCCTGCCCAGTCGCCCACCTGC
GTGTGA

*p vs. taxol = 0.00004

*p = 0.0005 vs. Herceptin

Figure 52A
Figure 52B
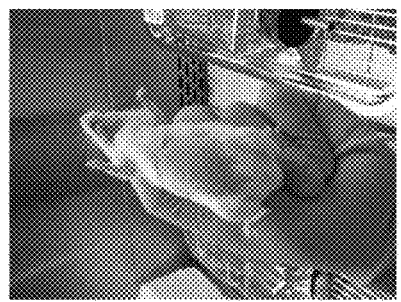
7/10
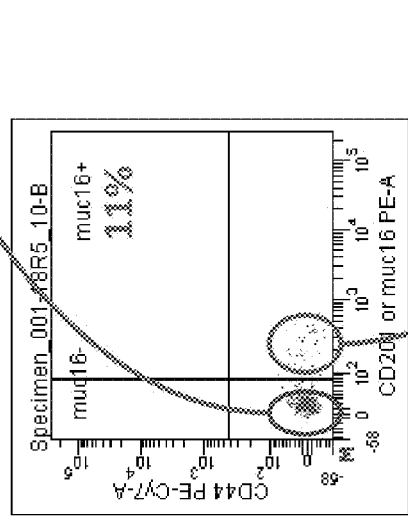
75 cells/mouse
0/10 after transient growth

Figure 62

| Cyclic peptides | Clone# |
|---|---|
| CPLYFPLYC (SEQ ID NO:98) | 3 |
| CPLVWPLIC (SEQ ID NO:99) | 4 |
| CPLAWPLIC (SEQ ID NO:100) | 8 |
| CPVKYPLVC (SEQ ID NO:101) | 13 |
| CPLRFPLFC (SEQ ID NO:102) | 15 |
| CPLAWPLIC (SEQ ID NO:103) | 16 |
| CPVAFPLYC (SEQ ID NO:104) | 17 |
| CPVNYPLYC (SEQ ID NO:105) | 18 |
| CPVKFPLYC (SEQ ID NO:106) | 20 |
| CPLTYPLIC (SEQ ID NO:107) | 22 |
| CPLRWPLMC (SEQ ID NO:108) | 24 |
| CPLQYPLMC (SEQ ID NO:109) | 25 |
| CPLSFPLYC (SEQ ID NO:110) | 26 |
| CPLNWPLMC (SEQ ID NO:111) | 27 |

| Linear peptides | Clone# |
|---|---|
| DTLSALIERGLM (SEQ ID NO:113) | 2 |
| DVWWLGSTWLKR (SEQ ID NO:114) | 28 |
| FGNYLNDVRFLI (SEQ ID NO:115) | 6 |
| TNLADIAHWISG (SEQ ID NO:116) | 12 |

Consensus: C, P, (L/V), X, (Y/F/W), P, L, (Y/F/I/V/M), C    (SEQ ID NO:112)

Figure 65 h-FZD1 amino acids 116-227 (SEQ ID NO:117):
CQPISIPLCTDIAYNQTIMPNLLGHTNQEDAGLEVHQFYPLVKVQCSAELKFFLCSMYAPVCT
VLEQALPPCRSLCERARQGCEALMNKFGFQWPDTLKCEKFPVHGAGELC h-FZD2 amino acids 39-150 (SEQ ID NO:118):
CQPISIPLCTDIAYNQTIMPNLLGHTNQEDAGLEVHQFYPLVKVQCSPELRFFLCSMYAPVCT
VLEQAIPPCRSICERARQGCEALMNKFGFQWPERLRCEHFPRHGAEQIC h-FZD3 amino acids 28-133 (SEQ ID NO:119):
CEPITLRMCQDLPYNTTFMPNLLNHYDQQTAALAMEPFHPMVNLDCSRDFRPFLCALYAPIC
MEYGRVTLPCRRLCQRAYSECSKLMEMFGVPWPEDMECSRFPDC h-FZD4 amino acids 48-161 (SEQ ID NO:120):
CDPIRISMCQNLGYNVTKMPNLVGHELQTDAELQLTTFTPLIQYGCSSQLQFFLCSVYVPMC
TEKINIPIGPCGGMCLSVKRRCEPVLKEFGFAWPESLNCSKFPPQNDHNHMC h-FZD5 amino acids 33-147 (SEQ ID NO:121):
CQEITVPMCRGIGYNLTHMPNQFNHDTQDEAGLEVHQFWPLVEIQCSPDLRFFLCSMYTPIC
LPDYHKPLPPCRSVCERAKAGCSPLMRQYGFAWPERMSCDRLPVLGRDAEVLC

Figure 66 h-FZD6 amino acids 24-129 (SEQ ID NO:122):
CEPITVPRCMKMAYNMTFFPNLMGHYDQSIAAVEMEHFLPLANLECSPNIETFLCKAFVPTCIE
QIHVVPPCRKLCEKVYSDCKKLIDTFGIRWPEELECDRLQYC h-FZD7 amino acids 49-160 (SEQ ID NO:123):
CQPISIPLCTDIAYNQTILPNLLGHTNQEDAGLEVHQFYPLVKVQCSPELRFFLCSMYAPVCTV
LDQAIPPCRSLCERARQGCEALMNKFGFQWPERLRCENFPVHGAGEIC h-FZD8 amino acids 35-148 (SEQ ID NO:124):
CQEITVPLCKGIGYNYTYMPNQFNHDTQDEAGLEVHQFWPLVEIQCSPDLKFFLCSMYTPICL
EDYKKPLPPCRSVCERAKAGCAPLMRQYGFAWPDRMRCDRLPEQGNPDTLC h-FZD9 amino acids 39-152 (SEQ ID NO:125):
CQAVEIPMCRGIGYNLTRMPNLLGHTSQGEAAAELAEFAPLVQYGCHSHLRFFLCSLYAPMCT
DQVSTPIPACRPMCEQARLRCAPIMEQFNFGWPDSLDCARLPTRNDPHALC h-FZD10 amino acids 34-147 (SEQ ID NO:126):
CQPIEIPMCKDIGYNMTRMPNLMGHENQREAAIQLHEFAPLVEYGCHGHLRFFLCSLYAPMCT
EQVSTPIPACRVMCEQARLKCSPIMEQFNFKWPDSLDCRKLPNKNDPNYLC

FRIZZLED-BINDING AGENTS AND USES THEREOF

CROSS-REFERENCE TO RELATED APPLICATIONS

This application is a divisional application of U.S. application Ser. No. 13/078,728, filed Apr. 1, 2011, now U.S. Pat. No. 8,551,789, which claims the priority benefit of U.S. Provisional Application No. 61/320,175, filed Apr. 1, 2010, each of which is incorporated by reference herein in its entirety.

REFERENCE TO A SEQUENCE LISTING SUBMITTED ELECTRONICALLY VIA EFS-WEB

The content of the electronically submitted sequence listing (Name: sequencelisting_ascii.txt. Size: 182 kilobytes; and Date of Creation: Aug. 21, 2013) is herein incorporated by reference in its entirety.

FIELD OF THE INVENTION

The field of this invention generally relates to polypeptides and other agents that bind to human frizzled receptor(s), as well as to methods of using the polypeptides or other agents for the treatment of diseases, such as cancer.

BACKGROUND OF THE INVENTION

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which-breast, lung, colorectal, and prostate—account for over half of all new cases (Jemal et al., 2003, *Cancer J. Clin.* 53:5-26).

The Wnt signaling pathway has been identified as a potential target for cancer therapy. The Wnt signaling pathway is one of several critical regulators of embryonic pattern formation, post-embryonic tissue maintenance, and stem cell biology. More specifically, Wnt signaling plays an important role in the generation of cell polarity and cell fate specification including self-renewal by stem cell populations. Unregulated activation of the Wnt pathway is associated with numerous human cancers where it can alter the developmental fate of tumor cells to maintain them in an undifferentiated and proliferative state. Thus carcinogenesis can proceed by usurping homeostatic mechanisms controlling normal development and tissue repair by stem cells (reviewed in Reya & Clevers, 2005, *Nature* 434:843; Beachy et al., 2004, *Nature* 432:324).

The Wnt signaling pathway was first elucidated in the *Drosophila* developmental mutant wingless (wg) and from the murine proto-oncogene int-1, now Wnt1 (Nusse & Varmus, 1982, *Cell* 31:99-109; Van Ooyen & Nusse, 1984, *Cell* 39:233-40; Cabrera et al., 1987. *Cell* 50:659-63; Rijsewijk et al., 1987, *Cell* 50:649-57). Wnt genes encode secreted lipid-modified glycoproteins of which 19 have been identified in mammals. These secreted ligands activate a receptor complex consisting of a Frizzled (Fzd) receptor family member and low-density lipoprotein (LDL) receptor-related protein 5 or 6 (LPR5/6). The Fzd receptors are seven transmembrane domain proteins of the G-protein coupled receptor (GPCR) superfamily and contain a large extracellular N-terminal ligand binding domain with 10 conserved cysteines, known as a cysteine-rich domain (CRD) or Fri domain. There are ten human FZD receptors: FZD1-10. Different Fzd CRDs have different binding affinities for specific Wnts (Wu & Nusse, 2002. *J. Biol. Chem.* 277: 41762-9), and Fzd receptors have been grouped into those that activate the canonical β-catenin pathway and those that activate non-canonical pathways described below (Miller et al., 1999, *Oncogene* 18:7860-72). To form the receptor complex that binds the FZD ligands. FZD receptors interact with LRP5/6, single pass transmembrane proteins with four extracellular EGF-like domains separated by six YWTD amino acid repeats (Johnson et al., 2004, *J. Bone Mineral Res.* 19:1749).

The canonical Wnt signaling pathway activated upon receptor binding is mediated by the cytoplasmic protein Dishevelled (Dsh) interacting directly with the Fzd receptor and results in the cytoplasmic stabilization and accumulation of β-catenin. In the absence of a Wnt signal, β-catenin is localized to a cytoplasmic destruction complex that includes the tumor suppressor proteins adenomatous polyposis coli (APC) and Axin. These proteins function as critical scaffolds to allow glycogen synthase kinase (GSK)-3β to bind and phosphorylate β-catenin, marking it for degradation via the ubiquitin/proteasome pathway. Activation of Dsh results in phosphorylation of GSK3β and the dissociation of the destruction complex. Accumulated cytoplasmic β-catenin is then transported into the nucleus where it interacts with the DNA-binding proteins of the Tcf/Lef family to activate transcription.

In addition to the canonical signaling pathway, Wnt ligands also activate β-catenin-independent pathways (Veeman et al., 2003. *Dev. Cell* 5:367-77). Non-canonical Wnt signaling has been implicated in numerous processes but most convincingly in gastrulation movements via a mechanism similar to the *Drosophila* planar cell polarity (PCP) pathway. Other potential mechanisms of non-canonical Wnt signaling include calcium flux, JNK, and both small and heterotrimeric G-proteins. Antagonism is often observed between the canonical and non-canonical pathways, and some evidence indicates that non-canonical signaling can suppress cancer formation (Olson & Gibo, 1998, *Exp. Cell Res.* 241:134; Topol et al., 2003, *J. Cell Biol.* 162:899-908). Thus, in certain contexts, Fzd receptors act as negative regulators of the canonical Wnt signaling pathway. For example, FZD6 represses Wnt-3a-induced canonical signaling when co-expressed with FZD1 via the TAK1-NLK pathway (Golan et al., 2004, *JBC* 279:14879-88). Similarly, Fzd2 antagonized canonical Wnt signaling in the presence of Wnt-5a via the TAK1-NLK MAPK cascade (Ishitani et al. 2003. *Mol. Cell. Biol.* 23:131-9).

The canonical Wnt signaling pathway also plays a central role in the maintenance of stem cell populations in the small intestine and colon, and the inappropriate activation of this pathway plays a prominent role in colorectal cancers (Reya & Clevers, 2005, *Nature* 434:843). The absorptive epithelium of the intestines is arranged into villi and crypts. Stem cells reside in the crypts and slowly divide to produce rapidly proliferating cells that give rise to all the differentiated cell populations that move up out of the crypts to occupy the intestinal villi. The Wnt signaling cascade plays a dominant role in controlling cell fates along the crypt-villi axis and is essential for the maintenance of the stem cell population. Disruption of Wnt signaling either by genetic loss of Tcf7/2 by homologous recombination (Korinek et al., 1998, *Nat. Genet.* 19:379) or overexpression of Dickkopf-1

(Dkk1), a potent secreted Wnt antagonist (Pinto et al., 2003, *Genes Dev.* 17:1709-13; Kuhnert et al. 2004, *Proc. Nat'l. Acad. Sci.* 101:266-71), results in depletion of intestinal stem cell populations.

Colorectal cancer is most commonly initiated by activating mutations in the Wnt signaling cascade. Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Mutations have also been identified in other Wnt pathway components including Axin and β-catenin. Individual adenomas are clonal outgrowths of epithelial cell containing a second inactivated allele, and the large number of FAP adenomas inevitably results in the development of adenocarcinomas through addition mutations in oncogenes and/or tumor suppressor genes. Furthermore, activation of the Wnt signaling pathway, including gain-of-function mutations in APC and β-catenin, can induce hyperplastic development and tumor growth in mouse models (Oshima et al. 1997, *Cancer Res.* 57:1644-9; Harada et al., 1999, *EMBO J.* 18:5931-42).

A role for Wnt signaling in cancer was first uncovered with the identification of Wnt1 (originally int1) as an oncogene in mammary tumors transformed by the nearby insertion of a murine virus (Nusse & Varmus, 1982, *Cell* 31:99-109). Additional evidence for the role of Wnt signaling in breast cancer has since accumulated. For instance, transgenic overexpression of β-catenin in the mammary glands results in hyperplasias and adenocarcinomas (Imbert et al., 2001, *J. Cell Biol.* 153:555-68: Michaelson & Leder, 2001, *Oncogene* 20:5093-9) whereas loss of Wnt signaling disrupts normal mammary gland development (Tepera et al., 2003, *J. Cell Sci.* 116:1137-49; Hatsell et al., 2003, *J. Mammary Gland Biol. Neoplasia* 8:145-58). More recently mammary stem cells have been shown to be activated by Wnt signaling (Liu et al., 2004, *Proc. Nat'l Acad. Sci.* 101:4158). In human breast cancer, β-catenin accumulation implicates activated Wnt signaling in over 50% of carcinomas, and though specific mutations have not been identified, upregulation of Frizzled receptor expression has been observed (Brennan & Brown, 2004, *J. Mammary Gland Neoplasia* 9:119-31; Malovanovic et al., 2004, *Int. J. Oncol.* 25:1337-42).

FZD10, FZD8, FZD7, FZD4, and FZD5 are five often identified human Wnt receptors. Fzd10 is co-expressed with Wnt7b in the lungs, and cell transfection studies have demonstrated that the Fzd10/LRP5 co-receptor activates the canonical Wnt signaling pathway in response to Wnt7b (Wang et al., 2005, *Mol. Cell. Biol.* 25:5022-30). FZD10 mRNA is upregulated in numerous cancer cell lines, including cervical, gastric, and glioblastoma cell lines, and in primary cancers including approximately 40% of primary gastric cancers, colon cancers, and synovial sarcomas (Saitoh et al., 2002, *Int. J. Oncol.* 20:117-20; Terasaki et al., 2002, *Int. J. Mol. Med.* 9:107-12; Nagayama et al., 2005, *Oncogene* 1-12). FZD8 is upregulated in several human cancer cell lines, primary gastric cancers, and renal carcinomas (Saitoh et al. 2001. *Int. J. Oncol.* 18:991-96; Kirikoshi et al., 2001, *Int. J. Oncol.* 19:111-5: Janssens et al., 2004, *Tumor Biol.* 25:161-71). FZD7 is expressed throughout the gastrointestinal tract and is up-regulated in one out of six cases of human primary gastric cancer (Kirikoshi et al., 2001, *Int. J. Oncol.* 19:111-5). Expression of the FZD7 ectodomain by a colon cancer cell line induced morphological changes and decreased tumor growth in a xenograft model (Vincan et al. 2005, *Differentiation* 73:142-53). FZD5 plays an essential role in yolk sac and placental angiogenesis (Ishikawa et al., 2001, *Dev.* 128:25-33) and is upregulated in renal carcinomas in association with activation of Wnt/β-catenin signaling (Janssens et al., 2004, *Tumor Biology* 25:161-71). FZD4 is highly expressed in intestinal crypt epithelial cells and is one of several factors that display differential expression in normal versus neoplastic tissue (Gregorieff et al., 2005, *Gastroenterology* 129:626-38). The identification of FZD receptors as markers of cancer stem cells thus makes these proteins ideal targets for cancer therapeutics.

SUMMARY OF THE INVENTION

The present invention provides novel agents that bind to one or more human frizzled receptors (FZDs), including, but not limited to, antibodies or other agents that bind two or more human frizzled receptors, and methods of using the agents. The present invention further provides novel polypeptides, such as antibodies that bind one or more human frizzled receptors, fragments of such antibodies, and other polypeptides related to such antibodies. In certain embodiments, the agent, antibodies, other polypeptides, or agents that bind a FZD, bind to a region of the FZD referred to herein as the Biological Binding Site (BBS) that the inventors have now for the first time identified as a target for inhibiting Wnt signaling and/or tumor growth. Antibodies and other polypeptides that comprise an antigen-binding site that binds more than one FZD are also provided. Polynucleotides comprising nucleic acid sequences encoding the polypeptides are also provided, as are vectors comprising the polynucleotides. Cells comprising the polypeptides and/or polynucleotides of the invention are further provided. Compositions (e.g., pharmaceutical compositions) comprising the novel FZD-binding agents or antibodies are also provided. In addition, methods of making and using the novel FZD-binding agents or antibodies are also provided, such as methods of using the novel FZD-binding agents or antibodies to inhibit tumor growth and/or treat cancer.

Thus, in one aspect, the invention provides an agent that specifically binds a human frizzled receptor. In certain embodiments, the agent inhibits the binding of a ligand (e.g., a Wnt) to the Biological Binding Site (BBS) of the human frizzled receptor. In certain embodiments, the agent binds to at least part of the Biological Binding Site (BBS) within the human frizzled receptor. In certain embodiments, the binding of the agent to the BBS results in an inhibition of Wnt signaling and/or tumor growth. In certain embodiments, the human frizzled receptor is FZD8 and the agent binds to at least a part of (a) a conformational epitope of FZD8 formed by amino acids 72(F), 74-75(PL), 78(I), 92(Y), 121-122 (LM), and 129-132(WPDR (SEQ ID NO:70)); (b) a region of FZD8 consisting of the sequence QDEAGLEVHQFWPL (SEQ ID NO:67); and/or (c) a region of FZD8 consisting of the sequence QYGFA (SEQ ID NO:66).

In certain embodiments, the human frizzled receptor bound by the agent is selected from the group consisting of FZD1, FZD2, FZD5, FZD7, or FZD8, and the agent binds to at least part of the sequence Q(DE/ED)AGLEVHQF(Y/W)PL (SEQ ID NO:24) within the human frizzled receptor. For instance, in certain embodiments, the human frizzled receptor is FZD8 and the agent binds to at least part of the sequence QDEAGLEVHQFWPL (SEQ ID NO:67) within FZD8. In certain embodiments, the agent binds to at least part of the sequence GLEVHQ (SEQ ID NO:25). In certain embodiments, the human frizzled receptor is FZD1, FZD2, FZD3, FZD4, FZD5, FZD6. FZD7, FZD9, or FZD10, and the agent binds to at least part of a region of the human frizzled receptor corresponding to the region of FZD8 consisting of QDEAGLEVHQFWPL (SEQ ID NO:67). In certain embodiments, the agent binds to at least part of a sequence (K/Q)(F/Y)GF(Q/A) (SEQ ID NO:69) within FZD1. FZD2, FZD5, FZD7, and/or FZD8. For example, in certain embodiments, the human frizzled receptor is FZD8 and the agent binds to at least part of a sequence QYGFA (SEQ ID NO:66) within FZD8. In certain alternative embodiments, the human frizzled receptor is FZD1, FZD2, FZD3, FZD4, FZD5, FZD6, FZD7, FZD9, or FZD10, and the agent binds to at least part of a region of the human frizzled receptor corresponding to the region of FZD8 consisting of QYGFA (SEQ ID NO:66). In certain embodiments, the agent specifically binds to two or more, three or more, or four or more human frizzled receptors. In certain embodiments, the agent specifically binds to human frizzled receptors comprising FZD5 and FZD8.

In certain alternative embodiments, the FZD-binding agent is an agent that binds a human FZD receptor (e.g., FZD8) in the cleft of its BBS. By way of nonlimiting example, the agent may bind one or more cleft residues listed in Table 16. In certain embodiments, the agent binds L75 of FZD8. In certain embodiments, the agent comprises a polypeptide comprising a sequence having at least about 80% sequence identity to a sequence selected from the group consisting of SEQ ID NOs:98-111 and SEQ ID NOs:113-116. In certain embodiments, the agent comprises SEQ ID NO:112. In some instances, the agent may comprise SEQ ID NO: 108.

In another aspect, the invention provides an agent that competes for specific binding to a human frizzled receptor with an antibody (e.g., in an in vitro competitive binding assay), wherein the antibody comprises a heavy chain variable region comprising SEQ ID NO:10 and a light chain variable region comprising SEQ ID NO:12 or SEQ ID NO:14. In certain embodiments, the antibody comprises a heavy chain variable region comprising SEQ ID NO:10 and a light chain variable region comprising SEQ ID NO:14. In certain embodiments, the agent competes for specific binding to two or more, three or more, or four or more human frizzled receptors. In certain embodiments, the agent competes for specific binding to FZD1, FZD2, FZD5, FZD7, or FZD8.

In another aspect, the invention provides an agent that competes for specific binding to a human FZD5 and/or FZD8 with an antibody that comprises a heavy chain variable region comprising SEQ ID NO:85 and a light chain variable region comprising SEQ ID NO:86.

In a further aspect, the invention provides a FZD-binding agent that (a) competes for binding to the BBS of FZD8 with a polypeptide and/or (b) is capable of displacing from FZD8 a polypeptide that is bound to the BBS of FZD8. In certain embodiments, the polypeptide comprises a sequence having at least 80% identity with a sequence selected from the group consisting of SEQ ID NOs:98-111 and SEQ ID NOs:113-116. In certain alternative embodiments, the polypeptide comprises the sequence of SEQ ID NO: 112.

In another aspect, the invention provides an agent that specifically binds to two or more human frizzled receptors. In certain embodiments, the two or more frizzled receptors comprise: (a) FZD1 and a second frizzled receptor selected from the group consisting of FZD2, FZD5. FZD7, and FZD8: (b) FZD2 and a second frizzled receptor selected from the group consisting of FZD5, FZD7, and FZD8; (c) FZD5 and FZD7; or (d) FZD7 and FZD8. In certain embodiments, the agent specifically binds three or more (i.e., 3, 4, or 5) human frizzled receptors, wherein the three or more human frizzled receptors comprise FZD1, FZD2, FZD5, FZD7, and/or FZD8. In certain embodiments, the three or more human receptors comprise FZD5 and FZD8. In certain embodiments, the three or more human frizzled receptors further comprise FZD3, FZD4, FZD6, FZD9, and/or FZD10.

In a further aspect, the invention provides a polypeptide that specifically binds a human frizzled receptor, wherein the polypeptide comprises a heavy chain variable region comprising: (a) a heavy chain CDR1 comprising GFTFSHYTLS (SEQ ID NO:1), or a variant thereof comprising 1, 2, 3, or 4 amino acid substitutions; (b) a heavy chain CDR2 comprising VISGDGSYTYYADSVKG (SEQ ID NO:2), or a variant thereof comprising 1, 2, 3, or 4 amino acid substitutions; and/or (c) a heavy chain CDR3 comprising NFIKYVFAN (SEQ ID NO:3), or a variant thereof comprising 1, 2, 3, or 4 amino acid substitutions. In certain embodiments, the polypeptide specifically binds FZD1, FZD2, FZD5, FZD7, and/or FZD8. In certain embodiments, the polypeptide specifically binds two or more human frizzled receptors including FZD5 and FZD8. In certain embodiments, the amino acid substitutions are conservative substitutions.

In an additional aspect, the invention provides a polypeptide that specifically binds a human frizzled receptor, wherein the polypeptide comprises a light chain variable region comprising: (a) a light chain CDR1 comprising SGDKLGKKYAS (SEQ ID NO:4) or SGDNIGSFYVH (SEQ ID NO:7), or a variant of SEQ ID NO:4 or SEQ ID NO:7 comprising 1, 2, 3, or 4 amino acid substitutions; (b) a light chain CDR2 comprising EKDNRPSG (SEQ ID NO:5) or DKSNRPSG (SEQ ID NO:8), or a variant of SEQ ID NO:5 or SEQ ID NO:8 comprising 1, 2, 3, or 4 amino acid substitutions; and/or (c) a light chain CDR3 comprising SSFAGNSLE (SEQ ID NO:6) or QSYANTLSL (SEQ ID NO:9), or a variant of SEQ ID NO:6 or SEQ ID NO:9 comprising 1, 2, 3, or 4 amino acid substitutions. In certain embodiments, the polypeptide specifically binds FZD1, FZD2, FZD5, FZD7, and/or FZD8. In certain embodiments, the polypeptide specifically binds two or more human frizzled receptors including FZD5 and FZD8. In certain embodiments, the amino acid substitutions are conservative substitutions.

In another aspect, the invention provides a polypeptide comprising: (a) a heavy chain CDR1 comprising GFTFSHYTLS (SEQ ID NO:1), a heavy chain CDR2 comprising VISGDGSYTYYADSVKG (SEQ ID NO:2), and a heavy chain CDR3 comprising NFIKYVFAN (SEQ ID NO:3); and/or (b) a light chain CDR1 comprising SGDKLGKKYAS (SEQ ID NO:4) or SGDNIGSFYVH (SEQ ID NO:7), a light chain CDR2 comprising EKDNRPSG (SEQ ID NO:5) or DKSNRPSG (SEQ ID NO:8), and a light chain CDR3 comprising SSFAGNSLE (SEQ ID NO:6) or QSYANTLSL (SEQ ID NO:9). In certain embodiments, the polypeptide specifically binds a human frizzled receptor. In certain embodiments, the polypeptide specifically binds two or more (e.g., at least FZD5 and FZD8), three or more, or four or more human frizzled receptors.

In a further aspect, the invention provides an antibody that specifically binds a human frizzled receptor selected from the group consisting of FZD1, FZD2, FZD5, FZD7, and FZD8, wherein the antibody comprises a heavy chain variable region comprising: (a) a heavy chain CDR1 comprising GFTFSHYTLS (SEQ ID NO:1), or a variant thereof comprising 1, 2, or 3 amino acid substitutions; a heavy chain CDR2 comprising VISGDGSYTYYADSVKG (SEQ ID NO:2), or a variant thereof comprising 1, 2, 3, or 4 amino acid substitutions; and a heavy chain CDR3 comprising NFIKYVFAN (SEQ ID NO:3), or a variant thereof comprising 1, 2, 3, or 4 amino acid substitutions; and/or (b) a light chain CDR1 comprising SGDKLGKKYAS (SEQ ID NO:4), SGDNIGSFYVH (SEQ ID NO:7), or a variant of either SEQ ID NO:4 or SEQ ID NO:7 comprising 1, 2, 3, or 4 conservative amino acid substitutions; a light chain CDR2 comprising EKDNRPSG (SEQ ID NO:5), DKSNRPSG (SEQ ID NO:8), or a variant of either SEQ ID NO:5 or SEQ ID NO:8 comprising 1, 2, 3, or 4 conservative amino acid substitutions; and a light chain CDR3 comprising SSF-AGNSLE (SEQ ID NO:6), QSYANTLSL (SEQ ID NO:9), or a variant of either SEQ ID NO:6 or SEQ ID NO:9 comprising 1, 2, 3, or 4 conservative amino acid substitutions. In certain embodiments, the antibody comprises (a) a heavy chain CDR1 comprising GFTFSHYTLS (SEQ ID NO:1), a heavy chain CDR2 comprising VISGDGSYTYY-ADSVKG (SEQ ID NO:2), and a heavy chain CDR3 comprising NFIKYVFAN (SEQ ID NO:3); and/or (b) a light chain CDR1 comprising SGDKLGKKYAS (SEQ ID NO:4) or SGDNIGSFYVH (SEQ ID NO:7), a light chain CDR2 comprising EKDNRPSG (SEQ ID NO:5) or DKSNRPSG (SEQ ID NO:8), and a light chain CDR3 comprising SSF-AGNSLE (SEQ ID NO:6) or QSYANTLSL (SEQ ID NO:9). In certain embodiments, the antibody comprises (a) a heavy chain CDR1 comprising GFTFSHYTLS (SEQ ID NO:1), a heavy chain CDR2 comprising VISGDGSYTYYADSVKG (SEQ ID NO:2), and a heavy chain CDR3 comprising NFIKYVFAN (SEQ ID NO:3); and/or (b) a light chain CDR1 comprising SGDNIGSFYVH (SEQ ID NO:7), a light chain CDR2 comprising DKSNRPSG (SEQ ID NO:8), and a light chain CDR3 comprising QSYANTLSL (SEQ ID NO:9).

In another aspect, the invention provides a polypeptide comprising (a) a polypeptide having at least about 80% sequence identity to SEQ ID NO:10; and/or (b) a polypeptide having at least about 80% sequence identity to SEQ ID NO:12 or SEQ ID NO: 14. In certain embodiments, the invention provides a polypeptide comprising (a) a polypeptide having at least about 80% sequence identity to SEQ ID NO:10; and/or (b) a polypeptide having at least about 80% sequence identity to SEQ ID NO:14. In certain embodiments, the polypeptide specifically binds a human frizzled receptor. In certain embodiments, the polypeptide specifically binds two or more, three or more, or four or more human frizzled receptors. In certain embodiments, the human frizzled receptor(s) are selected from the group consisting of FZD1, FZD2, FZD5, FZD7, and FZD8.

In still another aspect, the invention provides an agent such as an antibody that specifically binds human FZD5 and/or FZD8, wherein the antibody comprises: (a) a heavy chain CDR1 comprising GFTFSSYYIT (SEQ ID NO:77), or a variant thereof comprising 1, 2, 3, or 4 conservative amino acid substitutions; a heavy chain CDR2 comprising TISYS-SSNTYYADSVKG (SEQ ID NO:78), or a variant thereof comprising 1, 2, 3, or 4 conservative amino acid substitutions; and a heavy chain CDR3 comprising SIVFDY (SEQ ID NO:79), or a variant thereof comprising 1, 2, 3, or 4 conservative amino acid substitutions; and/or (b) a light chain CDR1 comprising SGDALGNRYVY (SEQ ID NO:80), or a variant thereof comprising 1, 2, 3, or 4 conservative amino acid substitutions; a light chain CDR2 comprising SG (SEQ ID NO:81), or a variant thereof comprising 1, 2, 3, or 4 conservative amino acid substitutions; and a light chain CDR3 comprising GSWDTRPYPKY (SEQ ID NO:82), or a variant thereof comprising 1, 2, 3, or 4 conservative amino acid substitutions. In certain embodiments, the antibody comprises: (a) a heavy chain CDR1 comprising GFTFSSYYIT (SEQ ID NO:77), a heavy chain CDR2 comprising TISYSSSNTYY-ADSVKG (SEQ ID NO:78), and a heavy chain CDR3 comprising SIVFDY (SEQ ID NO:79); and/or (b) a light chain CDR1 comprising SGDALGNRYVY (SEQ ID NO:80), a light chain CDR2 comprising SG (SEQ ID NO:81), and a light chain CDR3 comprising GSWDTRPYPKY (SEQ ID NO:82).

In an additional aspect, the invention provides a polypeptide that specifically binds FZD5 and/or FZD8, wherein said polypeptide comprises: (a) a polypeptide having at least about 80% identity to SEQ ID NO:85; and/or (b) a polypeptide having at least about 80% identity to SEQ ID NO: 86.

In a further aspect, the invention provides an agent that competes for specific binding to human FZD1, FZD2, FZD5, FZD7, and/or FZD8 with any one of the following IgG antibodies: 18R8, 18R5, 18R4605, and 18R4805.

In a still further aspect, the invention provides an agent that competes for specific binding to human FZD5 and/or FZD8 with the anti-FZD IgG antibody 44R24.

In certain embodiments of each of the aforementioned aspects, as well as other aspects described herein, the agent or polypeptide is an antibody. In certain alternative embodiments, the agent is not an antibody.

In certain embodiments of each of the aforementioned aspects, as well as other aspects described herein, the agent or polypeptide or antibody specifically binds to the extracellular domain (ECD) of the human frizzled receptor or receptors to which it binds. In certain embodiments of each of the aforementioned aspects, as well as other aspects described herein, the agent or polypeptide or antibody specifically binds to the Fri domain (Fri) of the human frizzled receptor or receptors to which it binds.

In certain embodiments of each of the aforementioned aspects, as well as other aspects described elsewhere herein, an individual antigen-binding site of the antibody or other polypeptide specifically binds (or is capable of binding) more than one human frizzled receptor.

In certain embodiments of each of the aforementioned aspects, as well as other aspects described herein, the agent or polypeptide or antibody inhibits binding of a ligand to the human frizzled receptor(s). In certain embodiments, the ligand is a Wnt, including, but not limited to Wnt3a In certain embodiments, of each of the aforementioned aspects, as well as other aspects described herein, the agent or polypeptide or antibody that binds to the FZD(s) is an antagonist of the FZD(s).

In certain embodiments of each of the aforementioned aspects, as well as other aspects described herein, the agent or polypeptide or antibody inhibits Wnt signaling. In certain embodiments, the Wnt signaling that is inhibited is canonical Wnt signaling. In some embodiments, the Wnt signaling that is inhibited by the FZD-binding agent is non-canonical Wnt signaling. In certain embodiments, the Wnt signaling is non-canonical Wnt signaling.

In certain embodiments of each of the aforementioned aspects, as well as other aspects described herein, the FZD-binding agent or polypeptide or antibody inhibits tumor growth.

The invention further provides the antibodies 18R8, 18R5, 18R4605, 44R24, and 18R4805, as well as fragments thereof.

The invention further provides compositions, such as pharmaceutical compositions, comprising a FZD-binding agent, polypeptide, or antibody.

Methods of inhibiting Wnt signaling (e.g., canonical Wnt signaling) and/or inhibiting tumor growth in a subject comprising administering a therapeutically effective amount of the FZD-binding agent or polypeptide or antibody are provided.

Methods of reducing the tumorigenicity of a tumor that comprises cancer stem cells are also provided. In certain embodiments, the methods comprise administering a therapeutically effective amount of the FZD-binding agent or polypeptide or antibody to a subject comprising the tumor. In certain embodiments, the frequency of cancer stem cells in the tumor is reduced by administration of the antibody. In certain embodiments, administration of the FZD-binding agent results in the differentiation of tumorigenic cells in the tumor to a non-tumorigenic state.

Also provided are methods of inducing cells in a tumor in a subject to differentiate, said methods comprising administering a therapeutically effective amount of the FZD-binding, agent, polypeptide, or antibody to the subject.

Methods of treating cancer in a subject, comprising administering a therapeutically effective amount of the FZD-binding agent, polypeptide, or antibody to the subject are further provided.

In addition, methods of reducing myofibroblast activation in the stroma of a solid tumor, comprising contacting the stroma with an effective amount of the FZD-binding agent, polypeptide, or antibody are also provided.

In other aspects, methods of treating a disease associated with Wnt-signaling activation are provided. In certain embodiments, the methods comprise administering to a subject in need thereof an effective amount of a FZD-binding agent, polypeptide, or antibody. In certain embodiments, the disease is cancer. In certain alternative embodiments, the disease is polycystic kidney disease. In certain embodiments, the FZD-binding agent is a polypeptide that binds to the BBS of one or more human FZD receptors. In certain embodiments, the FZD-binding polypeptide comprises a sequence having at least 80% identity with a sequence selected from the group consisting of SEQ ID NOs:98-111 and SEQ ID NOs:113-116. In some embodiments, the FZD-binding polypeptide comprises the sequence of SEQ ID NO: 112. In certain alternative embodiments, the FZD-binding polypeptide is 18R5.

In certain embodiments, the methods comprising administration of the FZD-binding agent, polypeptide, or antibody further comprise administering a second anti-cancer agent (e.g., a chemotherapeutic agent) to the subject. In certain embodiments, the second agent is gemcitabine, irinotecan, or paclitaxel. In certain embodiments, the second agent is an angiogenesis inhibitor and/or an inhibitor of Notch signaling.

In another aspect, the invention provides a polypeptide comprising a sequence selected from the group consisting of SEQ ID NOs: 10-15. Polypeptides comprising a sequence selected from the group consisting of SEQ ID NOs: 85-86 are likewise provided. Polynucleotides comprising nucleic acid sequences encoding such polypeptides are also provided.

In a further aspect, the invention provides a polynucleotide comprising a sequence selected from the group consisting of SEQ ID NOs: 17-22. Polynucleotides comprising a sequence selected from the group consisting of SEQ ID NOs: 87-90, 92, and 94-95 are further provided.

In a still further aspect, the invention provides a polynucleotide that comprises a polynucleotide that hybridizes to a polynucleotide selected from the group consisting of SEQ ID NOs: 17, 19, 21, 87-90, 92, and 94-95, or a polynucleotide encoding a polypeptide selected from the group consisting of SEQ ID NOs: 10, 12, 14, and 85-86 under conditions of high stringency. In certain embodiments, the invention comprises a polynucleotide that hybridizes to a polynucleotide consisting of a sequence SEQ ID NOs: 17, 19, or 21, or a polynucleotide encoding SEQ ID NOs: 10, 12, or 14 under conditions of high stringency.

In certain embodiments of each of the aforementioned aspects, as well as other aspects described herein, the agent or polypeptide or antibody or polynucleotide is isolated. In certain embodiments, the agent or polypeptide or antibody or polynucleotide is substantially pure.

The present invention further provides a Wnt gene signature useful for the identification of tumors and/or patients likely to respond to treatment with a FZD-binding agent (e.g., an antagonist of a human frizzled receptor and/or an inhibitor of Wnt signaling) or other inhibitors of Wnt signaling. Methods of using the Wnt gene signature to select patients for treatment with a FZD-binding agent or other inhibitor of Wnt signaling are also provided. In certain embodiments, the methods involve the assessment of the level of one or more genes in the Wnt gene signature. Methods of screening drug candidates against tumors identified using the Wnt gene signature are also provided. Arrays, kits, and other compositions useful in the methods are also provided.

The present invention also provides methods of screening for inhibitors of Wnt signaling, potential drug candidates, or other agents. These methods include, but are not limited to, methods comprising comparing the levels of one or more differentiation markers in a first solid tumor that has been exposed to the agent relative to the levels of the one or more differentiation markers in a second solid tumor that has not been exposed to the agent. In certain embodiments, these methods include comprising (a) exposing a first solid tumor, but not a second solid tumor, to the agent; (b) assessing the levels of one or more differentiation markers in the first and second solid tumors; and (c) comparing the levels of the one or more differentiation markers in the first and second solid tumors. In certain alternative embodiments, the methods involve the use of FZD receptors or derivatives of FZD receptors which comprise one or more substitutions in the BBS or polypeptides or other agents which have already been identified as binding to portions of the BBS. Agents identified using the screening methods, or having the characteristics of agents identified using the screening methods, are likewise provided, as are methods of using such agents to inhibit Wnt signaling and/or in therapy.

In one aspect the invention provides a method of screening a test compound for activity or possible activity as an inhibitor of Wnt signaling. In certain embodiments, the method comprises comparing (a) the binding affinity of the test compound for a first polypeptide comprising the Fri domain of a human FZD receptor (e.g., FZD8) having one or more substitutions in its BBS with (b) the binding affinity of the compound for a second polypeptide comprising the wild-type Fri domain. If the test compound has greater affinity for the second polypeptide than the first polypeptide, the compound is identified as an inhibitor of Wnt signaling or a possible inhibitor of Wnt signaling. In certain embodiments, the method further comprises the additional steps of first determining the binding affinity of the test compound for the first and second polypeptides. Reagents useful in such methods including the mutant Fri domain are also provided. Agents identified as inhibitors of Wnt signaling (or at least potential Wnt inhibitors) by such methods are likewise provided.

In another aspect, the invention provides a method of screening a test compound for activity or possible activity as an inhibitor of Wnt signaling that comprises determining whether the test compound can compete with a FZD-binding agent (that binds the BBS) for binding to a human FZD receptor. In certain embodiments, the ability of the compound to compete for binding with the polypeptide indicates the compound has activity or possible activity as an inhibitor of Wnt signaling.

In another aspect, the invention provides alternative methods of screening a test compound for activity or possible activity as an inhibitor of Wnt signaling. In certain embodiments the method comprises determining whether the test compound can displace a FZD-binding agent (that binds the BBS) from the human FZD receptor to which it is bound. If the test compound can displace the FZD-binding agent, the compound has activity or possible activity as an inhibitor of Wnt signaling. Reagents useful in the above-indicated competitive binding and displacement assays, including, without limitation, polypeptides comprising a sequence that is at least about 80% identical to a sequence selected from the group consisting of SEQ ID NOs:98-111 and SEQ ID NOs:113-116, are provided. Agents identified as inhibitors of Wnt signaling (or at least potential Wnt inhibitors) by such competitive binding and displacement assays are likewise provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

BRIEF DESCRIPTIONS OF THE DRAWINGS

FIG. 1. 18R8 binds multiple human frizzled receptors. FACS analysis demonstrated that 18R8 binds to FZD1, FZD2, FZD5, FZD7, and FZD8 sequences on transiently transfected HEK293 cells. FACS plots are shown for the binding of 18R8 to HEK293 cells transfected with expression vectors encoding the indicated FZD and an expression vector for GFP. 18R8 binding is indicated by elevated staining within the co-transfected (GFP positive) cell population. FACS plots for FZD1, FZD2, FZD5, FZD7 and FZD8 are boxed with thick line to highlight the FZDs showing binding to 18R8.

Figure 2:
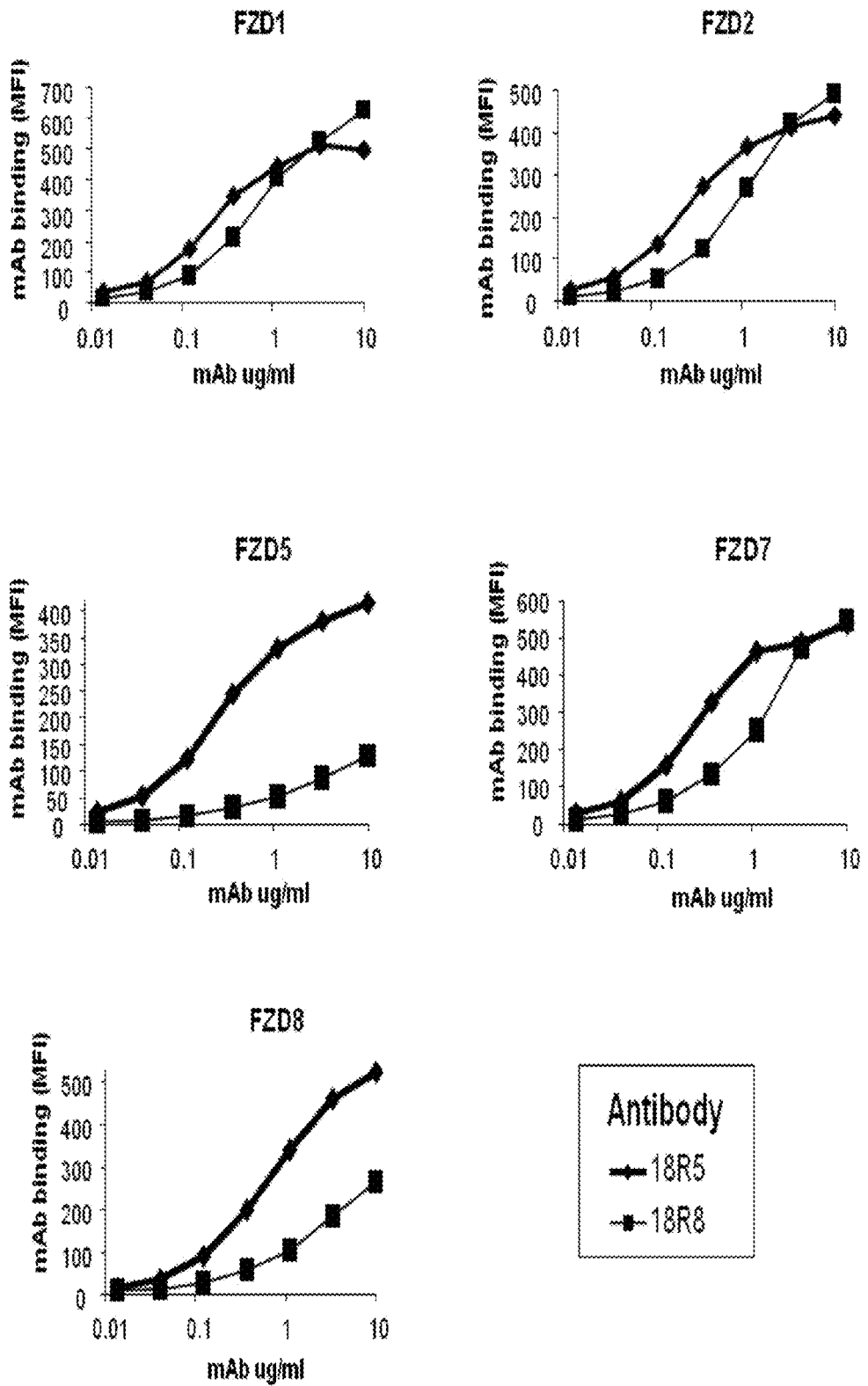

FIG. 2. Anti-FZD antibody 18R5 binds multiple human frizzled receptors on cells. FACS analysis demonstrated that 18R5, like 18R8, binds to FZD1, FZD2, FZD5. FZD7, and FZD8 sequences on cells. Antibodies 18R8 and 18R5 were incubated at a range of concentrations with the HEK293 cells overexpressing the indicated FZD and antibody binding was assessed by flow cytometry. While both 18R8 and 18R5 bind to FZD1. FZD2, FZD5, FZD7 and FZD8, 18R5 binds with greater affinity.

Figure 3:
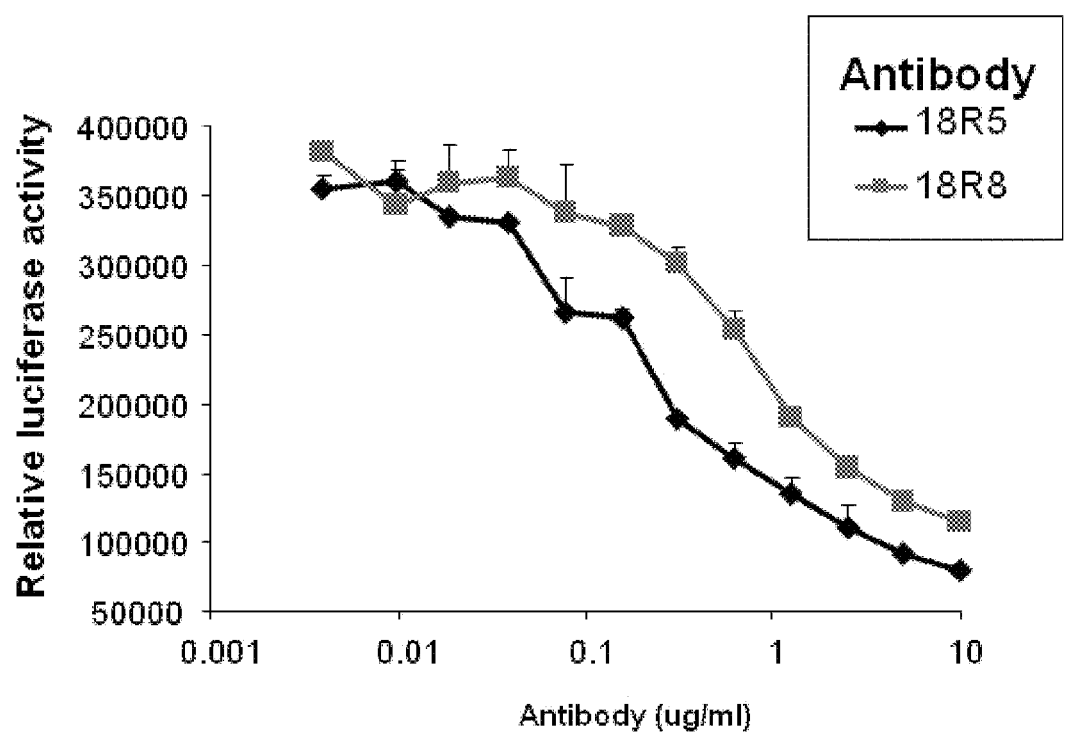

FIG. 3. Luciferase reporter assays were carried out in STF293 cells that stably express 8xTCF promoter element linked to luciferase. Cells were treated with conditioned medium containing Wnt3A as well as a range of concentrations of 18R8 and 18R5 and then assayed 18 hours later using the Dual-Glo luciferase assay reporter system (Promega). The results demonstrate that both 18R8 and 18R5 inhibit Wnt signaling and that 18R5 binds with greater affinity than 18R8.

Figure 4:
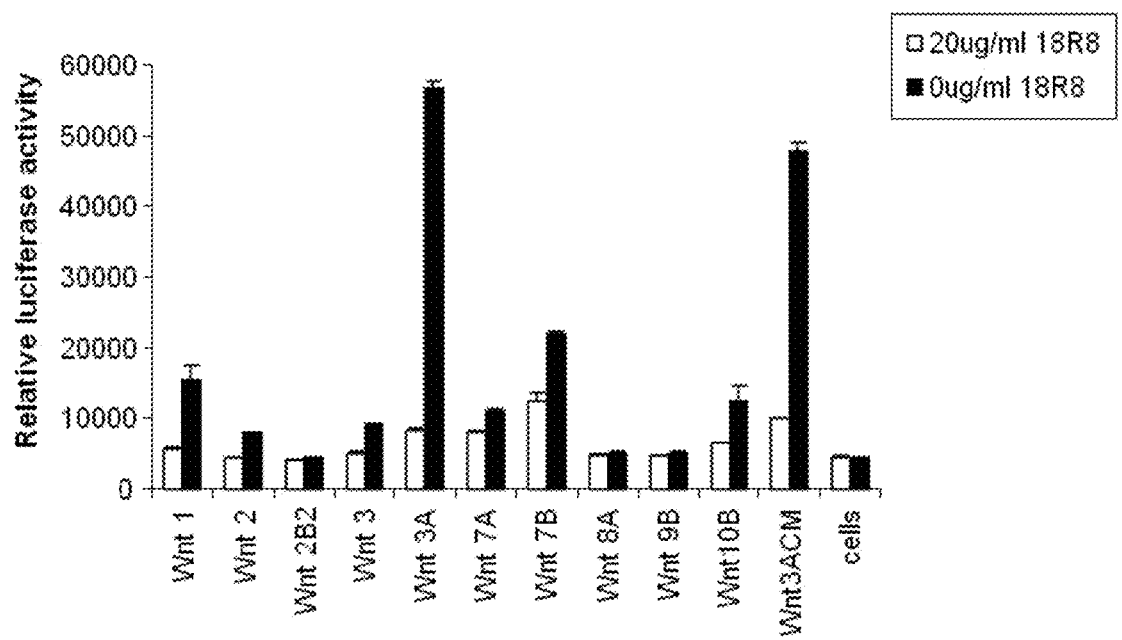

FIG. 4. 18R8 blocks TCF signaling by multiple Wnts. Luciferase reporter assays were carried out in STF293 cells that stably express 8xTCF promoter element linked to luciferase. Various Wnt-overexpressing cells were generated by transfecting HEK293 cells (ATCC) with expression vectors encoding indicated Wnt proteins using Fugene 6 (Roche). STF293 cells were treated with 18R8 and added Wnts overexpressed HEK293 cells and assayed 18 hours later using the Dual-Glo luciferase assay reporter system.

Figure 5:
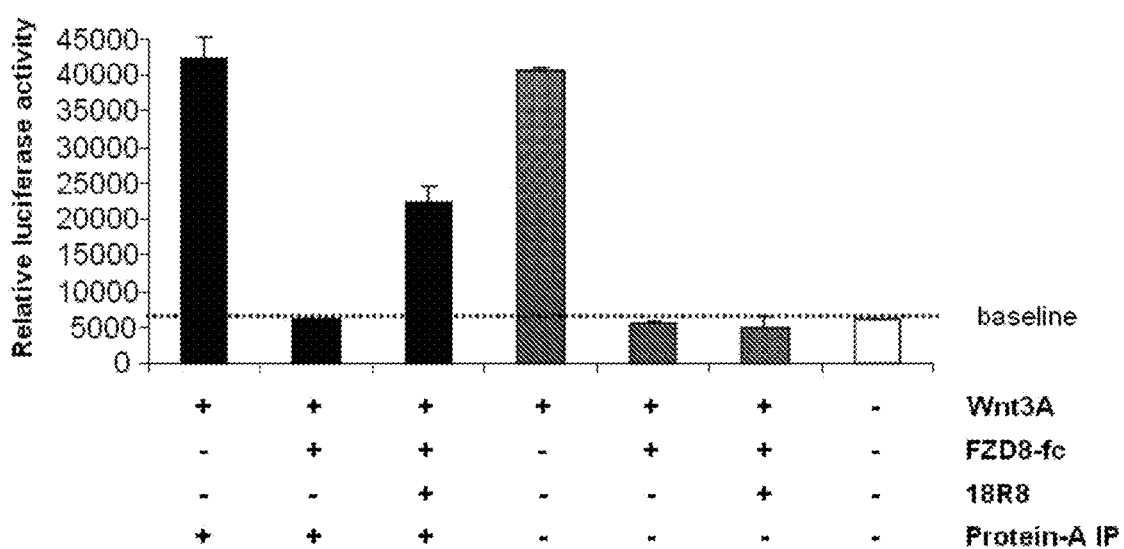

FIG. 5. 18R8 directly inhibits Wnt binding to FZD. Luciferase reporter assays were carried out in STF293 cells that stably express 8xTCF promoter element. A mixture containing Wnt3A conditioned medium, purified FZD8-Fc, and/or 18R8 were co-incubated as indicated for 2 hrs at 4° C. with/without protein A sepharose beads. After the incubation, the protein A sepharose beads were removed and added to STF293 cells. The treated STF293 cells were assayed 18 hours later using the Dual-Glo luciferase assay reporter system. This experiment shows that in the absence of 18R8, Fzd8-Fc is able to inhibit the ability of Wnt3A to stimulate signaling, but that 18R8 is able to block the ability of FZD8 to bind Wnt3A, as evidenced by the restoration of signaling when the sepharose A beads are used to remove the FZD8-Fc (and 18R8) from the co-incubation.

Figure 6:
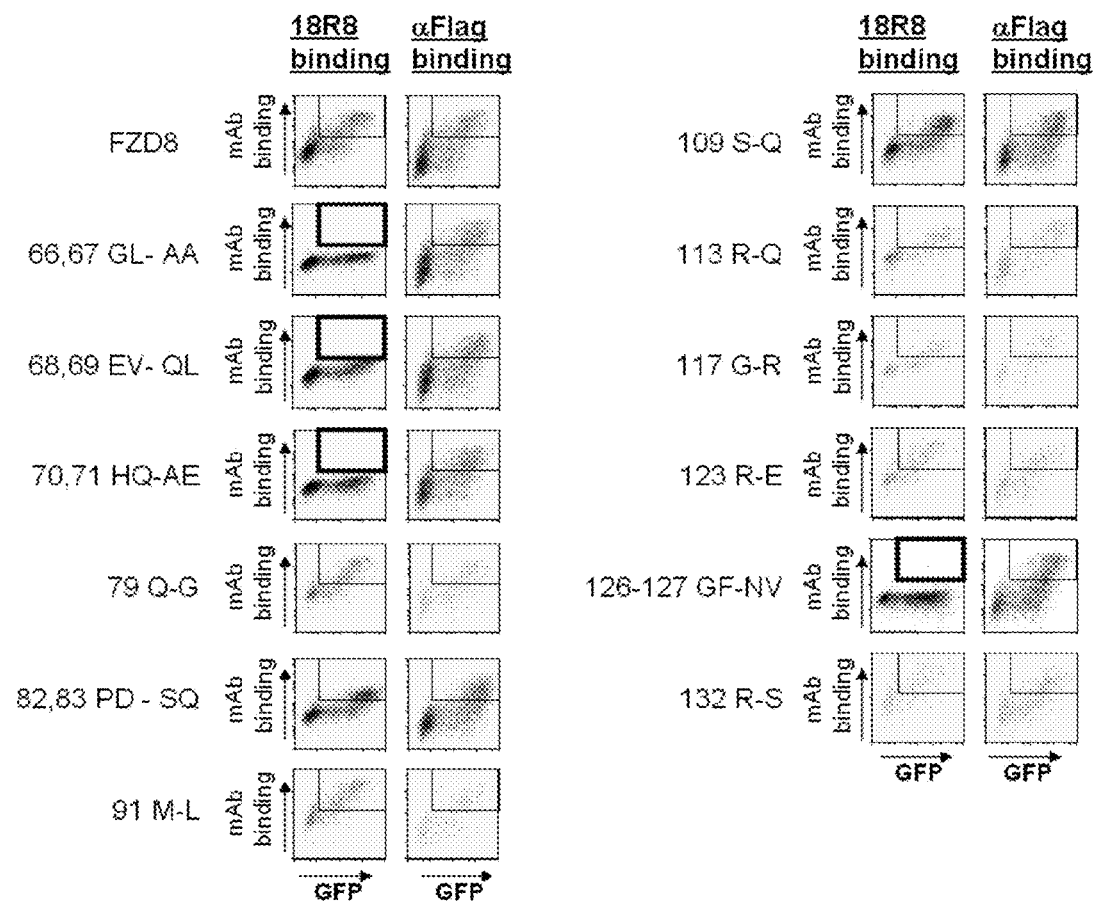

FIG. 6. FACS analysis of binding of 18R8 to mutant FZD8 compared to wild-type FZD8. To assess the epitope of 18R8 on FZD, epitope mapping studies were performed. An expression construct that enabled the expression of the Fri domain of human FZD8 with an N-terminal FLAG tag, and a C-terminal CD4 transmembrane domain and intracellular domain was used in transient transfection studies together with an expression vector encoding GFP. Variants of this expression vector were also prepared which contained selected amino acid substitutions within the FZD8 sequence to encode the amino acids at the corresponding position within the Fri domain of other particular FZDs not bound by 18R8. The ability of 18R8 to bind to these variant FZD8 sequences was then assessed by flow cytometry. Certain positions including amino acids 66-71 and 126-127 of FZD8 were found to be required for 18R8 binding as indicated by reduced staining within the co-transfected (GFP positive) cell population. The region of the FACS plot showing binding of 18R8 to the cotransfected cell population is highlighted by a box and the box is shown in thick lines for those amino acid substitutions showing markedly reduced 18R8 binding.

Figure 7:
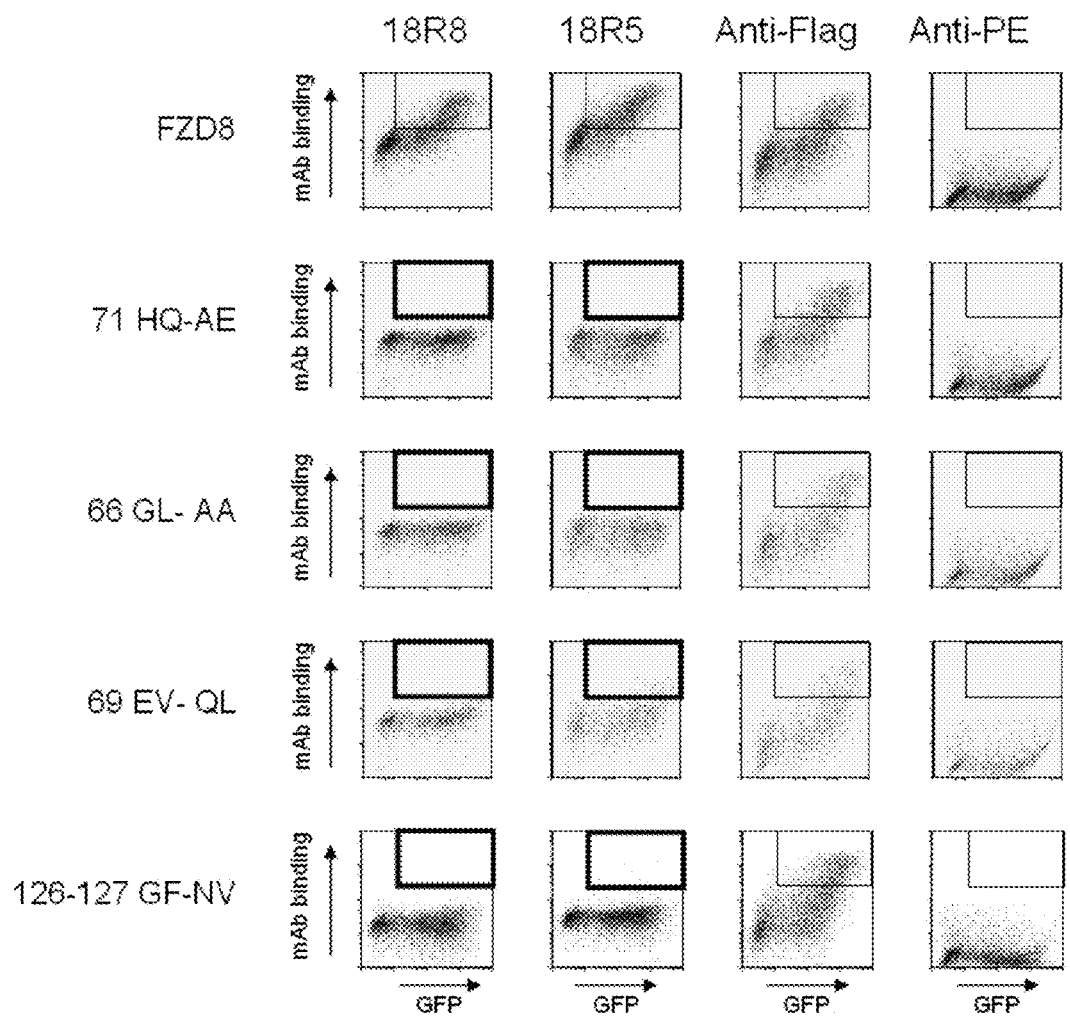

FIG. 7. 18R5 and 18R8 are shown to have a similar binding epitope on human FZD8. The ability of 18R5 to bind to a similar epitope as 18R8 was assessed by flow cytometry using a series of amino acid variants previous shown to disrupt binding of 18R8. Positions including amino acids 66-71 and 126-127 of FZD8 were found to be required for binding both 18R8 and 18R5 as indicated by reduced staining within the co-transfected (GFP positive) cell population. The region of the FACS plot showing binding of 18R8 to the cotransfected cell population is highlighted by a box and the box is shown in thick lines for those amino acid substitutions showing markedly reduced 18R8 and 18R5 binding.

Figure 8:
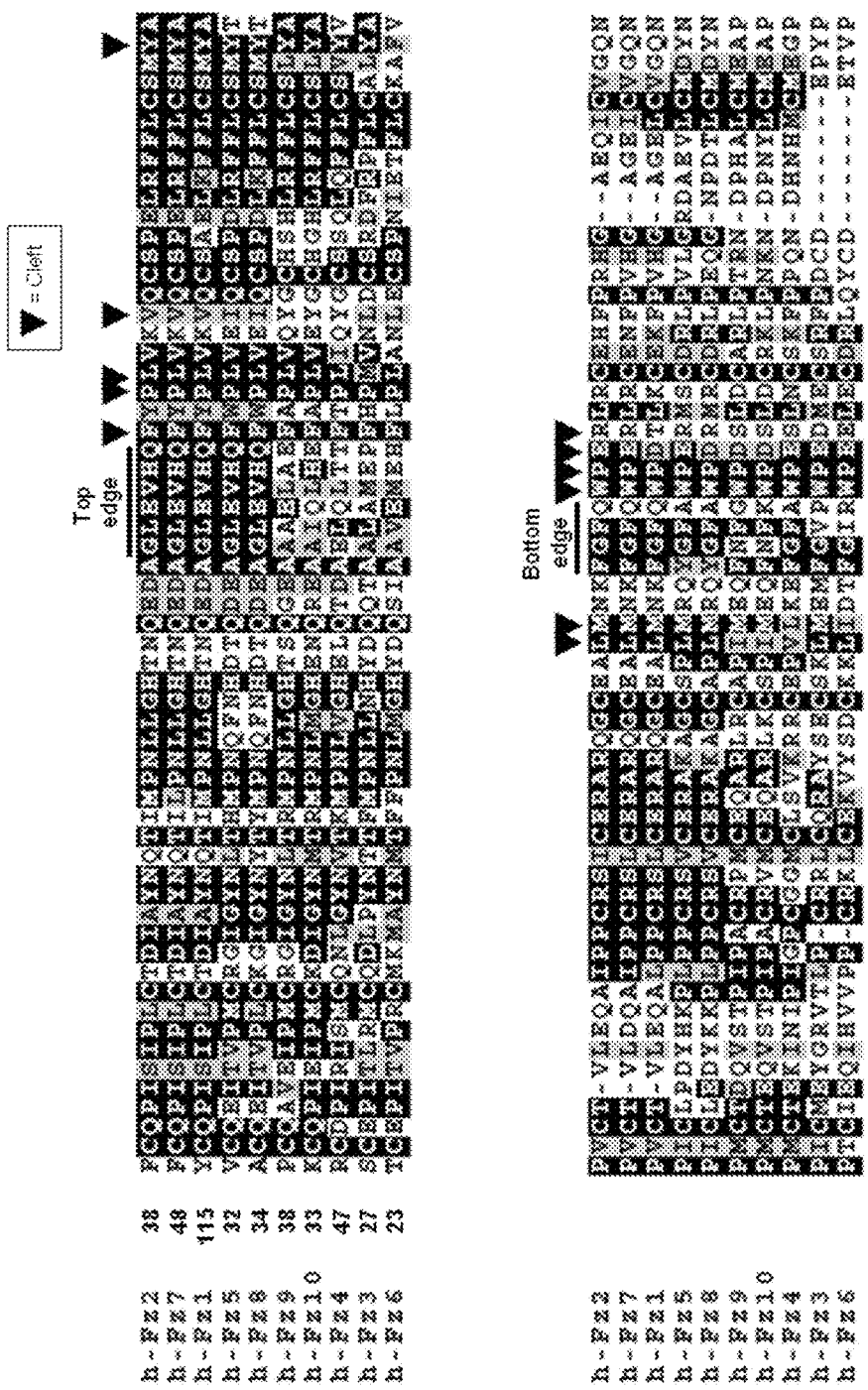

FIG. 8. Comparison of the amino acid sequences of portions of the Fri domain sequences of the human frizzled receptors. Sites with conserved residues are shaded in black; sites with similar amino acid residues are shaded in gray.

The FZD epitope of 18R8 and 18R5 contains the regions denoted by underline and labeled as "top edge" and "bottom edge." The terms "top edge" and "bottom edge" reflect the recognition, based on examination of Fri domain crystal structure, that these regions flank a cleft on the surface of the FZD protein. This cleft contains multiple highly conserved residues. The amino acids that comprise this cleft are highlighted by carrot symbols above each corresponding position within the alignment. This region has not previously been ascribed specific function. The discovery of antibodies that bind to this region and the discovery that these antibodies inhibit Wnt binding and Wnt signaling as well as our recognition of the conserved nature of this cleft have enabled us to identify this region as a key functional aspect of the FZD proteins.

Figure 9:
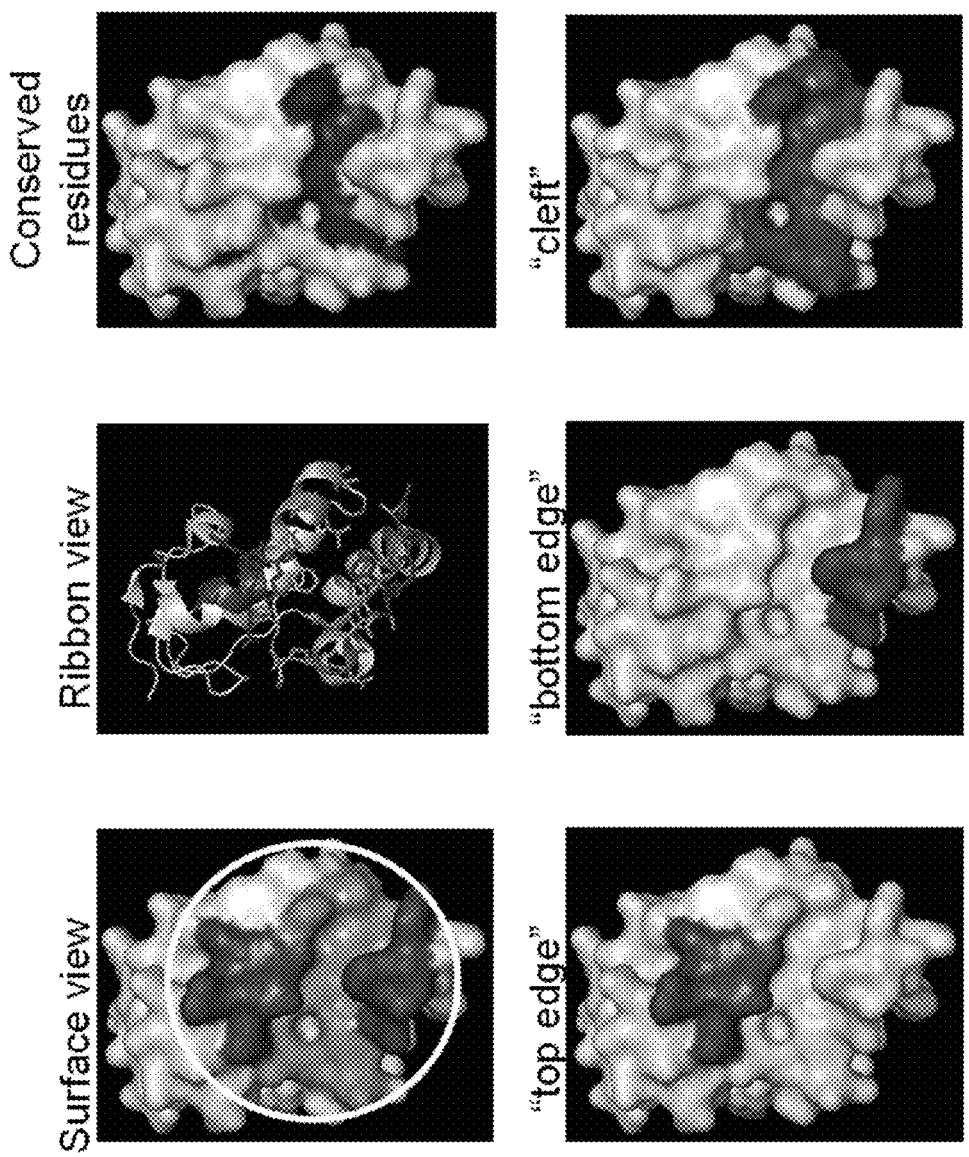

FIG. 9. The Biological Binding Site (BBS) of FZD. Shown are images of the structure of a Fzd fri domain. The images are based on analysis of the previously reported crystal structure of mouse FZD8 (Dann C E et al., Nature 412 (6842) 86-90, 2001) and analysis done using the software program Pymol. Shown in the upper left image is a surface view of the FZD Fri domain with the region of the Fzd protein comprising the biological binding site (BBS) that the inventors have discovered (encircled by a white oval). This is the region bound by the antibodies 18R8 and 18R5. This region contains structural elements we term the "top edge" the "bottom edge" and the "cleft." Each of these is highlighted in darker surface coloration in separate images at the bottom of the panel. The upper right image highlights in darker surface the residues that are conserved in nine or ten of the ten human Fzd family members and highlights the recognition that a distinct grouping of these residues occurs within the center of the "cleft" region flanked by the epitope that binds antibodies that inhibit Fzd function.

Figure 10:
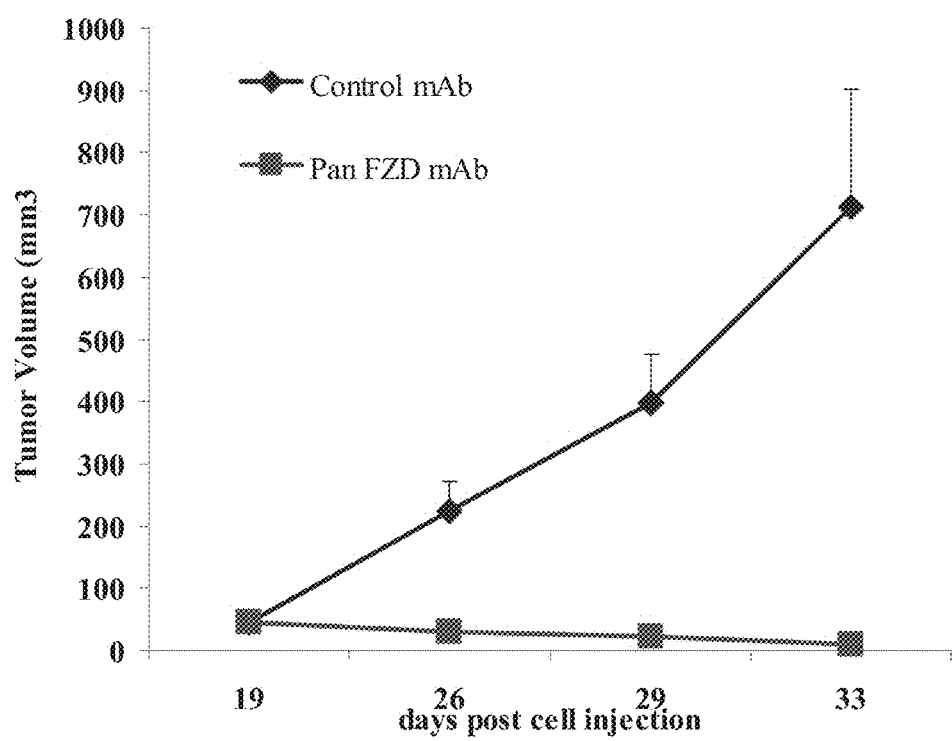

FIG. 10. Prevention of Wnt-dependent tumor growth by anti-FZD mAb. NOD/SCID mice injected with 50,000 MMTV WNT1 tumor derived cells and tumor growth was monitored weekly until growth was detected, then tumor growth was measured twice a week. Ten mice with established tumors were treated with either 18R8 or a control antibody as a control. Tumor growth in animals treated with 18R8 was virtually eliminated compared to that observed in animals treated with control antibody.

Figure 11:
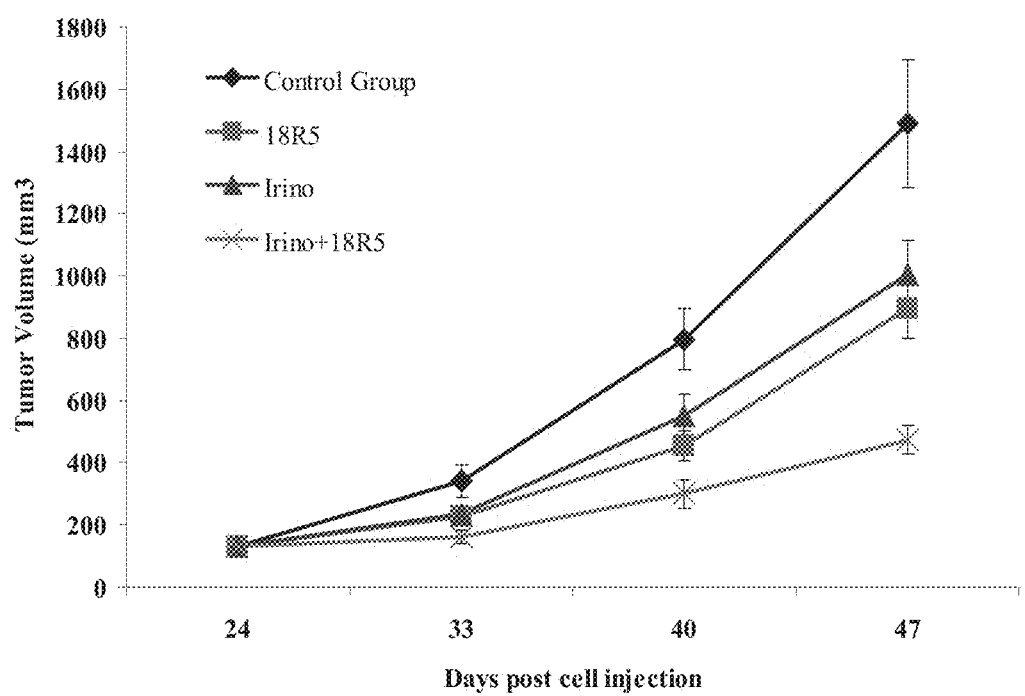

FIG. 11. Reduction of OMP-C28 xenograft tumor growth by combination treatment of 18R5 and irinotecan. NOD/SCID mice were injected with 10,000 OMP-C28 colon tumor cells, and on day 24, mice with tumors of average volume of 129 mm$^3$ were randomized and the indicated treatments were initiated. Tumor growth was monitored weekly. Tumor growth in animals treated with 18R5 was significantly reduced. Further, the combination of 18R5 and irinotecan was significantly reduced over treatment with either agent alone.

Figure 12:
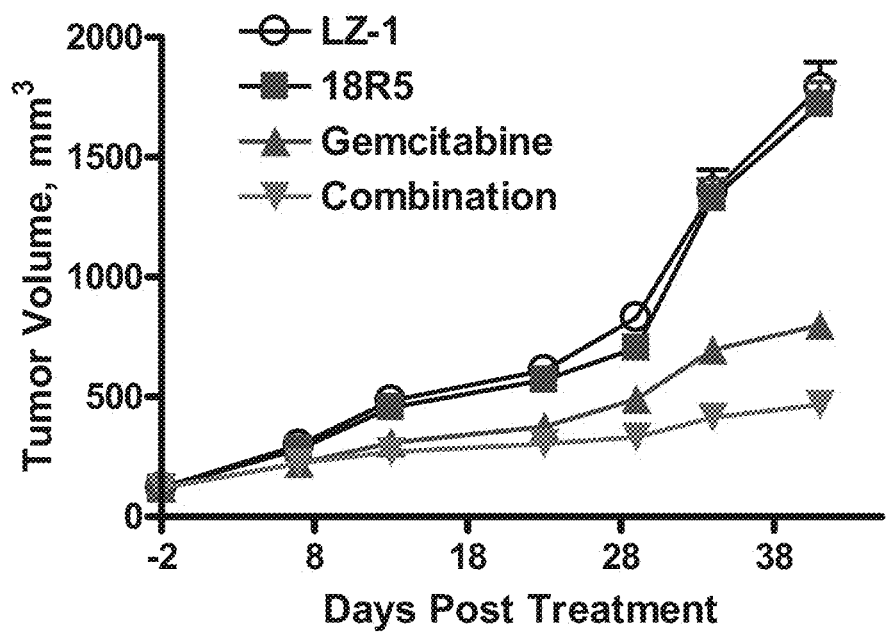

FIG. 12. Reduction of OMP-PN4 xenograft tumor growth by combination treatment of 18R5 and gemcitabine. NOD/SCID mice injected with 50,000 OMP-PN4 pancreatic tumor cells and on day 38, mice with tumors of average volume of about 120 mm$^3$ were randomized, and the indicated treatments were initiated two days later. Tumor growth in animals treated with the combination of 18R5 and gemcitabine was significantly reduced over treatment with gemcitabine alone.

FIG. 13. Heavy chain and light chain amino acid sequences for 18R8 and 18R5, including VH and VL sequences.

FIG. 14. Nucleotide sequences encoding the heavy chain and VH sequences of 18R8 and 18R5.

FIG. 15. Nucleotide sequences encoding the light chain and VL sequences of 18R8 and 18R5.

FIG. 16. Amino acid sequence of FZD7 ECD Fc protein and nucleotide sequence encoding same.

FIG. 17. Amino acid sequences of human FZD1 (SEQ ID NO:26), the extracellular domain (ECD) of FZD1 (SEQ ID NO:27, shown as underlined amino acids 1-321 of SEQ ID NO:26), and the Fri domain of FZD1 (SEQ ID NO:28).

FIG. 18. Amino acid sequences of human FZD2 (SEQ ID NO:30), the extracellular domain (ECD) of FZD2 (SEQ ID NO:31, shown as underlined amino acids 1-250 of SEQ ID NO:30), and the Fri domain of FZD2 (SEQ ID NO:32).

FIG. 19. Nucleotide sequence encoding human FZD1.

FIG. 20. Nucleotide sequence encoding human FZD2.

FIG. 21. Amino acid sequences of human FZD3 (SEQ ID NO:34), the extracellular domain (ECD) of FZD3 (SEQ ID NO:35, shown as underlined amino acids 1-204 of SEQ ID NO:34), and the Fri domain of FZD3 (SEQ ID NO:36).

FIG. 22. Amino acid sequences of human FZD4 (SEQ ID NO:38), the extracellular domain (ECD) of FZD4 (SEQ ID NO:39, shown as underlined amino acids 1-224 of SEQ ID NO:38), and the Fri domain of FZD4 (SEQ ID NO:40).

FIG. 23. Nucleotide sequence encoding human FZD3.

FIG. 24. Nucleotide sequence encoding human FZD4.

FIG. 25. Amino acid sequences of human FZD5 (SEQ ID NO:42), the extracellular domain (ECD) of FZD5 (SEQ ID NO:43, shown as underlined amino acids 1-233 of SEQ ID NO:42), and the Fri domain of FZD5 (SEQ ID NO:44).

FIG. 26. Amino acid sequences of human FZD6 (SEQ ID NO:46), the extracellular domain (ECD) of FZD6 (SEQ ID NO:47, shown as underlined amino acids 1-207 of SEQ ID NO:46), and the Fri domain of FZD6 (SEQ ID NO:48).

FIG. 27. Nucleotide sequence encoding human FZD5.

FIG. 28. Nucleotide sequence encoding human FZD6.

FIG. 29. Amino acid sequences of human FZD7 (SEQ ID NO:50), the extracellular domain (ECD) of FZD7 (SEQ ID NO:51, shown as underlined amino acids 1-255 of SEQ ID NO:50), and the Fri domain of FZD7 (SEQ ID NO:52).

FIG. 30. Amino acid sequences of human FZD8 (SEQ ID NO:54), the extracellular domain (ECD) of FZD8 (SEQ ID NO:55, shown as underlined amino acids 1-277 of SEQ ID NO:54), and the Fri domain of FZD8 (SEQ ID NO:56).

FIG. 31. Nucleotide sequence encoding human FZD7.

FIG. 32. Nucleotide sequence encoding human FZD8.

FIG. 33. Amino acid sequences of human FZD9 (SEQ ID NO:58), the extracellular domain (ECD) of FZD9 (SEQ ID NO:59, shown as underlined amino acids 1-230 of SEQ ID NO:58), and the Fri domain of FZD9 (SEQ ID NO:60).

FIG. 34. Amino acid sequences of human FZD10 (SEQ ID NO:62), the extracellular domain (ECD) of FZD10 (SEQ ID NO:63, shown as underlined amino acids 1-227 of SEQ ID NO:62), and the Fri domain of FZD10 (SEQ ID NO:64).

FIG. 35. Nucleotide sequence encoding human FZD9.

FIG. 36. Nucleotide sequence encoding human FZD10.

Figure 37:
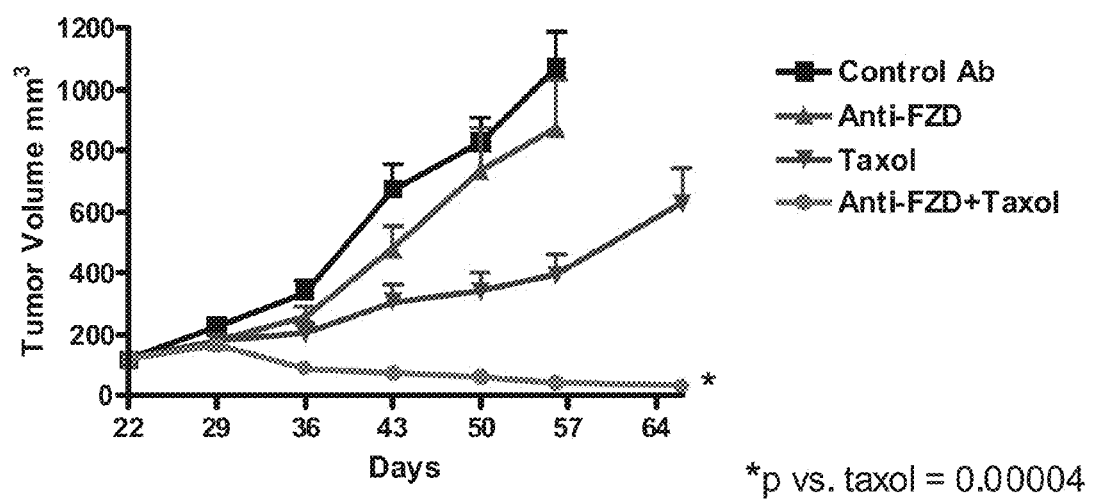

FIG. 37. Reduction of PE-13 breast tumor growth with combination treatment of 18R5 antibody and paclitaxel. NOD/SCID mice were injected with 10,000 PE-13 breast tumor cells and on day 22, mice with tumors of average volume of about 120 mm$^3$ were randomized. The mice were then treated with either a control antibody ("Control Ab"), 18R5 antibody ("Anti-FZD"), paclitaxel ("Taxol"), or a combination of 18R5 antibody plus paclitaxel ("Anti-FZD+Taxol"). Treatment with 18R5 antibody in combination with paclitaxel resulted in anti-tumor activity.

Figure 38:
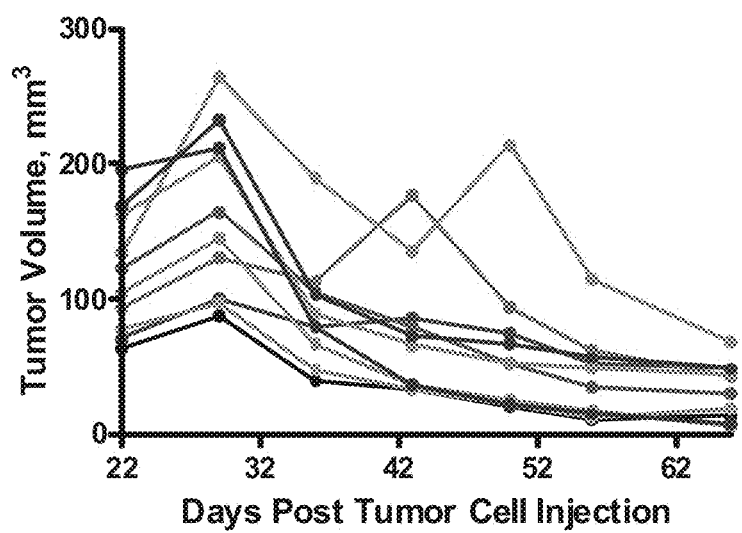

FIG. 38. Breast tumor growth in individual animals treated with the combination of 18R5 antibody plus paclitaxel. Treatment with 18R5 antibody in combination with paclitaxel resulted in regression of established breast tumors.

Figure 39:
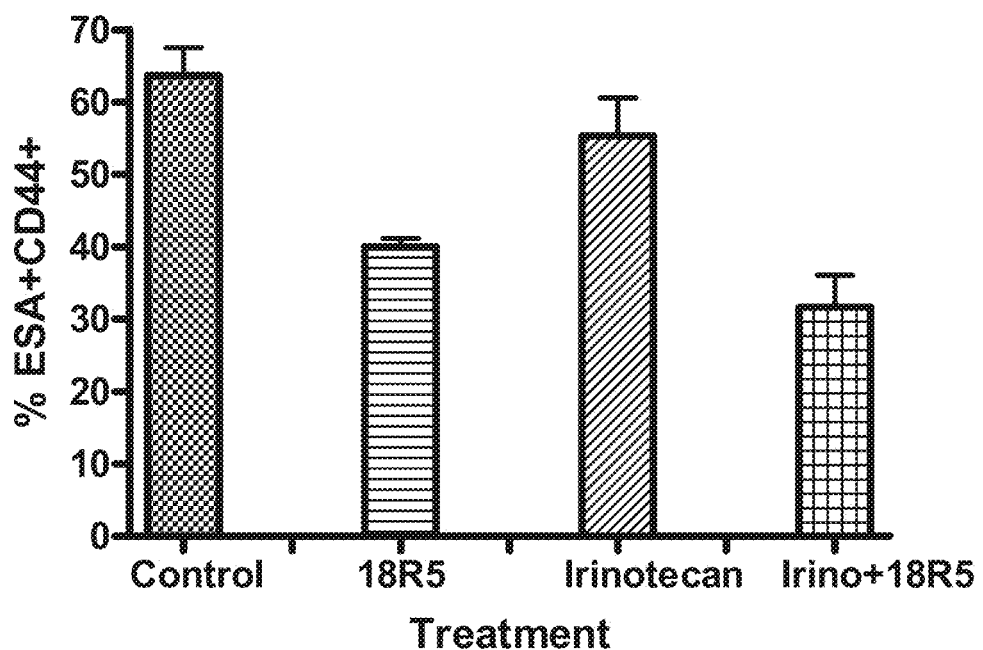

FIG. 39. Flow cytometry analysis of colorectal tumor cells following treatment with control antibody, 18R5 antibody, irinotecan, or both 18R5 antibody and irinotecan.

Figure 40:
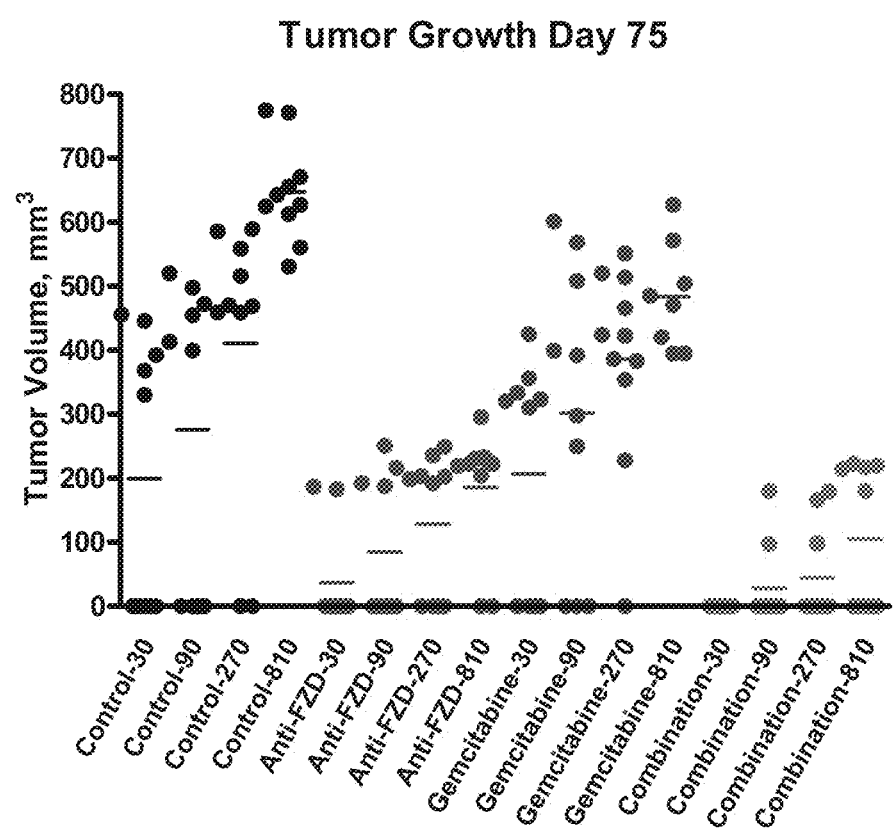

FIG. 40. Tumor growth in mice following implantation of 30, 90, 270, or 810 tumor cells obtained from mice that had been treated for 41 days with either control antibody ("Control"), 18R5 antibody ("Anti-FZD"), gemcitabine ("Gemcitabine"), or the combination of 18R5 plus gemcitabine ("Combination").

Figure 41:
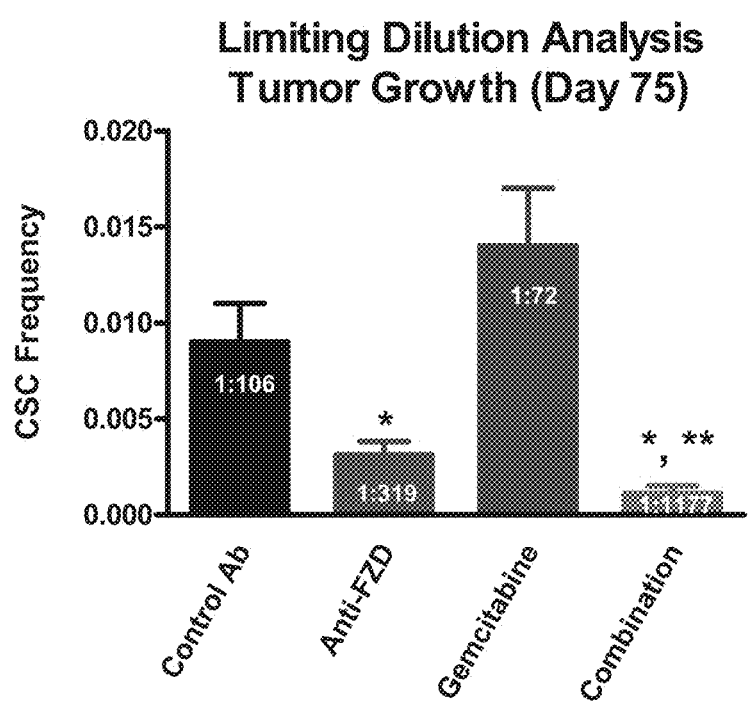

FIG. 41. Cancer stem cell (CSC) frequency in PN-4 pancreatic tumors following treatment with control antibody ("Control Ab"), 18R5 antibody alone ("Anti-FZD"), gemcitabine alone ("Gemcitabine"), or the combination of 18R5 antibody and gemcitabine ("Combination"), as determined by limiting dilution analysis.

Figure 42:
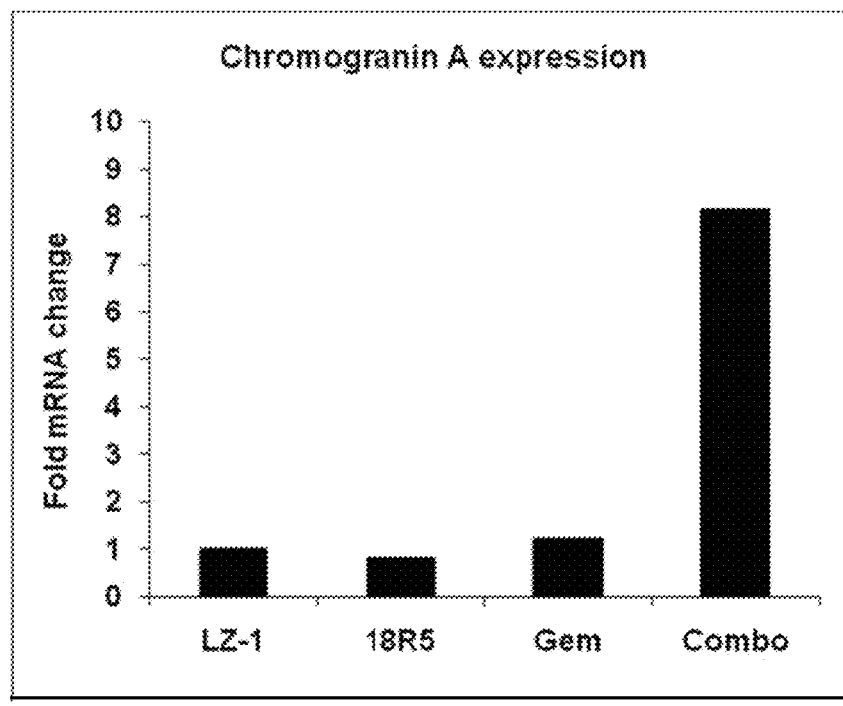

FIG. 42. Chromatogram gene expression in pancreatic tumor cells that have been treated with control antibody ("LZ-1"), 18R5 antibody alone ("18R5"), gemcitabine alone ("Gem"), or a combination of gemcitabine and 18R5 ("Combo").

Figure 43:
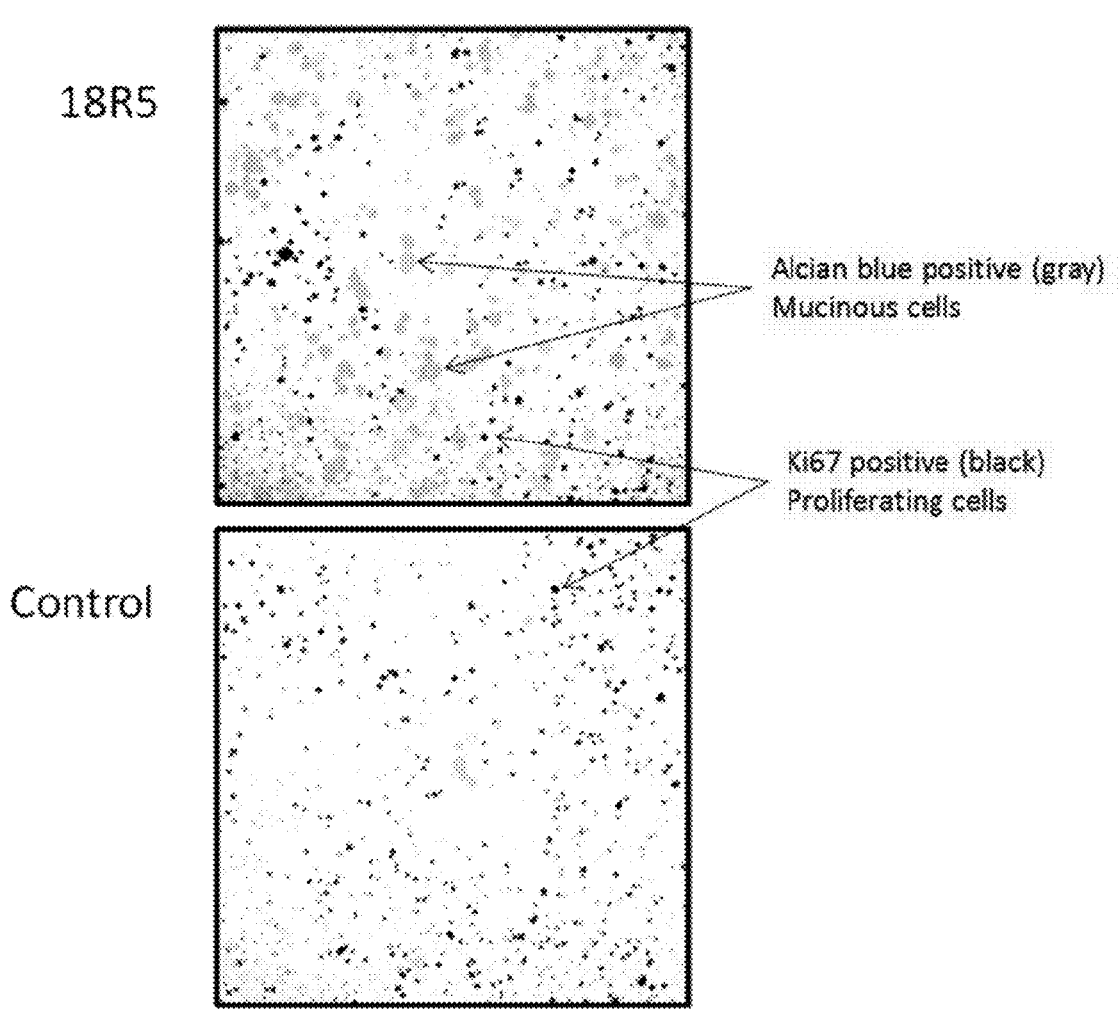

FIG. 43. Treatment with anti-FZD antibody 18R5 promotes differentiation of tumor cells into non-proliferative mucinous cells. NOD/SCID mice were injected with 50,000 OMP-PN13 pancreatic tumor cells and on day 23, mice with tumors of average volume of about 107 mm$^3$ were randomized, and treatment with control antibody or 18R5 was initiated four days later. After 20 days tumors were collected and sectioned. Tumor sections from 18R5 treated mice or control antibody treated mice were stained with alcian blue stain to reveal mucinous cells and by immunohistochemistry with antibody to ki67 to reveal proliferative cells. Exemplary mucinous cells and proliferative cells are highlighted by arrows.

Figure 44:
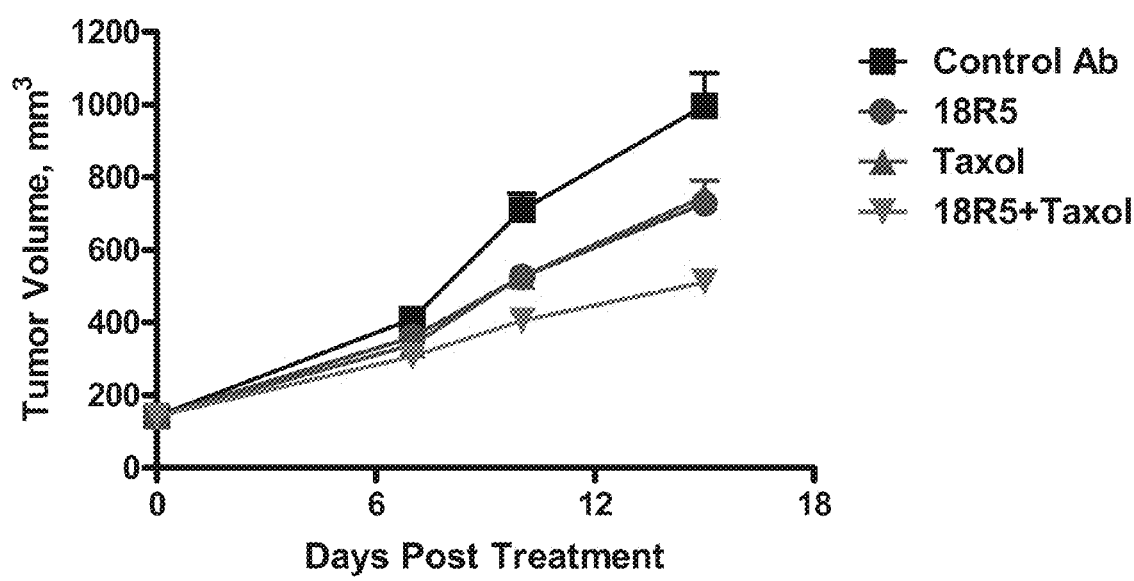

FIG. 44. Anti-FZD antibody 18R5, both alone and in combination with Taxol® (paclitaxel), inhibits OMP-LU24 xenograft tumor growth. Mice bearing OMP-LU24 human lung tumors were treated with either control antibody ("Control Ab"), anti-FZD 18R5 ("18R5"), Taxol® ("Taxol") or the combination of 18R5 plus Taxol® ("18R5+Taxol").

Figure 45:
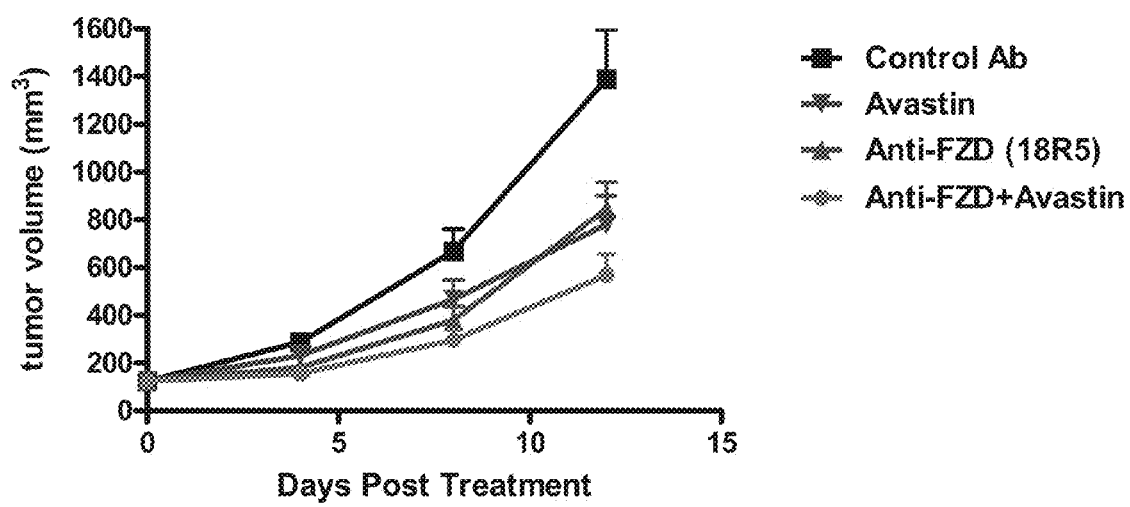

FIG. 45. Anti-FZD antibody 18R5, both alone and in combination with Avastin® (bevacizumab), inhibits OMP-LU33 xenograft tumor growth. Mice bearing OMP-LU33 human lung tumors were treated with either control antibody (squares), Avastin® (triangles pointing up), anti-FZD 18R5 (triangles pointing down), or the combination of 18R5 plus Avastin® (circles).

Figure 46:
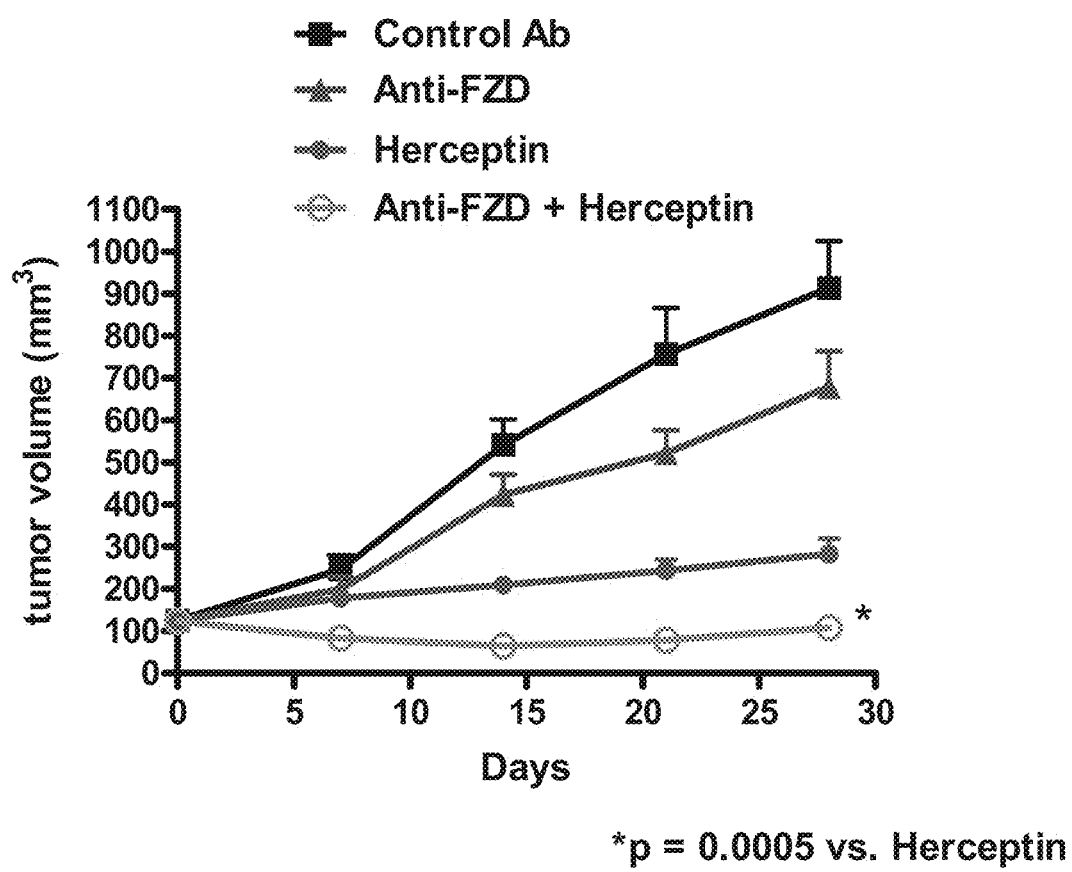

FIG. 46. The combination of anti-FZD antibody 18R5 with Herceptin® (trastuzumab) inhibits the growth of T3 xenograft tumor growth. Mice carrying T3 human breast tumors were treated with either control antibody (squares), anti-FZD 18R5 (triangles), Herceptin® (filled circles), or the combination of 18R5 plus Herceptin® (open circles).

FIG. 4. 7, 18R5 and 44R24Fzd binding profiles. Dose-reponse curve representing the binding of each mAb to Fzd 1, 2, 5, 7 and 8.

Figure 48:
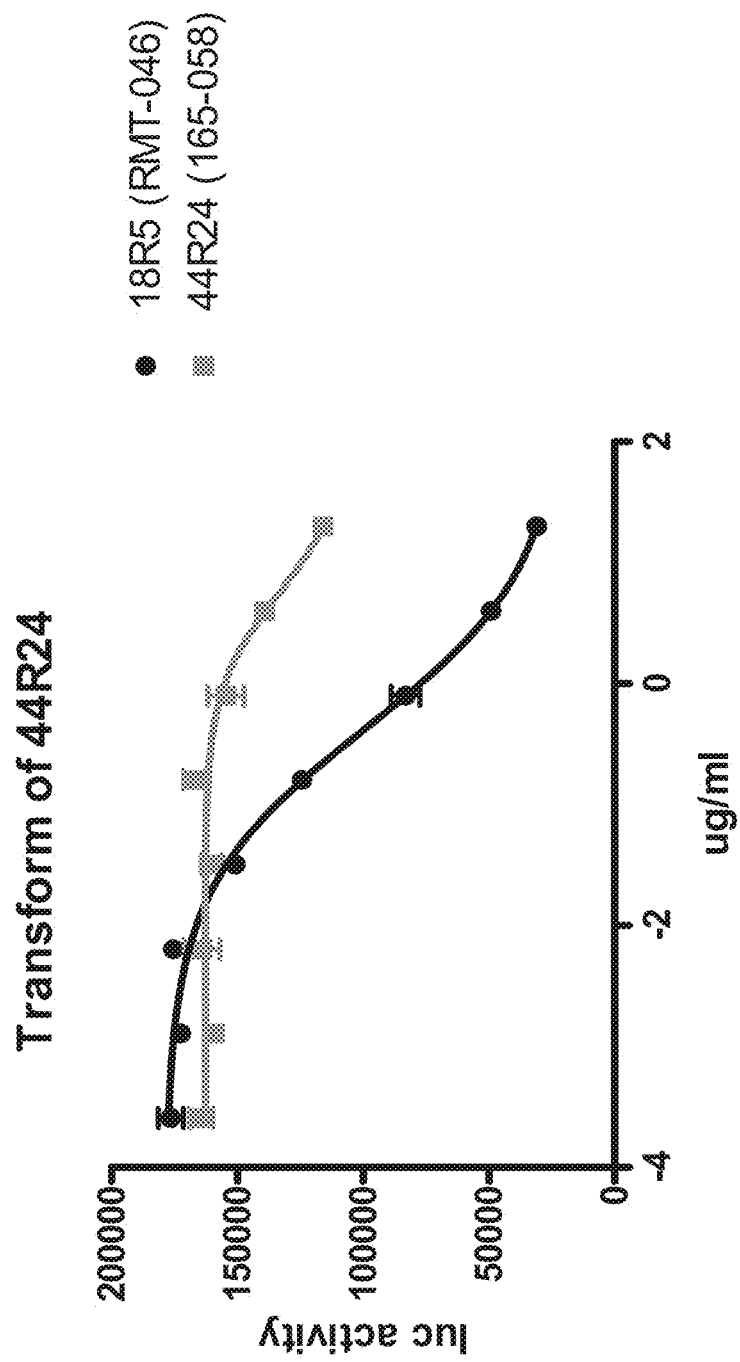

FIG. 48. Inhibition of Wnt3a-induced reporter activity in STF cells by 18R5 and 44R24 (dose response curves).

Figure 49:
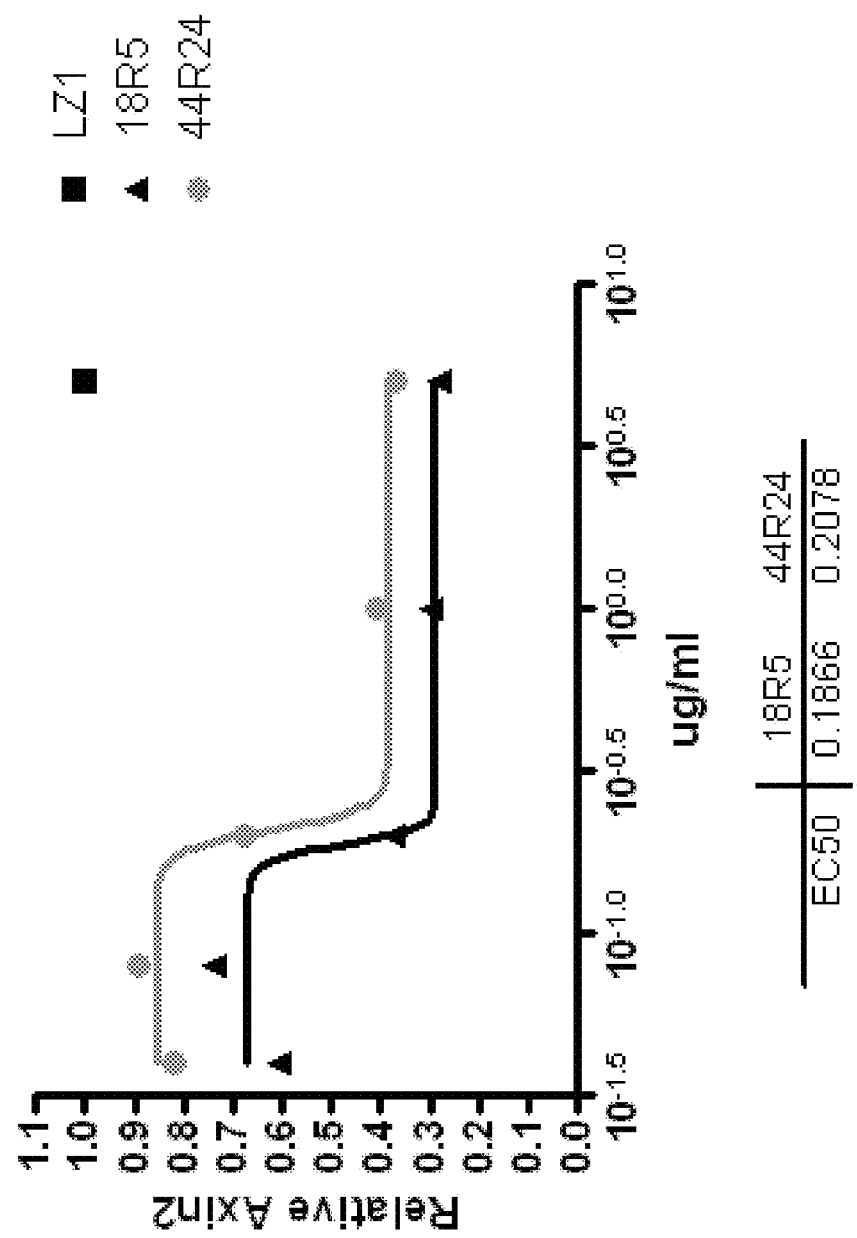

FIG. 49. Inhibition of basal level of axin2 gene expression by 18R5 and 44R24.

Figure 50:
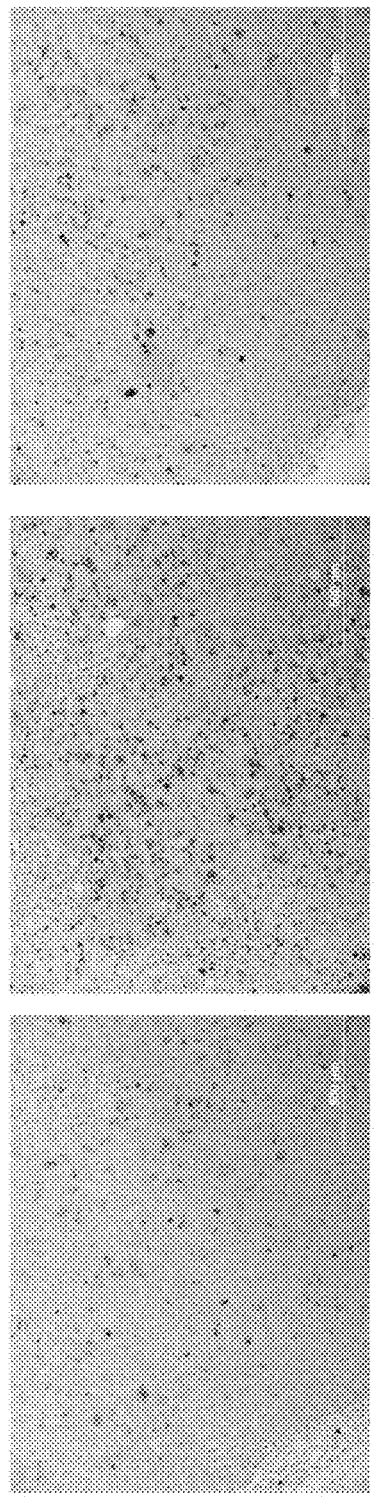

FIG. 50. THC detection of Muc16 in 18R5 and 44R24-treated OMP-PN13 tumors.

Figure 51A:
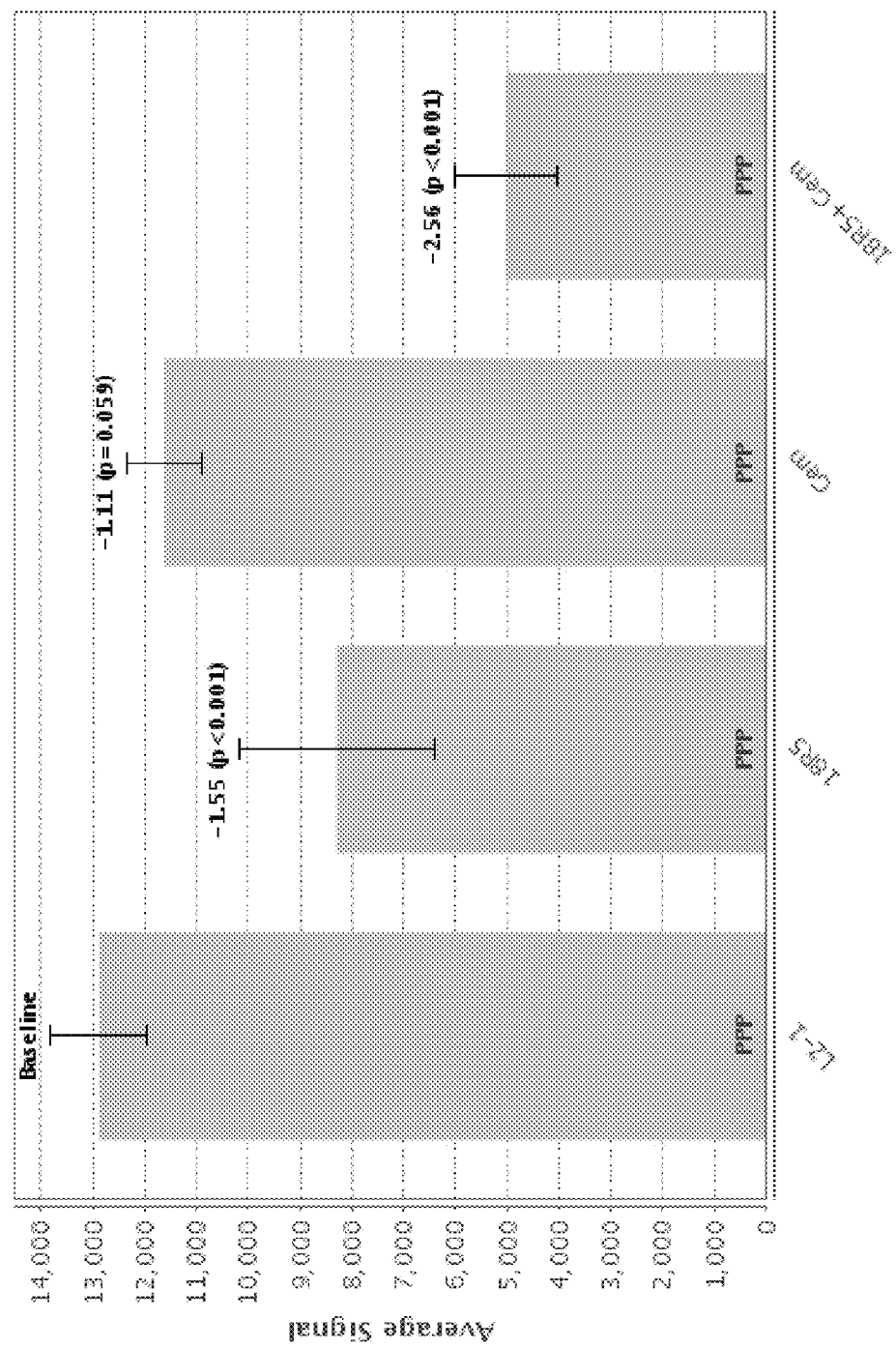
Figure 51B:
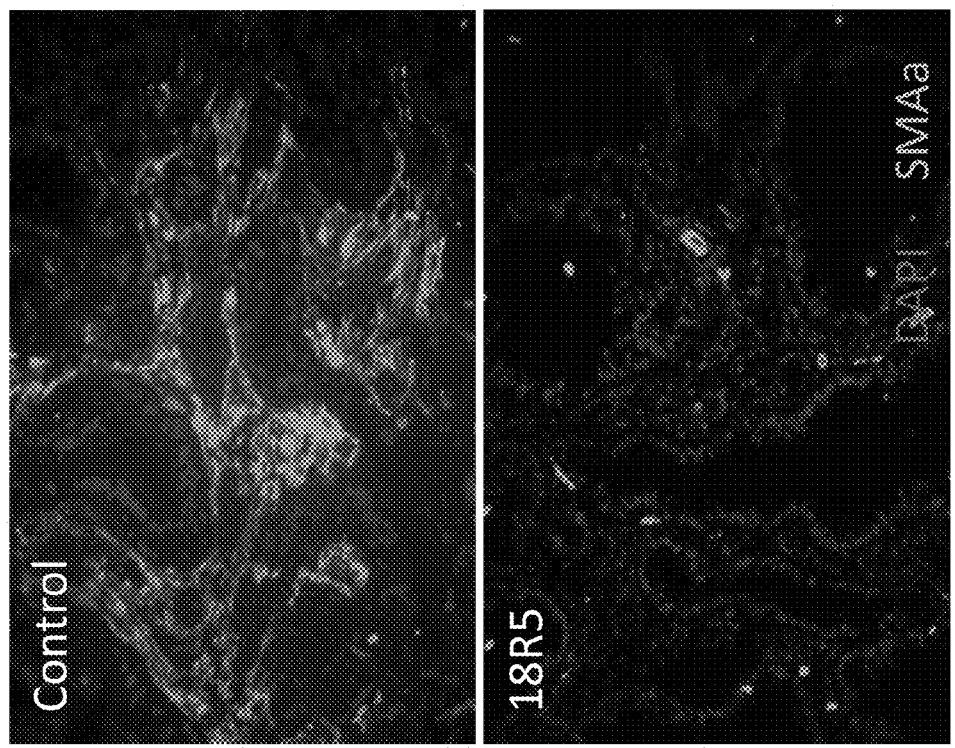

FIGS. 51A and B. Inhibition of smooth muscle actin in 18R5-treated pancreatic tumor. FIG. 51A. ACTA2 gene expression levels as detected by microarray. FIG. 51B. SMA detection on control mAb (upper panel) and 18R5 (lower panel)-treated OMP-PN4 tumors.

Figure 52C:
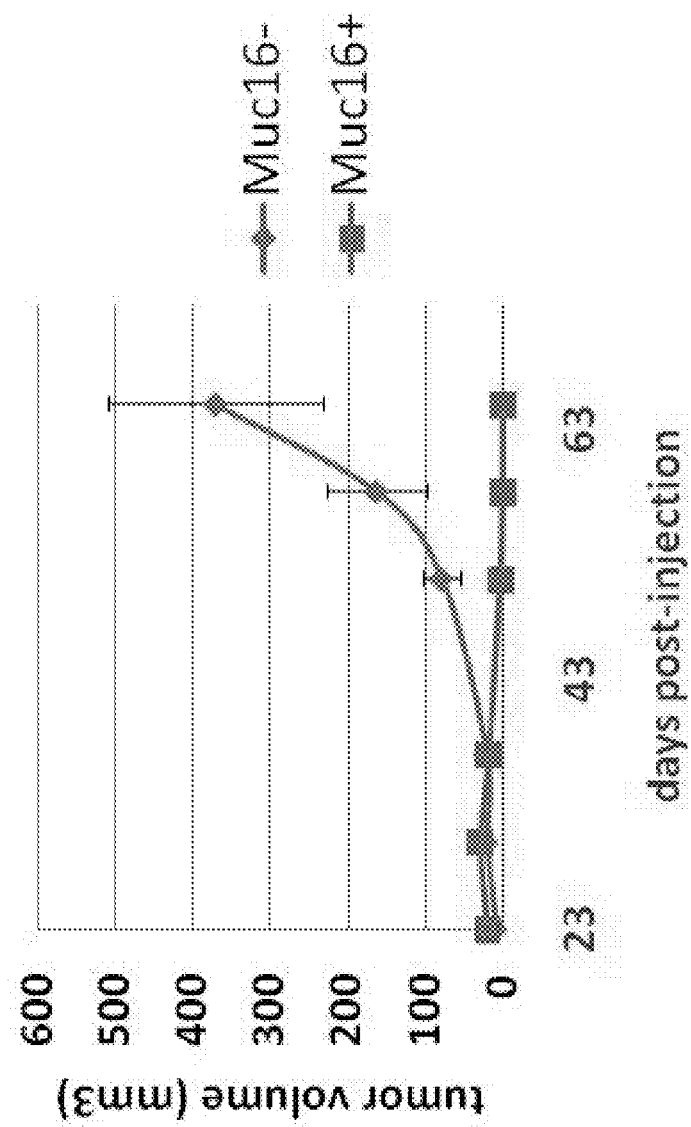

FIGS. 52A-C. Testing the tumorgenicity of 18R5-induced Muc16+OMP-PN13 cells. FIG. 52A. FACS plot of lin-depleted OMP-PN13 tumor cells stained for Muc16. The 2 sorted populations are circled. FIG. 52B. Representative pictures of tumors resulting from the injection of Muc16− (upper panel) and Muc16+(lower panel) cells. FIG. 52C. Tumor growth curves.

Figure 53:
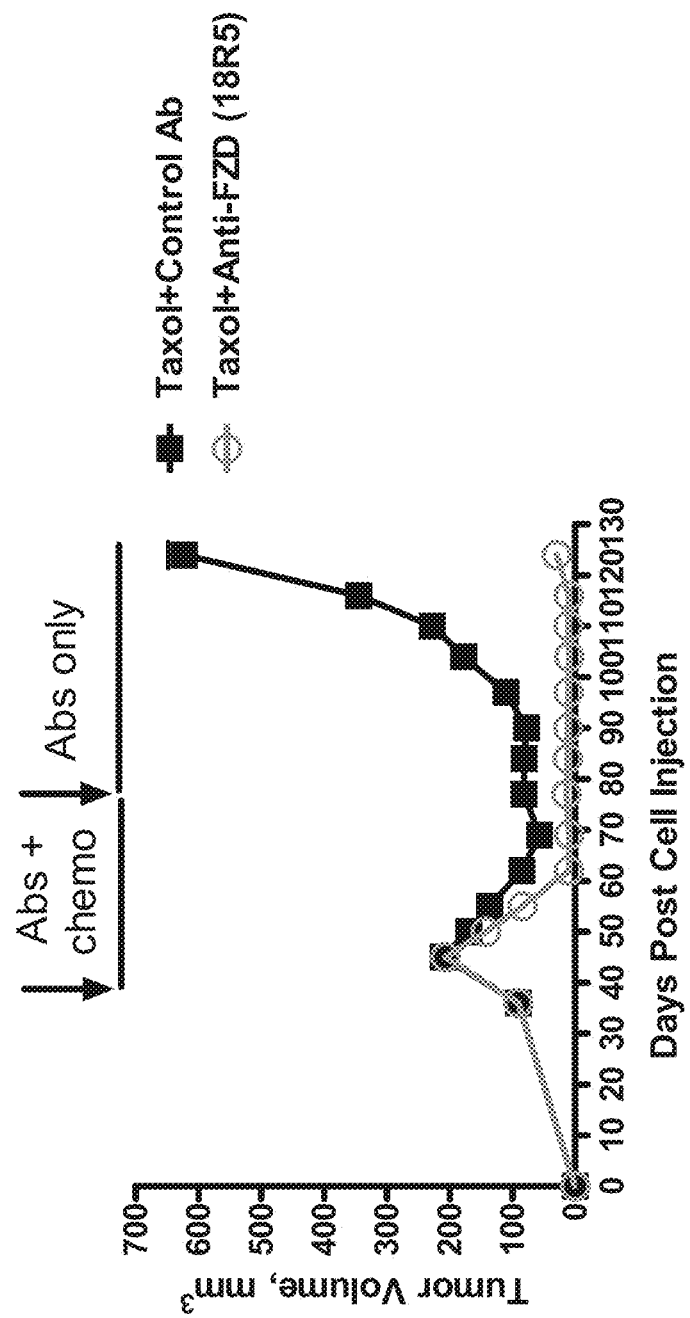

FIG. 53. Inhibition of tumor recurrence by anti-FZD mAb 18R5 in PE13 breast tumor xenograft.

Figure 54:
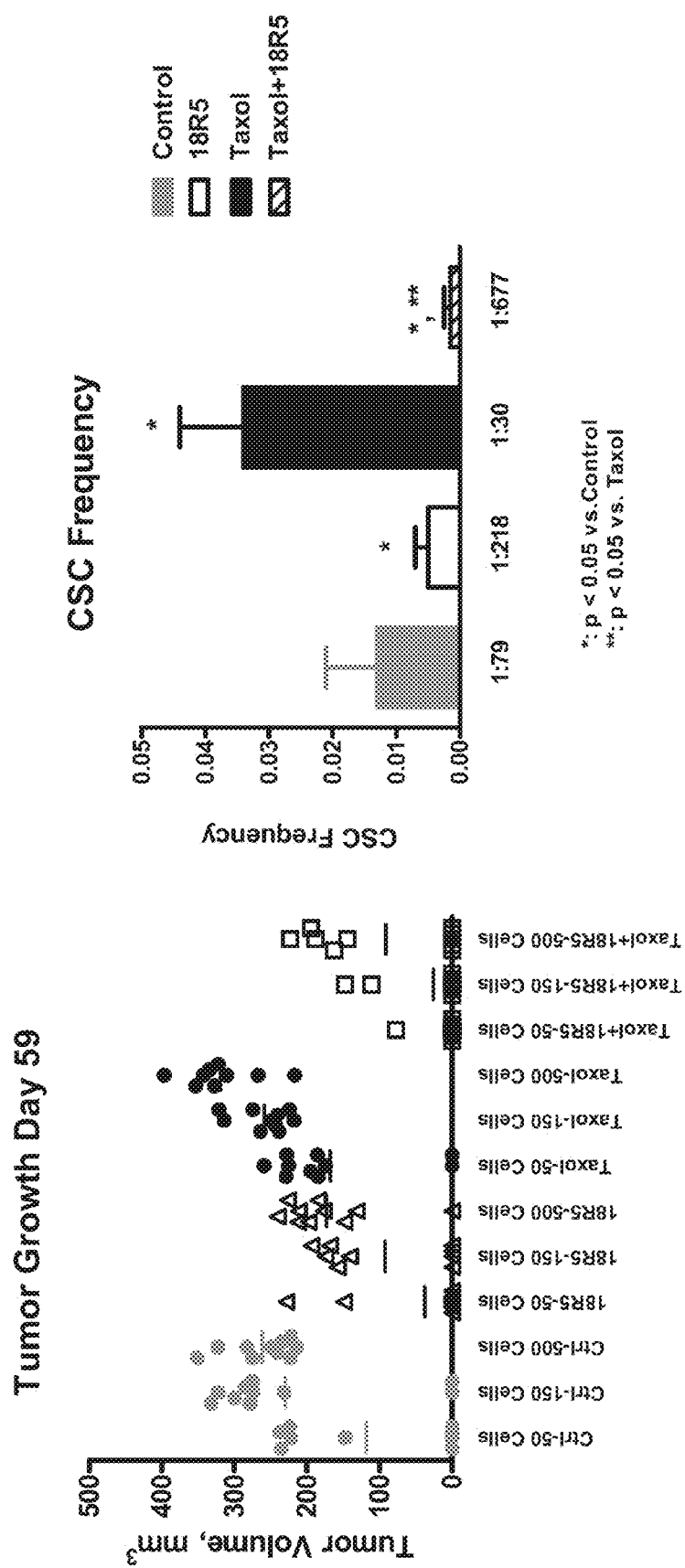

FIG. 54. Reduction of breast cancer stem cell frequency by anti-FZD mAb18R5.

Figure 55:
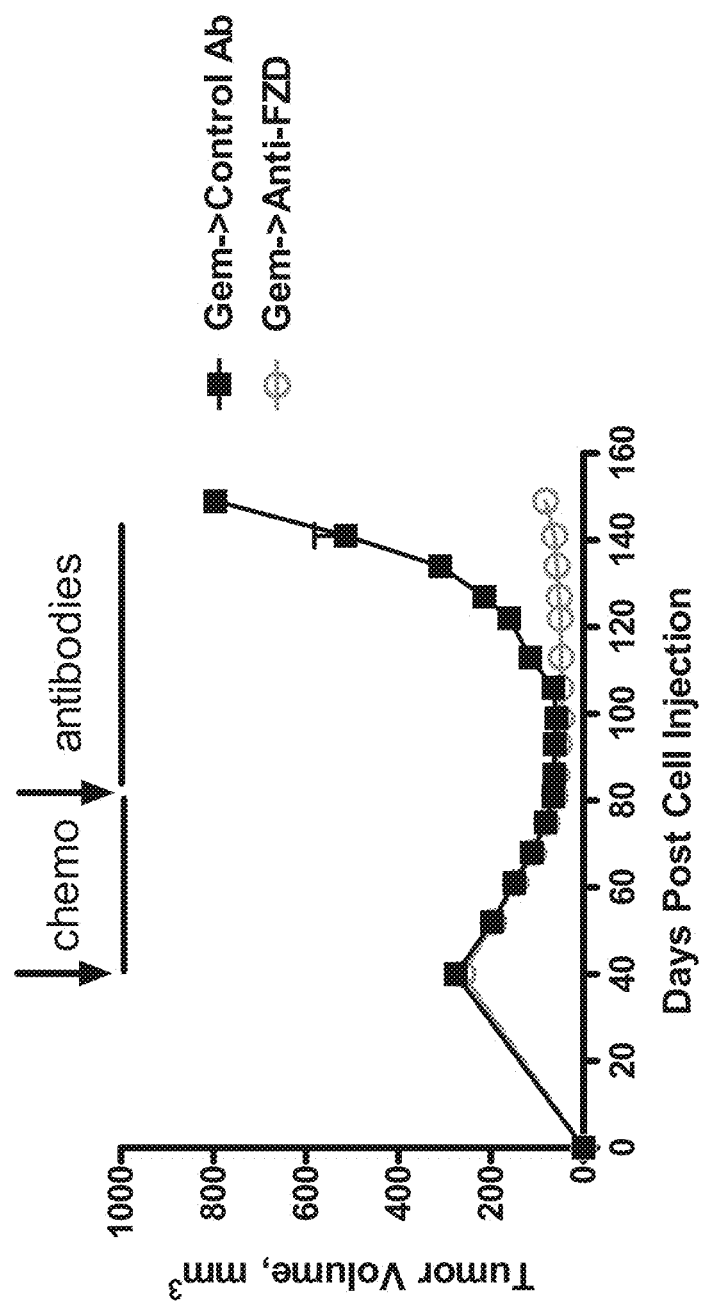

FIG. 55. Inhibition of tumor recurrence by anti-FZD mAb 18R5 in PN4 pancreatic tumor xenograft.

Figure 56:
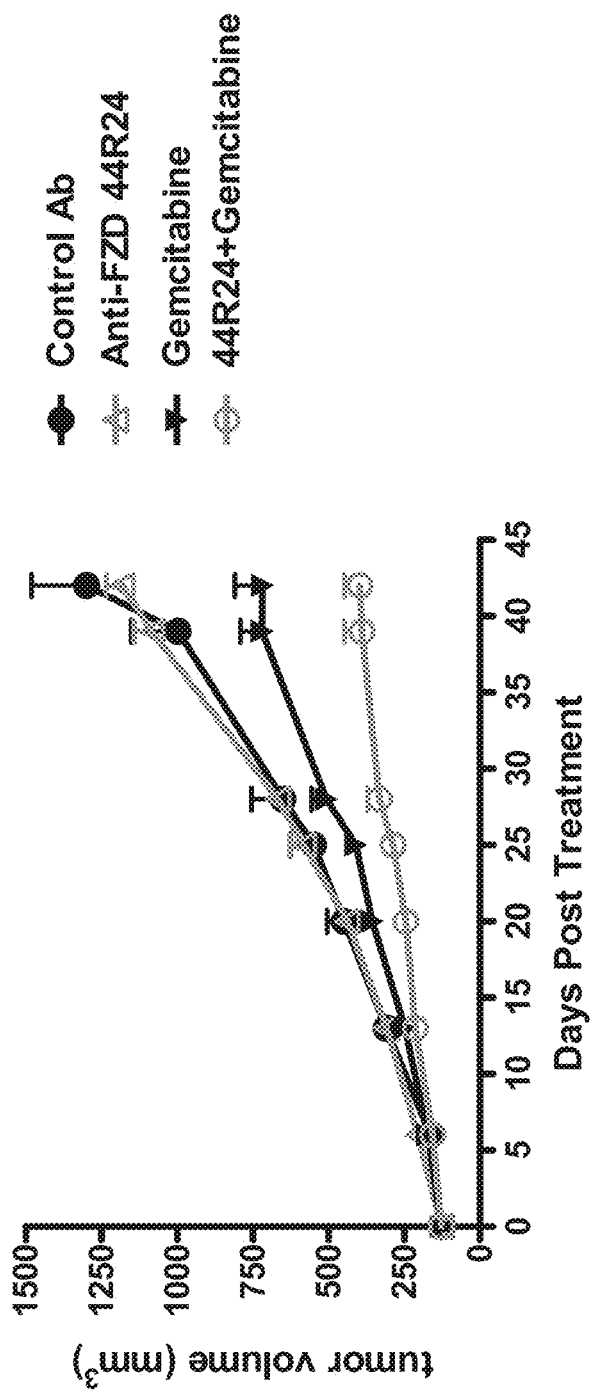

FIG. 56. Inhibition of tumor growth by anti-FZD mAb 44R24 in combination with gemcitabine in PN4 pancreatic tumor xenograft.

Figure 57:
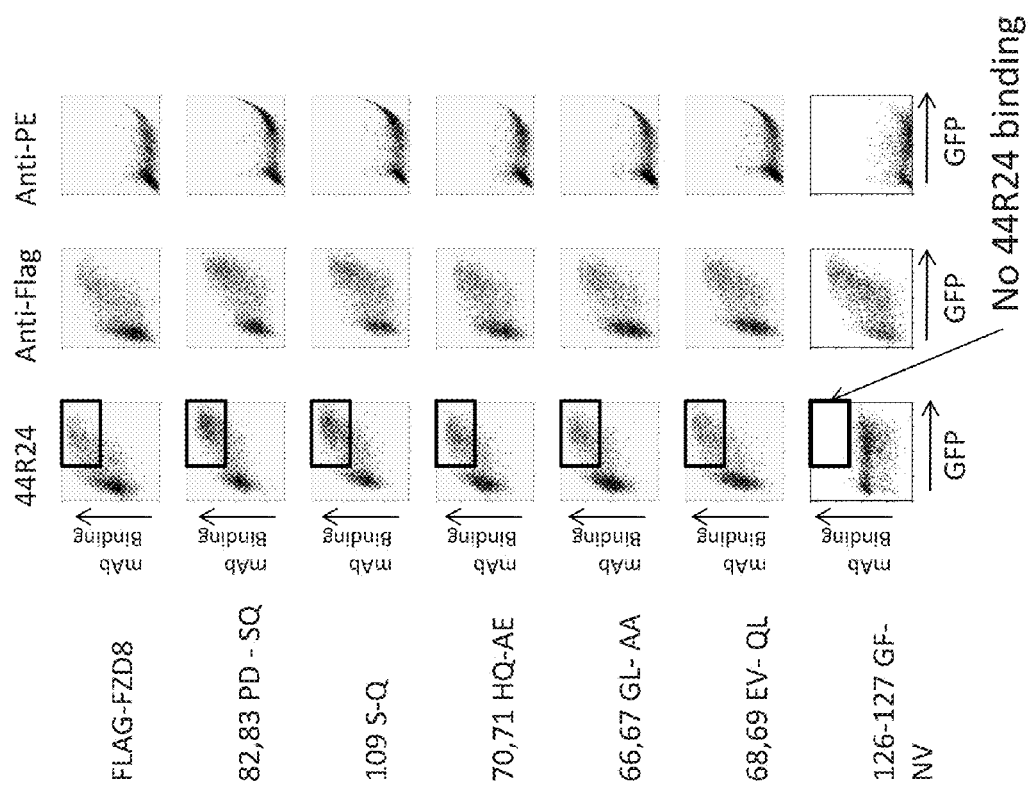

FIG. 57. FACS analysis of binding of anti-FZD mAb 44R24 to mutant FZD8 relative to wild-type FZD8. The region of the FACS plot showing binding of 44R24 to the cotransfected cell population is highlighted by a box. The box for those amino acid substitutions showing markedly reduced 44R24 binding is marked with an arrow.

Figure 58:
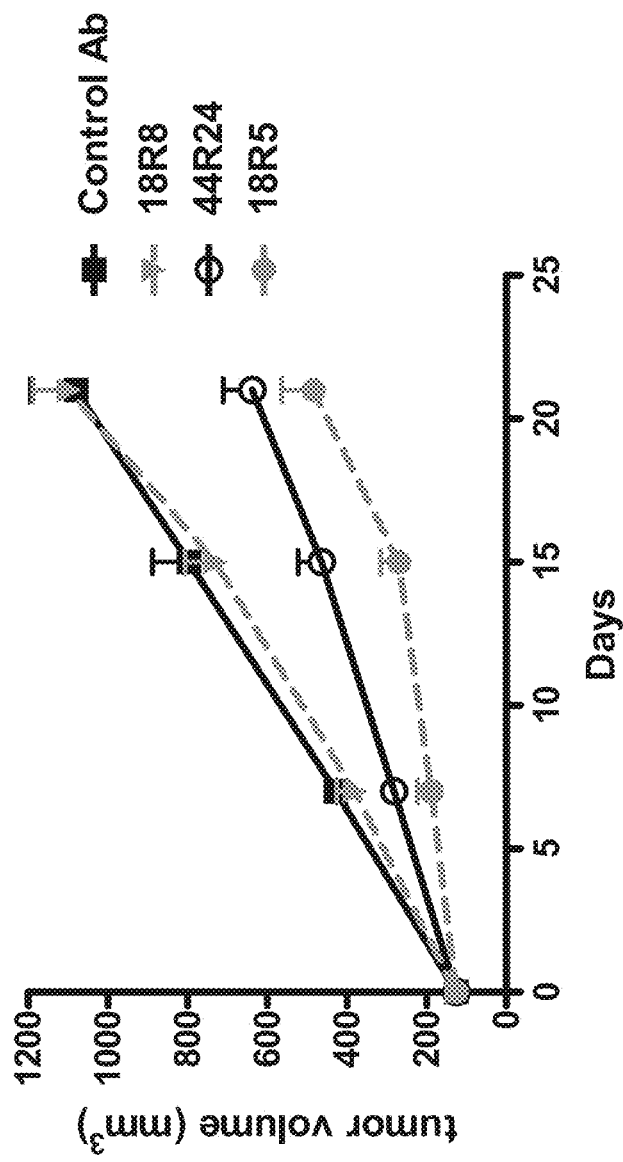

FIG. 58. Anti-Tumor activity of anti-FZD Antibodies 44R24 and 18R5 in C28 colon tumor xenografts.

Figure 59:
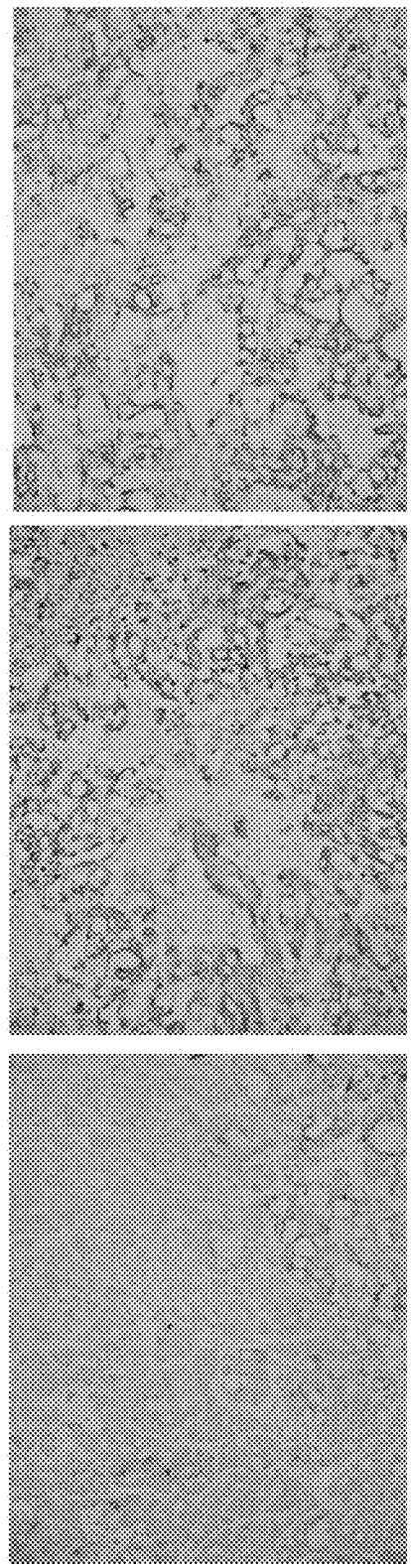

FIG. 59. Induction of cytokeratin 7 expression in C28 colon tumor xenografts treated with anti-FZD antibodies 44R24 or 18R5.

Figure 60B:
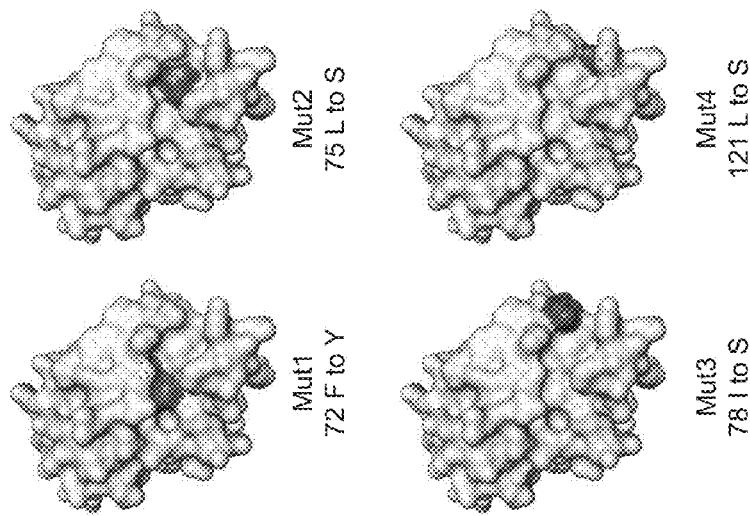
Figure 60A:
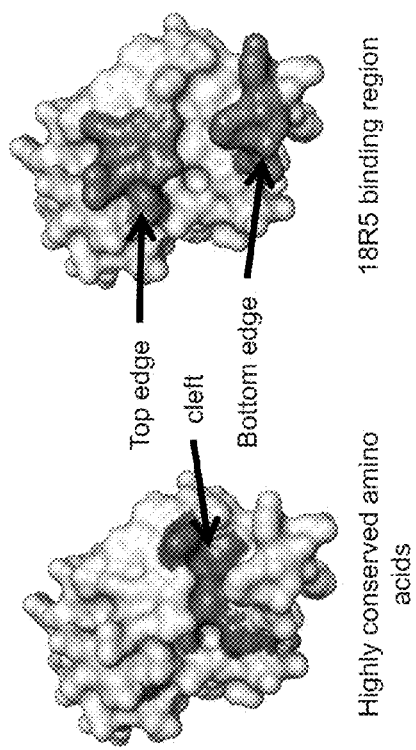
Figure 60C:
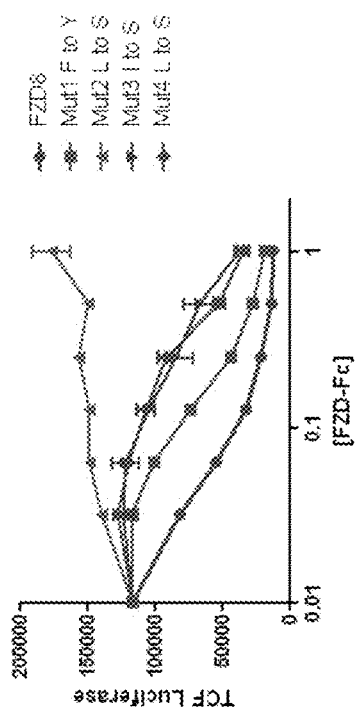

FIGS. 60A-C. Residues within the OMP-18R5 binding site impact Wnt binding. FIG. 60A. Shown are images of the structure of a Fzd fri domain. The images are based on analysis of the previously reported crystal structure of mouse FZD8 (Dann C E et al., Nature 412 (6842) 86-90, 2001) and analysis done using the software program Pymol. This region contains structural elements we term the "top edge" the "bottom edge" and the "cleft". Shown in the upper left image is a surface view of the FZD fri domain with the region of the Fzd protein highlighting residues conserved in nine or ten of the human frizzled receptors. The upper right highlights some of the residues bound by 18R5. FIG. 60B. Shown are images depicting the position of four amino acid substitutions within the cleft region by grey highlight. The position and amino acid substitution (single letter amino acid code) within human FZD8 is listed. FIG. 60C. The ability of FZD8-Fc fusion proteins including the variants containing amino acid substitutions within the cleft region to act as soluble decoy molecules to bind Wnt3A is examined. Luciferase reporter assays were carried out in STF293 cells that stably express 8×TCF promoter element. Cells were exposed to Wnt3A-containing medium and a range of dilutions of medium contain FZD8-Fc variants for 18 hours and then luciferase activity was measured with the Dual-Glo luciferase assay reporter system (Promega). The results demonstrate that FZD8-Fc variants that contain amino acid substitutions with the cleft region are less able to bind to Wnt3A and inhibit its ability to elicit Wnt signaling with the STF293 cells.

Figure 61:
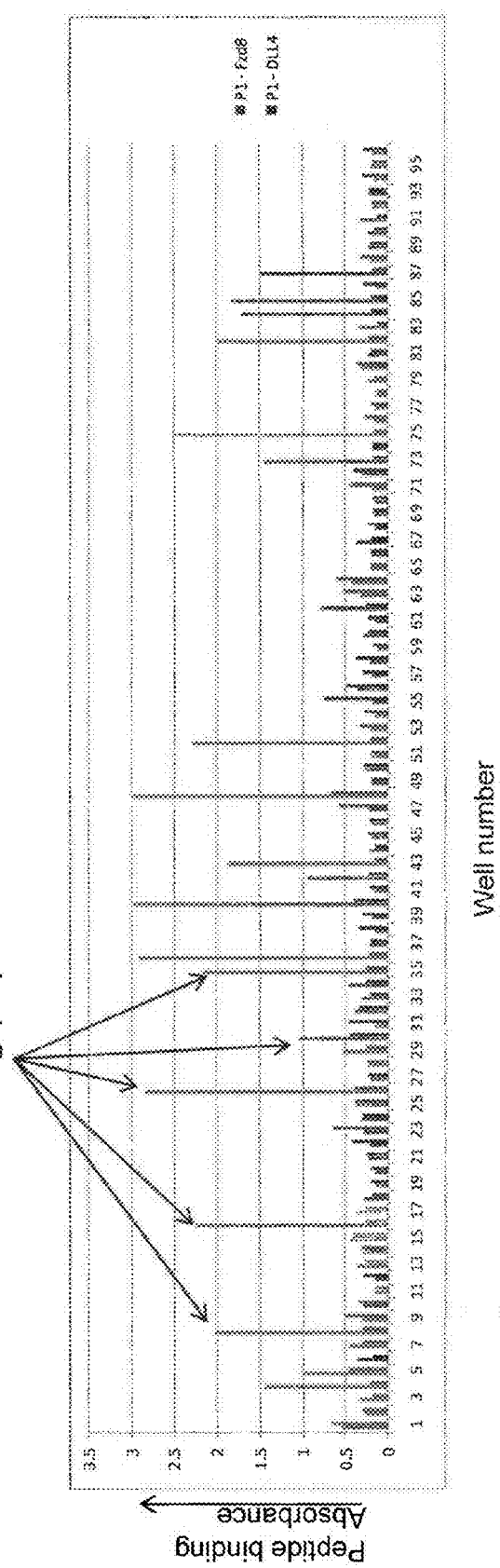

FIG. 61. Identification of peptides that bind to FZD. Shown is ELISA data testing the ability of individual phage clones expressing peptides to bind to FZD8-Fc or a negative control protein, DLL4-Fc. Arrows highlight several positive clones by way of example.

FIG. 62. Analysis of FZD binding peptide sequences. Shown are peptide sequences found to bind specifically to FZD. Both cyclic and linear peptide sequences were identified. The cyclic peptides show a clear sequence similarity enabling the definition of a consensus sequence. Because the peptide library is unlikely to contain all possible amino acid variations related to this consensus, it is likely that additional variants outside of this consensus would also be capable of binding to FZD. The linear peptides did not display strong consensus similarity. However, several of these sequences (e.g. clone#2 DTLSALIERGLM (SEQ ID NO: 113)) were potent FZD binders to the 18R5 binding region of FZD and bound within the cleft region found to be important for Wnt-FZD interaction.

Figure 63:
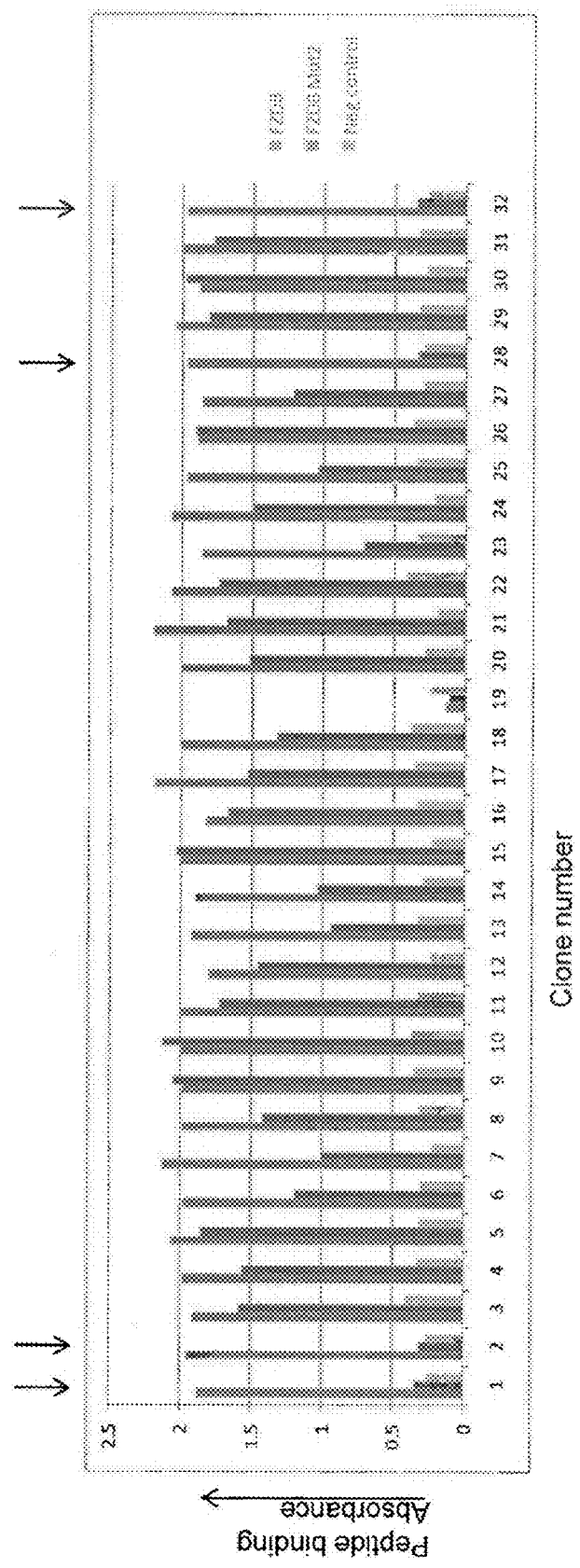

FIG. 63. FZD binding peptides bind within the "cleft" in 18R5 binding/Wnt binding region. To examine the ability of the FZD binding peptides to interact with the "cleft" within the 18R5 binding region, ELISA was conducted testing the ability of individual phage clones expressing peptides to bind to FZD8-FC or a FZD8-Fc variant (Mut2) containing an amino acid substitution within the cleft, or a negative control protein, DLL4-Fc. Many of the peptides bound the FZD8-Mut2 protein much less well than wild-type FZD8. Several peptides, as highlighted by arrows, displayed little if any binding to the FZD8-Mut2 protein indicating that they bound specifically within the "cleft". An example of such a peptide, clone#2, had the sequence DTLSALIERGLM (SEQ ID NO:113).

Figure 64:
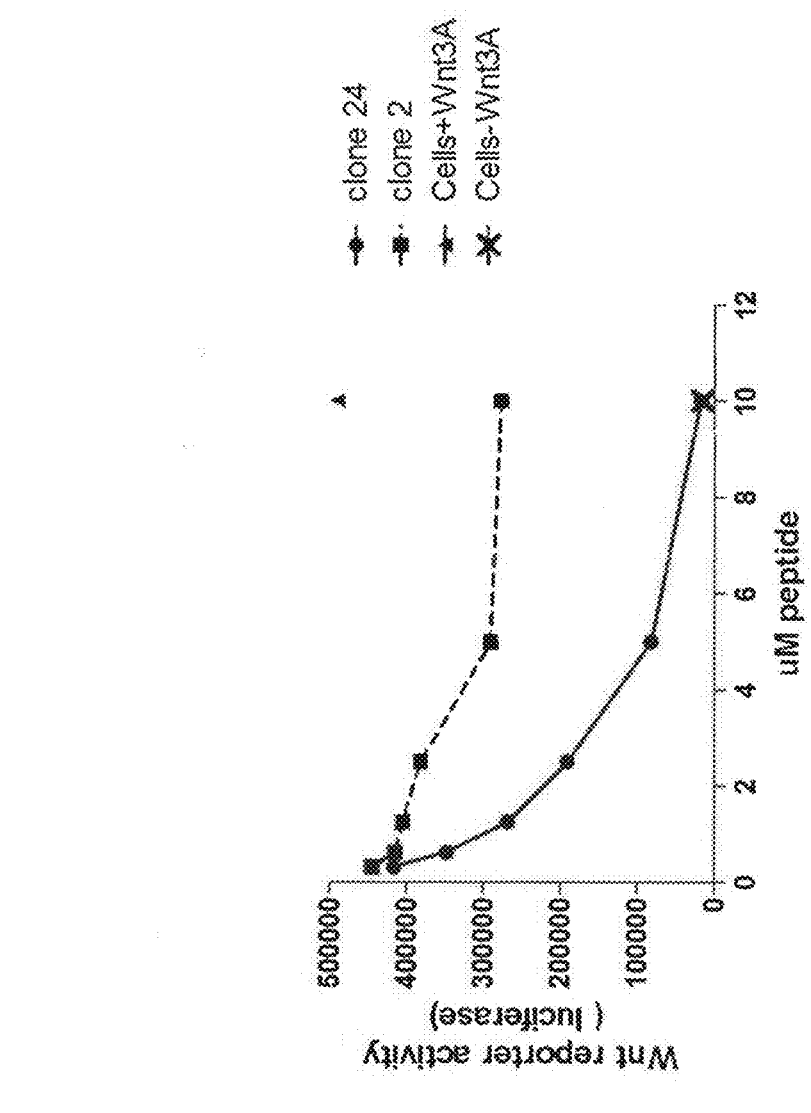

FIG. 64. Inhibition of Wnt signaling by peptides that bind to FZD. Shown are the results of Wnt dependent luciferase reporter studies examining the ability of two peptides (clones #2 and #24) to inhibit Wnt signaling. The two peptides were generated by chemical synthesis. The peptides were dissolved into dimethyl sulfoxide (DMSO) and then diluted into the reported assay at the concentrations indicated. The reporter assay utilized HEK293 cells transfected with a plasmid containing the Wnt responsive 8×TCF luciferase reporter. Cells were exposed to Wnt3A and the indicated peptide and then incubated for 16 hours. Wnt activity was determined using the Dual-glo luciferase assay (Promega).

FIG. 65. Minimum Fri domains of human FZD1-5.

FIG. 66. Minimum Fri domains of human FZD6-10.

Figure 67:
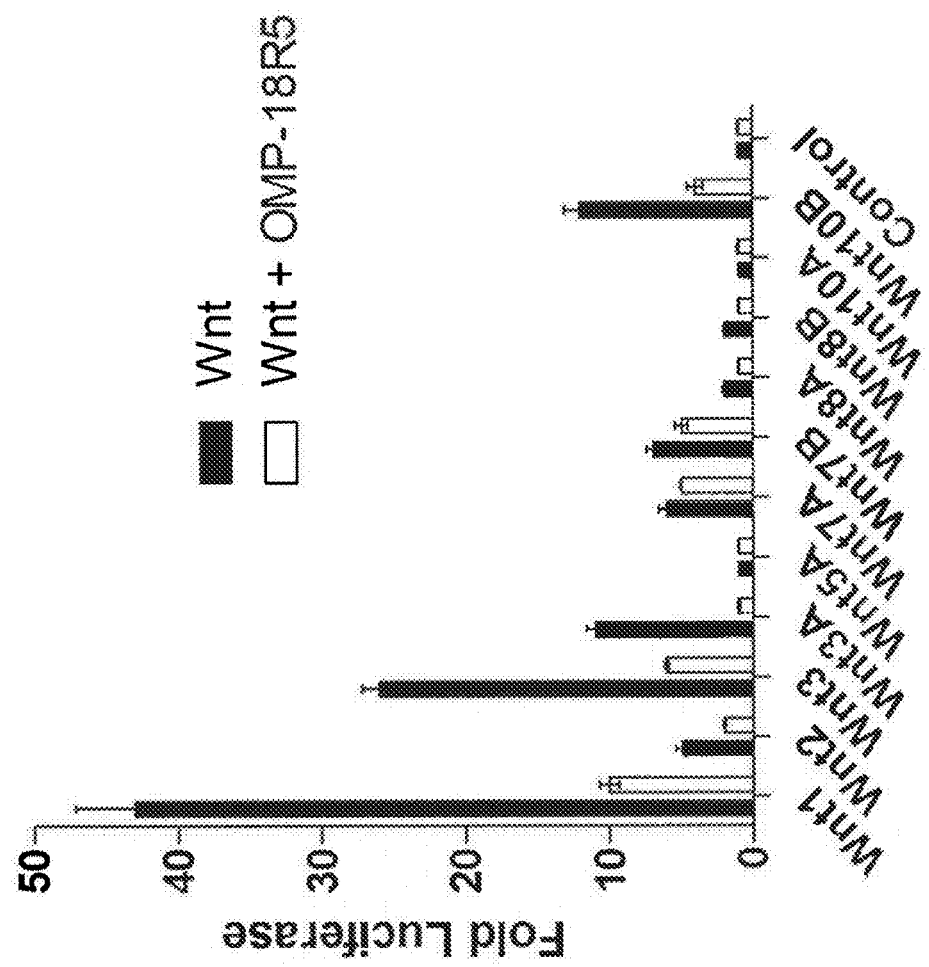

FIG. 67. Anti-FZD antibody 18R5 inhibits the ability of several Wnts to induce canonical signaling.

Figure 68:
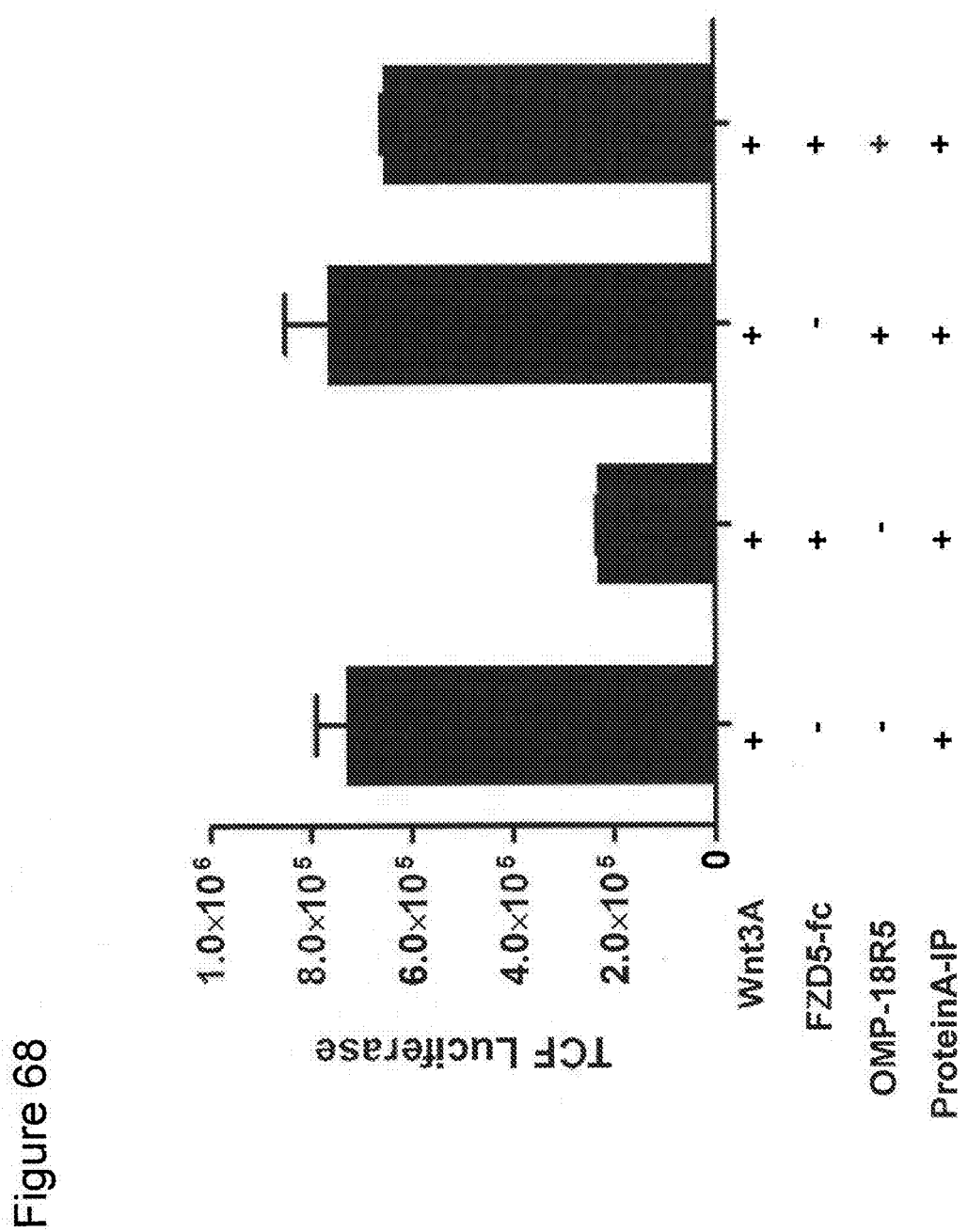

FIG. 68. Binding of 18R5 to FZD inhibits the interaction of WNT with FZD.

DETAILED DESCRIPTION OF THE INVENTION

The present invention provides novel agents, including, but not limited to polypeptides such as antibodies, that bind to one or more human frizzled receptors (FZDs). Related polypeptides and polynucleotides, compositions comprising the FZD-binding agents, and methods of making the FZD-binding agents are also provided. Methods of using the novel FZD-binding agents, such as methods of inhibiting tumor growth and/or treating cancer, are further provided.

The invention is based, in part, on the identification of a region within human frizzled receptors that is a suitable target for FZD-binding, anti-cancer agents. Two anti-FZD antibodies. 18R8 and 18R5, were found to specifically bind to FZD7, but also to cross-react with FZD1, FZD2, FZD5, and FZD8 (Examples 1 and 2, below). In vitro experiments with the 18R8 antibody indicated that the antibody is capable of inhibiting Wnt signaling (Example 3, below) and inhibiting binding of Wnt ligands to FZD8 (Example 4, below). The 18R5 antibody has also been demonstrated to likewise be capable of inhibiting Wnt signaling in cell-based assays (Examples 3 and 20, below). In vivo experiments with the 18R5 antibody demonstrated that the antibody is capable of inhibiting tumor growth or recurrence (Examples 7, 17, and 23, below). The inventors have also shown the anti-FZD antibody 18R5 to be capable of reducing the frequency of cancer stem cells in tumors (Examples, 8 and 23, below) and inducing the differentiation and/or reducing the tumorigenicity of tumor cells (Examples 16, 21, 22, and 25, below). Epitope mapping experiments with these active 18R8 and 18R5 antibodies indicated that both of the antibodies bind to at least part of the sequence GLEVHQ (SEQ ID NO:25) and at least part of the sequence YGFA (SEQ ID NO:74) within FZD8 (Example 5, below). In light of the demonstrated biological activity of these two antibodies, the crystal structure of mouse Frizzled 8 (Dann et al., Nature, 412: 86-90 (2001)) was analyzed and an extracellular region of frizzled proteins comprising these sequences that had not previously been ascribed any specific function was identified for the first time as playing an important functional role in FZD biology and Wnt signaling (Example 6). This region of human frizzled receptors, designated the Biological Binding Site (BBS), is a suitable target for anti-cancer therapies.

In addition, a third antibody, 44R24, was found to specifically bind to human FZD5 and FZD8 (Example 19, below). This antibody has also been shown to be capable of inhibiting Wnt signaling in cell-based assays (Example 20, below) and of anti-tumor efficacy in vivo (Examples 23 and 25, below). Like treatment with the anti-FZD antibodies 18R8 and 18R5, treatment of a tumor with 44R24 resulted in increased levels of a differentiation marker in the tumor (Example 25, below). Epitope mapping has also shown that the epitope of the anti-FZD antibody 44R24 overlaps with that of the anti-FZD antibodies 18R8 and 18R5. More specifically. 44R24 has been shown to bind to at least part of the region YGFA (SEQ ID NO:74) in the BBS (Example 24, below).

I. Definitions

To facilitate an understanding of the present invention, a number of terms and phrases are defined below.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA. IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g. murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability (Jones et al., 1986, Nature. 321:522-525; Riechmann et al., 1988, Nature. 332:323-327; Verhoeyen et al. 1988, Science. 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

That an antibody "specifically binds" to an epitope or protein means that the antibody reacts or associates more frequently, more rapidly, with greater duration, with greater affinity, or with some combination of the above to an epitope or protein than with alternative substances, including unrelated proteins. In certain embodiments, "specifically binds" means, for instance, that an antibody binds to a protein with a $K_D$ of about 0.1 mM or less, but more usually less than about 1 µM. In certain embodiments, "specifically binds" means that an antibody binds to a protein at times with a $K_D$ of at least about 0.1 µM or less, and at other times at least about 0.01 µM or less. Because of the sequence identity between homologous proteins in different species, specific binding can include an antibody that recognizes a particular protein such as a frizzled receptor in more than one species. Likewise, because of homology between different FZD receptors (e.g., FZD5 and FZD8) in certain regions of the polypeptide sequences of the receptors, specific binding can include an antibody (or other polypeptide or agent) that recognizes more than one frizzled receptor. It is understood that an antibody or binding moiety that specifically binds to a first target may or may not specifically bind to a second target. As such, "specific binding" does not necessarily require (although it can include) exclusive binding, i.e. binding to a single target. Thus, an antibody may, in certain embodiments, specifically bind to more than one target (e.g., human FZD1, FZD2. FZD5, FZD7, and/or FZD8). In certain embodiments, the multiple targets may be bound by the same antigen-binding site on the antibody. For example, an antibody may, in certain instances, comprise two identical antigen-binding sites, each of which specifically binds two or more human frizzled receptors (e.g., human FZD1, FZD2, FZD5, FZD7, and/or FZD8). In certain alternative embodiments, an antibody may be bispecific and comprise at least two antigen-binding sites with differing specificities. By way of non-limiting example, a bispecific antibody may comprise one antigen-binding site that recognizes an epitope on one frizzled receptor, such as human FZD5, and further comprises a second, different antigen-binding site that recognizes a different epitope on a second frizzled receptor, such as human FZD8. Generally, but not necessarily, reference to binding means specific binding.

A polypeptide, antibody, polynucleotide, vector, cell, or composition which is "isolated" is polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), more preferably at least 90% pure, more preferably at least 95% pure, more preferably at least 98% pure, more preferably at least 99% pure.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

"Tumor" and "neoplasm" refer to any mass of tissue that result from excessive cell growth or proliferation, either benign (noncancerous) or malignant (cancerous) including pre-cancerous lesions.

The terms "cancer stem cell," "tumor stem cell," or "solid tumor stem cell" are used interchangeably herein and refer to a population of cells from a solid tumor that: (1) have extensive proliferative capacity; 2) are capable of asymmetric cell division to generate one or more kinds of differentiated progeny with reduced proliferative or developmental potential; and (3) are capable of symmetric cell divisions for self-renewal or self-maintenance. These properties of "cancer stem cells," "tumor stem cells," or "solid tumor stem cells" confer on those cancer stem cells the ability to form palpable tumors upon serial transplantation into an immunocompromised mouse compared to the majority of tumor cells that fail to form tumors. Cancer stem cells undergo self-renewal versus differentiation in a chaotic manner to form tumors with abnormal cell types that can change over time as mutations occur.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor. These properties of self-renewal and proliferation to generate all other tumor cells confer on cancer stem cells the ability to form palpable tumors upon serial transplantation into an immunocompromised mouse compared to non-tumorigenic tumor cells, which are unable to form tumors upon serial transplantation. It has been observed that non-tumorigenic tumor cells may form a tumor upon primary transplantation into an immunocompromised mouse after obtaining the tumor cells from a solid tumor, but those non-tumorigenic tumor cells do not give rise to a tumor upon serial transplantation.

The term "subject" refers to any animal (e.g. a mammal), including, but not limited to humans, non-human primates, rodents, and the like, which is to be the recipient of a particular treatment. Typically, the terms "subject" and "patient" are used interchangeably herein in reference to a human subject.

"Pharmaceutically acceptable salt" refers to a salt of a compound that is pharmaceutically acceptable and that possesses the desired pharmacological activity of the parent compound.

"Pharmaceutically acceptable excipient, carrier or adjuvant" refers to an excipient, carrier or adjuvant that can be administered to a subject, together with at least one antibody of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient, or carrier with which at least one antibody of the present disclosure is administered.

The term "therapeutically effective amount" refers to an amount of an antibody, polypeptide, polynucleotide, small organic molecule, or other drug effective to "treat" a disease or disorder in a subject or mammal. In the case of cancer, the therapeutically effective amount of the drug can reduce the number of cancer cells; reduce the tumor size; inhibit or stop cancer cell infiltration into peripheral organs including, for example, the spread of cancer into soft tissue and bone; inhibit and stop tumor metastasis; inhibit and stop tumor growth; relieve to some extent one or more of the symptoms associated with the cancer; reduce morbidity and mortality; improve quality of life; decrease tumorigenicity, tumorgenic frequency, or tumorgenic capacity of a tumor; reduce the number or frequency of cancer stem cells in a tumor; differentiate tumorigenic cells to a non-tumorigenic state; or a combination of such effects. To the extent the drug prevents growth and/or kills existing cancer cells, it can be referred to as cytostatic and/or cytotoxic.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorgenic frequency, or tumorgenic capacity, of a tumor; reduction in the number or frequency of cancer stem cells in a tumor; differentiation of tumorigenic cells to a non-tumorigenic state; or some combination of effects.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g. methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-. 2'-O-allyl. 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R', P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) *J. Molec. Biol.* 273:927-948)). In addition, combinations of these two approaches are sometimes used in the art to determine CDRs.

The term "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents. DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software are known in the art that may be used to obtain alignments of amino acid or nucleotide sequences. One such non-limiting example of a sequence alignment algorithm is the algorithm described in Karlin et al, 1990, *Proc. Natl. Acad. Sci.,* 87:2264-2268, as modified in Karlin et al., 1993, *Proc. Natl. Acad. Sci.* 90:5873-5877, and incorporated into the NBLAST and XBLAST programs (Altschul et al., 1991, *Nucleic Acids Res.,* 25:3389-3402). In certain embodiments, Gapped BLAST may be used as described in Altschul et al., 1997, *Nucleic Acids Res.* 25:3389-3402. BLAST-2, WU-BLAST-2 (Altschul et al., 1996, *Methods in Enzymologyv,* 266:460-480), ALIGN. ALIGN-2 (Genentech. South San Francisco, Calif.) or Megalign (DNASTAR) are additional publicly available software programs that can be used to align sequences. In certain embodiments, the percent identity between two nucleotide sequences is determined using the GAP program in GCG software (e.g. using a NWSgap-dna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453 (1970)) may be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity may be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%. 97%. 98%, or 99% identical) to a reference sequence can, in certain embodiments, be determined using the Bestfit program (Wisconsin Sequence Analysis Package, Version 8 for Unix, Genetics Computer Group. University Research Park, 575 Science Drive, Madison, Wis. 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, preferably at least 80%, more preferably at least 85%, more preferably at least 90%, and in some embodiments at least 95%, 96%, 97%. 98%, 99% nucleotide or amino acid residue identity, when compared and aligned for maximum correspondence, as measured using a sequence comparison algorithm or by visual inspection. Preferably, identity exists over a region of the sequences that is at least about 10, preferably about 20, more preferable about 40-60 residues in length or any integral value therebetween, preferably over a longer region than 60-80 residues, more preferably at least about 90-100 residues, and most preferably the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence, to the antigen(s), i.e., the one or more human frizzled receptors to which the polypeptide or antibody binds. Methods of identifying nucleotide and amino acid conservative substitutions which do not eliminate antigen binding are well-known in the art (see, e.g., Brummell et al., *Biochem.* 32: 1180-1 187 (1993); Kobayashi et al. *Protein Eng.* 12(10):879-884 (1999); and Burks et al. *Proc. Natl. Acad. Sci. USA* 94:412-417 (1997)).

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

"Conditions of high stringency." may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

II. FZD-Binding Agents

The present invention provides agents that specifically bind one or more human frizzled receptors (FZDs). These agents are referred to herein as "FZD-binding agents." In certain embodiments, the agents specifically bind two, three, four, five, six, seven, eight, nine, or ten frizzled receptors. The human frizzled receptor or receptors bound by the agent may be selected from the group consisting of FZD1, FZD2, FZD3, FZD4, FZD5. FZD6, FZD7. FZD8, FZD9, and FZD10. In certain embodiments, the one or more human frizzled receptors comprise FZD1, FZD2, FZD5, FZD7, and/or FZD8. In certain embodiments, the one or more human frizzled receptors comprise FZD7. In certain embodiments, the one or more human frizzled receptors comprise FZD5 and/or FZD8. In certain embodiments, the agent specifically binds FZD1, FZD2, FZD5, FZD7, and FZD8. The full-length amino acid (aa) and nucleotide (nt) sequences for FZD1-10 are known in the art and also provided herein as SEQ ID NO:26 (FZD1 aa), SEQ ID NO:30 (FZD2 aa). SEQ ID NO:34 (FZD3 aa), SEQ ID NO:38 (FZD4 aa), SEQ ID NO:42 (FZD5 aa). SEQ ID NO:46 (FZD6 aa), SEQ ID NO:50 (FZD7 aa). SEQ ID NO:54 (FZD8 aa), SEQ ID NO:58 (FZD9 aa), SEQ ID NO:62 (FZD10 aa), SEQ ID NO:29 (FZD1 nt), SEQ ID NO:33 (FZD2 nt), SEQ ID NO:37 (FZD3 nt), SEQ ID NO:41 (FZD4 nt), SEQ ID NO:45 (FZD5 nt), SEQ ID NO:49 (FZD6 nt). SEQ ID NO:53 (FZD7 nt). SEQ ID NO:57 (FZD8 nt), SEQ ID NO:61 (FZD9 nt), and SEQ ID NO:65 (FZD10 nt).

In certain embodiments, the antibody or other polypeptide or agent described herein specifically binds FZD7. In certain embodiments, that antibody, polypeptide, or agent may further specifically bind or cross-react with one or more additional human frizzled receptors.

In certain embodiments, the antibody or other polypeptide or agent described herein specifically binds FZD5. In certain embodiments, that antibody, polypeptide, or agent may further specifically bind or cross-react with one or more additional human frizzled receptors.

In certain embodiments, the agent specifically binds to two or more human frizzled receptors. In certain embodiments, the two or more human frizzled receptors are selected from the group consisting of FZD2, FZD5, FZD7, and FZD8. In certain embodiments, the two or more frizzled receptors comprise FZD1 and a second frizzled receptor selected from the group consisting of FZD2, FZD5. FZD7, and FZD8. In certain embodiments, the two or more frizzled receptors comprise FZD2 and a second frizzled receptor selected from the group consisting of FZD1, FZD5, FZD7, and FZD8. In certain embodiments, the two or more frizzled receptors comprise FZD5 and a second frizzled receptor selected from the group consisting of FZD1, FZD2, FZD7, and FZD8. In certain embodiments, the two or more frizzled receptors comprise both FZD5 and FZD8. In certain embodiments, the two or more frizzled receptors comprise FZD7 and a second frizzled receptor selected from the group consisting of FZD1, FZD2, FZD5, and FZD8.

In certain embodiments, the agent specifically binds to three or more human frizzled receptors. In certain embodiments, the three or more human frizzled receptors comprise three or more frizzled receptors selected from the group consisting of FZD1, FZD2. FZD5, FZD7, and FZD8. In certain embodiments, the agent further specifically binds to one or more additional human frizzled receptors.

In certain embodiments, the agent or antibody specifically binds to the extracellular domain (ECD) within the one or more human frizzled receptors to which it binds. Sequences of the extracellular domain of each of the human frizzled receptors are known in the art and are also provided as SEQ ID NO:27 (FZD1 ECD), SEQ ID NO:31 (FZD2 ECD). SEQ ID NO:35 (FZD3 ECD), SEQ ID NO:39 (FZD4 ECD), SEQ ID NO:43 (FZD5 ECD), SEQ ID NO:47 (FZD6 ECD), SEQ ID NO:51 (FZD7 ECD), SEQ ID NO:55 (FZD8 ECD). SEQ ID NO:59 (FZD9 ECD), and SEQ ID NO:63 (FZD10 ECD).

In certain embodiments, the agent or antibody specifically binds to the Fri domain (FRI) (also known as the cysteine-rich domain (CRD)) within the human frizzled receptor(s) to which it binds. Sequences of the Fri domain of each of the human frizzled receptors are known in the art and are also provided as SEQ ID NO:28 (FZD1 FRI), SEQ ID NO:32 (FZD2 FRI), SEQ ID NO:36 (FZD3 FRI). SEQ ID NO:40 (FZD4 FRI), SEQ ID NO:44 (FZD5 FRI), SEQ ID NO:48 (FZD6 FRI), SEQ ID NO:52 (FZD7 FRI), SEQ ID NO:56 (FZD8 FRI), SEQ ID NO:60 (FZD9 FRI), and SEQ ID NO:64 (FZD10 FRI).

In certain embodiments, an individual antigen-binding site of a FZD-binding antibody or polypeptide described herein is capable of binding (or binds) the one, two, three, four, or five (or more) human frizzled receptors. In certain embodiments, an individual antigen-binding site of the FZD-binding antibody or polypeptide is capable of specifically binding one, two, three, four, or five human frizzled receptors selected from the group consisting of FZD1, FZD2, FZD5, FZD7, and FZD8. In certain embodiments, an individual binding site of the antibody or polypeptide specifically binds to at least FZD5 and FZD8.

In certain embodiments, the FZD-binding agent or antibody binds to one or more (for example, two or more, three or more, or four or more) human frizzled receptors with a dissociation constant ($K_D$) of about 1 μM or less, about 100 nM or less, about 40 nM or less, about 20 nM or less, or about 10 nM or less. For example, in certain embodiments, a FZD-binding agent or antibody described herein that binds to more than one FZD, binds to those FZDs with a $K_D$ of about 100 nM or less, about 20 nM or less, or about 10 nM or less. In certain embodiments, the FZD-binding agent or antibody binds to each of one or more (e.g., 1, 2, 3, 4, or 5) of the following FZDs with a dissociation constant of about 40 nM or less: FZD1, FZD2, FZD5, FZD7, and FZD8. In certain embodiments, the FZD-binding agent or antibody binds to each of one or more of the following FZDs with a dissociation constant of about 10 nM or less: FZD1, FZD2, FZD5, FZD7, and FZD8. In certain embodiments, the FZD-binding agent or antibody binds to each of the following FZDs with a dissociation constant of about 10 nM or less: FZD1, FZD2. FZD5, FZD7, and FZD8. In certain embodiments, the dissociation constant of the agent or antibody to a particular FZD is the dissociation constant determined using an FZD-Fc fusion protein comprising the FZD extracellular domain or Fri domain immobilized on a Biacore chip.

In certain embodiments, the FZD-binding agent or antibody binds to each of one or more of the following FZDs with a dissociation constant between about 1 nM and about 10 nM: FZD1, FZD2, FZD5, FZD7, and FZD8. Alternatively, the FZD-binding agent or antibody binds to two or more (or three or more) of the following FZDs with a dissociation constant between about 1 nM and about 10 nM: FZD1, FZD2, FZD5, FZD7, and FZD8. In certain further embodiments, the FZD-binding agent or antibody binds to each of both FZD5 and FZD8 with a dissociation constant between about 1 nM and about 10 nM.

In certain embodiments, the FZD-binding agent or antibody binds to FZD8 with a dissociation contant of at least about 3 nM. In certain embodiments, the FZD-binding agent or antibody binds to FZD8 with a dissociation constant between about 3 nM and 30 nM. In certain alternative embodiments, the dissociation constant for binding of FZD8 may be between about 3 nM and 10 nM.

In certain embodiments, the FZD-binding agent or antibody binds to one or more (for example, two or more, three or more, or four or more) human frizzled receptors with an $EC_{50}$ of about 1 μM or less, about 100 nM or less, about 40 nM or less, about 20 nM or less, about 10 nM or less, or about 1 nM or less. For example, in certain embodiments, a FZD-binding agent or antibody described herein that binds to more than one FZD has an $EC_{50}$ of about 40 nM or less, about 20 nM or less, or about 10 nM or less, with respect to those FZDs. In certain embodiments, the FZD-binding agent or antibody has an $EC_{50}$ of about 20 nM or less with respect to one or more (e.g., 1, 2, 3, 4, or 5) of the following FZDs: FZD1, FZD2, FZD5, FZD7, and FZD8. In certain embodiments, the FZD-binding agent or antibody has an $EC_{50}$ of about 10 nM or less with respect to one or more (e.g., 1, 2, 3, 4, or 5) of the following FZDs: FZD1, FZD2, FZD5.

FZD7, and FZD8. In certain embodiments, the FZD-binding agent or antibody has an EC50 of about 40 nM or less or 20 nM or less with respect to binding of FZD5 and/or FZD8.

In certain embodiments, the FZD-binding agent (e.g., antibody) binds to the same epitope as or binds to an epitope that overlaps with the epitope of an antibody comprising a heavy chain variable region comprising SEQ ID NO:10 and a light chain variable region comprising SEQ ID NO:12 or SEQ ID NO:14 (e.g., the 18R5 or 18R8 IgG antibody). In certain embodiments, the FZD-binding agent or antibody binds to the same epitope as or binds to an epitope that overlaps with the epitope of an antibody comprising a heavy chain comprising the sequence of SEQ ID NO: 11 and a light chain comprising the sequence of SEQ ID NO:13 or SEQ ID NO:15. In certain embodiments, the FZD-binding agent binds to the same epitope as or binds to an epitope that overlaps with the epitope of an antibody comprising a heavy chain variable region comprising SEQ ID NO:85 and a light chain variable region comprising SEQ ID NO:86 (e.g. the 44R24 IgG antibody).

In certain embodiments, the FZD-binding agent competes for specific binding to a human frizzled receptor with an antibody in a competitive binding assay, wherein the antibody comprises a heavy chain variable region comprising SEQ ID NO:10 and a light chain variable region comprising SEQ ID NO:12 or SEQ ID NO: 14. In certain embodiments, the FZD-binding agent competes for specific binding to a human frizzled receptor with an antibody comprising a heavy chain comprising the sequence of SEQ ID NO: 11 and a light chain comprising the sequence of SEQ ID NO:13 or SEQ ID NO:15. In certain embodiments, the antibody with which the agent competes for specific binding to the human frizzled receptor is an 18R5 IgG antibody. In certain alternative embodiments, the antibody is an 18R8 IgG antibody.

In certain embodiments, the FZD-binding agent competes for specific binding to a human frizzled receptor with an antibody in a competitive binding assay, wherein the antibody comprises a heavy chain variable region comprising SEQ ID NO:85 and a light chain variable region comprising SEQ ID NO:86.

In certain embodiments, the FZD-binding agent directly competes for binding or directly inhibits binding of Wnt on the FZD(s).

In certain embodiments, the FZD-binding agent or antibody binds to at least part of a region of a human frizzled receptor designated by the inventors as the Biological Binding Site (BBS) (FIG. 9, Example 6). In human FZD8 (SEQ ID NO:54), the BBS consists of the following: (a) a conformational epitope consisting of amino acids 72(F), 74-75 (PL). 78(I), 92(Y), 121-122(LM), and 129-132(WPDR (SEQ ID NO:70)) (the "cleft" of the BBS shown in FIGS. 8 and 9): (b) a region of FZD8 consisting of the sequence GLEVHQ (SEQ ID NO:25) (the "top edge" of the BBS shown in FIGS. 8 and 9); and (c) a region of FZD8 consisting of the sequence YGFA (SEQ ID NO:74) (the "bottom edge" of the BBS shown in FIGS. 8 and 9). The corresponding residues of the BBS on FZD1-7, FZD9, and FZD10 are identified in Table 1, below, and FIG. 8. In certain embodiments, an agent that blocks binding of a ligand (e.g., a Wnt) to the FZD inhibits the binding of the ligand to the BBS. It is understood that in certain embodiments, the agents which bind to at least part of the BBS may also bind one or more regions elsewhere (i.e., outside of the BBS) on the human frizzled receptor. In other words, in certain embodiments, the epitope to which the FZD-binding agent or antibody binds is a region within the extracellular domain of the FZD receptor that overlaps with the BBS, but is not entirely contained within the BBS. In certain alternative embodiments, the epitope to which the FZD-binding agent or antibody binds is entirely contained within the BBS (i.e., the BBS comprises the entire epitope to which the FZD binding antibody or other agent binds).

TABLE 1

Biological Binding Sites (BBS) of FZD Receptors

| Human Frizzled Receptor (aa sequence) | Amino acid residues forming the Biological Binding Site (BBS) |
|---|---|
| FZD1 (SEQ ID NO: 26) | 147-153(GLEVHQF), 155-156(PL), 159(V), 173(Y), 201-202(LM), 205-212(FGFQWPDT) |
| FZD2 (SEQ ID NO: 30) | 70-76(GLEVHQF), 78-79(PL), 82(V), 96(Y), 124-125(LM), 128-135(FGFQWPER) |
| FZD3 (SEQ ID NO: 34) | 59-65(ALAMEPF), 67-68(PM), 71(L), 85(Y), 113-114(LM), 117-124(FGVPWPED) |
| FZD4 (SEQ ID NO: 38) | 79-85(ELQLTTF), 87-88(PL), 91(Y), 105(Y), 134-135(VL), 138-145(FGFAWPES) |
| FZD5 (SEQ ID NO: 42) | 64-70(GLEVHQF), 72-73(PL), 76(I) 90(Y), 119-120(LM), 123-130(YGFAWPER) |
| FZD6 (SEQ ID NO: 46) | 55-61(AVEMEHF), 63-64(PL), 67(L), 81(F), 109-110(LI), 113-120(FGIRWPEE) |
| FZD7 (SEQ ID NO: 50) | 80-86(GLEVHQF), 88-89(PL), 92(V), 106(Y), 134-135(LM), 138-145(FGFQWPER) |
| FZD8 (SEQ ID NO: 54) | 66-72(GLEVHQF), 74-75(PL), 78(I), 92(Y), 121-122(LM), and 125-132(YGFAWPDR) |
| FZD9 (SEQ ID NO: 58) | 70-76(AAELAEF), 78-79(PL), 82(Y), 96(Y), 125-126(IM), 129-136(FNFGWPDS) |
| FZD10 (SEQ ID NO: 62) | 65-71(AIQLHEF), 73-74(PL), 77(Y), 91(Y), 120-121(IM), 124-131(FNFKWPDS) |

Without being bound by theory, the BBS is believed to comprise a possible ligand binding site, such as a binding site for Wnt. On FZD8, this possible ligand binding site comprises the conformational epitope formed by amino acids 72(F), 74-75(PL), 78(I), 92(Y), 121-122(LM), and 129-132(WPDR (SEQ ID NO:70)) (the "cleft" of the BBS shown in FIGS. 8 and 9). The corresponding residues of the possible ligand binding site on FZD1-7, FZD9, and FZD10 are shown in the alignment of sequences in FIG. 8. In certain embodiments, an agent that blocks binding of a ligand (e.g, a Wnt) to the BBS inhibits the binding of the ligand to this conformational epitope. It is understood that in certain embodiments, the agents which bind to at least a part of this ligand binding site may also bind to a region elsewhere (e.g., outside of the BBS) on the human frizzled receptor. In certain alternative embodiments, the agent does not bind to any portion of the FZD outside of the conformational epitope.

In certain embodiments, the agent binds to at least part of the sequence QDEAGLEVHQFWPL (SEQ ID NO:67) within the human frizzled receptor if the human frizzled receptor is FZD8, or the corresponding sequence if the human frizzled receptor is FZD1-7, FZD9, or FZD10. This region on the FZDs comprises the "top edge" of the BBS identified in FIGS. 8 and 9. The sequences corresponding to the epitope QDEAGLEVHQFWPL (SEQ ID NO:67) of FZD8 in the various frizzled receptors are identified in Table 2, below, and are also apparent from the alignment in FIG. 8. In certain embodiments, the agent specifically binds to a human frizzled receptor selected from the group consisting of FZD1, FZD2, FZD5, FZD7, and FZD8, and the agent binds to at least part of the sequence Q(DE/ED)AG-LEVHQF(Y/W)PL (SEQ ID NO:24) within the human frizzled receptor. In certain embodiments, the agent specifically binds to at least part of the sequence AGLEVHQF (SEQ ID NO:68) within the human frizzled receptor(s) FZD1, FZD2, FZD5, FZD7, and/or FZD8. In certain embodiments, the agent binds to at least part of a sequence in FZD3, FZD4, FZD6, FZD9, and/or FZD10 that corresponds to the sequence AGLEVHQF (SEQ ID NO:68) in FZD8. In certain embodiments, the agent specifically binds to at least part of the sequence GLEVHQ (SEQ ID NO: 25) within the human frizzled receptor(s) FZD1, FZD2, FZD5, FZD7, and/or FZD8. This sequence is the "top edge" of the BBS shown in FIG. 9. In certain embodiments, the agent binds to at least part of the sequence in FZD3, FZD4, FZD6, FZD9, and/or FZD10 that corresponds to the sequence GLEVHQ (SEQ ID NO: 25) in FZD8. Sequences which correspond to the sequence GLEVHQ (SEQ ID NO: 25) of FZD8 are underlined in the second and third columns of Table 2 below and are apparent from the sequence alignment in FIG. 8. In certain embodiments, an agent that binds to at least part of SEQ ID NO:67 or 68 in FZD8, or to a corresponding epitope in another FZD, inhibits binding of a ligand (e.g., a Wnt) to the FZD (e.g., to the BBS of the FZD). In certain embodiments, the agents which bind to the above indicated regions may also bind to additional regions elsewhere (i.e., outside of the above-specified regions) on the human frizzled receptor.

TABLE 2

Corresponding regions on human frizzled receptors

| FZD (aa seq) | aa corresponding to aa 62-75 (QDEAGLEVHQFWPL; SEQ ID NO: 67) of FZD8 (SEQ ID NO: 54)[a] | aa corresponding to aa 65-72 (AGLEVHQF; SEQ ID NO: 68) of FZD8 (SEQ ID NO: 54)[b] | aa corresponding to aa 124-128 (QYGFA; SEQ ID NO: 66) of FZD8 (SEQ HD |
|---|---|---|---|
| FZD1 (SEQ ID NO: 26) | 143-156 (QEDA<u>GLEVHQ</u>FYPL) | 146-153 (A<u>GLEVHQ</u>F) | 204-208 (K<u>FGFQ</u>) |
| FZD2 (SEQ ID NO: 30) | 66-79 (QEDA<u>GLEVHQ</u>FYPL) | 69-76 (A<u>GLEVHQ</u>F) | 127-131 (K<u>FGFQ</u>) |
| FZD3 (SEQ ID NO: 34) | 55-68 (QQTA<u>ALAMEP</u>FHPM) | 58-65 (A<u>ALAMEP</u>F) | 116-120 (M<u>FGVP</u>) |
| FZD4 (SEQ ID NO: 38) | 75-88 (QTDA<u>ELQLTT</u>FTPL) | 78-85 (A<u>ELQLTT</u>F) | 137-141 (E<u>FGFA</u>) |
| FZD5 (SEQ ID NO: 42) | 60-73 (QDEA<u>GLEVHQ</u>FWPL) | 63-70 (A<u>GLEVHQ</u>F) | 122-126 (Q<u>YGFA</u>) |
| FZD6 (SEQ ID NO: 46) | 51-64 (QSIA<u>AVEMEH</u>FLPL) | 54-61 (A<u>AVEMEH</u>F) | 112-116 (T<u>FGIR</u>) |
| FZD7 (SEQ ID NO: 50) | 76-89 (QEDA<u>GLEVHQ</u>FYPL) | 79-86 (A<u>GLEVHQ</u>F) | 137-141 (K<u>FGFQ</u>) |
| FZD9 (SEQ ID NO: 58) | 66-79 (QGEA<u>AAELAE</u>FAPL) | 69-76 (A<u>AAELAE</u>F) | 128-132 (Q<u>FNFG</u>) |
| FZD10 (SEQ ID NO: 62) | 61-74 (QREA<u>AIQLHE</u>FAPL) | 64-71 (A<u>AIQLHE</u>F) | 123-127 (Q<u>FNFK</u>) |

[a]Sequences corresponding to as 66-71 GLEVHQ (SEQ ID NO: 25) of FZD8 (SEq ID NO: 54) are underlined.
[b]Sequences corresponding to as 125-128 YGFA (SEQ ID NO: 74) of FZD8 (SEQ ID NO: 54) are underlined.

In certain embodiments, the FZD-binding agent binds to at least part of a region consisting of the sequence QYGFA (SEQ ID NO:66) if the human frizzled receptor is FZD8, which comprises the "bottom edge" of the BBS, or the corresponding sequence if the human frizzled receptor is FZD1-7, FZD9, or FZD10. The sequences corresponding to the region QYGFA (SEQ ID NO:66) in the various frizzled receptors are identified in FIG. 8 and Table 2 above. In certain embodiments, the FZD-binding agent binds to at least part of a region consisting of the sequence YGFA (SEQ ID NO:74), the "bottom edge" of the BBS, if the human frizzled receptor is FZD8, or the corresponding sequence if the human frizzled receptor is FZD1-7, FZD9, or FZD10. The sequences corresponding to the region YGFA (SEQ ID NO:74) in the various frizzled receptors are identified in FIG. 8 and underlined in the fourth column of Table 2 above. In certain embodiments, an agent that binds to at least part of SEQ ID NO:66 or SEQ ID NO:74 in FZD8, or to its corresponding sequence in another FZD, inhibits binding of a ligand (e.g., a Wnt) to the FZD (e.g., the BBS of the FZD). In certain embodiments, the agents which bind to this region may also bind to one or more amino acid residues elsewhere (i.e. outside of this region) on the human frizzled receptor.

In certain embodiments, FZD-binding agent binds at least part of the region forming the "top edge" of the BBS, as well as at least a part of the region forming the "bottom edge" of the BBS. In certain embodiments, the FZD-binding agent that binds to at least part of Q(DE/ED)AGLEVHQF(Y/W) PL (SEQ ID NO:24) within FZD1, FZD2, FZD5, FZD7, and/or FZD8, QDEAGLEVHQFWPL (SEQ ID NO:67) within FZD8, AGLEVHQF (SEQ ID NO:68) within FZD8, and/or GLEVHQ (SEQ ID NO:25) within FZD8, and/or a sequence corresponding to any of these sequences in a different human frizzled receptor (as defined in Table 2, above) further binds to at least part of QYGFA (SEQ ID NO:66) within FZD8 or YGFA (SEQ ID NO:74) within FZD8, and/or a sequence corresponding to one of these sequences within FZD1-7, FZD9, or FZD10 (as defined in Table 2, above). In certain embodiments, the FZD binding agent binds to at least part of the sequence GLEVHQ (SEQ ID NO:25) within FZD8, as well as to at least part of the sequence YGFA (SEQ ID NO:74) within FZD8. In certain embodiments, the FZD-binding agent binds to at least part of a region of FZD1-7, FZD9, or FZD10 corresponding to the sequence GLEVHQ (SEQ ID NO:25) in FZD8, as well as to at least part of a region of FZD1-7, FZD9, or FZD10 corresponding to the sequence YGFA (SEQ ID NO:74) in FZD8. In certain embodiments, the FZD-binding agent that binds to the indicated sequences also binds to one or more sequences elsewhere within the human frizzled receptor(s) to which it binds. In other words, in certain embodiments, the epitope to which the FZD-binding agent or antibody binds is a region within the FZD extracellular domain that overlaps only partially with the above-indicated sequences. In certain alternative embodiments, the entire epitope to which the FZD-binding agent binds is entirely contained within the above-indicated sequences.

In certain embodiments, the FZD-binding agent binds a human FZD receptor (e.g., FZD8) in the cleft of its BBS. See, e.g., the cleft residues listed in Table 16 in the Examples below. In certain embodiments, L75 of FZD8 is necessary for binding of the agent. In certain embodiments, the FZD-binding agent which binds in the cleft of the BBS, may have a molecular weight of less than about 2000 Daltons or less than about 1000 Daltons. The FZD-binding agent may be a polypeptide, a lipid, an aptamer, a small molecule or other compound. In certain embodiments, the FZD-binding agent comprises a polypeptide comprising about 100 amino acids or less. In certain embodiments, the polypeptide comprises less than about 20 amino acids. The polypeptide may be modified or unmodified. In certain embodiments, the agent comprises a polypeptide comprising a sequence having at least about 80% sequence identity to a sequence selected from the group consisting of SEQ ID NOs: 98-111 and 113-116. In certain embodiments, the agent comprises SEQ ID NO:112. In some instances, the agent may comprise SEQ ID NO: 108.

In certain embodiments, the agent is a polypeptide. In certain embodiments, the agent or polypeptide is an antibody. In certain embodiments, the antibody is an IgG1 antibody or an IgG2 antibody. In certain embodiments, the antibody is a monoclonal antibody. In certain embodiments, the antibody is a human antibody or a humanized antibody. In certain embodiments, the antibody is an antibody fragment.

The antibodies or other agents of the present invention can be assayed for specific binding by any method known in the art. The immunoassays which can be used include, but are not limited to competitive and non-competitive assay systems using techniques such as BIAcore analysis. FACS analysis, immunofluorescence, immunocytochemistry, Western blots, radioimmunoassays, ELISA, "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, and protein A immunoassays. Such assays are routine and well known in the art (see, e.g., Ausubel et al, eds. 1994, Current Protocols in Molecular Biology, Vol. 1, John Wiley & Sons, Inc., New York, which is incorporated by reference herein in its entirety).

For example, the specific binding of an antibody to a human frizzled receptor may be determined using ELISA. An ELISA assay comprises preparing antigen, coating wells of a 96 well microtiter plate with antigen, adding the FZD-binding antibody or other FZD-binding agent conjugated to a detectable compound such as an enzymatic substrate (e.g. horseradish peroxidase or alkaline phosphatase) to the well, incubating for a period of time and detecting the presence of the antigen. In some embodiments, the FZD-binding antibody or agent is not conjugated to a detectable compound, but instead a second conjugated antibody that recognizes the FZD-binding antibody or agent is added to the well. In some embodiments, instead of coating the well with the antigen, the FZD-binding antibody or agent can be coated to the well and a second antibody conjugated to a detectable compound can be added following the addition of the antigen to the coated well. One of skill in the art would be knowledgeable as to the parameters that can be modified to increase the signal detected as well as other variations of ELISAs known in the art (see e.g. Ausubel et al, eds, 1994, Current Protocols in Molecular Biology, Vol. 1, John Wiley & Sons, Inc., New York at 11.2.1).

The binding affinity of an antibody or other agent to a human frizzled receptor and the off-rate of an antibody-antigen interaction can be determined by competitive binding assays. One example of a competitive binding assay is a radioimmunoassay comprising the incubation of labeled antigen (e.g. $^3$H or $^{125}$I), or fragment or variant thereof, with the antibody of interest in the presence of increasing amounts of unlabeled antigen followed by the detection of the antibody bound to the labeled antigen. The affinity of the antibody against a frizzled receptor and the binding off-rates can be determined from the data by scatchard plot analysis. In some embodiments, BIAcore kinetic analysis is used to determine the binding on and off rates of antibodies or agents that bind one or more human frizzled receptors. BIAcore kinetic analysis comprises analyzing the binding and dissociation of antibodies from chips with immobilized FZD antigens on their surface.

In certain embodiments, the agent (e.g. antibody) is an antagonist of at least one human frizzled receptor (i.e., 1, 2, 3, 4, 5, 6, 7, 8, 9, or 10 FZDs) bound by the agent. In certain embodiments, the agent inhibits at least about 10%, at least about 20%, at least about 30%, at least about 50%, at least about 75%, at least about 90%, or about 100% of one or more activity of the bound human frizzled receptor.

In certain embodiments, the FZD-binding agent inhibits binding of a ligand to the at least one human frizzled receptor. In certain embodiments, the FZD-binding agent inhibits binding of a ligand to the Biological Binding site (BBS) of the human frizzled receptor. In certain embodiments, the ligand is a human Wnt protein. Nineteen human Wnt proteins have been identified: WNT1, WNT2, WNT2B/ 13, WNT3, WNT3A, WNT4, WNT5A, WNT5B, WNT6. WNT7A, WNT7B. WNT8A, WNT8B. WNT9A (previously WNT14), WNT9B (previously WNT15), WNT10A, WNT10B, WNT11, and WNT16. In certain embodiments, the agent inhibits binding of WNT3A to FZD8. In certain embodiments, the inhibition of binding of a particular ligand to a particular human frizzled protein provided by the FZD-binding agent is at least about 10%, at least about 25%, at least about 50%, at least about 75%, at least about 90%, or at least about 95%. In certain embodiments, an agent that inhibits binding of a ligand such as a Wnt to a FZD, further inhibits Wnt signaling (e.g., inhibits canonical Wnt signaling).

In certain embodiments, the FZD-binding agent inhibits Wnt signaling. It is understood that a FZD-binding agent that inhibits Wnt signaling may, in certain embodiments, inhibit signaling by one or more Wnts, but not necessarily by all Wnts. In certain alternative embodiments, signaling by all human Wnts may be inhibited. In certain embodiments, signaling by one or more Wnts selected from the group consisting of WNT1, WNT2, WNT2B/13, WNT3, WNT3A, WNT4, WNT5A, WNT5B, WNT6, WNT7A, WNT7B, WNT8A, WNT8B, WNT9A (previously WNT14), WNT9B (previously WNT15), WNT10A, WNT10B, WNT11, and WNT16 is inhibited. In certain embodiments, the Wnt signaling that is inhibited is signaling by WNT1, WNT2. WNT3, WNT3A, WNT7a, WNT7b, and/or WNT10B. In certain embodiments, the agent inhibits signaling by (at least) WNT1, WNT3A, WNT7b, and WNT10B. In particular embodiments, the agent inhibits signaling by (at least) WNT3A. In certain embodiments, the inhibition of signaling by a Wnt provided by the FZD-binding agent is a reduction in the level of signaling by the Wnt of at least about 10%, at least about 25%, at least about 50%, at least about 75%, at least about 90%, or at least about 95%. In certain embodiments, the Wnt signaling that is inhibited is canonical Wnt signaling.

In vivo and in vitro assays for determining whether a FZD-binding agent (or candidate FZD-binding agent) inhibits Wnt signaling are known in the art. For example, cell-based, luciferase reporter assays utilizing a TCF/Luc reporter vector containing multiple copies of the TCF-binding domain upstream of a firefly luciferase reporter gene may be used to measure canonical Wnt signaling levels in vitro (Gazit et al., 1999, Oncogene 18; 5959-66). The level of Wnt signaling in the presence of one or more Wnts (e.g., Wnt(s) expressed by transfected cells or provided by Wnt-conditioned media) with the FZD-binding agent present is compared to the level of signaling without the FZD-binding agent present. Non-limiting, specific examples of the use of such a luciferase reporter assay to assess inhibition of canonical Wnt signaling are provided in Examples 3 and 11, below. In addition to the TCF/luc reporter assay, the effect of a FZD-binding agent (or candidate agent) on canonical Wnt signaling may be measured in vitro or in vivo by measuring the effect of the agent on the level of expression of beta-catenin regulated genes, such as c-myc (He et al., Science. 281:1509-12 (1998)), cyclin D1 (Tetsu et al., Nature, 398: 422-6 (1999)) and/or fibronectin (Gradl et al. Mol. Cell. Biol., 19:5576-87 (1999)). In certain embodiments, the effect of an agent on Wnt signaling may also be assessed by measuring the effect of the agent on the phosphorylation state of Dishevelled-1, Dishevelled-2, Dishevelled-3, LRP5, LRP6, and/or beta-catenin. In still further embodiments, the effect of a FZD-binding agent on Wnt signaling is determined by assessing the impact of the FZD-binding agent on the expression level of one or more genes in a Wnt signature.

In certain embodiments, the FZD-binding agents have one or more of the following effects: inhibit proliferation of tumor cells, reduce the tumorigenicity of a tumor by reducing the frequency of cancer stem cells in the tumor, inhibit tumor growth, increase survival, trigger cell death of tumor cells, differentiate tumorigenic cells to a non-tumorigenic state, or prevent metastasis of tumor cells.

In embodiments, antibodies or other agents that specifically bind one or more human frizzled receptors trigger cell death via a conjugated toxin, chemotherapeutic agent, radioisotope, or other such agent. For example, in certain embodiments, an antibody to a human frizzled antibody is conjugated to a toxin that is activated in tumor cells expressing the FZD by protein internalization. In certain alternative embodiments, the agent or antibody is not conjugated to a toxin, chemotherapeutic agent, or radioisotope.

In certain embodiments, the FZD-binding agents are capable of inhibiting tumor growth. In certain embodiments, the FZD-binding agents are capable of inhibiting tumor growth in vivo (e.g., in a xenograft mouse model and/or in a human having cancer).

In certain embodiments, the FZD-binding agents are capable of reducing the tumorigenicity of a tumor. In certain embodiments, the agent or antibody is capable of reducing the tumorigenicity of a tumor comprising cancer stem cells in an animal model, such as a mouse xenograft model. In certain embodiments, the number or frequency of cancer stem cells in a tumor is reduced by at least about two-fold, about three-fold, about five-fold, about ten-fold, about 50-fold, about 100-fold, or about 1000-fold. In certain embodiments, the reduction in the number or frequency of cancer stem cells is determined by limiting dilution assay using an animal model. An example of a limiting dilution assay used to test the efficacy of an anti-FZD antibody is provided in Example 8, below. Additional examples and guidance regarding the use of limiting dilution assays to determine a reduction in the number or frequency of cancer stem cells in a tumor can be found, e.g., in International Publication Number WO 2008/042236, U.S. Patent Application Publication No. 2008/0064049, and U.S. Patent Application Publication No. 2008/0178305, each of which is incorporated by reference herein in its entirety.

In certain embodiments, antibodies to human frizzled receptors mediate cell death of a cell expressing the FZD protein via antibody-dependent cellular cytotoxicity (ADCC). ADCC involves cell lysis by effector cells that recognize the Fcc portion of an antibody. Many lymphocytes, monocytes, tissue macrophages, granulocytes and eosinophiles, for example, have Fc receptors and can mediate cytolysis (Dillman, 1994. J. Clin. Oncol. 12:1497).

In certain embodiments, antibodies to one or more FZDs trigger cell death of a cell expressing the FZD protein(s) by activating complement-dependent cytotoxicity (CDC). CDC involves binding of serum complement to the Fc portion of an antibody and subsequent activation of the complement protein cascade, resulting in cell membrane damage and eventual cell death. Biological activity of antibodies is known to be determined, to a large extent, by the constant domains or Fc region of the antibody molecule (Uananue and Benacerraf, Textbook of Immunology, 2nd Edition. Williams & Wilkins, p. 218 (1984)). Antibodies of different classes and subclasses differ in this respect, as do antibodies of the same subclass but from different species. Of human antibodies. 1 µM is the most efficient class of antibodies to bind complement, followed by IgG1, IgG3, and IgG2 whereas IgG4 appears quite deficient in activating the complement cascade (Dillman, 1994, J. Clin. Oncol. 12:1497; Jefferis et al., 1998, Immunol. Rev. 163:59-76). According to the present invention, antibodies of those classes having the desired biological activity are prepared.

The ability of any particular antibody against one or more FZDs to mediate lysis of the target cell by complement activation and/or ADCC can be assayed. The cells of interest are grown and labeled in vitro; the antibody is added to the cell culture in combination with either serum complement or immune cells which can be activated by the antigen antibody complexes. Cytolysis of the target cells is detected, for example, by the release of label from the lysed cells. In fact, antibodies can be screened using the patient's own serum as a source of complement and/or immune cells. The antibody that is capable of activating complement or mediating ADCC in the in vitro test can then be used therapeutically in that particular patient.

The invention provides polypeptides, including, but not limited to, antibodies that specifically bind to one or more human frizzled receptors, that comprise one, two, three, four, five and/or six of the CDRs of 18R5 and/or 18R8 (see Table 4 of Example 1 below) with up to four (i.e., 0, 1, 2, 3, or 4) conservative amino acid substitutions per CDR. Thus, the invention provides polypeptides, including, but not limited to, antibodies that specifically bind to one or more human frizzled receptors that comprise one, two, three, four, five and/or six of the CDRs of 18R5 and/or 18R8. In certain embodiments, the polypeptides comprise the heavy chain CDR3 of 18R8 and/or the light chain CDR3 of 18R5 or 18R8. In certain embodiments, the heavy chain CDR(s) are contained within a heavy chain variable region and/or the light chain CDR(s) are contained within a light chain variable region.

For example, the invention provides a polypeptide (e.g., an antibody) that specifically binds a human frizzled receptor, wherein the polypeptide comprises a heavy chain variable region comprising: (a) a heavy chain CDR1 comprising GFTFSHYTLS (SEQ ID NO:1), or a variant thereof comprising 1, 2, 3, or 4 amino acid substitutions; (b) a heavy chain CDR2 comprising VISGDGSYTYYADSVKG (SEQ ID NO:2), or a variant thereof comprising 1, 2, 3, or 4 amino acid substitutions; and/or (c) a heavy chain CDR3 comprising NFIKYVFAN (SEQ ID NO:3), or a variant thereof comprising 1, 2, 3, or 4 amino acid substitutions. In certain embodiments, the polypeptide further comprises a light chain variable region comprising: (a) a light chain CDR1 comprising SGDKLGKKYAS (SEQ ID NO:4) or SGDNIGSFYVH (SEQ ID NO:7), or a variant of SEQ ID NO:4 or SEQ ID NO:7 comprising 1, 2, 3, or 4 amino acid substitutions; (b) a light chain CDR2 comprising EKDNRPSG (SEQ ID NO:5) or DKSNRPSG (SEQ ID NO:8), or a variant of SEQ ID NO:5 or SEQ ID NO:8 comprising 1, 2, 3, or 4 amino acid substitutions; and/or (c) a light chain CDR3 comprising SSFAGNSLE (SEQ ID NO:6) or QSYANTLSL (SEQ ID NO:9), or a variant of SEQ ID NO:6 or SEQ ID NO:9 comprising 1, 2, 3, or 4 amino acid substitutions. In certain embodiments, the amino acid substitutions are conservative substitutions.

Thus, the invention provides polypeptides or antibodies that comprise a heavy chain CDR1 comprising GFTFSHYTLS (SEQ ID NO:1), a heavy chain CDR2 comprising VISGDGSYTYYADSVKG (SEQ ID NO:2), and/or a heavy chain CDR3 comprising NFIKYVFAN (SEQ ID NO:3). In certain embodiments, the light chain CDR(s) are contained within a variable region of an antibody heavy chain. In certain embodiments, the polypeptide or antibody comprising the one or more of heavy chain CDRs specifically binds one or more human frizzled receptors. In certain embodiments, the CDR(s) have been modified with 1, 2, 3, or 4 conservative amino acid substitutions. In certain embodiments, each of the heavy chain CDR(s) has been modified by no more than 1-2 conservative amino acid substitutions.

The invention also provides an antibody that specifically binds a human frizzled receptor, wherein the antibody comprises a heavy chain variable region comprising: (a) a heavy chain CDR I comprising GFTFSHYTLS (SEQ ID NO:1), or a variant thereof comprising 1, 2, 3, or 4 amino acid substitutions: (b) a heavy chain CDR2 comprising VISGDGSYTYYADSVKG (SEQ ID NO:2), or a variant thereof comprising 1, 2, 3, or 4 amino acid substitutions; and (c) a heavy chain CDR3 comprising NFIKYVFAN (SEQ ID NO:3), or a variant thereof comprising 1, 2, 3, or 4 amino acid substitutions. In certain embodiments, the antibody further comprises a light chain variable region comprising: (a) a light chain CDR1 comprising SGDKLGKKYAS (SEQ ID NO:4) or SGDNIGSFYVH (SEQ ID NO:7), or a variant of SEQ ID NO:4 or SEQ ID NO:7 comprising 1, 2, 3, or 4 amino acid substitutions; (b) a light chain CDR2 comprising EKDNRPSG (SEQ ID NO:5) or DKSNRPSG (SEQ ID NO:8), or a variant of SEQ ID NO:5 or SEQ ID NO:8 comprising 1, 2, 3, or 4 amino acid substitutions; and (c) a light chain CDR3 comprising SSFAGNSLE (SEQ ID NO:6) or QSYANTLSL (SEQ ID NO:9), or a variant of SEQ ID NO:6 or SEQ ID NO:9 comprising 1, 2, 3, or 4 amino acid substitutions. In some alternative embodiments, the antibody instead further comprises a light chain variable region comprising: (a) a light chain CDR1 comprising SGDKLGKKYAS (SEQ ID NO:4) or SGDNIGSFYVH (SEQ ID NO:7); (b) a light chain CDR2 comprising EKDNRPSG (SEQ ID NO:5) or DKSNRPSG (SEQ ID NO:8); and (c) a light chain CDR3 comprising SSFAGNSLE (SEQ ID NO:6) or QSYANTLSL (SEQ ID NO:9). In certain embodiments, the antibody specifically binds FZD1, FZD2, FZD5, FZD7, and/or FZD8. In certain embodiments, the antibody specifically binds two or more human frizzled receptors including FZD5 and FZD8. In certain embodiments, the amino acid substitutions are conservative substitutions.

The invention further provides a polypeptide (e.g., an antibody) that specifically binds a human frizzled receptor, wherein the polypeptide comprises a light chain variable region comprising: (a) a light chain CDR1 comprising SGDKLGKKYAS (SEQ ID NO:4) or SGDNIGSFYVH (SEQ ID NO:7), or a variant of SEQ ID NO:4 or SEQ ID NO:7 comprising 1, 2, 3, or 4 amino acid substitutions; (b) a light chain CDR2 comprising EKDNRPSG (SEQ ID NO:5) or DKSNRPSG (SEQ ID NO:8), or a variant of SEQ ID NO:5 or SEQ ID NO:8 comprising 1, 2, 3, or 4 amino acid substitutions: and/or (c) a light chain CDR3 comprising SSFAGNSLE (SEQ ID NO:6) or QSYANTLSL (SEQ ID NO:9), or a variant of SEQ ID NO:6 or SEQ ID NO:9 comprising 1, 2, 3, or 4 amino acid substitutions. In certain embodiments, the amino acid substitutions are conservative substitutions.

Also provided are polypeptides or antibodies that comprise (a) a light chain CDR1 comprising the sequence SGD(K/N)(L/I)G(K/S)(K/F)Y(A/V)(S/H) (SEQ ID NO:71) or the sequence of SEQ ID NO:71 with up to four (i.e., 0, 1, 2, 3, or 4) conservative amino acid substitutions, (b) a light chain CDR2 comprising the sequence (E/D)K(D/S)NRPSG (SEQ ID NO:72) or the sequence of SEQ ID NO:72 with up to four conservative amino acid substitutions, and/or (c) a light chain CDR3 comprising the sequence (S/Q)S(F/Y)A(G/N)(N/T)(no aa/L)SL(E/no aa) (where "no aa/L" indicates either L or no amino acid and "E/no aa" indicates either E or no amino acid; SEQ NO:73) or the sequence of SEQ ID NO:73 with up to four conservative amino acid substitutions.

The invention also provides polypeptides or antibodies that comprise a light chain CDR1 comprising SGDKLGKKYAS (SEQ ID NO:4) or SGDNIGSFYVH (SEQ ID NO:7), a light chain CDR2 comprising EKDNRPSG (SEQ ID NO:5) or DKSNRPSG (SEQ ID NO:8), and/or a light chain CDR3 comprising SSFAGNSLE (SEQ ID NO:6) or QSYANTLSL (SEQ ID NO:9). In certain embodiments, the polypeptide or antibody comprises a light chain CDR1 comprising SGDNIGSFYVH (SEQ ID NO:7), a light chain CDR2 comprising DKSNRPSG (SEQ ID NO:8), and a light chain CDR3 comprising QSYANTLSL (SEQ ID NO:9). In certain alternative embodiments, the polypeptide or antibody comprises a light chain CDR1 comprising SGDKLGKKYAS (SEQ ID NO:4), a light chain CDR2 comprising EKDNRPSG (SEQ ID NO:5), and a light chain CDR3 comprising SSFAGNSLE (SEQ ID NO:6). In certain embodiments, the light chain CDR(s) are contained within a variable region of an antibody light chain. In certain embodiments, the polypeptide or antibody specifically binds one or more human frizzled receptors. In certain embodiments, the polypeptide or antibody comprising the one or more of light chain CDRs specifically binds one or more human frizzled receptors. In certain embodiments, the CDR(s) have been modified with 1, 2, 3, or 4 conservative modifications. In certain embodiments, each of the light chain CDR(s) has been modified by no more than 1-2 conservative amino acid substitutions.

In certain embodiments, the antibody comprises (a) a heavy chain CDR1 comprising GFTFSHYTLS (SEQ ID NO:1), a heavy chain CDR2 comprising VISGDGSYTYYADSVKG (SEQ ID NO:2), and a heavy chain CDR3 comprising NFTKYVFAN (SEQ ID NO:3); and/or (b) a light chain CDR1 comprising SGDKLGKKYAS (SEQ ID NO:4) or SGDNIGSFYVH (SEQ ID NO:7), a light chain CDR2 comprising EKDNRPSG (SEQ ID NO:5) or DKSNRPSG (SEQ ID NO:8), and a light chain CDR3 comprising SSFAGNSLE (SEQ ID NO:6) or QSYANTLSL (SEQ ID NO:9). In certain embodiments, the antibody comprises (a) a heavy chain CDR1 comprising GFTFSHYTLS (SEQ ID NO:1), a heavy chain CDR2 comprising VISGDGSYTYYADSVKG (SEQ ID NO:2), and a heavy chain CDR3 comprising NFIKYVFAN (SEQ ID NO:3); and (b) a light chain CDR1 comprising SGDKLGKKYAS (SEQ ID NO:4), a light chain CDR2 comprising EKDNRPSG (SEQ ID NO:5), and a light chain CDR3 comprising SSFAGNSLE (SEQ ID NO:6). In certain embodiments, the antibody comprises (a) a heavy chain CDR1 comprising GFTFSHYTLS (SEQ ID NO: 1), a heavy chain CDR2 comprising VISGDGSYTYYADSVKG (SEQ ID NO:2), and a heavy chain CDR3 comprising NFIKYVFAN (SEQ ID NO:3) and (b) a light chain CDR1 comprising SGDNIGSFYVH (SEQ ID NO:7), a light chain CDR2 comprising DKSNRPSG (SEQ ID NO:8), and a light chain CDR3 comprising QSYANTLSL (SEQ ID NO:9). In certain embodiments, the CDR(s) have been modified with 1, 2, 3, or 4 conservative amino acid substitutions. In certain embodiments, each of the CDR(s) has been modified by no more than 1-2 conservative amino acid substitutions.

The invention further provides polypeptides, including, but not limited to, antibodies that specifically bind to one or more human frizzled receptors, that comprise one, two, three, four, five and/or six of the CDRs of the anti-FZD antibody 44R24 (see Table 7 of Example 18 below) with up to four (i.e., 0, 1, 2, 3, or 4) conservative amino acid substitutions per CDR. Thus, the invention provides polypeptides, including, but not limited to, antibodies that specifically bind to one or more human frizzled receptors that comprise one, two, three, four, five and/or six of the CDRs of 44R24. In certain embodiments, the polypeptides comprise the heavy chain CDR3 of 44R24 and/or the light chain CDR3 of 44R24. In certain embodiments, the heavy chain CDR(s) are contained within a heavy chain variable region and/or the light chain CDR(s) are contained within a light chain variable region.

The invention also provides a polypeptide (e.g. an antibody) that specifically binds human FZD5 and/or FZD8, wherein the antibody comprises: (a) a heavy chain CDR1 comprising GFTFSSYYIT (SEQ ID NO:77), or a variant thereof comprising 1, 2, 3, or 4 conservative amino acid substitutions; a heavy chain CDR2 comprising TISYSSSNTYYADSVKG (SEQ ID NO:78), or a variant thereof comprising 1, 2, 3, or 4 conservative amino acid substitutions; and a heavy chain CDR3 comprising SIVFDY (SEQ ID NO:79), or a variant thereof comprising 1, 2, 3, or 4 conservative amino acid substitutions; and/or (b) a light chain CDR1 comprising SGDALGNRYVY (SEQ ID NO:80), or a variant thereof comprising 1, 2, 3, or 4 conservative amino acid substitutions; a light chain CDR2 comprising SG (SEQ ID NO:81), or a variant thereof comprising 1, 2, 3, or 4 conservative amino acid substitutions; and a light chain CDR3 comprising GSWDTRPYPKY (SEQ ID NO:82), or a variant thereof comprising 1, 2, 3, or 4 conservative amino acid substitutions. In certain embodiments, the antibody (or other FZD-binding polypeptide) comprises: (a) a heavy chain CDR1 comprising GFTFSSYYIT (SEQ ID NO:77), a heavy chain CDR2 comprising TISYSSSNTYYADSVKG (SEQ ID NO:78), and a heavy chain CDR3 comprising SIVFDY (SEQ ID NO:79); and/or (b) a light chain CDR1 comprising SGDALGNRYVY (SEQ ID NO:80), a light chain CDR2 comprising SG (SEQ ID NO:81), and a light chain CDR3 comprising GSWDTRPYPKY (SEQ ID NO:82).

Polypeptides comprising one of the individual light chains or heavy chains described herein, as well as polypeptides (e.g., antibodies) comprising both a light chain and a heavy chain are also provided.

Also provided are polypeptides that comprise: (a) a polypeptide having at least about 80% sequence identity to SEQ ID NO: 10; and/or (b) a polypeptide having at least about 80% sequence identity to SEQ ID NO:12 or SEQ ID NO:14. In certain embodiments, the polypeptide comprises a polypeptide having at least about 85%, at least about 90%, at least about 95%, at least about 97%, or at least about 99% sequence identity to SEQ ID NOs:10, 12, or 14. Thus, in certain embodiments, the polypeptide comprises (a) a polypeptide having at least about 95% sequence identity to SEQ ID NO:10, and/or (b) a polypeptide having at least about 95% sequence identity to SEQ ID NO:12 or 14. In certain embodiments, the polypeptide comprises (a) a polypeptide having the amino acid sequence of SEQ ID NO: 10; and/or (b) a polypeptide having the amino acid sequence of SEQ ID NO:12 or SEQ ID NO:14. In certain embodiments, the polypeptide comprises (a) a polypeptide having the amino acid sequence of SEQ ID NO: 11: and/or (b) a polypeptide having the amino acid sequence of SEQ ID NO:13 or SEQ ID NO:15. In certain embodiments, the polypeptide is an antibody and/or the polypeptide specifically binds one or more human frizzled receptors (e.g., FZD1, FZD2. FZD5, FZD7 and/or FZD8). For example, the invention provides an antibody that specifically binds a human frizzled receptor that comprises (a) a polypeptide having the amino acid sequence of SEQ ID NO: 10; and (b) a polypeptide having the amino acid sequence of SEQ ID NO: 14. In certain embodiments the polypeptide comprising SEQ ID NO:10 is a heavy chain variable region. In certain embodiments, the polypeptide comprising SEQ ID NO:12 or 14 is a light chain variable region. In certain embodiments, the polypeptide having a certain percentage of sequence identity to SEQ ID NO:10, 12, or 14 differs from SEQ ID NO:10, 12, or 14 by conservative amino acid substitutions only.

In certain embodiments the polypeptide or antibody comprises: (a) SEQ ID NO:10 and SEQ ID NO: 12; (b) SEQ ID NO: 10 and SEQ ID NO:14; (c) SEQ ID NO:11 and SEQ ID NO:13; or (d) SEQ ID NO:11 and SEQ ID NO: 15.

The invention further provides an antibody or other polypeptide that specifically binds to FZD5 and/or FZD8 and comprises: (a) a polypeptide having at least about 80%, at least about 85%, at least about 90%, at least about 95%, at least about 97%, or at least about 99% identity to SEQ ID NO:85; and/or (b) a polypeptide having at least about 80%, at least about 85%, at least about 90%, at least about 95%, at least about 97%, or at least about 99% identity to SEQ ID NO:86. In certain alternative embodiments, the polypeptide or antibody comprises SEQ ID NO:85 and/or SEQ ID NO:86.

In certain embodiments, the FZD-binding agent comprises, consists essentially of, or consists of an anti-FZD antibody selected from the group consisting of 18R8, 18R5, 18R4605, 18R4805, and 44R24 IgG antibodies.

In certain embodiments, the FZD-binding agent is not the 44M1, 44M2, 44M13, 44M15, 44M17, 44M18, 18M4, 18M6, 18M17, 18M18, 54M1, 54M2, 54M3, 54M4, 54M5, 54M6, or 54M7 antibody reported in U.S. Patent Application Publication No. US 2007/0116701, which is incorporated by reference herein in its entirety. In certain embodiments, the FZD-binding agent is an antibody that binds FZD5, but is not 44M13.

In certain embodiments, the FZD-binding agent comprises the heavy chains and light chains of the 18R8 IgG2 antibody (with or without the leader sequence). In certain embodiments, the FZD-binding agent is the 18R8 IgG2 antibody. DNA encoding the heavy chains and light chains of the 18R8 IgG2 antibody was deposited with the American Type Culture Collection (ATCC), 10801 University Boulevard, Manassas, Va., USA, under the conditions of the Budapest Treaty on Sep. 29, 2008, and assigned ATCC deposit designation number PTA-9540. In certain embodiments, the FZD-binding agent comprises the heavy chains and light chains of the 18R5 IgG2 antibody (with or without the leader sequence). In certain embodiments, the FZD-binding agent is the 18R5 IgG2 antibody. DNA encoding the heavy chains and light chains of the 18R5 IgG2 antibody was deposited with the ATCC, under the conditions of the Budapest Treaty on Sep. 29, 2008, and assigned ATCC deposit designation number PTA-9541.

In certain embodiments, the FZD-binding agent is an IgG antibody encoded by the plasmid deposited with the ATCC on Aug. 26, 2009, and assigned deposit designation number PTA-10307. PTA-10309, or PTA-10311.

In certain embodiments, the FZD-binding agent is an agent that competes for specific binding to FZD1, FZD2, FZD5, FZD7, and/or FZD8 with an antibody encoded by the plasmid having ATCC deposit designation number PTA-9540, PTA-9541, PTA-10307, or PTA-10309 (e.g., in a competitive binding assay). In certain alternative embodiments, the FZD-binding agent is an agent that competes for specific binding to FZD5 and/or FZD8 with an antibody encoded by the plasmid having ATCC deposit designation number PTA-10311.

In certain embodiments, the FZD-binding agent has a circulating half-life in mice, cynomologous monkeys, or humans of at least about 10 hours, at least about 24 hours, at least about 3 days, at least about 1 week, or at least about 2 weeks. In certain embodiments, the FZD-binding agent is an IgG (e.g., IgG1 or IgG2) antibody that has a circulating half-life in mice, cynomologous monkeys, or humans of at least about 10 hours, at least about 24 hours, at least about 3 days, at least about 1 week, or at least about 2 weeks. Methods of increasing the half-life of agents such as polypeptides and antibodies are known in the art. For example, known methods of increasing the circulating half-life of IgG antibodies include the introduction of mutations in the Fc region which increase the pH-dependent binding of the antibody to the neonatal Fc receptor (FcRn) at pH 6.0 (see, e.g. U.S. Pat. Pub. Nos. 2005/0276799, 2007/0148164, and 2007/0122403). Known methods of increasing the circulating half-life of antibody fragments lacking the Fc region include such techniques as PEGylation.

Polyclonal antibodies can be prepared by any known method. Polyclonal antibodies are raised by immunizing an animal (e.g. a rabbit, rat, mouse, donkey, etc) by multiple subcutaneous or intraperitoneal injections of the relevant antigen (a purified peptide fragment, full-length recombinant protein, fusion protein, etc) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature. 352:624-628; and Marks et al., 1991. J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the human frizzled receptor(s) is a humanized antibody. In certain embodiments, such antibodies are used therapeutically to reduce antigenicity and HAMA (human anti-mouse antibody) responses when administered to a human subject. Humanized antibodies can be produced using various techniques known in the art. In certain alternative embodiments, the antibody to the human frizzled receptor(s) is a human antibody. In certain embodiments, the agent is an antibody, such as a monoclonal antibody, that is not a murine antibody.

Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety). Affinity maturation strategies and chain shuffling strategies (Marks et al., 1992, Bio/Technology 10:779-783, incorporated by reference in its entirety) are known in the art and may be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize a human frizzled receptor. Bispecific antibodies are antibodies that are capable of specifically recognizing and binding at least two different epitopes. The different epitopes can either be within the same molecule (e.g. the same human frizzled receptor) or on different molecules such that both, for example, the antibodies can specifically recognize and bind a human frizzled receptor as well as, for example, 1) an effector molecule on a leukocyte such as a T-cell receptor (e.g. CD3) or Fc receptor (e.g. CD64, CD32, or CD16) or 2) a cytotoxic agent as described in detail below. In certain embodiments, the bispecific antibody specifically binds at least one human frizzled receptor, as well as either VEGF, a Notch ligand, such as a delta-like ligand (for example, DLL4) or jagged, or at least one Notch receptor selected from the group consisting of Notch 1, Notch 2, Notch 3, and Notch 4. Bispecific antibodies can be intact antibodies or antibody fragments.

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g. CD2, CD3, CD28, or B7), or Fc receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Techniques for making bispecific antibodies are common in the art (Millstein et al., 1983, Nature 305:537-539; Brennan et al., 1985, Science 229:81; Suresh et al, 1986. Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148:1547-1553; Gruber et al., 1994, J. Immunol. 152:5368; and U.S. Pat. No. 5,731,168). Antibodies with more than two valencies are also contemplated. For example, trispecific antibodies can be prepared (Tutt et al., J. Immunol. 147:60 (1991)). Thus, in certain embodiments the antibodies to human frizzled receptor(s) are multispecific.

Alternatively, in certain alternative embodiments, the FZD-binding agents of the invention are not bispecific antibodies. In certain embodiments, each of the antigen-binding sites of the antibody is identical to the other(s).

In certain embodiments, an individual antigen-binding site binds to a region that is homologous between two or more frizzled receptors (e.g., FZD1, FZD2, FZD5, FZD7, and/or FZD8). In certain embodiments, an antigen-binding site binds to a region in the BBS that is homologous between two or more frizzled receptors.

In certain embodiments, the antibodies (or other polypeptides) described herein may be monospecific. For example, in certain embodiments, each of the one or more antigen-binding sites that an antibody contains is capable of binding (or binds) the same one or more human FZD receptors (e.g., FZD1, FZD2, FZD5, FZD7, or FZD8, or a homologous epitope on some combination of the FZDs). In certain embodiments, an antigen-binding site of a monospecific antibody described herein is capable of binding (or binds) one, two, three, four, or five (or more) human frizzled receptors.

In certain embodiments are provided an antibody fragment to, for example, increase tumor penetration. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

According to the present invention, techniques can be adapted for the production of single-chain antibodies specific to one or more human frizzled receptors (see U.S. Pat. No. 4,946,778). In addition, methods can be adapted for the construction of Fab expression libraries (Huse, et al., Science 246:1275-1281 (1989)) to allow rapid and effective identification of monoclonal Fab fragments with the desired specificity for a FZD receptor, or derivatives, fragments, analogs or homologs thereof. Antibody fragments may be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the polypeptides of a human FZD receptor. In this regard, the variable region may comprise or be derived from any type of mammal that can be induced to mount a humoral response and generate immunoglobulins against the desired tumor associated antigen. As such, the variable region of the modified antibodies can be, for example, of human, murine, non-human primate (e.g. cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies (e.g. full-length antibodies or immunoreactive fragments thereof) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein may comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ΔCH2 constructs). In some embodiments, the omitted constant region domain will be replaced by a short amino acid spacer (e.g. 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain embodiments, the FZD-binding antibodies provide for altered effector functions that, in turn, affect the biological profile of the administered antibody. For example, the deletion or inactivation (through point mutations or other means) of a constant region domain may reduce Fc receptor binding of the circulating modified antibody thereby increasing tumor localization. In other cases it may be that constant region modifications, consistent with this invention, moderate complement binding and thus reduce the serum half life and nonspecific association of a conjugated cytotoxin. Yet other modifications of the constant region may be used to eliminate disulfide linkages or oligosaccharide moieties that allow for enhanced localization due to increased antigen specificity or antibody flexibility. Similarly, modifications to the constant region in accordance with this invention may easily be made using well known biochemical or molecular engineering techniques well within the purview of the skilled artisan.

In certain embodiments, a FZD-binding agent that is an antibody does not have one or more effector functions. For instance, in some embodiments, the antibody has no antibody-dependent cellular cytotoxicity (ADCC) activity and/or no complement-dependent cytoxicity (CDC) activity. In certain embodiments, the antibody does not bind to an Fc receptor and/or complement factors. In certain embodiments, the antibody has no effector function.

It will be noted that in certain embodiments, the modified antibodies may be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer may be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic, or even omitted altogether, so as to maintain the desired biochemical qualities of the modified antibodies.

Besides the deletion of whole constant region domains, it will be appreciated that the antibodies of the present invention may be provided by the partial deletion or substitution of a few or even a single amino acid. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement CLQ binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention also pertains to immunoconjugates comprising an antibody conjugated to a cytotoxic agent. Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Enzymatically active toxins and fragments thereof that can be used include diphtheria A chain, nonbinding active fragments of diphtheria toxin, exotoxin A chain, ricin A chain, abrin A chain, modeccin A chain, alpha-sarcin, *Aleurites fordii* proteins, dianthin proteins. *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies including 212Bi, 131I, 131In, 90Y, and 186Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Conjugates of an antibody and one or more small molecule toxins, such as a calicheamicin, maytansinoids, a trichothene, and CC1065, and the derivatives of these toxins that have toxin activity, can also be used.

Conjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

Regardless of how useful quantities are obtained, the antibodies of the present invention can be used in any one of a number of conjugated (i.e. an immunoconjugate) or unconjugated forms. Alternatively, the antibodies of this invention can be used in a nonconjugated or "naked" form. In certain embodiments, the antibodies are used in nonconjugated form to harness the subject's natural defense mechanisms including complement-dependent cytotoxicity (CDC) and antibody dependent cellular toxicity (ADCC) to eliminate the malignant cells. In some embodiments, the antibodies can be conjugated to radioisotopes, such as $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re using anyone of a number of well known chelators or direct labeling. In other embodiments, the disclosed compositions can comprise antibodies coupled to drugs, prodrugs or biological response modifiers such as methotrexate, adriamycin, and lymphokines such as interferon. Still other embodiments of the present invention comprise the use of antibodies conjugated to specific biotoxins such as ricin or diptheria toxin. In yet other embodiments the modified antibodies can be complexed with other immunologically active ligands (e.g. antibodies or fragments thereof) wherein the resulting molecule binds to both the neoplastic cell and an effector cell such as a T cell. The selection of which conjugated or unconjugated modified antibody to use will depend of the type and stage of cancer, use of adjunct treatment (e.g., chemotherapy or external radiation) and patient condition. It will be appreciated that one skilled in the art could readily make such a selection in view of the teachings herein.

The polypeptides of the present invention can be recombinant polypeptides, natural polypeptides, or synthetic polypeptides comprising an antibody, or fragment thereof, against a human FZD receptor. It will be recognized in the art that some amino acid sequences of the invention can be varied without significant effect of the structure or function of the protein. Thus, the invention further includes variations of the polypeptides which show substantial activity or which include regions of an antibody, or fragment thereof, against a human FZD receptor protein. Such mutants include deletions, insertions, inversions, repeats, and type substitutions.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against human frizzled receptors. Recombinant expression vectors are replicable DNA constructs which have synthetic or cDNA-derived DNA fragments encoding a polypeptide chain of an anti-FZD antibody, or fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Esherichia coli*, including pCR 1, pBR322, pMB9 and their derivatives, wider host range plasmids, such as M13 and filamentous single-stranded DNA phages.

Suitable host cells for expression of a FZD-binding polypeptide or antibody (or a FZD protein to use as an antigen) include prokaryotes, yeast, insect or higher eukaryotic cells under the control of appropriate promoters. Prokaryotes include gram negative or gram positive organisms, for example E. coli or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO). HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a FZD-binding agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication No. 2008/0312425, 2008/0177048, and 2009/0187005, each of which is hereby incorporated by reference herein in its entirety.

In certain embodiments, the FZD-binding agent is a polypeptide that is not an antibody. A variety of methods for identifying and producing non-antibody polypeptides that bind with high affinity to a protein target are known in the art. See, e g., Skerra, Curr. Opin. Biotechnol., 18:295-304 (2007), Hosse et al., Protein Science. 15:14-27 (2006), Gill et al. Curr. Opin. Biotechnol., 17:653-658 (2006), Nygren, FEBS J., 275:2668-76 (2008), and Skerra, FEBS J., 275: 2677-83 (2008), each of which is incorporated by reference herein in its entirety In certain embodiments, phage display technology has been used to identify/produce the FZD-binding polypeptide. In certain embodiments, the polypeptide comprises a protein scaffold of a type selected from the group consisting of protein A, a lipocalin, a fribronectin domain, an ankyrin consensus repeat domain, and thioredoxin.

In certain embodiments, the polypeptide has been naturally or unnaturally modified. By way of non-limiting example, the polypeptide may be labeled. In certain embodiments, the polypeptide is glycosylated, pegylated, phosphorylated, or acetylated, amidated. In certain embodiments, the modifications increase stability and/or the in vivo half-life of the polypeptide. In certain embodiments, the polypeptides are cyclic. In certain further embodiments, the polypeptides comprise one or more N-methyl amino acids.

In certain embodiments, the FZD-binding agent is (or comprises) a polypeptide comprising (a) a sequence selected from the group consisting of SEQ ID NOs:98-112 or (b) a sequence having at least about 80% amino acid sequence identity to a sequence selected from the group consisting of SEQ ID NOs:98-111. In certain embodiments, the polypeptide comprises a sequence having at least about 85%, at least about 88%, or at least about 90% amino acid sequence identity to a sequence selected from the group consisting of SEQ ID NOs:98-11. In certain embodiments, the polypeptides comprise, consist essentially of, or consist of a cyclic peptide selected from the group consisting of SEQ ID NOs:98-112. In certain embodiments, the sequence is SEQ ID NO:108. In certain alternative embodiments, the sequence is SEQ ID NO: 112.

In certain alternative embodiments, the FZD-binding agent is (or comprises) a polypeptide having at least about 80%, at least about 85%, at least about 88%, or at least about 90% amino acid sequence identity to a sequence selected from the group consisting of SEQ ID NOs:113-116. In certain alternative embodiments, the FZD-binding agent is (or comprises) a polypeptide comprising, consisting essentially of, or consisting of a sequence selected from the group consisting of SEQ ID NOs: 113-116.

In certain embodiments, the FZD-binding polypeptide may be less than about 500 amino acids in length, less than about 200 amino acids in length, less than about 100 amino acids in length, less than about 50 amino acids in length, less than about 20 amino acids amino acids in length, or less than about 15 amino acids in length. Such polypeptides may be at least about 3, at least about 5, or at least about 7 amino acids in length. Accordingly, in certain embodiments the polypeptide may be between about 5 and about 20 amino acids in length. In some embodiments, the polypeptide is between about 7 and about 15 amino acids in length.

In some embodiments, the agent is a non-protein molecule. In certain embodiments, the agent is a small molecule. Combinatorial chemistry libraries and techniques useful in the identification of non-protein FZD-binding agents are known to those skilled in the art. See, e.g., Kennedy et al., J. Comb. Chem., 10:345-354 (2008), Dolle et al, J. Comb. Chem., 9:855-902 (2007), and Bhattacharyya. Curr. Med. Chem., 8:1383-404 (2001), each of which is incorporated by reference herein in its entirety. In certain further embodiments, the agent is a carbohydrate, a glycosaminoglycan, a glycoprotein, or a proteoglycan.

In certain embodiments, the agent comprises a lipid. For instance, in some instances, the agent may comprise a fatty acid or a derivative thereof. In certain embodiments, the fatty acid is myristoleic acid, palmitoleic acid, sapienic acid, oleic acid, linoleic acid, α-linolenic acid, arachidonic acid, eicosapentaenoic acid, erucic acid, or docosahexaenoic acid. Because the cleft of the BBS is hydrophobic, agents comprising one or more lipids are particularly suitable for targeting the cleft.

In certain embodiments, the agent is a nucleic acid aptamer. Aptamers are polynucleotide molecules that have been selected (e.g., from random or mutagenized pools) on the basis of their ability to bind to another molecule. In some embodiments, the aptamer comprises a DNA polynucleotide. In certain alternative embodiments, the aptamer comprises an RNA polynucleotide. In certain embodiments, the aptamer comprises one or more modified nucleic acid residues. Methods of generating and screening nucleic acid aptamers for binding to proteins are well known in the art. See, e.g., U.S. Pat. No. 5,270,163, U.S. Pat. No. 5,683,867, U.S. Pat. No. 5,763,595, U.S. Pat. No. 6,344,321, U.S. Pat. No. 7,368,236, U.S. Pat. No. 5,582,981, U.S. Pat. No. 5,756,291, U.S. Pat. No. 5,840,867. U.S. Pat. No. 7,312,325, U.S. Pat. No. 7,329,742. International Patent Publication No. WO 02/077262, International Patent Publication No. WO 03/070984, U.S. Patent Application Publication No. 2005/0239134, U.S. Patent Application Publication No. 2005/0124565, and U.S. Patent Application Publication No. 2008/0227735, each of which is incorporated by reference herein in its entirety.

In certain embodiments, the agent has a molecular weight of at least about 100 daltons. In certain embodiments, the agent has a molecular weight of at least about 1000 daltons. In certain embodiments, the agent has a molecular weight of less than about 2000 daltons or less than about 1000 daltons.

The present invention further provides methods of screening agents for efficacy in inhibiting Wnt signaling, for anti-tumor efficacy, and/or efficacy against cancer stem cells. These methods include, but are not limited to, methods comprising comparing the levels of one or more differentiation markers in a first solid tumor that has been exposed to the agent relative to the levels of the one or more differentiation markers in a second solid tumor that has not been exposed to the agent. In certain embodiments, these methods include (a) exposing a first solid tumor, but not a second solid tumor, to the agent: (b) assessing the levels of one or more differentiation markers in the first and second solid tumors; and (c) comparing the levels of the one or more differentiation markers in the first and second solid tumors. In certain embodiments, the agent is an inhibitor of the canonical Wnt signaling pathway, and Lor inhibits binding of one or more human Wnt proteins to one or more human frizzled receptors. In certain embodiments, the agent is an antibody that specifically binds to one or more human frizzled receptor. In certain embodiments, increased levels of one or more differentiation markers in the first solid tumor relative to the second solid tumor indicates efficacy against solid tumor stem cells. In certain alternative embodiments, decreased levels of one or more differentiation markers (i.e., negative markers for differentiation) in the first solid tumor relative to the second solid tumor indicates efficacy against solid tumor stem cells. In certain embodiments, the solid tumor is a pancreatic tumor. In certain embodiments, the solid tumor is a pancreatic tumor and the one or more differentiation markers may comprise one or more mucins (e.g., Muc16) and/or chromogranin A (CHGA). In certain alternative embodiments, the solid tumor is a colon tumor. In some embodiments, the solid tumor is a colon tumor and the one or more differentiation markers comprise cytokeratin 7. Other potential differentiation markers for pancreas and colon as well as other tumor types are known to those skilled in the art. The usefulness of potential differentiation markers in a screening method can be readily assessed by one skilled in the art by treating the desired tumor type with one or more of the anti-FZD antibodies disclosed herein such as 18R5 and/or 44R24 and then assessing for changes in expression of the marker by the treated tumor relative to control. Non-limiting examples of such methods, can for instance, be found in the specific Examples below.

Useful reagents for additional screening assays include mutant FZD derivatives. For instance, polypeptides comprising the Fri domain of a frizzled receptor in which one or more (e.g., 1, 2, 3, 4, 5, 6, 7 or more) amino acid substitutions have been made in the Biological Binding Site (BBS). In certain embodiments, the mutant polypeptides exhibit a reduced binding affinity to a Wnt (e.g., Wnt3a), relative to the binding affinity that a polypeptide comprising the wild-type Fri domain of the frizzled receptor has for the Wnt. In certain embodiments, the wild-type Fri domain comprises a minimum Fri domain sequence such as a sequence selected from the group consisting of SEQ ID NOs. 117-126. Alternatively, the wild-type Fri domain comprises a polypeptide having a FZD Fri domain sequence selected from the group consisting of SEQ ID NOs. 28, 32, 36, 40, 44, 48, 52, 56, 60, and 64. In certain embodiments, one or more of the amino acid substitutions can be made at the site of a cleft residue selected from Table 16 and/or Table 17. In certain embodiments, the Fri domain is a FZD4, FZD5, or FZD8 Fri domain. In certain embodiments, the Fri domain is a FZD8 Fri domain comprising one or more substitutions at F72, L75, I78, or L121. In certain embodiments, the FZD8 Fri domain comprising a mutation at L75. An amino acid substitution(s) in the cleft of the BBS may, for example, be an amino acid residue(s) that is less hydrophobic than the amino acid residue at that same site in the wild-type FZD sequence. Alternatively, the one or more substitutions may be made in the top overhang and/or the bottom overhang of the BBS. In certain embodiments, the mutant FZD polypeptide is soluble. In certain embodiments, the mutant FZD polypeptide is a soluble FZD receptor and may comprise an Fc region, such as a human Fc region.

In certain embodiments, the invention provides a polypeptide comprising the Fri domain of FZD8 in which one or more substitutions have been made in the BBS which impair binding of FZD8 to Wnt. For example, the one or more substitutions may have been made in the cleft of the BBS. In certain embodiments, one or more substitutions have been made at F72, L75, I78, and/or L121. Non-limiting examples of possible substitutions include F72Y, L75S, I78S, or L121S. In certain embodiments, a substitution has been made at L75 (e.g., L75S). Assays for screening for agents which bind to the BBS of a FZD receptor (e.g., a human FZD receptor), inhibit Wnt signaling and/or can be used as therapeutic agents, such as anti-cancer agents, include assays in which a compound is screened for preferential binding to a wild-type FZD Fri domain sequence relative to a mutant FZD polypeptide in which one or more amino acid substitutions have been made in the BBS. For example, the invention provides a method of screening a compound for possible activity as an inhibitor of Wnt signaling. In one embodiment, the method comprises determining the binding affinity (qualitatively or quantitatively) of a compound for a first polypeptide comprising the Fri domain of a frizzled receptor, wherein the Fri domain comprises one or more substitutions in the Biological Binding Site (BBS). The method further comprises determining the binding affinity of the compound for a second polypeptide comprising the wild-type sequence of the Fri domain of the human Frizzled receptor of the first polypeptide, and then comparing the binding affinity of the compound for the first polypeptide with the binding affinity of the compound for the second polypeptide. If the compound has greater affinity for the second (wild-type FZD Fri domain) polypeptide than the first (mutant BBS) polypeptide, the compound is identified as a possible inhibitor of Wnt signaling (and candidate anti-cancer agent).

In certain embodiments, the FZD receptors in the above-described assays or other assays described herein are human FZD receptors. A human FZD receptor may be FZD1, FZD2, FZD3, FZD4, FZD5, FZD6, FZD7. FZD8, FZD9, or FZD10. Likewise, in certain embodiments of the aforementioned assays, or other assays described elsewhere herein, the Wnt protein is a human Wnt protein. For example, in certain embodiments, the Wnt protein is human Wnt3a, or another human Wnt protein described elsewhere herein.

The invention further provides additional polypeptides (e.g., FZD-binding polypeptides) useful in screening assays. For instance, the invention provides polypeptides comprising a sequence selected from the group consisting of SEQ ID NOs:98-112. In certain embodiments, the polypeptides comprise, consist essentially of, or consist of a cyclic peptide selected from the group consisting of SEQ ID NOs:98-112. The invention also provides isolated polypeptides comprising, consisting essentially of, or consisting of a sequence selected from the group consisting of SEQ ID NOs:113-116. In certain embodiments, the sequence is SEQ ID NO:108. In certain embodiments, the sequence is SEQ ID NO: 112. In certain alternative embodiments, the sequence is SEQ ID NO:113. The polypeptides used in the competitive binding assays and/or displacement assays are, in some instances, labeled or modified. Generally, any of the FZD-binding agents described herein can be used in such assays. In certain alternative embodiments, the FZD-binding polypeptide used in a competitive binding assay is the antibody 18R5.

Screening methods involving the use of the FZD-binding polypeptides described in the preceding paragraph or elsewhere herein are also provided (e.g. FZD-binding agents that bind to one or more residues in the cleft of the BBS). In one embodiment, a method of screening a compound for possible activity as an inhibitor of Wnt signaling comprises determining whether the compound can compete with a FZD-binding polypeptide for binding to a human FZD receptor (and/or displace the polypeptide from the FZD receptor to which it is bound.). In such a method, the ability of the compound to compete for binding with the polypeptide (and/or displace the polypeptide from the FZD receptor to which it is bound) indicates the compound has possible activity as an inhibitor of Wnt signaling. In certain embodiments, the FZD receptor is FZD8. In certain embodiments, the human FZD receptor molecule actually used in the screening assay is in a soluble form (e.g., a FZD-Fc molecule such as FZD8Fc, which comprises the extracellular domain or at least the Fri domain of the FZD protein fused to an Fc region).

In certain embodiments, the screening assays and/or other assays described herein have been used to identify the FZD-binding agents. For example, the agent may have been identified by a competitive binding or displacement assay using a polypeptide comprising one of SEQ ID NOs:98-116. Alternatively, the agent may have, for example been identified by reduced binding to a FZD containing one or more substitutions in the BBS relative to the wild-type FZD.

III. Polynucleotides

In certain embodiments, the invention encompasses polynucleotides comprising polynucleotides that encode a polypeptide that specifically binds a human FZD receptor or a fragment of such a polypeptide. For example, the invention provides a polynucleotide comprising a nucleic acid sequence that encodes an antibody to a human frizzled receptor or encodes a fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotides are isolated. In certain embodiments, the polynucleotides are substantially pure.

The invention provides a polynucleotide comprising a polynucleotide encoding a polypeptide comprising a sequence selected from the group consisting of SEQ ID NOs:10, 12, 14. The invention further provides a polynucleotide comprising a polynucleotide encoding a polypeptide comprising a sequence selected from the group consisting of SEQ ID NOs: 85-86. A polynucleotide comprising polynucleotides encoding a polypeptide comprising SEQ ID NOs: 11, 13, or 15 is also provided.

Also provided is a polynucleotide comprising a polynucleotide that encodes a polypeptide comprising a sequence selected from the group consisting of SEQ ID NOs:98-111 and SEQ ID NOs:113-116. In certain embodiments, the polynucleotide comprises a polynucleotide that encodes SEQ ID NO: 108.

The invention further provides a polynucleotide comprising a sequence selected from the group consisting of SEQ ID NOs:17, 19, and 21. Alternatively, in certain embodiments, the polynucleotide may comprise a sequence selected from the group consisting of SEQ ID NOs: 87-90, 92, and 94-95. Polynucleotide sequences comprising SEQ ID NO: 18, 20, or 22 are also provided.

Also provided is a polynucleotide that comprises a polynucleotide that hybridizes to a polynucleotide having the sequence of SEQ ID NO: 17, 19, or 21 and/or to a polynucleotide encoding a polypeptide having the sequence of SEQ ID NO:10, 12, or 14. Also provided is a polynucleotide that comprises a polynucleotide that hybridizes to a polynucleotide having a sequence selected from the group consisting of SEQ ID NOs: 87-90, 92, and 94-95 and/or to a polynucleotide encoding a polypeptide having the sequence of SEQ ID NO: 85 or 86. In certain embodiments, the hybridization is under conditions of high stringency.

In certain embodiments the polynucleotides comprise the coding sequence for the mature polypeptide fused in the same reading frame to a polynucleotide which aids, for example, in expression and secretion of a polypeptide from a host cell (e.g. a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g. COS-7 cells) is used.

The present invention further relates to variants of the hereinabove described polynucleotides encoding, for example, fragments, analogs, and derivatives.

In certain embodiments, the present invention provides isolated polynucleotides comprising polynucleotides having a nucleotide sequence at least 80% identical, at least 85% identical, at least 90% identical, at least 95% identical, and in some embodiments, at least 96%. 97%. 98% or 99% identical to a polynucleotide encoding a polypeptide comprising an antibody, or fragment thereof, to a human FZD receptor described herein.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons. e.g., to optimize codon expression for a particular host (change codons in the human mRNA to those preferred by a bacterial host such as E. coli).

Vectors and cells comprising the polynucleotides described herein are also provided.

IV. Methods of Use and Pharmaceutical Compositions

The FZD-binding agents (including polypeptides and antibodies) of the invention are useful in a variety of applications including, but not limited to, therapeutic treatment methods, such as the treatment of cancer. In certain embodiments, the agents are useful for inhibiting Wnt signaling (e.g. canonical Wnt signaling), inhibiting tumor growth, inducing differentiation, reducing tumor volume, and/or reducing the tumorigenicity of a tumor. The methods of use may be in vitro, ex vivo, or in vivo methods. In certain embodiments, the FZD-binding agent or polypeptide or antibody is an antagonist of the one or more human frizzled receptors to which it binds.

In certain embodiments, the FZD-binding agents or antagonists are used in the treatment of a disease associated with Wnt signaling activation. In certain embodiments, the methods comprise administering an effective amount of the FZD-binding agent to a subject. In certain embodiments, the disease is cancer or polycystic kidney disease. In particular embodiments, the disease is a disease dependent upon Wnt signaling. In particular embodiments, the Wnt signaling is canonical Wnt signaling. In certain embodiments, the FZD-binding agents or antagonists are used in the treatment of disorders characterized by increased levels of stem cells and/or progenitor cells.

In certain embodiments, the disease treated with the FZD-binding agent or antagonist (e.g., an anti-FZD antibody) is a cancer. In certain embodiments, the cancer is characterized by Wnt-dependent tumors. In certain embodiments, the cancer is characterized by tumors expressing one or frizzled receptors to which the FZD-binding agent (e.g., antibody) binds. In certain embodiments, the cancer is characterized by tumors expressing one or more genes in a Wnt gene signature.

In certain embodiments, the disease treated with the FZD-binding agent or antagonist is not a cancer. For example, the disease may be a metabolic disorder such as obesity or diabetes (e.g., type II diabetes) (Jin T., Diabetologia, 2008 October; 51(10):1771-80). Alternatively, the disease may be a bone disorder such as osteoporosis, osteoarthritis, or rheumatoid arthritis (Corr M., Nat Clin Pract Rheumatol, 2008 October; 4(10):550-6: Day et al., Bone Joint Surg Am, 2008 February; 90 Suppl 1:19-24). The disease may also be a kidney disorder, such as a polycystic kidney disease (Harris et al., Annu Rev Med, 2008 Oct. 23; Schmidt-Ott et al., Kidney Int, 2008 October; 74(8):1004-8; Benzing et al., J Am Soc Nephrol, 2007 May; 18(5): 1389-98). Alternatively, eye disorders including, but not limited to, macular degeneration and familial exudative vitreoretinopathy may be treated (Lad et al., Stem Cells Dev, 2008 Aug. 8). Cardiovascular disorders, including myocardial infarction, atherosclerosis, valve disorders, and cardiac hypertrophy may also be treated (Al-Aly Z., Transl Res, 2008 May; 151(5):233-9; Kobayashi et al., Nat Cell Biol, 2009 January; 11(1):46-55; van Gijn et al., Cardiovasc Res, 2002 July; 55(1):16-24; Christman et al., Am J Physiol Heart Circ Physiol, 2008 June; 294(6):H2864-70; Malekar et al., Hypertension, 2010 April; 55(4):939-45 (Epub 2010 Feb. 22).). In some embodiments, the disease is a pulmonary disorder such as idiopathic pulmonary arterial hypertension or pulmonary fibrosis (Laumanns et al., Am J Respir Cell Mol Biol, 2008 Nov. 21; Kinigshoff et al., PLoS ONE, 2008 May 14; 3(5):e2142). In some embodiments, the disease treated with the FZD-binding agent is a liver disease, such as cirrhosis or liver fibrosis (Cheng et al., Am J Physiol Gastrointest Liver Physiol, 2008 January; 294(1):G39-49).

Accordingly, the present invention provides for methods of treating polycystic kidney disease comprising administering to a subject in need thereof an effective amount of a FZD-binding agent, polypeptide, or antibody. In certain embodiments, the FZD-binding agent, polypeptide, or antibody binds to the BBS of a human FZD receptor (e.g., FZD8). In certain embodiments, the FZD-binding polypeptide comprises a sequence having at least 80% identity with a sequence selected from the group consisting of SEQ ID NOs:98-111 and SEQ ID NOs:113-116. In certain alternative embodiments, the polypeptide comprises the sequence of SEQ ID NO: 112. In still further embodiments, the FZD-binding agent is 18R5.

The present invention provides for methods of treating cancer comprising administering a therapeutically effective amount of a FZD-binding agent to a subject (e.g. a subject in need of treatment). In certain embodiments, the cancer is a cancer selected from the group consisting of colorectal cancer, pancreatic cancer, lung cancer, ovarian cancer, liver cancer, breast cancer, kidney cancer, prostate cancer, gastrointestinal cancer, melanoma, cervical cancer, bladder cancer, glioblastoma, and head and neck cancer. In certain embodiments, the cancer is pancreatic cancer. In certain embodiments, the cancer is colorectal cancer. In certain embodiments, the subject is a human.

The present invention further provides methods for inhibiting tumor growth using the antibodies or other agents described herein. In certain embodiments, the method of inhibiting the tumor growth comprises contacting a tumor or tumor cells with an effective amount of a FZD-binding agent (e.g., an antibody or other polypeptide) in vitro. For example, an immortalized cell line or a cancer cell line that expresses the targeted FZD(s) is cultured in medium to which is added the antibody or other agent to inhibit tumor growth. In some embodiments, tumor cells are isolated from a patient sample such as, for example, a tissue biopsy, pleural effusion, or blood sample and cultured in medium to which is added an FZD-binding agent to inhibit tumor growth.

In some embodiments, the method of inhibiting tumor growth comprises contacting the tumor or tumor cells with an effective amount of the FZD-binding agent (e.g., antibody) in vivo. In certain embodiments, contacting a tumor or tumor cell with a FZD-binding agent is undertaken in an animal model. For example, FZD-binding agents may be administered to xenografts expressing one or more FZDs that have been grown in immunocompromised mice (e.g. NOD/SCID mice) to inhibit tumor growth. In some embodiments, cancer stem cells are isolated from a patient sample such as, for example, a tissue biopsy, pleural effusion, or blood sample and injected into immunocompromised mice that are then administered a FZD-binding agent to inhibit tumor cell growth. In some embodiments, the FZD-binding agent is administered at the same time or shortly after introduction of tumorigenic cells into the animal to prevent tumor growth. In some embodiments, the FZD-binding agent is administered as a therapeutic after the tumorigenic cells have grown to a specified size.

In certain embodiments, the method of inhibiting tumor growth comprises administering to a subject a therapeutically effective amount of a FZD-binding agent. In certain embodiments, the subject is a human. In certain embodiments, the subject has a tumor or has had a tumor removed.

In certain embodiments, the tumor is a tumor in which Wnt signaling is active. In certain embodiment, the Wnt signaling that is active is canonical Wnt signaling. In certain embodiments, the tumor is a Wnt-dependent tumor. For example, in some embodiments, the tumor is sensitive to axin over-expression. In certain embodiments, the tumor does not comprise an inactivating mutation (e.g., a truncating mutation) in the adenomatous polyposis coli (APC) tumor suppressor gene or an activating mutation in the beta-catenin gene. In certain embodiments, the tumor expresses one or more genes in a Wnt gene signature. In certain embodiments, the cancer for which a subject is being treated involves such a tumor.

In certain embodiments, the tumor expresses the one or more human frizzled receptors to which the FZD-binding agent or antibody binds. In certain embodiments, the tumor overexpresses the human frizzled receptor(s).

In certain embodiments, the tumor is a tumor selected from the group consisting of colorectal tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. In certain embodiments, the tumor is a colorectal tumor. In certain embodiments, the tumor is a pancreatic tumor.

The invention also provides a method of inhibiting Wnt signaling in a cell comprising contacting the cell with an effective amount of a FZD-binding agent. In certain embodiments, the cell is a tumor cell. In certain embodiments, the method is an in vivo method wherein the step of contacting the cell with the agent comprises administering a therapeutically effective amount of the agent to the subject. In some alternative embodiments, the method is an in vitro or ex vivo method. In certain embodiments, the Wnt signaling that is inhibited is canonical Wnt signaling. In certain embodiments, the Wnt signaling is signaling by WNT1, WNT2, WNT3, WNT3A. WNT7a, WNT7b, and/or WNT10B. In certain embodiments, the Wnt signaling is signaling by WNT1, WNT3A, WNT7b, and/or WNT10B.

In addition, the invention provides a method of reducing the tumorigenicity of a tumor in a subject, comprising contacting the tumor with an effective amount of a FZD-binding agent or administering a therapeutically effective amount of a FZD-binding agent to the subject. In certain embodiments, the tumor comprises cancer stem cells. In certain embodiments, the frequency of cancer stem cells in the tumor is reduced by administration of the agent.

Thus, the invention also provides a method of reducing the frequency of cancer stem cells in a tumor, comprising contacting the tumor with an effective amount of a FZD-binding agent (e.g. an anti-FZD antibody or other FZD-binding polypeptide).

The invention further provides methods of differentiating tumorigenic cells into non-tumorigenic cells comprising contacting the tumorigenic cells with a FZD-binding agent (for example, by administering the FZD-binding agent to a subject that has a tumor comprising the tumorigenic cells or that has had such a tumor removed. In certain embodiments, the tumorigenic cells are pancreatic tumor cells. In certain alternative embodiments, the tumorigenic cells are colon tumor cells.

The use of the FZD-binding agents, polypeptides, or antibodies described herein to induce the differentiation of cells, including, but not limited to tumor cells, is also provided. For example, methods of inducing cells to differentiate comprising contacting the cells with an effective amount of a FZD-binding agent (e.g., an anti-FZD antibody or other FZD-binding polypeptide) described herein are envisioned. Methods of inducing cells in a tumor in a subject to differentiate comprising administering a therapeutically effective amount of a FZD-binding agent, polypeptide, or antibody to the subject are also provided. In certain embodiments, the tumor is a pancreatic tumor. In certain other embodiments, the tumor is a colon tumor.

Methods of treating a disease or disorder in a subject, wherein the disease or disorder is associated with Wnt signaling activation and/or is characterized by an increased level of stem cells and/or progenitor cells are further provided. In some embodiments, the treatment methods comprise administering a therapeutically effective amount of the FZD-binding agent, polypeptide, or antibody to the subject. In certain embodiments, the Wnt signaling is canonical Wnt signaling.

The present invention further provides methods of reducing myofibrolblast activation in the stroma of a solid tumor, comprising contacting the stroma with an effective amount of the FZD-binding agent, polypeptide or antibody.

The present invention further provides pharmaceutical compositions comprising one or more of the FZD-binding agents described herein. In certain embodiments, the pharmaceutical compositions further comprise a pharmaceutically acceptable vehicle. These pharmaceutical compositions find use in inhibiting tumor growth and treating cancer in human patients.

In certain embodiments, formulations are prepared for storage and use by combining a purified antibody or agent of the present invention with a pharmaceutically acceptable vehicle (e.g. carrier, excipient) (Remington, The Science and Practice of Pharmacy 20th Edition Mack Publishing. 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride: benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

In certain embodiments, the pharmaceutical composition is frozen. In certain alternative embodiments, the pharmaceutical composition is lyophilized.

The invention provides formulations for the antibodies described herein, such as 18R5, which comprise one or more (or all) of the following components: 30-50 mM Histidine, 70-110 mM Sodium Chloride, 60-100 mM Sucrose, and/or 0.01%-0.04% Polysorbate-20, with a pH of 5.5 to 5.9. In certain embodiments, the formulation comprises 40 mM Histidine, 86 mM Sodium Chloride, 82 mM Sucrose, and 0.02% Polysorbate-20, pH 5.7. Thus, in one embodiment, an 18R5 formulation comprises 5-20 mg/mL 18R5, 40 mM Histidine, 86 mM Sodium Chloride, 82 mM Sucrose, and 0.02% Polysorbate-20, pH 5.7. In another embodiment, an 18R5 formulation comprises 5-20 mg/mL 18R5, 56 mM Histidine, 86 mM Sodium Chloride, 82 mM Sucrose, and 0.02% Polysorbate-20, pH 5.7. In certain embodiments, the concentration of 18R5 in the formulation is 10 mg/mL. In certain embodiments, the pharmaceutical composition is frozen.

The pharmaceutical compositions of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g. water) to form a solid preformulation composition containing a homogeneous mixture of a compound of the present invention, or a non-toxic pharmaceutically acceptable salt thereof. The solid preformulation composition is then subdivided into unit dosage forms of the type described above. The tablets, pills, etc of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

The antibodies or agents can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions as described in Remington, The Science and Practice of Pharmacy 20th Ed. Mack Publishing (2000).

In certain embodiments, pharmaceutical formulations include antibodies or other agents of the present invention complexed with liposomes (Epstein, et al., 1985, Proc. Natl. Acad. Sci. USA 82:3688; Hwang, et al., 1980, Proc. Natl. Acad. Sci. USA 77:4030; and U.S. Pat. Nos. 4,485,045 and 4,544,545). Liposomes with enhanced circulation time are disclosed in U.S. Pat. No. 5,013,556. Some liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

In addition sustained-release preparations can be prepared. Suitable examples of sustained-release preparations include semipermeable matrices of solid hydrophobic polymers containing the antibody, which matrices are in the form of shaped articles (e.g. films, or microcapsules). Examples of sustained-release matrices include polyesters, hydrogels such as poly(2-hydroxyethyl-methacrylate) or poly(v nylalcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In certain embodiments, in addition to administering the FZD-binding agent, the method or treatment further comprises administering a second anti-cancer agent (prior to, concurrently with, and/or subsequently to administration of the FZD-binding agent). Pharmaceutical compositions comprising the FZD-binding agent and the second anti-cancer agent are also provided. In certain embodiments, the administration of the combination of the FZD-binding agent and a second anti-cancer agent has a synergistic effect, such as a synergistic effect on the frequency of cancer stem cells.

It will be appreciated that the combination of a FZD-binding agent and a second anti-cancer agent may be administered in any order or concurrently. In selected embodiments, the FZD-binding agents will be administered to patients that have previously undergone treatment with the second anti-cancer agent. In certain other embodiments, the FZD-binding agent and the second anti-cancer agent will be administered substantially simultaneously or concurrently. For example, a subject may be given the FZD-binding agent while undergoing a course of treatment with the second anti-cancer agent (e.g. chemotherapy). In certain embodiments, the FZD-binding agent will be administered within 1 year of the treatment with the second anti-cancer agent. In certain alternative embodiments, the FZD-binding agent will be administered within 10, 8, 6, 4, or 2 months of any treatment with the second anti-cancer agent. In certain other embodiments, the FZD-binding agent will be administered within 4, 3, 2, or 1 week of any treatment with the second anti-cancer agent. In some embodiments, the FZD-binding agent will be administered within 5, 4, 3, 2, or 1 days of any treatment with the second anti-cancer agent. It will further be appreciated that the two agents or treatment may be administered to the subject within a matter of hours or minutes (i.e., substantially simultaneously).

Useful classes of anti-cancer agents include, for example, antitubulin agents, auristatins, DNA minor groove binders, DNA replication inhibitiors, alkylating agents (e.g., platinum complexes such as cis-platin, mono(platinum), bis (platinum) and tri-nuclear platinum complexes and carboplatin), anthracyclines, antibiotics antifolates, antimetabolites, chemotherapy sensitizers, duocarmycins, etoposides, fluorinated pyrimidines, ionophores, lexitropsins, nitrosoureas, platinols, performing compounds, purine antimetabolites, puromycins, radiation sensitizers, steroids, taxanes, topoisomerase inhibitors, vinca alkaloids, or the like. In certain embodiments, the second anti-cancer agent is an antimetabolite, an antimitotic, a topoisomerase inhibitor, or an angiogenesis inhibitor.

Anticancer agents that may be administered in combination with the FZD-binding agents include chemotherapeutic agents. Thus, in some embodiments, the method or treatment involves the combined administration of an antibody or agent of the present invention and a chemotherapeutic agent or cocktail of multiple different chemotherapeutic agents. Treatment with an antibody can occur prior to, concurrently with, or subsequent to administration of chemotherapies. Chemotherapies contemplated by the invention include chemical substances or drugs which are known in the art and are commercially available, such as Gemcitabine, Irinotecan, Doxorubicin, 5-Fluorouracil, Cytosine arabinoside ("Ara-C"), Cyclophosphamide, Thiotepa, Busulfan, Cytoxin, TAXOL, Methotrexate, Cisplatin, Melphalan, Vinblastine and Carboplatin. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in Chemotherapy Service Ed. M. C. Perry, Williams & Wilkins, Baltimore, Md. (1992).

Chemotherapeutic agents useful in the instant invention also include, but are not limited to, alkylating agents such as thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylencthiophosphaoramidc and trimethylolomelamime nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate: purine analogs such as fludarabine. 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; antiadrenals such as aminoglutethimide, mitotane, trilostane: folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.; razoxane; sizofuran; spirogermanium; tenuazonic acid; triaziquone; 2,2', 2"-trichlorotriethylamine; urethan; vindesine: dacarbazine; mannomustine; mitobronitol; mitolactol; pipobroman; gacytosine; arabinoside ("Ara-C"); cyclophosphamide; thiotepa; taxoids, e.g. paclitaxel (TAXOL. Bristol-Myers Squibb Oncology, Princeton, N.J.) and doxetaxel (TAXOTERE, Rhone-Poulenc Rorer. Antony. France); chlorambucil; gemcitabine: 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine (DMFO); retinoic acid; esperamicins; capecitabine; and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and antiandrogens such as flutamide, nilutamide, bicalutamide, leuprolide, and goserelin; and pharmaceutically acceptable salts, acids or derivatives of any of the above.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCL, daunorubicin citrate, mitoxantrone HCL, actinomycin D, etoposide, Topotecan HCL, teniposide (VM-26), and irinotecan. In certain embodiments, the second anticancer agent is irinotecan. In certain embodiments, the tumor to be treated is a colorectal tumor and the second anticancer agent is a topoisomerase inhibitor, such as irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, Pemetrexed, tegafur, cytosine arabinoside, THIOGUANINE (GlaxoSmithKline), 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the second anticancer agent is gemcitabine. In certain embodiments, the tumor to be treated is a pancreatic tumor and the second anticancer agent is an anti-metabolite (e.g., gemcitabine).

In certain embodiments, the chemotherapeutic agent is an antimitotic agent, including, but not limited to, agents that bind tubulin. By way of non-limiting example, the agent comprises a taxane. In certain embodiments, the agent comprises paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (e.g., ABRAXANE), DHA-paclitaxel, or PG-paclitaxel. In certain alternative embodiments, the antimitotic agent comprises a vinka alkaloid, such as vincristine, binblastine, vinorelbine, or vindesine, or pharmaceutically acceptable salts, acids, or derivatives thereof. In some embodiments, the antimitotic agent is an inhibitor of Eg5 kinesin or an inhibitor of a mitotic kinase such as Aurora A or Plk1. In certain embodiments where the chemotherapeutic agent administered in combination with the FZD-binding agent or polypeptide or antibody comprises an antimitotic agent, the cancer or tumor being treated is breast cancer or a breast tumor.

In certain embodiments, the treatment involves the combined administration of an antibody (or other agent) of the present invention and radiation therapy. Treatment with the antibody (or agent) can occur prior to, concurrently with, or subsequent to administration of radiation therapy. Any dosing schedules for such radiation therapy can be used as determined by the skilled practitioner.

In some embodiments, the second anti-cancer agent comprises an antibody. Thus, treatment can involve the combined administration of antibodies (or other agents) of the present invention with other antibodies against additional tumor-associated antigens including, but not limited to, antibodies that bind to EGFR, ErbB2, HER2, DLL4, Notch and/or VEGF. Exemplary, anti-DLL4 antibodies, are described, for example, in U.S. Patent Application Publication No. US 2008/0187532, incorporated by reference herein in its entirety. In certain embodiments, the second anti-cancer agent is an antibody that is an angiogenesis inhibitor (e.g., an anti-VEGF antibody). Additional anti-DLL4 antibodies are described in, e.g., International Patent Publication Nos. WO 2008/091222 and WO 2008/0793326, and U.S. Patent Application Publication Nos. US 2008/0014196, US 2008/0175847, US 2008/0181899, and US 2008/0107648, each of which is incorporated by reference herein in its entirety. Exemplary anti-Notch antibodies, are described, for example, in U.S. Patent Application Publication No. US 2008/0131434, incorporated by reference herein in its entirety. In certain embodiments, the second anti-cancer agent is an antibody that is an angiogenesis inhibitor (e.g., an anti-VEGF antibody). In certain embodiments, the second anti-cancer agent is an inhibitor of Notch signaling. In certain embodiments, the second anti-cancer agent is AVASTIN (Bevacizumab), Herceptin (Trastuzumab), VECTIBIX (Panitumumab), or Erbitux (Cetuximab). Combined administration can include co-administration, either in a single pharmaceutical formulation or using separate formulations, or consecutive administration in either order but generally within a time period such that all active agents can exert their biological activities simultaneously.

Furthermore, treatment can include administration of one or more cytokines (e.g., lymphokines, interleukins, tumor necrosis factors, and/or growth factors) or can be accompanied by surgical removal of cancer cells or any other therapy deemed necessary by a treating physician.

For the treatment of the disease, the appropriate dosage of an antibody or agent of the present invention depends on the type of disease to be treated, the severity and course of the disease, the responsiveness of the disease, whether the antibody or agent is administered for therapeutic or preventative purposes, previous therapy, patient's clinical history, and so on all at the discretion of the treating physician. The antibody or agent can be administered one time or over a series of treatments lasting from several days to several months, or until a cure is effected or a diminution of the disease state is achieved (e.g. reduction in tumor size).

Optimal dosing schedules can be calculated from measurements of drug accumulation in the body of the patient and will vary depending on the relative potency of an individual antibody or agent. The administering physician can easily determine optimum dosages, dosing methodologies and repetition rates. In certain embodiments, dosage is from 0.01 µg to 100 mg per kg of body weight, and can be given once or more daily, weekly, monthly or yearly. In certain embodiments, the antibody or other FZD-binding agent is given once every two weeks or once every three weeks. In certain embodiments, the dosage of the antibody or other FZD-binding agent is from about 0.1 mg to about 20 mg per kg of body weight. The treating physician can estimate repetition rates for dosing based on measured residence times and concentrations of the drug in bodily fluids or tissues.

V. Wnt Gene Signature and Uses Thereof

The present invention further provides a Wnt gene signature, a gene signature indicative of Wnt signaling activity in tumors, which may be used in the selection of tumors, patients, and/or therapy.

The Wnt gene signature comprises the differential expression of a set of genes in tumors in which Wnt signaling is activated (and/or which are dependent upon Wnt signaling), relative to tumors in which Wnt signaling is not activated. In certain embodiments, the Wnt signaling is canonical Wnt signaling. The Wnt gene signature is useful for the identification of tumors and/or patients likely to respond to treatment with an inhibitor of Wnt signaling (e.g. a FZD-binding agent that is an antagonist of at least one human frizzled receptor and/or an inhibitor of Wnt signaling).

In certain embodiments, the Wnt gene signature comprises one or more genes (i.e. 1, 2, 3, 4, 5, 6, 7, 8, 9, 10, 11, 12, 13, 14, 15, 16, 17, 18, or 19 genes) listed in Table 3, below. The "Probe Set ID" numbers are the probe set ID numbers for the GeneChip® Human Genome U133 Plus 2.0 Array ("HG_UI33_Plus_2"; Affymetrix, Santa Clara, Calif.). In tumors in which Wnt signaling is active (i.e., tumors which are positive for a Wnt gene signature), the expression level(s) of the gene(s) in Table 3 that comprise the Wnt gene signature are elevated relative to tumors in which Wnt signaling is not active. In some embodiments, the Wnt gene signature comprises two or more genes listed in Table 3, below. In some embodiments, the Wnt gene signature comprises three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, or nineteen of the genes listed in Table 3, below. In certain embodiments, the tumor being assessed for expression levels of the one or more genes in Table 3 is a colorectal tumor. In certain embodiments, the Wnt gene signature comprises AXIN2 and/or FOXQ1. In certain embodiments, the tumor is a colorectal tumor and the Wnt gene signature comprises AXIN2, LGR5, and/or FOXQ1.

TABLE 3

Exemplary Wnt gene signature genes

| HG_U133_Plus_2 Probe Set ID | Gene Symbol | Description |
| --- | --- | --- |
| 222696_at | AXIN2 | axin 2 (conductin, axil) |
| 206286_s_at | TDGF1 | teratocarcinoma-derived growth factor 1 |
| 213880_at | LGR5 | leucine-rich repeal-containing G protein-coupled receptor 5 |
| 207217_s_at | NOX1 | NADPH oxidase 1 |

TABLE 3-continued

Exemplary Wnt gene signature genes

| HG_U133_Plus_2 Probe Set ID | Gene Symbol | Description |
| --- | --- | --- |
| 209588_at | EPHB2 | EPH receptor B2 |
| 212850_s_at | LRP4 | low density lipoprotein receptor-related protein 4 |
| 205107_s_at | EFNA4 | ephrin-A4 |
| 214058_at | MYCL1 | v-myc myelocytomatosis viral oncogene homolog 1, lung carcinoma derived (avian) |
| 209864_at | FRAT2 | frequently rearranged in advanced T-cell lymphomas 2 |
| 208121_s_at | PTPRO | protein tyrosine phosphatase, receptor type, O |
| 229376_at | | unknown expressed sequence tag (EST) |
| 202431_s_at | MYC | v-myc myelocytomatosis viral oncogene homolog (avian) |
| 212444_at | GPCR5A | G protein-coupled receptor, family C, group 5, member A |
| 222938_x_at | ENPP3 | ectonucleotide pyrophosphatase/phosphodiesterase 3 |
| 241607_at | LOC730102 | hypothetical protein LOC730102 |
| 227475_at | FOXQ1 | forkhead box Q1 |
| 230398_at | TNS4 | tensin 4 |
| 40284_at | FOXA2 | forkhead box A2 |
| 219704_at | YBX2 | Y box binding protein 2 |

Methods of using the Wnt gene signature to select patients (or to identify a patient) suitable for treatment with a Wnt pathway inhibitor or for assessing the efficacy of a particular therapy are also provided. In certain embodiments, the Wnt signaling inhibitor is a FZD-binding agent, such as an antagonistic FZD antibody. For example, a patient may be identified as being suitable for treatment with a FZD-binding agent (or FZD-binding agents) by determining whether a tumor in the patient or that has been removed from the patient exhibits a Wnt gene signature. In certain embodiments, detecting the Wnt gene signature comprises assessing the expression level of one or more genes in Table 3 in the tumor. If expression levels of the one or more genes in Table 3 that comprise the Wnt gene signature are elevated in the tumor (thus indicating that Wnt signaling is active in the tumor), the patient is identified as being suitable for treatment with a FZD-binding agent, such as an anti-FZD antibody that inhibits Wnt signaling. Methods of using the Wnt gene signature to select a suitable therapy for a particular patient are likewise provided.

The invention provides a method of treating cancer in a patient having a tumor or from whom a tumor has been removed, comprising (a) providing the expression level of one or more genes in Table 3 in the tumor (b) selecting the patient for beginning or continuing treatment with a FZD-binding agent based on the expression level of the one or more genes, and (c) administering the FZD-binding agent to the patient. In certain embodiments, the method comprises measuring the expression level of the one or more genes in the tumor. In certain embodiments, the expression level of the one or more genes is compared to a control or reference level.

Methods of identifying tumor which may be responsive to treatment with an inhibitor of Wnt signaling are also provided. In certain embodiments, the inhibitor of Wnt signaling is a FZD-binding agent. In certain embodiments, the methods comprise testing the tumor for a Wnt gene signature. In certain embodiments, the methods comprise assessing the expression level of one or more genes in Table 3 in the tumor.

Methods of screening drug candidates against tumors identified as exhibiting the Wnt gene signature are also provided. In certain embodiments, the drug candidates are Wnt signaling inhibitors. Such drug candidates are preferably tested for efficacy on those tumors in which Wnt signaling is active and/or which are dependent upon Wnt signaling. The present invention also provides a method of screening a drug candidate comprising assessing the expression level of one or more genes in Table 3 in a tumor (b) selecting the tumor for testing with the drug candidate based (at least in part) on the expression level of the one or more genes, and (c) testing the effect of the drug candidate on the tumor.

In addition, in certain embodiments, the effect of a drug on the Wnt gene signature may be determined and used to assess the efficacy of a treatment of a tumor in which Wnt signaling is active. In certain embodiments, this provides a method of monitoring treatment of a patient. In some alternative embodiments, this provides a method of assessing the efficacy of a drug candidate. In certain embodiments, a decrease in the expression levels of one or more genes in Table 3 (i.e., a reduction in or elimination of the Wnt gene signature) indicates efficacy of the treatment.

In certain embodiments, assessing the level of one or more genes in a Wnt gene signature comprises determining the expression levels of polynucleotides of the one or more genes. In certain embodiments, detecting a Wnt gene signature comprises detecting mRNA expression of polynucleotides of the one or more genes that comprise the signature. In some embodiments, the detection of mRNA expression is via Northern blot. In some embodiments, the detection of mRNA expression is via RT-PCR, real-time PCR or quantitative PCR using primer sets that specifically amplify the polynucleotides comprising the cancer stem cell signature. In certain embodiments, the detection of mRNA comprises exposing a sample to nucleic acid probes complementary to polynucleotides comprising a cancer stem cell gene signature. In some embodiments, the mRNA of the sample is converted to cDNA prior to detection. In some embodiments, the detection of mRNA is via microarrays that comprise polynucleotides that hybridize to one or more genes in the Wnt gene signature.

In certain embodiments, assessing the level of one or more genes in a Wnt gene signature comprises detecting polypeptides encoded by the one or more genes. In some embodiments, the assessment of levels of the polypeptide expression products of the one or more genes comprises exposing a sample to antibodies specific to the polypeptides and detecting the binding of the antibodies to the polypeptides by, for example, quantitative immunofluorescence, or ELISA. Other detection means are known to one of ordinary skill in the art see e.g., U.S. Pat. No. 6,057,105.

An array comprising polynucleotides that hybridize under stringent conditions to one or more genes in Table 3 are also provided. A kit comprising the array is also provided.

Kits comprising antibodies that bind the expression product of one or more genes in Table 3 are also provided.

VI. Kits Comprising Fzd-Binding Agents

The present invention provides kits that comprise the antibodies or other agents described herein and that can be used to perform the methods described herein. In certain embodiments, a kit comprises at least one purified antibody against one or more human frizzled receptors in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed antibodies or agents of the present invention can be readily incorporated into one of the established kit formats which are well known in the art.

Further provided are kits comprising a FZD-binding agent (e.g., a FZD-binding antibody), as well as a second anti-cancer agent. In certain embodiments, the second anti-cancer agent is a chemotherapeutic agent (e.g., gemcitabine or irinotecan). In certain embodiments, the second anti-cancer agent is an angiogenesis inhibitor. In certain embodiments, the second anti-cancer agent is an inhibitor of Notch signaling (e.g., an anti-DLL4 or anti-Notch antibody).

Also provided are kits comprising a FZD-binding agent and a reagent or reagents for assessing the expression of one or more gene in Table 3, above ("Exemplary Wnt gene signature genes").

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, may be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application.

Example 1

Identification/Generation of Anti-FZD Antibodies

Human antibodies that specifically recognize one or more human Frizzled receptors can be isolated using phage display. For example, a synthetic antibody library containing human antibody variable domains may be panned for specific and high affinity recognition of the extracellular domain of the human FZD7 receptor. Once a specific Fab with the desired characteristics has been identified, the human variable regions of the Fab are then cloned into an Ig expression vector containing human IgG2 heavy-chain and light-chain (kappa or lambda) for expression of human antibodies in CHO cells.

Phage display was used to identify a specific Fab, 18R8, that binds to the extracellular domain of FZD7. $2 \times 10^{13}$ Fab displaying phage particles from a human Fab phage library were incubated with passively immobilized recombinant FZD7 ECD Fc protein. The non-specific phage were washed off, and then specific phage were eluted with DTT. The eluted output was used to infect TG1 F+ bacteria, rescued with helper phage. Fab display was then induced with IPTG (0.25 mM). The output of this rescued round one served as the starting point for further selection rounds. The selections were continued to round 3, and then the output was screened in ELISA for specific Fabs to recombinant FZD7 ECD Fc protein. A Fab that specifically bound to human FZD7 was identified.

The sequences of the variable regions of the identified Fab were obtained. An N-linked glycosylation site was removed from the parent sequence through site-directed mutagenesis. The N-linked glycosylation site. Asn, in the heavy chain CDR1 was changed to His. This mutation was made to prevent glycosylation during expression in mammalian systems. The resulting Fab was designated 18R8. The heavy chain and light chain CDR sequences of 18R8 are shown below in Table 4, below. The VH and VL sequences of 18R8 are provided in SEQ ID NO: 10 and SEQ ID NO: 12, respectively.

TABLE 5

Affinity of 18R8 and 18R5 IgG antibodies

| FZD | 18R8 $K_D$ (nM) | 18R5 $K_D$ (nM) |
|---|---|---|
| 1 | 15.6 | 4.6 |
| 2 | 6.2 | 3.3 |
| 5 | 4.2 | 1.9 |

TABLE 4

CDRs of 18R8 and 18R5 human antibodies

| | Heavy Chain | | | Light Chain | | |
|---|---|---|---|---|---|---|
| Lead | CDR1 | CDR2 | CDR3 | CDR1 | CDR2 | CDR3 |
| 18R8 | GFTFS<u>H</u>YTLS (SEQ ID NO: 1) | VISGDGSYTYYADSVKG (SEQ ID NO: 2) | NFIKYVFAN (SEQ ID NO: 3) | SGDKLGKKYAS (SEQ ID NO: 4) | EKDNRPSG (SEQ. ID NO: 5) | SSFAGNSLE (SEQ ID NO: 6) |
| 18R5 | GFTFS<u>H</u>YTLS (SEQ ID NO: 1) | VISGDGSYTYYADSVKG (SEQ. ID NO: 2) | NFIKYVFAN (SEQ ID NO: 3) | SGDNIGSFYVH (SEQ ID NO: 7) | DKSNRPSG (SEQ ID NO: 8) | QSYANTLSL (SEQ ID NO: 9) |

*Site directed change to remove N-linked glycosylation site is underlined.

Anti-FZD Fab 18R5 was generated by associating the VH-CH1 chains of 18R8Fab with a variety of VL-CL chains from the original Fab phage library from which 18R8 was identified. 18R5 was isolated from the library after three rounds of panning with immobilized recombinant FZD7 ECD Fc protein. The sequences of the CDRs of 18R5 are shown in Table 4, above. The VL of the 18R5 antibody has the sequence shown in SEQ ID NO:14. The heavy chain CDRs and the VH of the 18R5 antibody are identical to that of the 18R8 antibody.

The human variable regions of the 18R8 and 18R5Fabs were cloned into Ig expression vector containing human IgG2 heavy-chain and light-chain (lambda) for expression in CHO cells. The amino acid sequence of the heavy chain and light chain of the 18R8 IgG antibody (including signal sequences) are provided in SEQ ID NO: 11 and SEQ ID NO: 13, respectively. The signal sequence at the N-terminus of the amino acid sequence of each of the chains is cleaved upon secretion. The nucleic acid sequences encoding the heavy and light chains of the 18R8 IgG antibody are provided in SEQ ID NO:18 and SEQ ID NO:20, respectively. The amino acid sequence of the heavy chain and light chain of the 18R5 IgG antibody are provided in SEQ ID NO:11 and SEQ ID NO:15, respectively. (Again, the signal sequence at the N-terminus of the amino acid sequence of each of the chains is cleaved upon secretion.) The nucleic acid sequences encoding the heavy and light chains of the 18R5 IgG antibody are provided in SEQ ID NO:18 and SEQ ID NO:22, respectively. Protein A purification was used to purify the antibodies.

The $K_D$s of 18R8 and 18R5 antibodies were determined using the Biacore 2000 system from Biacore Lifescience (GE Healthcare). Specifically, purified anti-Fzd7 antibodies were serially diluted in 2-fold increments from 100 to 0.78 nM in HBS-P (0.01 M HEPES pH 7.4, 0.15 M NaCl, 0.005% v/v Surfactant P20). Each dilution was tested against recombinant Fzd Fc proteins immobilized onto a CM5 Biacore chip. The association and dissociation rates were measured and $K_D$ values determined using the Biaevaluation software program (Table 5, below).

TABLE 5-continued

Affinity of 18R8 and 18R5 IgG antibodies

| FZD | 18R8 $K_D$ (nM) | 18R5 $K_D$ (nM) |
|---|---|---|
| 7 | 5.2 | 1.8 |
| 8 | 29.3 | 5.8 |

Another anti-FZD antibody, 18R0512, was also prepared.

Example 2

FACS Analysis of Anti-FZD Antibodies Demonstrates Binding to Multiple Cell-Surface Human FZDs Flow cytometry analysis was utilized to determine the ability of antibodies to bind to cell surface expressed FZD proteins.

To enable robust cell surface expression of selected FZD proteins, mammalian expression plasmids comprising a CMV promoter upstream of polynucleotides that encode FZD were generated using standard recombinant DNA technology (such constructs were termed "FL no FLAG"). Similar expression plasmids were generated for each of the ten human frizzled proteins. Alternative versions of the FZD expression vectors were also prepared in which polynucleotides encoding an N-terminal signal sequence-FLAG epitope tag fused to the N-terminus of the mature FZD protein were also generated by standard recombinant technology (such constructs were termed "FL flag"). Additionally, expression plasmids were designed which encoded chimeric proteins comprised of either the CRD domain (also referred to as the "fri" domain) of the FZD or the entire N-terminal extracellular domain of the FZD protein fused to an N-terminal signal sequence-FLAG epitope (termed "fri flag" and "ECD flag" respectively), as well as a C-terminal section encoding the transmembrane and cytoplasmic domain of human CD4 protein.

To measure antibody binding to FZD by flow cytometry HEK293 cells were co-transfected with FZD expression vectors and the transfection marker GFP. Twenty-four to forty-eight hours post-transfection, cells were collected in suspension and incubated on ice with anti-FZD antibodies (10 µg/ml unless otherwise indicated) or control IgG to detect background antibody binding. The cells were washed and primary antibodies detected with Fc domain-specific secondary antibodies conjugated to a fluorescent chromophore (e.g. phycoerythrin conjugated anti-human IgG). Labeled cells were then analyzed by flow cytometry to identify anti-FZD antibodies that specifically recognize cell surface expression of FZD protein. Monoclonal antibodies 18R5 and 18R8 recognized FZD on transfected cells. As shown in FIG. 1 and FIG. 2, both 18R8 and 18R5 bind to multiple FZD including FZD1, FZD2, FZD5, FZD7, and FZD8. To examine the relative ability of 18R8 and 18R5 to bind to each FZD protein, titration analysis was conducted wherein the amount of antibody in the binding reaction was varied (FIG. 2). This analysis demonstrated that 18R5 displayed greater binding potency to each of the FZD receptors (FZD1, FZD2, FZD5. FZD7, and FZD8) than 18R8.

Example 3

Inhibition of Wnt Signaling by 18R8 and 18R5

The ability of the anti-FZD IgG antibodies 18R8 and 18R5 to block activation of the Wnt signaling pathway was determined in vitro using luciferase reporter assays.

STF293 cells were cultured in DMEM supplemented with antibiotics and 10% FCS. The STF293 cells are 293 cells in which the following have been stably integrated: (1) an 8×TCF Luc reporter vector containing seven copies of the TCF binding site linked to a promoter upstream of a firefly luciferase reporter gene to measure canonical Wnt signaling levels (Gazit et al., 1999, *Oncogene* 18:5959-66) and (2) a *Renilla* luciferase reporter (Promega; Madison, Wis.) as an internal control for transfection efficiency. The cells were added to cultures plates. The FZD antibodies to be tested (or no antibodies) were added. The cells were then incubated in the presence or absence of Wnt3A-conditioned medium that had been prepared from L cells that stably express Wnt3a (ATCC CRL-2647) or control conditioned media from L cells not overexpressing Wnt3A (ATCC cell line CRL-2648). After overnight incubation, luciferase levels were measured using a dual luciferase assay kit (Promega; Madison, Wis.) with firefly luciferase activity normalized to *Renilla* luciferase activity.

The ability of the 18R8 and 18R5 antibodies to inhibit Wnt-induced pathway activation was thus determined. STF293 cells were treated with different concentrations of 18R8 or 18R5 IgG antibodies and Wnt3A-conditioned medium was added. The cells were assayed 18 hours later using the dual luciferase assay kit. The results are shown in FIG. 3. Greater inhibition of the TCF signaling of the Wnt3a pathway was observed with the anti-FZD antibody 18R5.

In further experiments, the ability of the 18R8 antibody to antagonize signaling by different Wnt ligands was determined. HEK 293 cells were transfected with Wnt1, Wnt2, Wnt2b2, Wnt3, Wnt3a, Wnt7a, Wnt7b, Wnt8a, Wnt9b, and Wnt10b for forty eight hours by Fugene 6 (Roche). Wnt3A conditioned medium ("WNT3ACM") was used as a positive control of activation. STF293 cells, were cultured in DMEM supplemented with antibiotics and 10% FCS and treated with 20 µg/ml 18R8 antibody or no antibody. The Wnt-overexpressing HEK293 cells were then added. Eighteen hours following treatment, luciferase levels were measured using a dual luciferase assay kit. The results are shown in FIG. 4. The anti-FZD antibody 18R8 was shown to inhibit signaling of a variety of Wnts, including inhibiting Wnt1, Wnt2, Wnt3, Wnt7A, Wnt7B, and Wnt10B, in addition to Wnt3A.

In similar experiments, the ability of the 18R5 antibody to inhibit signaling by different Wnt ligands was determined. The results are shown in FIG. 67. 18R5 was found to inhibit beta-catenin signaling in response to each of the Wnt family members that was active in the cell-based reporter assay.

Example 4

18R8 Blocks Binding of FZD to Wnt

To assess the ability of 18R8 to block the binding of FZD to Wnt, 2 µl of 1.32 µg/µl soluble FZD8-Fc containing the Fri domain (amino acids 1-157 of FZD8 linked in-frame to human IgG1 Fc) was added to culture medium to bind Wnt3A (added as 20 µl of Wnt3A conditioned medium) either alone or in the presence of the 18R8 IgG antibody (added as 4 µl of 3.71 µg/µl). The mixtures were incubated either alone or in the presence of Protein A sepharose beads (GE Healthcare products; 20 µl of 50% solution in PBS) for two his at 4° C. After the incubation, the protein A beads (and any proteins complexed to the protein A beads) in each sample were removed by spinning and the supernatant was assayed for ability to induce 8×TCF luciferase activity. The supernatant was added to STF293 cells, which stably express 8×TCF (eight copies of the TCF-binding domain upstream of a firefly luciferase reporter gene) to measure canonical Wnt signaling levels and which were cultured in DMEM supplemented with antibiotics and 10% FCS. Eighteen hours following treatment of the STF293 cells, luciferase levels were measured using a dual luciferase assay kit (Promega; Madison, Wis.).

As seen in FIG. 5, Wnt 3A plus Protein A induces a strong activation of the reporter gene as measured by luciferase units (RLU) (FIG. 5, column 1). Addition of Fzd8-fc induces a complex between Wnt 3A-Fzd8 and the Fc fusion protein with the Protein A sepharose beads, and once the Protein A-Wnt3A-Fzd8 complex is removed by centrifugation, the resulting supernatant is no longer capable of activating the reporter gene (FIG. 5, column 2). Upon addition of 18R8, this complex is presumably disrupted by the blockade of the antibody upon the Wnt3A interacting domain of Fzd8, because although the Protein A-Fzd8-fc complex is removed along with 18R8 which can readily interact with Protein A through its own Fc portion, reporter activity can be readily observed, suggesting sufficient levels of uncomplexed Wnt 3A (FIG. 5, column 3). 18R8 also functions on the endogenous Fzd's present on the STF293 cells, because failure to remove 18R8 by Protein A does not show the return of Wnt 3A activation (FIG. 5, column 6).

The data in FIG. 5 show that the presence of the 18R8 IgG antibody in the incubation reaction resulted in retention of Wnt3A activity within the supernatant relative to the activity observed with FZD8-Fc alone. These results indicate that 18R8 blocked the ability of FZD8 to bind to Wnt3A and indicate that antibody binding to the epitope recognized by 18R8 is able to block Wnt-FZD interactions.

Similarly, to determine whether 18R5 directly blocked the ability of Wnt to interact with Fzd, additional binding studies were conducted. The results are shown in FIG. 68. Wnt3A, FZD5-Fc and 18R5 were co-incubated as indicated, and then 18R5 and FZD5-Fc were removed by protein A IP. Supernatant was then assayed for WNT activity in an 8×TCF luciferase reporter assay. 18R5 blocked Wnt3A binding to Fzd5-Fc, suggesting that a mechanism by which 18R5 inhibits Wnt signaling involves the direct inhibition of Wnt binding.

Example 5

Epitope Mapping of 18R8 and 18R5

To identify the FZD epitope recognized by the 18R8 IgG antibody, epitope mapping was performed. Flow cytometry analysis of cell surface expressed FZD was utilized to measure antibody binding. Mammalian expression plasmid vectors comprising a CMV promoter upstream of polynucleotides that encode an N-terminal signal sequence FLAG epitope tag fused to the N-terminus of the Fri domain of FZD8 in turn fused to the transmembrane domain and intracellular domain of CD4 protein were generated by standard recombinant technology. This expression construct allows expression of the FZD8 Fri domain on the cell surface, as well as expression of a FLAG epitope tag to monitor expression. Site-direct mutagenesis was then used to modify selected amino acids within the extracellular domain of FZD. HEK293 cells were co-transfected with expression vectors encoding the FZD and the transfection marker GFP. Forty-eight hours post-transfection, cells were collected in suspension and incubated on ice with anti-FZD antibody or control IgG to detect background antibody binding. The cells were washed and primary antibodies detected with anti-antibody secondary antibodies conjugated to a fluorescent chromophore. Labeled cells were then analyzed by flow cytometry to measure the binding of anti-FZD antibody to cell surface FZD.

In this manner, specific amino acids within the FZD extracellular domain that were important for the binding of anti-FZD antibodies were identified. When amino acid residues 82-83 of FZD8 were mutated from PD to SQ, binding of the FZD8 by 18R8 was largely unaffected (FIG. 6). Similarly, when amino acid 109S was changed to 109Q, no appreciable effect on binding was observed. On the other hand, when residues 70-71 of FZD8 were changed from HQ to AE, binding of the FZD8 on cells by 18R8 was clearly diminished (FIG. 6 and FIG. 7). When amino acids 66-67 were mutated from GL to AA, or when amino acids 68-69 were mutated from EV to QL, or when amino acids 126-127 were mutated from FG to NV, binding of the 18R8 antibody to FZD8 on the cells was similarly lost. The loss of binding to FZD when certain amino acids had been substituted the extracellular domain of FZD revealed specific recognition sites of the antibody. Thus, the antibody 18R8 was determined to bind to an epitope comprising amino acids 66-71 GLEVHQ (SEQ ID NO:25) of FZD8 and amino acids 124-128 GF of human FZD8. This epitope region is well conserved across the human frizzled receptors to which FZD8 binds (i.e., FZD1, FZD2, FZD5. FZD7, and FZD8), and not highly conserved in those human frizzled receptors to which FZD8 does not bind (i.e., FZD3, FZD4, FZD6, FZD9, or FZD10).

FACS experiments comparing the binding of 18R5 IgG and 18R8 IgG to the wild-type and mutant FZD8 on cells were also performed. These experiments demonstrated that the 18R8 antibody and the 18R5 antibody bind to a similar epitope on FZD8 (FIG. 7).

Example 6

Identification of the Biological Binding Site (BBS of the FZD Receptors)

The discovery of antibodies that inhibit Wnt signaling and the discovery of the epitope within the FZD protein bound by these antibodies has now enabled the analysis of which regions of the FZD protein structure are important for Wnt signaling. To examine this, the crystal structure of the Fri domain of mouse Fzd 8 was examined. We identified the binding epitope of 18R8 and 18R5 as lying within a region of the FZD structure for which a specific functional role had not previously been appreciated. Moreover the epitope contained two separate surface elements of the Fzd (which we termed "top edge" and "bottom edge") separated by a cleft. It was also discovered upon comparison of the ten human frizzled receptors that there was striking conservation of the identity of amino acids that lined the bottom of this cleft. The region comprising this cleft, as well as the "top edge" and "bottom edge" to which 18R8 and 18R5 bind has been designated the Biological Binding Site (BBS) of FZD. Shown in FIG. 9 are images of the structure of a Fzd Fri domain based on analysis of the previously reported crystal structure of mouse FZD8 (Dann C E et al., *Nature* 412 (6842) 86-90, 2001) and analysis done using the software program Pymol. Shown in the upper left image is a surface view of the FZD Fri domain with the region of the Fzd protein comprising the biological binding site (BBS) indicated by a white circle. The regions designated as the "top edge", "bottom edge" and the "cleft" of the BBS are each highlighted in darker surface coloration in separate images at the bottom of the panel. The upper right image of FIG. 9 highlights in a darker surface the residues that are conserved in 9 or 10 of ten human Fzd family members.

Example 7

Inhibition of Tumor Growth In Vivo by 18R5

Prevention of Wnt-Dependent Tumor Growth by 18R5

Female NOD/SCID mice were injected at age 5-7 weeks with 50,000 mouse mammary tumor virus (MMTV)-WNT1 tumor derived cells in the upper right mammary fat pad. Transgenic (MMTV)-Wnt-1 mice exhibit discrete steps of mammary tumorigenesis, including hyperplasia, invasive ductal carcinoma, and distant metastasis, and thus this mouse model of breast cancer provides a useful tool for analyzing the role of Wnts in tumor formation and growth (Nusse and Varmus (1982) *Cell* 31:99-109). Tumors from these mice were dissociated and these dissociated tumor cells used for tumor propagation purposes. Mice with tumor cells implanted in the mammary fat pad were monitored twice a week. Once tumors were palpable, tumors were measured twice weekly and tumor volume was determined using the formula $\frac{1}{2}(a \times b^2)$; where a=length, and b=breadth. Data are expressed as mean and mean±S.E.M. Group means were compared using Student's two-tailed, unpaired t test. Probability (p) values of <0.05 were interpreted as significantly different. On day 19, mice with average tumor volume of 44 mm$^3$ were randomized into 2 groups of 10 animals each. Animals were injected with either control antibody, or 18R5 IgG antibody (10 mg/kg). Administration of the antibodies was performed via injection into the intra-peritoneal cavity, twice weekly. Treatment with the antibody 18R5 completely abolished tumor growth as compared to tumors treated with control antibody (FIG. 10; p=0.002).

Reduction of OMP-C28 Xenograft Tumor Growth by Combination Treatment of 18R5 and Irinotecan In another embodiment anti-FZD antibodies were analyzed for their ability to reduce the growth of OMP-C28 colon tumor xenografts. Dissociated human OMP-C28 cells (10,000 per animal) were injected subcutaneously into 6-8 week old male NOD/SCID mice. Tumor growth was monitored weekly and tumor measurements were initiated once tumors were palpable. On day 24 mice with average tumor volume of 129 mm$^3$ were randomized into 4 groups of 10 animals each. Animals were injected with either control antibody, or 18R5 IgG antibody (10 mg/kg), or irinotecan (7.5 mg/kg) or combination of both 18R5 and irinotecan. Administration of the antibodies and irinotecan was performed via injection into the intra-peritoneal cavity, twice weekly. Tumors were measured twice a week and tumor volume was determined using the formula ½(a×b$^2$); where a=length, and b=breadth. Data are expressed as mean and mean±S.E.M. Group means were compared using Student's two-tailed, unpaired t test. Probability (p) values of <0.05 were interpreted as significantly different. Treatment with 18R5 resulted in a 40% reduction in tumor growth, as shown in FIG. 11 (p=0.02). Furthermore, treatment with 18R5 and irinotecan resulted in a 53% reduction of tumor growth relative to treatment with irinotecan alone (p=0.0002 vs. irinotecan alone) (FIG. 11). Thus, 18R5 demonstrated anti-tumor growth activity in OMP-C28 colon tumor model as a single agent as well as in combination with irinotecan.

Reduction of OMP-Pn4 Xenograft Tumor Growth by Combination Treatment of 18R5 and Gemcitabine In another embodiment, anti-FZD antibodies were analyzed for their ability to reduce the growth of OMP-Pn4 pancreatic tumor xenografts. NOD/SCID mice were purchased from Harlan (Indianapolis. Ind.) and allowed to acclimate for several days prior to the studies. The establishment and characterization of in vivo cancer stem cell-driven pancreas xenograft models were described previously (Li et al., *Cancer Res.*, 67:1030-7, 2007). For efficacy studies. OMP-Pn4 human pancreatic tumor cells were dissociated into single cell suspensions, resuspended in 1:1 (v/v) mixture of FACS buffer (Hank's balanced salt solution [HBSS] supplemented with 2% heat-inactivated fetal bovine serum and 20 mM Hepes) and Matrigel (BD Bioscience, San Jose, Calif.) and implanted subcutaneously into the right flank region of 6-7 weeks old male NOD/SCID mice with a 25-gauge needle containing 50,000 cells/100 μL. Tumor growth was monitored weekly and tumor measurements were initiated once tumors were palpable. At day 36, the mean tumor volumes reached about 120 mm$^3$ and the tumor-bearing animals were randomized (4 groups of 9 per group). Treatment was initiated two days later. Animals were injected with control antibody, with 18R5 IgG antibody (10 mg/kg), with gemcitabine (40 mg/kg), or with a combination of both 18R5 IgG antibody and gemcitabine. Administration of the antibodies and/or gemcitabine was performed via injection into the intra-peritoneal cavity, once weekly. Tumor growth was measured by with an electronic caliper (Coast Tools Company, San Leandro, Calif.). Tumors were measured once a week and tumor volume was determined using the formula ½(a×b$^2$); where a=length (longest axis of the tumor), and b=breadth (shortest axis of the tumor). Animals were weighed every day if they showed more than 15% body weight loss and euthanized if they showed 20% body weight. Data are expressed as mean±S.E.M. Differences in mean values between groups were analyzed by non-parimetric t test. Multiple comparisons used one-way ANOVA test with posthoc t test comparison. Differences of p<0.05 are considered significantly different. Software for statistical analysis was by GraphPad Prism4 (GraphPad Software Inc., San Diego, Calif.). At the end of the study, the mice were euthanized using a $CO_2$ chamber followed by cervical dislocation. Tumors were collected for RNA and histologic analysis. The remaining tumors were transferred into cold medium 199 for processing into single cell suspensions for analysis of cancer stem cell frequency.

The results of the OMP-Pn4 xenograft study are shown in FIG. 12. Treatment with the 18R5 antibody as monotherapy did not result in a significant reduction in tumor growth in this experiment. However, treatment with 18R5 and gemcitabine resulted in a reduction of tumor growth by 42% over treatment with gemcitabine (FIG. 12; p=<0.001 vs gemcitabine alone). Thus, 18R5 demonstrated synergistic anti-tumor growth activity in OMP-Pn4 pancreatic tumor model in combination with gemcitabine, an approved standard-of-care chemotherapy agent.

Reduction of PE-13 Breast Tumor Growth by Combination Treatment of 18R5 and Paclitaxel 10.000 PE-13 human breast tumor cells (HER2-negative) were implanted in NOD-SCID mice and allowed to grow for 22 days until they reached an average volume of approximately 120 mm$^3$. The animals were then randomized into 4 groups of 10 animals each and dosed with either a control antibody, anti-FZD 18R5, paclitaxel (TAXOL®®), or 18R5 plus paclitaxel. FIG. 37 shows the average tumor volumes of the mice dosed with control antibody, anti-FZD 18R5, paclitaxel, or 18R5 plus paclitaxel. Antibodies were dosed at 10 mg/kg, IP, twice per week. Paclitaxel was dosed at 10 mg/kg, IP, once per week. Tumors were measured on the days indicated in FIG. 37. FIG. 38 shows the tumor growth of the individual animals in the 18R5 plus paclitaxel group. 18R5 plus paclitaxel treatment was shown to result in anti-tumor activity and regression of established breast tumors.

Example 8

Assays to Determine Effect on Cancer Stem Cell Frequency

Limiting dilution assays (LDAs) can be used to assess the effect of a FZD-binding agent or antibody on solid tumor cancer stem cells and on the tumorigenicity of a tumor comprising the cancer stem cells. The assays can be used to determine the frequency of cancer stem cells in tumors from animals treated with the FZD-binding antibody or other agent and to compare that frequency to the frequency of cancer stem cells in tumors from control animals.

Effect of Combination Treatment of 18R5 and Irinotecan on Cancer Stem Cells in OMP-C28 Tumors Control and treated tumors from the OMP-C28 xenograft study described above (Example 7) were harvested at the end of the study (day 48). The tumors were processed and dissociated into single cells. Tumor cells were then incubated with biotinylated mouse antibodies (α-mouse CD45-biotin 1:200 dilution and rat α-mouse H2 Kd-biotin 1:100 dilution, BioLegend, San Diego, Calif.) on ice for 30 min followed by addition of streptavidin-labeled magnetic beads (Invitrogen, Carlsbad, Calif.) to remove mouse cells with the aid of a magnet.

For the LDA, the human cells in the suspension were harvested, counted, and appropriate cell doses (5, 25, and 125 cells) in FACS buffer were mixed in a 1:1 mixture with Matrigel and injected subcutaneously in NOD/SCID mice (10 mice per cell dose per treatment group). Tumors are allowed to grow for up to 4 months. At the desired time point, the percentage of mice with detectable tumors is determined in all groups injected with anti-FZD antibody treated tumor cells and compared to the percentage of mice with detectable tumors in the controls. For example, the number of mice injected with 125 control-treated tumor cells that have detectable tumors is determined and compared to the number of mice injected with 125 FZD-antibody treated tumor cells that have detectable tumors. The cancer stem cell frequency is then calculated using L-Calc™ software (Stem-Cell Technologies Inc.). Briefly, based on Poisson statistics, exactly one cancer stem cell exists among the known number of injected cells if 37% of the animals fail to develop tumors.

For analysis of cell surface markers, the single tumor cell suspension was stained with anti-ESA (Biomeda) and anti-CD44 (BD Biosciences) antibodies which were directly conjugated to fluorochromes. Dead cells were excluded by using the viability dye DAPI. Flow cytometry was performed using a FACS Aria (Becton Dickinson). Side scatter and forward scatter profiles were used to eliminate cell clumps. Analysis of the tumors treated with control antibody revealed that 64% of the bulk tumor population expressed both ESA and CD44 at high levels (FIG. 39). The double positive population was not significantly affected by treatment with irinotecan alone (55%), as shown in FIG. 39, but treatment with either 18R5 or the combination of 18R5 with irinotecan reduced the double positive population (40% and 32% respectively).

Effect of Combination Treatment of 18R5 and Gemcitabine on Cancer Stem Cells in OMP-Pn4 Tumors Control and treated tumors from the OMP-Pn4 xenograft study described above (Example 7) were harvested at the end of 41 days treatment. The tumors were processed and dissociated into single cells. Tumor cells were then incubated with biotinylated mouse antibodies (α-mouse CD45-biotin 1:200 dilution and rat α-mouse H2 Kd-biotin 1:100 dilution, BioLegend, San Diego, Calif.) on ice for 30 min followed by addition of streptavidin-labeled magnetic beads (Invitrogen, Carlsbad, Calif.) to remove mouse cells. The remaining human cells in the suspension were collected, counted and diluted to appropriate cell doses (30, 90, 270 and 810 cells), mixed in the mixture of 1:1 (v/v) FACS buffer and Matrigel and injected subcutaneously in NOD/SCID mice (10 mice per cell dose per treatment group). Tumors were allowed to grow for 75 days as shown in FIG. 40. Each dot in FIG. 40 represents the tumor volume of an individual mouse. The percentage of mice with detectable tumors was determined in all groups injected with anti-FZD antibody treated tumor cells and compared to the percentage of mice with detectable tumors in the controls. For example, the number of mice injected with 810 control-treated tumor cells that have detectable tumors was determined and compared to the number of mice injected with 810 FZD-antibody treated tumor cells that have detectable tumors. The tumor growth frequency was used to calculate the cancer stem cell frequency using L-Calc™ software. The calculated cancer stem cell frequencies for each of the treatment groups are shown in FIG. 41. Treatment with 18R5 alone and treatment with 18R5 in combination with gemcitabine reduced cancer stem cell frequency, while treatment with gemcitabine alone had no effect.

Example 9

Production of FZD Antibodies

Antigen Production

Recombinant polypeptide fragments of the extracellular domain (ECD) or Fri domain (Fri) of human FZD receptors (FZDs) are generated as antigens for antibody production. Standard recombinant DNA technology is used to isolate polynucleotides encoding the amino acids of these domains of the desired human frizzled receptor or receptors. These polynucleotides are ligated in-frame N-terminal to either a human Fc-tag or histidine-tag and cloned into a transfer plasmid vector for baculovirus mediated expression in insect cells. Standard transfection, infection, and cell culture protocols are used to produce recombinant insect cells expressing the corresponding FZD polypeptides (O'Reilley et al. Baculovirus expression vectors: A Laboratory Manual, Oxford: Oxford University Press (1994)).

Antigen protein is purified from insect cell conditioned medium using Protein A and Ni++-chelate affinity chromatography. Purified antigen protein is dialyzed against PBS (pH=7), concentrated to approximately 1 mg/ml, and sterile filtered in preparation for immunization.

Immunization

Mice are immunized with purified FZD antigen protein using standard techniques. Blood from individual mice are screened approximately 70 days after initial immunization for antigen recognition using ELISA and FACS analysis (described in detail below). The two animals with the highest antibody titers are selected for final antigen boost after which spleen cells are isolated for hybridoma production. Hybridoma cells are plated at 1 cell per well in 96 well plates, and the supernatant from each well are screened by ELISA and FACS analysis against antigen protein. Several hybridomas with high antibody titer are selected and scaled up in static flask culture. Antibodies are purified from the hybridoma supernatant using protein A or protein G agarose chromatography. Purified monoclonal antibodies are again tested by FACS and are isotyped to select for IgG and IgM antibodies.

Epilope Mapping

To identify antibodies that recognize specific regions of the FZD extracellular domain including the cysteine-rich domain, epitope mapping is performed. Mammalian expression plasmid vectors comprising a CMV promoter upstream of polynucleotides that encode fragments of the extracellular FZD domain are generated using standard recombinant DNA technology. Recombinant proteins are then expressed in cultured mammalian cells by transient transfection. Twenty-four to 48 hours following transfection, cells are harvested and cell lysate protein separated on SDS-PAGE acrylamide gels for Western blotting using antibodies from mice immunized with FZD antigen. Antibodies that recognize the ligand binding domain of FZD can be further analyzed for competitive binding with Wnt proteins by ELISA.

To identify specific epitopes within the extracellular domains recognized by an antibody against FZD the SPOTs system is used (Sigma Genosys, The Woodlands, Tex.). A series of 10-residue linear peptides overlapping by one amino acid and covering the entire FZD extracellular domain are synthesized and covalently bound to a cellulose membrane by the SPOT synthesis technique. The membrane is preincubated for 8 hours at room temperature with blocking buffer and hybridized with antibody overnight at 4° C. The membrane is then washed, incubated with a secondary antibody conjugated to horseradish peroxidase (HRP) (Amersham Bioscience. Piscataway. N.J.), re-washed, and visualized with signal development solution containing 3-amino-9-ethylcarbazole. Specific epitopes recognized by an antibody are thus determined.

FACS Analysis

To select monoclonal antibodies produced by hybridomas clones that recognize native cell-surface FZD protein. FACs analysis is used. HEK293 cells are transfected with an expression vector encoding a full-length cDNA clone of the corresponding FZD either alone or co-transfected with a vector expressing GFP. A Flag epitope tag may be introduced at the amino-terminus, which allows verification of expression of the tagged FZD receptors on the cell surface. Twenty-four to 48-hours post-transfection, cells are collected in suspension and incubated on ice with anti-FZD antibodies, FLAG antibodies, immune serum (for FZD5 expressing cells), or control IgG to detect background antibody binding. The cells are washed and primary antibodies detected with anti-mouse secondary antibodies conjugated to a fluorescent chromophore. Labeled cells are then sorted by FACS to identify anti-FZD antibodies that specifically recognize cell surface expression of the corresponding FZD receptor. Antibodies that recognize the desired human frizzled receptor(s) are identified.

Chimeric Antibodies

After monoclonal antibodies that specifically recognize a FZD receptor are identified, these antibodies are modified to overcome the human anti-mouse antibody (HAMA) immune response when rodent antibodies are used as therapeutics agents. The variable regions of the heavy-chain and light-chain of the selected monoclonal antibody are isolated by RT-PCR from hybridoma cells and ligated in-frame to human IgG1 heavy-chain and kappa light chain constant regions, respectively, in mammalian expression vectors. Alternatively a human Ig expression vector such as TCAE 5.3 is used that contains the human IgG1 heavy-chain and kappa light-chain constant region genes on the same plasmid (Preston et al., 1998, Infection & Immunity 66:4137-42). Expression vectors encoding chimeric heavy- and light-chains are then co-transfected into Chinese hamster ovary (CHO) cells for chimeric antibody production. Immunoreactivity and affinity of chimeric antibodies are compared to parental murine antibodies by ELISA and FACS.

Humanized Antibodies

As chimeric antibody therapeutics are still frequently antigenic, producing a human anti-chimeric antibody (HACA) immune response, chimeric antibodies against a FZD receptor can undergo further humanization. To generate humanized antibodies, key aspects of the specificity determining motifs of the antibody, potentially including elements from both the three short hypervariable sequences, or complementary determining regions (CDRs), and/or the framework regions required to correctly position the CDR regions of the antibody heavy- and light-chain variable domains described above are engineered using recombinant DNA technology into the germline DNA sequences of human heavy- and light-chain antibody genes, respectively, and then cloned into a mammalian expression vector for expression in CHO cells. The immunoreactivity and affinity of the humanized antibodies are compared to parental chimeric antibodies by ELISA and FACS. Additionally, site-directed or high-density mutagenesis of the variable region can be used to optimize specificity, affinity, etc. of the humanized antibody.

Human Antibodies

In some embodiments, human antibodies that specifically recognize the extracellular domain of a FZD receptor are isolated using phage display technology. A phage display antibody library containing human antibody variable domains displayed as single chain Fv or as fab domains is screened for specific and high affinity recognition of a FZD receptor antigen described above. The identified variable domain antibody sequences are then reformatted into an Ig expression vector containing human IgG1 heavy-chain and kappa light-chain for expression of human antibodies in CHO cells.

Example 10

Production of Antibodies that Recognize Specific Epitopes

Monoclonal Antibodies from Hybridomas

In certain embodiments, antibodies recognizing functional epitopes of FZD receptors are generated by immunizing mice with one or more of the FZD receptor antigens. Mice are immunized with the purified FZD antigen protein using standard techniques. In certain embodiments mice are immunized sequentially with distinct FZD receptor antigens. Blood from individual mice are screened approximately 70 days after initial immunization. Animals with the high antibody titer for the FZD antigen are selected for final antigen boost after which spleen cells are isolated for hybridoma production. Hybridoma cells are plated at 1 cell per well in 96 well plates, and the supernatants from each well are screened by ELISA and flow cytometry analysis. To identify monoclonal antibodies that recognize specific epitopes, including epitopes within or overlapping with the Biological Binding Site (BBS), the hybridoma supernatant is screened both for antibody binding to the desired FZD(s) and for failure to bind to FZD that have specific amino acid substitutions within the desired specific epitope (e.g. the BBS).

Human Antibodies

A phage display library may be used to identify antibodies that recognize the desired epitopes of the FZD receptors (e.g., epitopes common to multiple FZD and/or epitopes within or overlapping with the BBS or a portion thereof). For example, the Fri domain of a selected FZD is expressed as recombinant protein and coated on an appropriate surface at 10 µg/mL. A human phage library is then panned through two or more rounds of enrichment (See e.g. Griffiths et al., *EMBO J.* 12:715-34). Optionally, the subsequent rounds of panning may be performed using distinct FZD proteins. Optionally, each round of the panning may be performed in the presence of decoy soluble FZD protein containing specific amino acid substitutions within the desired target epitope region (e.g. including the epitopes within the Biological Binding Site (BBS)). Individual clones of the output from the panning selections are then screened for the ability to bind to desired FZD protein(s) by ELISA or flow cytometry analysis and binding to a desired epitope is assessed by lack of binding to FZD protein containing specific amino acid substitutions within the desired target epitope. Genes encoding the antigen binding domain are then recovered from the phage and used to construct a complete human antibody molecule by joining the antigen binding domain with constant regions for expression in a suitable host cell line. Antibodies are identified and tested for the ability to prevent tumor cell growth as described elsewhere herein.

Example 11

Additional In Vitro Assays to Evaluate Antibodies Against a FZD Receptor

This example describes representative in vitro assays to test the activity of antibodies generated against a FZD receptor on cell proliferation, pathway activation, and cytotoxicity.

Proliferation Assay

The expression of a FZD receptor by different cancer cell lines is quantified using Taqman analysis. Cell lines identified as expressing a FZD receptor are plated at a density of 10⁴ cell per well in 96-well tissue culture microplates and allowed to spread for 24 hours. Subsequently cells are cultured for an additional 12 hours in fresh DMEM with 2% FCS at which point anti-FZD antibodies versus control antibodies are added to the culture medium in the presence of 10 μmol/L BrdU. Following BrdU labeling, the culture media is removed, and the cells fixed at room temperature for 30 minutes in ethanol and reacted for 90 minutes with peroxidase-conjugated monoclonal anti-BrdU antibody (clone BMG 6H8, Fab fragments). The substrate is developed in a solution containing tetramethylbenzidine and stopped after 15 minutes with 25 μl of 1 mol/L $H_2SO_4$. The color reaction is measured with an automatic ELISA plate reader using a 450 nm filter (UV Microplate Reader; Bio-Rad Laboratories, Richmond, Calif.). All experiments are performed in triplicate. The ability of anti-FZD antibodies to inhibit cell proliferation compared to control antibodies is determined.

Pathway Activation Assay

In certain embodiments, the ability of antibodies against a FZD receptor to block activation of the Wnt signaling pathway is determined in vitro. For example, HEK 293 cells cultured in DMEM supplemented with antibiotics and 10% FCS are co-transfected with 1) Wnt7B and FZD10 expression vectors to activate the Wnt signaling pathway; 2) a TCF/Luc wild-type or mutant reporter vector containing three or eight copies of the TCF-binding domain upstream of a firefly luciferase reporter gene to measure canonical Wnt signaling levels (Gazit et al., 1999, *Oncogene* 18:5959-66); and 3) a *Renilla* luciferase reporter (Promega; Madison, Wis.) as an internal control for transfection efficiency. Anti-FZD10 and control antibodies are then added to the cell culture medium. Forty-eight hours following transfection, luciferase levels are measured using a dual luciferase assay kit (Promega; Madison, Wis.) with firefly luciferase activity normalized to *Renilla* luciferase activity. Three independent experiments are preformed in triplicate. The ability of the FZD antibodies to inhibit Wnt pathway activation is thus determined.

Complement-Dependent Cytotoxicity Assay

In certain embodiments, cancer cell lines expressing a FZD receptor or cancer stem cells isolated from a patient sample passaged as a xenograft in immunocompromised mice are used to measure complement dependent cytotoxicity (CDC) mediated by an antibody against a FZD receptor. Cells are suspended in 200 μl RPMI 1640 culture medium supplemented with antibiotics and 5% FBS at 10⁶ cells/ml. Suspended cells are then mixed with 200 μl serum or heat-inactivated serum with antibodies against a FZD receptor or control antibodies in triplicate. Cell mixtures are incubated for 1 to 4 hours at 37° C. in 5% $CO_2$. Treated cells are then collected, resuspended in 100 μl FITC-labeled annexin V diluted in culture medium and incubated at room temperature for 10 minutes. One hundred microliters of a propidium iodide solution (25 μg/ml) diluted in HBSS is added and incubated for 5 minutes at room temperature. Cells are collected, resuspended in culture medium and analyzed by flow cytometry. Flow cytometry of FITC stained cells provides total cell counts, and propidium iodide uptake by dead cells as a percentage of total cell numbers is used to measure cell death in the presence of serum and antibodies against a FZD compared to heat-inactivated serum and control antibodies. The ability of anti-FZD antibodies to mediate complement-dependent cytotoxicity is thus determined.

Antibody-Dependent Cellular Cytotoxicity Assay

Cancer cell lines expressing a FZD receptor or cancer stem cells isolated from a patient's sample passaged as a xenograft in immunocompromised mice may be used to measure antibody dependent cellular cytotoxicity (ADCC) mediated by an antibody against a FZD receptor. Cells are suspended in 200 μl phenol red-free RPMI 1640 culture medium supplemented with antibiotics and 5% FBS at 10⁶ cells/ml. Peripheral blood mononuclear cells (PBMCs) are isolated from heparinized peripheral blood by Ficoll-Paque density gradient centrifugation for use as effector cells. Target cells (T) are then mixed with PBMC effector cells (E) at E/T ratios of 25:1, 10:1, and 5:1 in 96-well plates in the presence of at least one FZD receptor antibody or a control antibody. Controls include incubation of target cells alone and effector cells alone in the presence of antibody. Cell mixtures are incubated for 1 to 6 hours at 37° C. in 5% CO2. Released lactate dehydrogenase (LDH), a stable cytosolic enzyme released upon cell lysis, is then measured by a colorimetric assay (CytoTox96 Non-radioactive Cytotoxicity Assay; Promega: Madison, Wis.). Absorbance data at 490 nm are collected with a standard 96-well plate reader and background corrected. The percentage of specific cytotoxicity is calculated according to the formula: % cytotoxicity=100×(experimental LDH release−effector spontaneous LDH release−target spontaneous LDH release)/(target maximal LDH release−target spontaneous LDH release). The ability of antibodies against a FZD receptor to mediate antibody dependent cellular cytotoxicity is thus determined.

Example 12

In Vivo Prevention of Tumor Growth Using Anti-FZD Receptor Antibodies

This example describes a use of anti-FZD receptor antibodies to prevent tumor growth in a xenograft model. In certain embodiments, tumor cells from a patient sample (solid tumor biopsy or pleural effusion) that have been passaged as a xenograft in mice are prepared for repassaging into experimental animals. Tumor tissue is removed under sterile conditions, cut up into small pieces, minced completely using sterile blades, and single cell suspensions obtained by enzymatic digestion and mechanical disruption. Specifically, pleural effusion cells or the resulting tumor pieces are mixed with ultra-pure collagenase III in culture medium (200-250 units of collagenase per mL) and incubated at 37° C. for 3-4 hours with pipetting up and down through a 10-mL pipette every 15-20 minutes. Digested cells are filtered through a 45 μM nylon mesh, washed with RPMI/20% FBS, and washed twice with HBSS. Dissociated tumor cells are then injected subcutaneously into the mammary fat pads of NOD/SCID mice to elicit tumor growth.

In certain embodiments, dissociated tumor cells are first sorted into tumorigenic and non-tumorigenic cells based on cell surface markers before injection into experimental animals. Specifically, tumor cells dissociated as described above are washed twice with Hepes buffered saline solution (HBSS) containing 2% heat-inactivated calf serum (HICS) and resuspended at 10⁶ cells per 100 μl. Antibodies are added and the cells incubated for 20 minutes on ice followed by two washes with HBSS/2% HICS. Antibodies include anti-ESA (Biomeda, Foster City, Calif.), anti-CD44, anti-CD24, and Lineage markers anti-CD2, -CD3, -CD10, -CD16, -CD18, -CD31, -CD64, and -CD140b (collectively referred to as Lin; PharMingen, San Jose, Calif.). Antibodies are directly conjugated to fluorochromes to positively or negatively select cells expressing these markers. Mouse cells are eliminated by selecting against H2Kd+ cells, and dead cells are eliminated by using the viability dye 7AAD. Flow cytometry is performed on a FACSVantage (Becton Dickinson, Franklin Lakes, N.J.). Side scatter and forward scatter profiles are used to eliminate cell clumps. Isolated ESA+, CD44+, CD24−/low, Lin− tumorigenic cells are then injected subcutaneously into NOD/SCID mice to elicit tumor growth.

By way of example, anti-FZD antibodies are analyzed for their ability to reduce the growth of tumor cells. Dissociated tumor cells (10,000 per animal) are injected subcutaneously into the flank region of 6-8 week old NOD/SCID mice. Two days after tumor cell injection, animals are injected intraperitoneal (i.p.) with 10 mg/kg either anti-FZD antibodies two times per week. Tumor growth is monitored weekly until growth is detected, after which point tumor growth is measured twice weekly for a total of 8 weeks. FZD-binding antibodies which significantly reduce tumor growth as compared to PBS injected controls are thus identified.

Example 13

In Vivo Treatment of Tumors Using Anti-FZD Receptor Antibodies

This example describes a use of anti-FZD receptor antibodies to treat cancer in a xenograft model. In certain embodiments, tumor cells from a patient sample (solid tumor biopsy or pleural effusion) that have been passaged as a xenograft in mice are prepared for repassaging into experimental animals. Tumor tissue is removed, cut up into small pieces, minced completely using sterile blades, and single cell suspensions obtained by enzymatic digestion and mechanical disruption. Dissociated tumor cells are then injected subcutaneously either into the mammary fat pads, for breast tumors, or into the flank, for non-breast tumors, of NOD/SCID mice to elicit tumor growth. Alternatively, ESA+, CD44+, CD24−/low, Lin− tumorigenic tumor cells are isolated as described above and injected.

Following tumor cell injection, animals are monitored for tumor growth. Once tumors reach an average size of approximately 150 to 200 mm, antibody treatment begins. Each animal receives 100 µg FZD receptor antibodies or control antibodies i.p. two to five times per week for a total of 6 weeks. Tumor size is assessed twice a week during these 6 weeks. The ability of FZD receptor antibodies to prevent further tumor growth or to reduce tumor size compared to control antibodies is thus determined.

At the end point of antibody treatment, tumors are harvested for further analysis. In some embodiments a portion of the tumor is analyzed by immunofluorescence to assess antibody penetration into the tumor and tumor response. A portion of each harvested tumor from anti-FZD receptor treated and control antibody treated mice is fresh-frozen in liquid nitrogen, embedded in O.C.T, and cut on a cryostat as 10 µm sections onto glass slides. In some embodiments, a portion of each tumor is formalin-fixed, paraffin-embedded, and cut on a microtome as 10 µm section onto glass slides. Sections are post-fixed and incubated with chromophore labeled antibodies that specifically recognize injected antibodies to detect anti-FZD receptor or control antibodies present in the tumor biopsy. Furthermore antibodies that detect different tumor and tumor-recruited cell types such as, for example, anti-VE cadherin (CD144) or anti-PECAM-1 (CD31) antibodies to detect vascular endothelial cells, anti-smooth muscle alpha-actin antibodies to detect vascular smooth muscle cells, anti-Ki67 antibodies to detect proliferating cells, TUNEL assays to detect dying cells, anti-β-catenin antibodies to detect Wnt signaling, and anti-intracellular domain (ICD) Notch fragment antibodies to detect Notch signaling can be used to assess the effects of antibody treatment on, for example, angiogenesis, tumor growth and tumor morphology.

In certain embodiments, the effect of anti-FZD receptor antibody treatment on tumor cell gene expression is also assessed. Total RNA is extracted from a portion of each harvested tumor from FZD antibody treated and control antibody treated mice and used for quantitative RT-PCR. Expression levels of FZD receptors, components of Wnt signaling pathway including, for example, Wnt1 and β-catenin, as well as addition cancer stem cell markers previously identified (e.g. CD44) are analyzed relative to the house-keeping gene GAPDH as an internal control. Changes in tumor cell gene expression upon FZD receptor antibody treatment are thus determined.

In addition, the effect of anti-FZD receptor antibody treatment on the frequency of cancer stem cells in a tumor is assessed. Tumor samples from FZD versus control antibody treated mice are cut up into small pieces, minced completely using sterile blades, and single cell suspensions obtained by enzymatic digestion and mechanical disruption. Dissociated tumor cells are then analyzed by FACS analysis for the presence of tumorigenic cancer stem cells based on ESA+, CD44+, CD24−/low, Lin− surface cell marker expression as described in detail above.

The tumorigenicity of cells isolated based on ESA+, CD44+, CD24−/low, Lin− expression following anti-FZD antibody treatment can then assessed. ESA+, CD44+, CD24−/low, Lin− cancer stem cells isolated from FZD antibody treated versus control antibody treated mice are re-injected subcutaneously into the mammary fat pads of NOD/SCID mice. The tumorigenicity of cancer stem cells based on the number of injected cells required for consistent tumor formation is then determined.

Example 14

Identification of a Wnt Gene Signature

Experiments were conducted to identify a group of genes whose expression is specific for Wnt signaling pathway activation in human colon tumors.

Abrogation of Tumor Growth by Axin Overexpression

Axin is an important regulator of the canonical Wnt pathway. It is part of the multiprotein complex that triggers β-catenin degradation, thus keeping the pathway silent in the absence of Wnt. This effect is reversed by Wnt, which removes axin from the destruction complex, allowing for β-catenin translocation and TCF-mediated activation of specific target genes. Both exogenous axin over-expression and expression of a dominant negative truncated form of TCF (DNTCF4) represent well-characterized means to block the Wnt signaling pathway.

We showed that lentivirus-mediated axin overexpression completely abrogated the growth of UM-PE13 and UM-T3 breast tumors as well as the growth of OMP-C11 and OMP-C17 colon tumors in NOD/SCID mice. Stable expression of DNTCF4 in UM-T3 tumor cells had the same effect. Taken together, these data demonstrate that intracellular Wnt blockade can negatively affect the development of different tumor types, supporting the Wnt pathway as a relevant target for the treatment of breast and colon cancers.

The Wnt signaling pathway is constitutively activated in many tumor types. In most colon tumors this activation is due to truncating mutation of APC or activating mutations of β-catenin. Such mutations have not been reported for other tissues, in which the Wnt signaling pathway could be activated through another set of mutations or an autocrine mechanism. In those tumors where the Wnt signaling pathway remains responsive to autocrine stimuli, blocking the pathway using extracellular means such as antibodies or other soluble protein inhibitors should be feasible and impact tumor development. Identifying such Wnt-dependent tumors would be helpful in developing anti-Wnt agents and defining tumor types to target in the clinic.

Immunohistochemical data showed that most OMP-C11 tumor cells express high levels of cytoplasmic/nuclear β-catenin, suggesting that the Wnt signaling pathway is constitutively activated in this tumor type. This was confirmed by the detection of high levels of β-catenin in OMP-C11 by Western blot. The combination of Wnt pathway activation and sensitivity to axin overexpression makes OMP-C11 a good tumor in which to study the regulation of gene expression in response to Wnt and Wnt blockade and from which to derive a Wnt gene signature.

Microarray Analysis of Differential Gene Expression in Response to Axin Overexpression The differential gene expression upon treatment of OMP-C11 colon tumor cells with axin was determined by microarray analysis.

Human colon OMP-C11 tumors freshly removed from NOD/SCID mice (xenograft tumor model) were used as a source for the colon tumor cells. Two lentiviral vectors were generated for the delivery of a constitutive axin-IRES-GFP expression cassette and a control IRES-GFP expression cassette that were termed LOM91 and LOM92, respectively.

OMP-C11 tumors were processed to a single cell suspension and depleted from the mouse lineage cells. The lin-depleted cells were infected with LOM91 (axin) or 92 (control) lentiviral vectors using a multiplicity of infection of 2.5, maintained in culture for 3-4 days and sorted for GFP expression. Total RNA was extracted from each sample of sorted cells. The RNAs were analyzed on the GeneChip® Human Genome U133 Plus 2.0 microarray (Affymetrix, Santa Clara, Calif.). The experiment was repeated twice.

A gene signature containing a core set of genes regulated by the Wnt pathway was generated by analysis of the genes that are differentially expressed following axin treatment and that also exhibit correlation with the expression of axin2 across a panel of normal and malignant colon tumor samples. Genes were identified from the axin microarray experiment (above) that showed down regulation in response to axis overexpression. The cutoff for this selection was down-regulation by 50% or more in Axin1 over-expressing samples comparing to control samples (log 2ratio of Axin1 over-expressing samples over control samples has to be −1 or smaller), with T test p value smaller than 0.1. As Axin1 is a known Wnt pathway inhibitor, genes down-regulated by Axin1 over expression will be direct or indirect Wnt pathway targets. This selection was then further refined by identification of those genes which showed high correlation (correlation value >0.3) with axin2 among a set of colon/intestine/other digestive tissue malignant tumor samples (232 samples). Since Axin2 is a known Wnt target, genes showing similar expression pattern as Axin2 will likely be Wnt target as well. This analysis produced a gene signature for Wnt pathway activity (Table 6). The expression levels of the genes in this signature can be used to assess whether individual tumor samples or different types of tumors show evidence of altered Wnt pathway signaling.

TABLE 6

Wnt gene signature list derived from colon tumors

| HG_U133_Plus_2 Probe Set ID | Correlation | log2ratio | Gene Symbol | Description |
| --- | --- | --- | --- | --- |
| 222696_at | 1 | −1.52705 | AXIN2 | axin 2 (conductin, axil) |
| 206286_s_at | 0.81941 | −1.15086 | TDGF1 | teratocarcinoma-derived growth factor 1 |
| 213880_at | 0.787599 | −3.32482 | LGR5 | leucine-rich repeat-containing G protein-coupled receptor 5 |
| 207217_s_at | 0.781543 | −1.15534 | NOX1 | NADPH oxidase 1 |
| 209588_at | 0.762464 | −1.09556 | EPHB2 | EPH receptor B2 |
| 212850_s_at | 0.75362 | −2.00386 | LRP4 | low density lipoprotein receptor-related protein 4 |
| 205107_s_at | 0.744062 | −1.01296 | EFNA4 | ephrin-A4 |
| 214058_at | 0.718735 | −1.74381 | MYCL1 | v-myc myelocytomatosis viral oncogene homolog 1, lung carcinoma derived (avian) |
| 209864_at | 0.714811 | −1.25716 | FRAT2 | frequently rearranged in advanced T-cell lymphomas 2 |
| 208121_s_at | 0.711694 | −1.87702 | PTPRO | protein tyrosine phosphatase, receptor type, O |
| 229376_at | 0.711672 | −1.73296 | | Unknown expressed sequence tag (EST) |
| 202431_s_at | 0.659255 | −1.49975 | MYC | v-myc myelocytomatosis viral oncogene homolog (avian) |
| 212444_at | 0.656023 | −2.15908 | GPCR5A | G protein-coupled receptor, family C, group 5, member A |
| 222938_x_at | 0.654955 | −2.43139 | ENPP3 | ectonucleotide pyrophosphatase/ phosphodiesterase 3 |
| 241607_at | 0.640554 | −1.00413 | LOC730102 | hypothetical protein LOC730102 |
| 227475_at | 0.637963 | −3.60987 | FOXQ1 | forkhead box Q1 |
| 230398_at | 0.628654 | −1.65124 | TNS4 | tensin 4 |
| 40284_at | 0.601382 | −1.21862 | FOXA2 | forkhead box A2 |
| 219704_at | 0.557276 | −1.33216 | YBX2 | Y box binding protein 2 |

Example 15

Treatment of Human Cancer Using Anti-FZD Receptor Antibodies

This example describes methods for treating cancer using antibodies against a FZD receptor to target tumors comprising cancer stem cells and/or tumor cells in which FZD receptor expression has been detected and/or tumor cells having a Wnt gene signature indicating that they are responsive to inhibition of Wnt signaling (e.g., the Wnt gene signature of Example 14).

The presence of cancer stem cell marker or FZD receptor or the expression of one or more genes in a Wnt gene signature can first be determined from a tumor biopsy. Tumor cells from a biopsy from a patient diagnosed with cancer are removed under sterile conditions. In some embodiments the tissue biopsy is fresh-frozen in liquid nitrogen, embedded in O.C.T., and cut on a cryostat as 10 µm sections onto glass slides. In some embodiments, the tissue biopsy is formalin-fixed, paraffin-embedded, and cut on a microtome as 10 µm section onto glass slides.

Sections are incubated with antibodies against a FZD receptor to detect FZD protein expression. Alternatively, sections can be analyzed for the presence of one or more genes in the Wnt gene signature as described in Example 14.

The presence of cancer stem cells also may be determined. Tissue biopsy samples are cut up into small pieces, minced completely using sterile blades, and cells subject to enzymatic digestion and mechanical disruption to obtain a single cell suspension. Dissociated tumor cells are then incubated with anti-ESA, -CD44, -CD24, -Lin, and -FZD antibodies to detect cancer stem cells, and the presence of ESA+. CD44+, CD24−/low, Lin−, FZD+ tumor stem cells is determined by flow cytometry as described in detail above.

Cancer patients whose tumors are diagnosed as expressing a FZD receptor and/or one or more genes in the Wnt gene signature are treated with anti-FZD receptor antibodies. In certain embodiments, humanized or human monoclonal anti-FZD receptor antibodies generated as described above are purified and formulated with a suitable pharmaceutical vehicle for injection. In some embodiments, patients are treated with the FZD antibodies at least once a month for at least 10 weeks. In some embodiments, patients are treated with the FZD antibodies at least once a week for at least about 14 weeks. Each administration of the antibody should be a pharmaceutically effective dose. In some embodiments, between about 2 to about 100 mg/ml of an anti-FZD antibody is administered. In some embodiments, between about 5 to about 40 mg/ml of an anti-FZD antibody is administered. The antibody can be administered prior to, concurrently with, or after standard radiotherapy regimens or chemotherapy regimens using one or more chemotherapeutic agent, such as oxaliplatin, fluorouracil, leucovorin, or streptozocin. Patients are monitored to determine whether such treatment has resulted in an anti-tumor response, for example, based on tumor regression, reduction in the incidences of new tumors, lower tumor antigen expression, decreased numbers of cancer stem cells, or other means of evaluating disease prognosis.

Example 16

Differentiation of Pancreatic Tumor Cells Following Treatment with 18R5 and Gemcitabine Gene Expression Analysis of Treated Pancreatic Tumor Cells by Quantitative PCR (Q-PCR)

PN4 xenograft tumors treated with either control Ab, 18R5 IgG antibody, gemcitabine, or the combination of gemcitabine and 18R5. IgG antibody as described above (Example 7) were analyzed for expression of chromogranin A (CHGA) by quantitative PCR analysis. CHGA is well known to be a marker for neuroendocrine differentiation of various tumors including breast, colon, lung and pancreatic tumors and elevated expression of CHGA in pancreatic tumors has been found to be associated with improved survival (Tezel et al. 2000. Cancer 89, 2230-6).

Total RNA was prepared from 5-tumors of each group in the PN4 xenograft study and was evaluated by one-step reverse transcription (RT)-PCR using Applied Biosystems Taqman® inventoried probes according to standard protocols. The probe-primer set (Hs00154441_m1) used for analysis of CHGA included a FAM-dye labeled probe and the following primer: 5'-CGCTCTCCAAGGCGC-CAAGGAGAGG-3' (SEQ ID NO:75). Gus B was used as internal control. Briefly, RT was done at 48° C. for 30 min, initial denaturation at 95° C. for 10 min, followed by 40 cycles of denaturation at 95° C. for 15 seconds, and extension at 60° C. for 1 min and the amplification/incorporation of fluorescent probes was observed real-time.

The islet beta cell marker CHGA was elevated significantly only in samples from mice treated with both gemcitabine and 18R5. Tumors from the control Ab, 18R5, and gemcitibine alone groups expressed similar levels of CHGA RNA while tumors from the combination group showed a clear increase in CHGA expression. CHGA levels were elevated 10-fold and 7-fold in two experiments in tumors treated with both 18R5 and gemcitabine. The results of a representative experiment are shown in FIG. 42.

Gene Expression Analysis of Treated Pancreatic Tumor Cells by Immunohistochemistry The increased expression of CHGA was also observed at the protein level by immunohistochemistry on tissue sections prepared from treated tumors (data not shown). Control Ab treated tumors showed intense staining of a small subset of cells scattered throughout tumors. Tumors treated with 18R5 alone or gemcitabine alone expressed CHGA at similar levels as the controls. In contrast, tumors treated with the combination of 18R5 and gemcitabine showed an increase in the number of CHGA-positive cells, consistent with the increased RNA expression detected by Q-PCR.

Staining with Alcian Blue and Antibody to Ki67

Another characteristic of endocrine, secretory or ductal cells is the production of mucin and these cells can be detected by alcian blue staining (van Es et al. 2005. Nature 435 959-63). It was observed during harvesting and processing of tumors that the 18R5 treated tumors were much more mucinous than control treated tumors. Therefore, PN4 tumors sections from mice treated with control antibody, gemcitabine alone, 18R5 alone, or 18R5 plus gemcitabine were stained with alcian blue. The 18R5 treated tumors showed a clear increase in alcian blue staining in both the 18R5 alone and the 18R5 plus gemcitabine groups relative to controls and the gemcitabine alone group (data not shown).

Increased mucinous cells were also noted in a second pancreatic tumor line, PN13, following treatment with 18R5 or control antibody (FIG. 43). In this experiment mice bearing PN13 tumors were treated as described above (Example 7). Tumors sections were stained with alcian blue to reveal mucinous cells and also stained by immunohistochemistry with an antibody to ki67 to reveal cells undergoing proliferation. The results show that 18R5 treatment resulted in greatly increased numbers of alcian blue positive mucinous cells. Additionally, the frequency of ki67 positive cells was reduced by 18R5 treatment. Interestingly there was not an overlap between the mucinious cells and cells that were ki67 positive, suggesting that the mucinous cells are not proliferative. This provides evidence that 18R5 treatment is promoting the differentiation of tumor cells into non-proliferative progeny.

In summary, the increased expression of CHGA, the increased production of mucins as evidenced by alcian blue staining, and the production of non-proliferative progeny as evidenced by staining with antibody to ki67 are consistent with a model that inhibiting Wnt-FZD signaling with 18R5 treatment promotes the differentiation of pancreatic tumor cells towards multiple distinct cell types with features characteristic of non-proliferative differentiated cells.

Example 17

Additional In Vivo Efficacy Studies with 18R5 Alone and/or in Combination with Other Anti-Cancer Agents Effect on OMP-L U24 Xenograft Tumor Growth The efficacy of anti-FZD antibody 18R5, both alone and in combination with Taxol® (paclitaxel), in inhibiting the growth of OMP-LU24 human lung tumors in vivo was assessed.

50,000 OMP-LU24 human lung tumor cells were injected subcutaneously in NOD-SCID mice. Tumors were allowed to grow for 27 days until they reached an average volume of 143 mm³. The animals were randomized into 4 groups (n=9 per group) and treated with either control antibody ("Control Ab"), anti-FZD 18R5 ("18R5"). Taxol® ("Taxol") or the combination of 18R5 plus Taxol® ("18R5+Taxol"). Tumor measurements were made on the days indicated in FIG. 44. Antibodies were dosed at 10 mg/kg intraperitoneal (IP), once per week and Taxol® was dosed at 15 mg/kg, IP, once per week.

The results are shown in FIG. 44. Anti-FZD treatment was seen to reduce tumor growth, and the combination treatment showed enhanced anti-tumor activity relative to Taxol®® alone.

Effect on OMP-LU33 Xenograft Tumor Growth

The efficacy of anti-FZD antibody 18R5, both alone and in combination with Avastin® (bevacizumab), in inhibiting the growth of OMP-LU33 human lung tumors in vivo was also tested.

10,000 OMP-LU33 human lung tumor cells were injected subcutaneously in NOD-SCID mice. Tumors were allowed to grow for 30 days until they reached an average volume of 124 mm³. The animals were randomized into 4 groups (n=10 per group) and treated with either control antibody (squares), Avastin® (triangles pointing down), anti-FZD 18R5 (triangles pointing up), or the combination of 18R5 plus Avastin® (circles). Tumor measurements were made on the days indicated in FIG. 45. Antibodies were dosed at 10 mg/kg IP, twice per week.

The results are shown in FIG. 45. Anti-FZD treatment was seen to reduce tumor growth, and the combination treatment showed enhanced anti-tumor activity relative to Avastin® alone.

Effect On T3 Xenograft Tumor Growth

The efficacy of anti-FZD antibody 18R5, both alone and in combination with Herceptin® (trastuzumab), in inhibiting the growth of T3 human HER2-positive breast tumors in vivo was also assessed.

50,000 T3 human breast tumor cells were injected subcutaneously in NOD-SCID mice. Tumors were allowed to grow for 32 days until they reached an average volume of 125 mm³. The animals were randomized into 4 groups (n=10 per group) and treated with either control antibody (squares), anti-FZD 18R5 (triangles), Herceptin, (small filled circles), or the combination of 185 plus Herceptin® (open circles). Tumor measurements were made on the days indicated in FIG. 46. Antibodies were dosed at 10 mg/kg IP, twice per week.

The results are shown in FIG. 46. The combination treatment with 18R5 and Herceptin® showed enhanced anti-tumor activity relative to Herceptin® alone.

Example 18

Anti-FZD Antibody Sequences

Heavy chain and light chain CDRs of anti-FZD antibodies are provided in Tables 7 and 8, below, respectively. The heavy chain variable regions (VH) and light chain variable regions (VL) of the anti-FZD antibodies and their coding sequences are identified in Table 9, below. The amino acid and polynucleotide sequences of the VH and VL listed in Table 9 are provided in FIGS. 13-15 or Tables 10 and 11, below. Sequences encoding the heavy chain or light chains of the anti-FZD antibodies are provided in FIGS. 14-15 or Table 12, below.

TABLE 7

Heavy chain CDRs of anti-FZD human antibodies

| Ab(s) | Heavy Chain | | |
|---|---|---|---|
| | CDR1 | CDR2 | CDR3 |
| 18R8 | GFTFSHYTLS (SEQ ID NO: 1) | VISGDGSYTYYADSVKG (SEQ ID NO: 2) | NFIKYVFAN (SEQ ID NO: 3) |
| 18R5 18R4605 18R4805 | GFTFSHYTLS (SEQ ID NO: 1) | VISGDGSYTYYADSVKG (SEQ ID NO: 2) | NFIKYVFAN (SEQ ID NO: 3) |
| 44R24 | GFTFSSYYIT (SEQ ID NO: 77) | TISYSSSNTYYADSVKG (SEQ ID NO: 78) | SIVFDY (SEQ ID NO: 79) |

TABLE 8

Light chain CDRs of anti-FZD human antibodies

| Ab(s) | Light Chain | | |
|---|---|---|---|
| | CDR1 | CDR2 | CDR3 |
| 18R8 | SGDKLGKKYAS (SEQ ID NO: 4) | EKDNRPSG (SEQ ID NO: 5) | SSFAGNSLE (SEQ ID NO: 6) |
| 18R5 18R4605 18R4805 | SGDNIGSFYVH (SEQ ID NO: 7) | DKSNRPSG (SEQ ID NO: 8) | QSYANTLSL (SEQ ID NO: 9) |
| 44R24 | SGDALGNRYVY (SEQ ID NO: 80) | SG (SEQ ID NO: 81) | GSWDTRPYPKY (SEQ ID NO: 82) |

TABLE 9

VH and VL of ant-FZD human antibodies

| Ab(s) | Heavy Chain Variable Region (VH) amino acid sequence | Light Chain Variable Region (VL) amino acid sequence | Heavy Chain Variable Region (VH) Coding Sequence | Light Chain Variable Region (VL) Coding Sequence |
|---|---|---|---|---|
| 18R8 | SEQ ID NO: 10 | SEQ ID NO: 12 | SEQ ID NO: 17 | SEQ ID NO: 19 |
| 18R8 (codon optimized) | SEQ ID NO: 10 | SEQ ID NO: 12 | SEQ ID NO: 87 | SEQ ID NO: 88 |
| 18R5 | SEQ ID NO: 10 | SEQ ID NO: 14 | SEQ ID NO: 17 | SEQ ID NO: 21 |
| 18R5 (codon optimized) | SEQ ID NO: 10 | SEQ ID NO: 14 | SEQ ID NO: 87 | SEQ ID NO: 89 |
| 18R4605 | SEQ ID NO: 10 | SEQ ID NO: 14 | SEQ ID NO: 87 | SEQ ID NO: 90 |
| 18R4805 | SEQ ID NO: 10 | SEQ ID NO: 14 | SEQ ID NO: 87 | SEQ ID NO: 92 |
| 44R24 | SEQ ID NO: 85 | SEQ ID NO: 86 | SEQ ID NO: 94 | SEQ ID NO: 95 |

TABLE 10

Additional anti-FZD VH and VL amino acid sequences
SEQUENCE (SEQ ID NO:)

44R24 VH (SEQ ID NO: 85):
EVQLVESGGGLVQPGGSLRLSCAASGFTFSSYYITWVRQAPGKGLEWVSTISYSSSNTYY

ADSVKGRFTISRDNSKNTLYLQMNSLRAEDTAVYYCARSIVFDYWGQGTLVTVSS

44R24 VL (SEQ ID NO: 86):
DIELTQPPSVSVAPGQTARISCSGDALGNRYVYWYQQKPGQAPVLVIPSGIPERFSGSNS

GNTATLTISGTQAEDEADYYCGSWDTRPYPKYVFGGGTKLTVLG

TABLE 11

Additional nucleotide sequences encoding VH and VL of
anti-FZD antibodies
SEQUENCE (SEQ ID NO:)

18R5/18R8 VH coding sequence (codon-optimized) (SEQ ID NO: 87):
GAGGTGCAGCTGGTCGAGTCTGGCGGCGGACTGGTGCAGCCTGGCGGCTCCCTGAGACTG

TCCTGCGCCGCCTCCGGCTTCACCTTCTCCCACTACACCCTGTCCTGGGTGCGCCAGGCA

GCCGACTCCGTGAAGGGCCGGTTCACCATCTCCTCCGACAACTCCAAGAACACCCTGTAC

CTGCAGATGAACTCTCTGAGAGCCGAGGACACCGCCGTGTACTACTGCGCCCGGAACTTC

ATCAAGTACGTGTTCGCCAACTGGGGCCAGGGCACCCTGGTGACCGTGTCCTCC

18R8 VL coding sequence (codon-optimized) (SEQ ID NO: 88):
GACATCGAGCTGACCCAGCCTCCCTCCGTGTCTGTGGCTCCTGGCCAGACCGCCCGGATC

TCCTGCTCCGGCGACAAGCTGGGCAAGAAGTACGCCTCCTGGTATCAGCAGAAGCCTGGA

CAGGCCCCTGTGCTGGTCATCTACGAGAAGGACAACCGGCCTAGCGGCATCCCTGAGCGG

TTCTCCGGCTCCAACTCCGGCAACACCGCCACCCTGACCATCTCCGGCACCCAGGCCGAG

GACGAGGCCGACTACTACTGCTCCTCCTTCGCCGGCAACTCCCTGGAAGTGTTCGGCGGA

GGCACCAAGCTGACCGTGCTGGGC

18R5 VL coding sequence (codon-optimized) (SEQ ID NO: 89):
GACATCGAGCTGACCCAGCCTCCCTCCGTGTCCGTGGCCCCTGGCCAGACCGCCCGGATC

TCCTGCTCCGGCGACAACATCGGCAGCTTCTACGTGCACTGGTATCAGCAGAAACCTGGA

CAGGCCCCTGTGCTGGTGATCTACGACAAGTCCAACCGGCCTTCCGGCATCCCTGAGCGG

TTCTCCGGCTCCAACTCCGGCAACACCGCCACCCTGACCATCTCCGGCACCCAGGCCGAG

TABLE 11-continued

Additional nucleotide sequences encoding VH and VL of
anti-FZD antibodies
SEQUENCE (SEQ ID NO:)

GACGAGGCCGACTACTACTGCCAGTCCTACGCCAACACCCTGTCCCTGGTGTTTGGCGGC

GGAACAAAGCTGACCGTGCTGGGC

18R4605 VL coding sequence (SEQ ID NO: 90):
GACATAGAACTAACTCAGCCACCCTCTGTTAGCGTTGCACCGGGACAGACGGCACGTATA

TCGTGCTCGGGAGACAATATAGGAAGTTTCTATGTACATTGGTATCAACAGAAACCTGGT

CAAGCACCTGTATTAGTAATCTATGACAAAAGTAACCGACCTTCCGGAATACCTGAGCGT

TTCAGTGGTTCGAACTCCGGCAACACTGCAACTTTAACTATATCTGGAACTCAGGCGGAG

GATGAGGCTGACTACTACTGCCAGAGTTACGCAAACACTCTGTCCCTGGTGTTTGGCGGC

GGAACAAAGTTAACCGTGCTGGGC

18R4805 VL coding sequence (SEQ ID NO: 92):
GACATAGAACTAACTCAGCCGCCGTCTGTTAGCGTTGCACCGGGACAGACGGCACGTATA

TCGTGCTCGGGAGACAATATTGGTTCTTTCTATGTACATTGGTATCAACAGAAACCTGGT

CAAGCACCTGTATTAGTAATATATGACAAAAGTAACCGTCCTTCGGGAATACCTGAGCGT

TTCAGTGGTTCGAACTCGGGCAACACTGCAACTTTAACTATATCTGGAACGCAGGCGGAG

GATGAGGCGGACTACTATTGCCAAAGTTACGCAAACACTCTATCCTTAGTGTTTGGTGGA

GGAACAAAGTTAACCGTGCTAGGC

44R24 VH coding sequence (SEQ ID NO: 94):
GAGGTGCAGCTGGTGGAGTCTGGCGGAGGACTGGTGCAGCCTGGCGGCTCCCTGAGACTG

TCTTGCGCCGCCTCCGGCTTCACCTTCTCCTCTTACTACATCACCTGGGTGCGCCAGGCT

CCTGGCAAGGGACTGGAATGGGTGTCCACCATCTCCTACTCCTCCAGCAACACCTACTAC

GCCGACTCCGTGAAGGGCCGGTTCACCATCTCCCGGGACAACTCCAAGAACACCCTGTAC

CTGCAGATGAACTCCCTGAGGGCCGAGGACACCGCCGTGTACTACTGCGCCCGGTCCATC

GTGTTCGACTACTGGGGCCAGGGCACCCTGGTGACCGTGTCCTCT

44R24 VL coding sequence (SEQ ID NO: 95):
GACATCGAGCTGACCCAGCCTCCCTCTGTGTCTGTGGCCCCTGGCCAGACCGCCAGGATC

TCTTGCTCTGGCGACGCCCTGGGCAACAGATACGTGTACTGGTATCAGCAGAAGCCAGGC

CAGGCCCCTGTGCTGGTGATCCCTTCCGGCATCCCTGAGCGGTTCTCCGGCTCCAACTCC

GGCAACACCGCCACCCTGACCATCTCTGGCACCCAGGCCGAGGACGAGGCCGACTACTAC

TGCGGCTCCTGGGACACCCGGCCTTACCCTAAGTACGTGTTCGGCGGAGGCACCAAGCTG

ACCGTGCTGGGC

TABLE 12

Additional nucleotide sequences encoding heavy chains (HC) or
light chains (LC) of anti-FZD IgG antibodies (including
signal sequences)
SEQUENCE (SEQ ID NO:)

18R5/18R8/18R4605/18R4805 IgG2 HC coding sequence
(codon-optimized) (SEQ ID NO: 96):
ATGAAGCACCTGTGGTTCTTTCTGCTGCTGGTCGCCGCTCCTAGATGGGTGCTGTCCGAG

GTGCAGCTGGTCGAGTCTGGCGGCGGACTGGTGCAGCCTGGCGGCTCCCTGAGACTGTCC

TGCGCCGCCTCCGGCTTCACCTTCTCCCACTACCCCTGTCCTGGGTGCGCCAGGCACCA

GGGAAGGGACTGGAGTGGGTCTCCGTGATCTCCGGCGACGGCTCCTACACCTACTACGCC

TABLE 12-continued

Additional nucleotide sequences encoding heavy chains (HC) or
light chains (LC) of anti-FZD IgG antibodies (including
signal sequences)
SEQUENCE (SEQ ID NO:)

GACTCCGTGAAGGGCCGGTTCACCATCTCCTCCGACAACTCCAAGAACACCCTGTACCTG

CAGATGAACTCTCTGAGAGCCGAGGACACCGCCGTGTACTACTGCGCCCGGAACTTCATC

AAGTACGTGTTCGCCAACTGGGGCCAGGGCACCCTGGTGACCGTGTCCTCCGCCTCCACC

AAGGGCCCTTCCGTGTTCCCTCTGGCCCCTTGCTCCCGGTCCACCTCCGAGTCCACCGCC

GCTCTGGGCTGCCTGGTGAAGGACTACTTCCCTGAGCCTGTGACAGTGTCCTGGAACTCT

GGCGCCCTGACCTCCGGCGTGCACACCTTCCCTGCCGTGCTGCAGTCCTCCGGCCTGTAC

TCCCTGTCCTCCGTGGTGACAGTGCCTTCCTCCAACTTCGGCACCCAGACCTACACCTGC

AACGTGGACCACAAGCCTTCCAACACCAAGGTGGACAAGACCGTGGAGCGGAAGTGCTGC

GTGGAGTGCCCTCCTTGCCCTGCCCCTCCTGTGGCTGGTCCTAGCGTGTTCCTGTTCCCT

CCTAAGCCTAAGGACACCCTGATGATCTCCCGGACCCCTGAGGTGACCTGCGTGGTGGTG

GACGTGTCCCACGAGGATCCTGAAGTCCAGTTCAATTGGTACGTGGACGGCGTGGAGGTG

CACAACGCCAAGACCAAGCCTCGGGAGGAGCAGTTCAACTCCACCTTCCGGGTGGTGTCC

GTGCTGACCGTGGTGCACCAGGACTGGCTGAACGGCAAAGAATACAAGTGCAAAGTCTCC

AACAAGGGCCTGCCTGCCCCTATCGAAAAGACCATCAGCAAGACCAAGGGCCAGCCTCGC

GAGCCTCAGGTGTACACCCTGCCTCCCTCTCGCGAAGAGATGACCAAGAACCAGGTGTCC

CTGACCTGTCTGGTGAAGGGCTTCTACCCTTCCGATATCGCCGTGGAGTGGGAGTCCAAC

TTCCTGTACTCCAAGCTGACAGTGGACAAGTCCCGGTGGCAGCAGGGCAACGTGTTCTCC

TGCTCCGTGATGCACGAGGCCCTGCACAATCACTACACCCAGAAGTCCCTGTCCCTGTCT

CCTGGCAAG

18R8 lambda LC coding sequence (codon-optimized)
(SEQ ID NO: 97):
ATGGCCTGGGCCCTGCTGCTGCTGACCCTGCTGACACAGGGCACCGGCTCTTGGGCCGAC

ATCGAGCTGACCCAGCCTCCCTCCGTGTCTGTGGCTCCTGGCCAGACCGCCCGGATCTCC

TGCTCCGGCGACAAGCTGGGCAAGAAGTACGCCTCCTGGTATCAGCAGAAGCCTGGACAG

GCCCCTGTGCTGGTCATCTACGAGAAGGACAACCGGCCTAGCGGCATCCCTGAGCGGTTC

TCCGGCTCCAACTCCGGCAACACCGCCACCCTGACCATCTCCGGCACCCAGGCCGAGGAC

GAGGCCGACTACTACTGCTCCTCCTTCGCCGGCAACTCCCTGGAAGTGTTCGGCGGAGGC

ACCAAGCTGACCGTGCTGGGCCAGCCTAAGGCCGCTCCTTCCGTGACCCTGTTCCCTCCT

TCCTCCGAGGAACTGCAGGCCAACAAGGCCACCCTGGTCTGCCTGATCTCCGACTTCTAC

CCTGGCGCCGTGACCGTGGCCTGGAAGGCCGACTCCTCCCCTGTGAAGGCCGGCGTGGAG

ACAACCACCCCTTCCAAGCAGTCCAACAACAAGTACGCCGCCTCCTCCTACCTGTCCCTG

ACCCCTGAGCAGTGGAAGTCCCACCGGTCCTACTCTTGCCAGGTCACCCACGAGGGCTCC

ACCGTGGAAAAGACAGTGGCCCCCACCGAGTGCTCC

18R5 LC coding sequence (codon-optimized) (SEQ ID NO: 76):
ATGGCCTGGGCCCTGCTGCTGCTGACCCTGCTGACACAGGGCACCGGCTCTTGGGCCGAC

ATCGAGCTGACCCAGCCTCCCTCCGTGTCCGTGGCCCCTGGCCAGACCGCCCGGATCTCC

TGCTCCGGCGACAACATCGGCAGCTTCTACGTGCACTGGTATCAGCAGAAACCTGGACAG

GCCCCTGTGCTGGTGATCTACGACAAGTCCAACCGGCCTTCCGGCATCCCTGAGCGGTTC

TCCGGCTCCAACTCCGGCAACACCGCCACCCTGACCATCTCCGGCACCCAGGCCGAGGAC

TABLE 12-continued

Additional nucleotide sequences encoding heavy chains (HC) or light chains (LC) of anti-FZD IgG antibodies (including signal sequences)
SEQUENCE (SEQ ID NO:)

GAGGCCGACTACTACTGCCAGTCCTACGCCAACACCCTGTCCCTGGTGTTTGGCGGCGGA

ACAAAGCTGACCGTGCTGGGCCAGCCTAAGGCCGCTCCTTCCGTGACCCTGTTCCCTCCT

TCCTCCGAGGAGCTGCAGGCCAACAAGGCCACCCTGGTGTGCCTGATCTCCGACTTCTAC

CCTGGCGCTGTGACTGTGGCTTGGAAGGCCGACTCCTCCCCTGTGAAGGCCGGCGTGGAG

ACAACCACCCCTTCCAAGCAGTCCAACAACAAGTACGCCGCCTCCTCCTACCTGTCCCTG

ACCCCTGAGCAGTGGAAGTCCCACCGGTCCTACTCTTGCCAGGTGACCCACGAGGGCTCC

ACCGTGGAAAAGACAGTGGCACCCACCGAGTGCTCC

18R4605 LC coding sequence (SEQ ID NO: 83):
ATGGCATGGGCATTATTGCTACTTACTCTATTGACGCAAGGAACGGGTTCATGGGCAGAC

ATAGAACTAACTCAGCCACCCTCTGTTAGCGTTGCACCGGGACAGACGGCACGTATATCG

TGCTCGGGAGACAATATAGGAAGTTTCTATGTACATTGGTATCAACAGAAACCTGGTCAA

GCACCTGTATTAGTAATCTATGACAAAAGTAACCGACCTTCCGGAATACCTGAGCGTTTC

AGTGGTTCGAACTCCGGCAACACTGCAACTTTAACTATATCTGGAACTCAGGCGGAGGAT

GAGGCTGACTACTACTGCCAGAGTTACGCAAACACTCTGTCCCTGGTGTTTGGCGGCGGA

ACAAAGTTAACCGTGCTGGGCCAGCCTAAGGCCGCACCTTCGGTGACCCTATTCCCTCCT

TCATCCGAGGAGCTACAGGCCAACAAGGCCACCTTAGTGTGCCTAATCTCCGACTTCTAT

CCTGGTGCTGTAACGGTAGCGTGGAAGGCCGACTCATCGCCGGTGAAGGCCGGTGTGGAG

ACAACGACTCCTTCCAAGCAGTCCAACAACAAATACGCCGCGTCCTCCTACCTGTCCCTA

ACCCCTGAGCAGTGGAAGTCCCACCGTTCATACTCGTGCCAGGTGACGCACGAGGGTTCA

ACGGTCGAAAAGACAGTAGCACCTACTGAATGCTCA

18R4805 LC coding sequence (SEQ ID NO: 84):
ATGGCATGGGCATTATTACTACTTACTCTACTTACGCAAGGAACGGGTTCATGGGCAGAC

ATAGAACTAACTCAGCCGCCGTCTGTTAGCGTTGCACCGGGACAGACGGCACGTATATCG

TGCTCGGGAGACAATATTGGTTCTTTCTATGTACATTGGTATCAACAGAAACCTGGTCAA

GCACCTGTATTAGTAATATATGACAAAAGTAACCGTCCTTCGGGAATACCTGAGCGTTTC

AGTGGTTCGAACTCGGGCAACACTGCAACTTTAACTATATCTGGAACGCAGGCGGAGGAT

GAGGCGGACTACTATTGCCAAAGTTACGCAAACACTCTATCCTTAGTGTTTGGTGGAGGA

ACAAAGTTAACCGTGCTAGGCCAGCCTAAGGCCGCACCTTCGGTGACCCTATTCCCTCCT

TCATCCGAGGAGCTACAGGCGAACAAAGCCACCTTAGTGTGCCTAATCTCAGACTTTTAT

CCTGGTGCTGTAACGGTAGCGTGGAAGGCGGACTCATCGCCGGTGAAGGCCGGTGTGGAG

ACAACGACTCCTTCCAAGCAGTCCAACAACAAATACGCAGCGAGTAGTTACCTGTCCCTA

ACCCCTGAGCAGTGGAAGTCGCACCGTTCATACTCGTGCCAGGTTACGCACGAGGGTTCA

ACGGTCGAAAAGACAGTAGCACCTACGGAATGCTCA

44R24 HC coding sequence (SEQ ID NO: 91):
ATGAAGCACCTGTGGTTCTTTCTGCTGCTGGTGGCCGCTCCTAGATGGGTGCTGTCC

GAGGTGCAGCTGGTGGAGTCTGGCGGAGGACTGGTGCAGCCTGGCGGCTCCCTGAGACTG

TCTTGCGCCGCCTCCGGCTTCACCTTCTCCTCTTACTACATCACCTGGGTGCGCCAGGCT

CCTGGCAAGGGACTGGAATGGGTGTCCACCATCTCCTACTCCTCCAGCAACACCTACTAC

TABLE 12-continued

Additional nucleotide sequences encoding heavy chains (HC) or light chains (LC) of anti-FZD IgG antibodies (including signal sequences)
SEQUENCE (SEQ ID NO:)

GCCGACTCCGTGAAGGGCCGGTTCACCATCTCCCGGGACAACTCCAAGAACACCCTGTAC

CTGCAGATGAACTCCCTGAGGGCCGAGGACACCGCCGTGTACTACTGCGCCCGGTCCATC

GTGTTCGACTACTGGGGCCAGGGCACCCTGGTGACCGTGTCCTCTTCCGTGTTCCCTCTG

GCCCCTTGCTCCCGGTCCACCTCTGAGTCTACCGCCGCTCTGGGCTGCCTGGTGAAGGAC

TACTTCCCTGAGCCTGTGACCGTGTCCTGGAACTCTGGCGCCCTGACCTCTGGCGTGCAC

ACCTTCCCTGCCGTGCTGCAGTCCTCCGGCCTGTACTCCCTGTCCTCCGTGGTGACCGTG

CCTTCCTCCAACTTCGGCACCCAGACCTACACCTGCAACGTGGACCACAAGCCTTCCAAC

ACCAAGGTGGACAAGACCGTGGAGCGGAAGTGCTGCGTGGAGTGCCCTCCTTGTCCTGCT

CCTCCTGTGGCTGGCCCTTCTGTGTTCCTGTTCCCTCCTAAGCCTAAGGACACCCTGATG

ATCTCCCGGACCCCTGAAGTGACCTGCGTGGTGGTGGACGTGTCCCACGAGGACCCTGAG

GTGCAGTTCAATTGGTACGTGGACGGCGTGGAGGTGCACAACGCCAAGACCAAGCCTCGG

GAGGAACAGTTCAACTCCACCTTCCGGGTGGTGTCTGTGCTGACCGTGGTGCACCAGGAC

TGGCTGAACGGCAAAGAATACAAGTGCAAGGTGTCCAACAAGGGCCTGCCTGCCCCTATC

GAAAAGACCATCTCTAAGACCAAGGGCCAGCCTCGCGAGCCTCAGGTCTACACCCTGCCT

CCTAGCCGGGAGGAAATGACCAAGAACCAGGTGTCCCTGACCTGTCTGGTGAAGGGCTTC

TACCCTTCCGATATCGCCGTGGAGTGGGAGTCTAACGGCCAGCCTGAGAACAACTACAAG

ACCACCCCTCCTATGCTGGACTCCGACGGCTCCTTCTTCCTGTACTCCAAGCTGACAGTG

GACAAGTCCCGGTGGCAGCAGGGCAACGTGTTCTCCTGCTCCGTGATGCACGAGGCCCTG

CACAACCACTACACCCAGAAGTCCCTGTCCCTGTCTCCTGGCAAGTGA

44R24 LC coding sequence (SEQ ID NO: 93):
ATGGCTTGGGCTCTGCTGCTGCTGACCCTGCTGACACAGGGCACCGGCTCTTGGGCC

GACATCGAGCTGACCCAGCCTCCCTCTGTGTCTGTGGCCCCTGGCCAGACCGCCAGGATC

TCTTGCTCTGGCGACGCCCTGGGCAACAGATACGTGTACTGGTATCAGCAGAAGCCAGGC

CAGGCCCCTGTGCTGGTGATCCCTTCCGGCATCCCTGAGCGGTTCTCCGGCTCCAACTCC

GGCAACACCGCCACCCTGACCATCTCTGGCACCCAGGCCGAGGACGAGGCCGACTACTAC

TGCGGCTCCTGGGACACCCGGCCTTACCCTAAGTACGTGTTCGGCGGAGGCACCAAGCTG

ACCGTGCTGGGCCCTTCCGTGACCCTGTTCCCTCCATCCTCCGAGGAACTGCAGGCCAAC

AAGGCCACCCTGGTGTGCCTGATCTCCGACTTCTACCCTGGCGCCGTGACCGTGGCTTGG

AAGGCCGACTCTAGCCCTGTGAAGGCCGGCGTGGAGACAACCACCCCTTCCAAGCAGTCC

AACAACAAGTACGCCGCCTCCTCCTACCTGTCCCTGACCCCTGAGCAGTGGAAGTCCCAC

CGGTCCTACTCTTGCCAGGTGACCCACGAGGGCTCCACCGTGGAAAAGACCGTGGCCCCT

ACCGAGTGCTCCTAG

Plasmids isolated from *E. coli* encoding the anti-FZD IgG antibodies 18R4605 (ATCC deposit no. PTA-10307), 18R4805 (ATCC deposit no. PTA-10309), and 44R24 (ATCC deposit no. PTA-10311) were deposited with the American Type Culture Collection (ATCC), 10801 University Boulevard, Manassas, Va., USA, under the conditions of the Budapest Treaty on Aug. 26, 2009.

Example 19

Binding Profiles of Anti-FZD Antibodies

FACS analysis was used to characterize the FZD1, 2, 5, 7 and 8 binding profiles of anti-FZD monoclonal antibodies (mAbs).

HEK293 cells were co-transfected with a plasmid DNA expressing full-length FZD1, 2, 5, 7 or 8 along with another plasmid expressing the reporter gene GFP used as a transfection marker. Fugene 6 (Roche) was used as transfection reagent according to the manufacturer directions. Transfected cells were incubated twenty-four to forty-eight hours at 37° C. and 5% $CO_2$. The anti-FZD mAbs were then diluted in a final volume of 50 µl starting with a concentration of 20 µg/ml and serially diluted 4-fold for a total of 8 dilutions. Each FZD/GFP 293 transiently tranfectant pool was collected in suspension and 100,000 transfected cells were incubated on ice 30-60 minutes with the diluted anti-FZD mAb to be tested. The cells were washed and bound anti-Fzd antibodies were detected with a secondary anti-human antibody conjugated to a fluorescent chromophore. Labeled cells were then detected and counted by FACS. The FACS data generated were expressed in Mean Fluorescence Intensity (MFI) units. GraphPad Prism software was used to graph and analyze the data. MFIs were plotted as a function of Ab concentration to establish dose-response curves. A non-linear regression was applied to the numbers to fit the curve and calculate EC50s.

Figure 47:
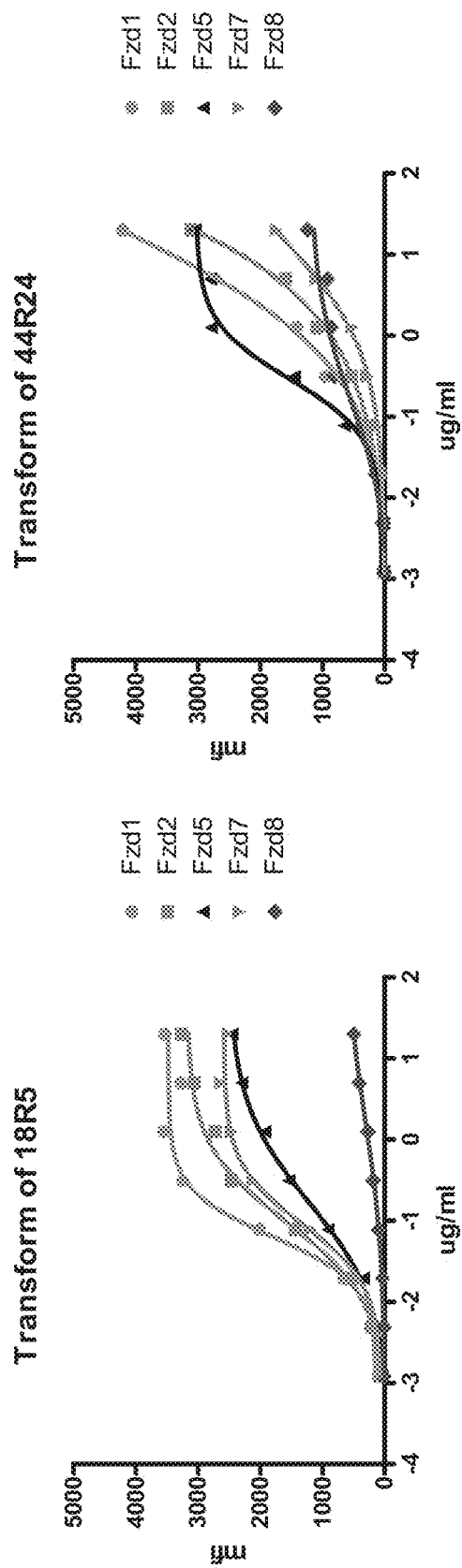

The binding profiles for the mAbs 18R5 and 44R24 were determined and compared. The dose-reponse curve representing the binding of each of 18R5 and 44R24 to Fzd1, 2, 5, 7 and 8 is shown in FIG. 47. The EC50s (nM) calculated for the two mAbs is shown in Table 13. 44R24 bound Fzd5 and Fzd8 with good affinity. A sigmoidal dose-response curve could not be established for the other 3 Fzd receptors, suggesting that 44R24 does not bind Fzd1, 2 and 7. High affinity binding of Fzd1, 2, 5 and 7 was confirmed for 18R5.

TABLE 13

EC50s (nM) for the mAbs 18R5 and 44R24

| EC50 (nM) | Fzd1 | Fzd2 | Fzd5 | Fzd7 | Fzd8 |
|---|---|---|---|---|---|
| 18R5 | 0.41 | 0.62 | 1.10 | 0.58 | 12.00 |
| 44R24 | 117.95 | no binding | 1.89 | 92.31 | 1.09 |

Example 20

Evaluation of Anti-Wnt Activity of Anti-FZD mAbs in Cell-Based Assays

The ability of 18R5 and 44R24 to inhibit Wnt signaling in STF-293 cells was determined and compared. STF cells are Human Embryonic Kidney (HEK)-293 cells stably transfected with the Super Top Flash (STF) reporter cassette in which the expression of the Luciferase (Luc) reporter gene is regulated by multiple copies of the TCF binding site upstream of a minimal promoter. A low basal Luc expression can be induced 30-60 fold in response to Wnt3a, providing a large window to assess the inhibitory activity of the anti-Fzd Abs.

To assess the mAbs, STF-293 cells were grown in DMEM-10% FBS. On day 1, 10,000 cells were plated per well in 96-well Optical Bottom White plates (Nunc #165306). The cells were incubated O.N. at 37° C. and 5% $CO_2$. On day 2, the Abs to be tested were diluted to a final concentration of 40 µg/µl using culture medium. Seven 5-fold serial dilutions were performed. The STF-293 cells culture medium was replaced with a mixture containing 50 µl Ab dilution, 25 µl Wnt3a-conditioned medium from Wnt3a stable L-cells and 25 µl DMEM-10% FBS. For each Ab, the final concentrations tested were 20, 4, 0.8, 0.16, 0.03, 0.006, 0.0013, 0.0003 µg/ml. Each Ab concentration was tested in triplicate. A human anti-hapten Ab. LZ1, was used as negative control Ab. A non-Wnt3a-conditioned medium from parental L-cells was used as negative control inducer. The plates were returned to the incubator. Luciferase activity was measured on day 3, using Promega Steady Glo kit (VWR#PAE2550-A) according to the manufacturer specifications. The results were expressed in photons per sec. GraphPad Prism software was used to graph and analyze the data. Luciferase activities were plotted as a function of Ab concentration to establish dose-response curves. A non-linear regression was applied to the numbers to fit the curve and calculate IC50s.

The ability of 44R24 and 18R5 to inhibit Wnt signaling in STF cells was likewise determined and compared as described above. The results are shown in FIG. 48 and Table 14. 44R24 activity was only detected at higher Ab concentrations, reflecting the antibody's low activity in the assay. 44R24's IC50 was calculated to be 13 fold lower than 18R5's.

TABLE 14

IC50s for inhibition of Wnt signaling in ST-293 cells by 18R5 and 44R24

|  | 18R5 | 44R24 |
|---|---|---|
| IC50 (nM) | 2.73 | 34.43 |

The ability of 18R5 and 44R24 to inhibit Wnt signaling in A549 cells was also determined. A549 cells are human lung carcinoma cells in which the Axin2 gene is highly expressed, translating endogenous activity of Wnt signaling. Axin2 is a well know Wnt target gene that responds to activation of the pathway by up-regulating its transcription and eventually down-regulating Wnt signaling through a feed-back loop mechanism. This system was used to test the impact of the anti-Fzd Abs on Axin2 mRNA levels by qPCR.

12-well plates were seeded with 30,000 A549 cells per well and grown for 3 days in DMEM+10% FBS. Antibodies were added at varying concentrations (5 µl, 0.2, 0.04, 0.008 µg/ml) for 24 hours and total RNA was extracted from the cells. LZ1, a nonbinding antibody, was used as negative control at only the highest concentration.

30,000 A549 cells were seeded into 12-well plates and grown for 3 days in DMEM+10% FBS. Anti-FZD antibody 18R5 or 44R24 were added at varying concentrations (5, 1, 0.2, 0.04, 0.008 ug/ml), and LZ1, a nonbinding antibody, was used as a negative control at only the highest concentration. RNA was made 24 hours post treatment and then treated with Dnase.

Axin2 is known to be a robust target gene in Wnt signaling and its expression level was examined by doing a Taqman relative expression (ΔΔCT) assay using an Applied Biosystems 7900 HT machine. 50 ng of RNA was used per point in triplicate and a GUSB probe was used for endogenous control. All results were normalized to Axin2 levels in the LZ1 control sample.

The dose response curve showing the inhibition of basal level of axin2 gene expression by 18R5 and 44R24 and the calculated EC50 values for these antibodies are shown in FIG. 49. 18R5 and 44R24 inhibit Axin2 basal levels relative to LZ1 control with comparable efficiencies.

Example 21

Evaluation of Anti-Tumor Activity of Anti-FZD mAbs in Pancreatic Xenograft Models OMP-PN13 Pancreatic Tumors:

Frozen OMP-PN13 tumor cells that have been passaged twice in mice were obtained from Oncomed's tumor bank. They were thawed and injected subcutaneously into the left flank of NOD/SCID mice immediately following thawing. ~25,000 viable cells were injected per animal. The mice were monitored weekly for tumor growth. After their onset, the size of the tumors was measured once weekly by caliper. 200-300 mm$^3$ tumor-bearing mice were dispatched in treatment groups that each contained 5 animals. The average tumor size was comparable in each group. Ab treatment was initiated the day after randomization. LZ1 was used as the negative control Ab. 3 doses of 10 mg/kg of Ab were administered via intra-peritoneal injection over a 12-day period. Mice were euthanized 24 hours after the last injection. Tumor, duodenum and liver were harvested.

Tumor tissues were fixed in formalin for paraffin embedding and sectioning. Muc16 detection was performed by immunohistochemical (IHC) to monitor the appearance of Mucin-producing cells. Mucins are specific for a subtype of differentiated cells in the pancreas, and as such are used as differentiation markers in the tumor model.

Formalin-fixed, paraffin-embedded (FFPE) sections were de-parrafinized. The slides were first de-parrafinized by sequential treatment with xylene twice for 5 minutes each. The tissue was then rehydrated by immersion in an ethanol series of 100% twice for 3 minutes each, 90% once for 1 minute, 80% once for 1 minute, and 70% once 1 minute in water. The tissue was washed with flowing distilled water for 1 minute.

Mucin 16 antibody (clone X325 from AbCAM, catalog ab10033) was used for IHC detection of mucin 16 expressing cells in FFPE tissue sections. Heat-induced antigen retrieval was carried out with 10 mM citrate buffer pH 6.0 in an autoclave. The slides were then kept at room temperature and the proteins allowed to recover antigenicity slowly (approximately 2 hours).

Tissue sections were blocked with 3% hydrogen peroxide solution in water, washed, and then blocked again using Normal Horse serum Blocking solution (for 50 mL; PBS (38.5 mL), 10% NHS (5 mL), 1% BSA (5 mL), 0.1% gelatin (500 μL), 0.1% Tx-100 (500 μL), 0.05% NaN3 (500 μL)) for 1 hour at room temperature. Sections were then stained with 1:200 dilution of Muc16 primary antibody in Da Vinci Green Diluent pH 7.3 (PD 900, Biocare Medical) for 1 hour at room temperature followed by three washes using phosphate buffered saline containing 0.1% triton X-100. Sections were then stained with 3 drops of ImmPress anti-mouse IgG HRP-conjugate (Catalog 101098-260, VWR) for 30 minutes at room temperature followed by three washes using phosphate buffered saline containing 0.1% triton X-100. Slides were placed in petridishes and developed using Vector NovaRed kit (SK4800, Vector labs) for 1-2 minutes. Reaction was stopped by adding distilled water. Slides were rinsed thoroughly under flowing distilled water. Tissue sections were then counterstained using Hematoxylin (Catalog H3401, Vector Labs Gill's formula) for 1 minute, washed, and then neutralized using blueing solution for 30 seconds. Slides were left to dry overnight and mounted using VectaMount (Vector Labs).

Representative fields of tumors treated with control Ab (LZ1), 18R5, or 44R24 are shown in FIG. 50. While LZ1 was associated with low intensity staining, higher levels of staining with Muc16 antibody were detected in the tumors treated with 18R5. This suggests that tumor cells were induced to differentiate towards the mucin-producing cell lineage by 18R5. Levels of Muc16 staining in the 44R24-treated tumors were more moderate than in the 18R5 treated tumors but still appeared to be slightly higher than in the LZ1-treated tumors in this experiment.

Total RNAs were also extracted from tumor, duodenum and liver for Wnt target gene expression analyses using qPCR.

Tissues were immediately transferred into RNAlater (QIAGEN) at the time of harvest. RNA was extracted using the QIAGEN RNeasy for Fibrous Tissue mini kit according to the manufacturer instructions. 50 ng total RNA were submitted to gene expression analyses using ABI one-step RT-PCR protocol and reagents. GusB gene expression was used as endogenous control. Triplicates were setup for each sample. All 5 tumors of each treatment group were analyzed. ABI 7900 TaqMan machine was used to run the experiments. ABI SDS 2.2.1 software was used to analyze the data and calculate DeltaCt values that were converted into relative quantities. The triplicate values of all 5 tumors were averaged for each treatment group. Fold inhibition factors were then calculated relative to control antibody (LZ1).

The results are shown in Table 15. Wnt target genes were variably affected by the anti-FZD Abs. 18R5 induced 2.3× and 8× inhibition in tumor and liver, while remaining unaffected in the duodenum. The changes induced by 44R24 were more moderate.

TABLE 15 qPCR gene expression analysis of Wnt target genes in 18R5- and 44R24-treated tissues.

| | tumor | Liver | | | | | duodenum | |
|---|---|---|---|---|---|---|---|---|
| | Axin2 | Axin2 | Rhbg | GluI | Lect2 | Lgr5 | Axin2 | Lgr5 |
| 18R5 | −2.3x | −8x | −6.5x | −19x | −8x | −26x | NS | −2.6x |
| | *−2.5x* | *−13x* | *−5x* | | | | | |
| 44R24 | *−1.8x* | *−2.4x* | *−1.9x* | ND | ND | ND | ND | ND |

ND: not done
Separate experiments are shown in italics

OMP-PN4 Pancreatic Tumors:

The impact of 18R5 on tumor stroma in the OMP-PN4 pancreatic tumor xenograft model was also investigated. Several genes were identified by microarray whose expression levels were altered by the treatment. Amongst them, ACTA2, which encodes for the smooth muscle actin (SMA) protein, is of particular interest. SMA has been shown to be associated with activated tumor stroma. Its down-regulation can therefore be viewed as a sign of decreased tumorigenic phenotype.

As described in Example 7 above, OMP-PN4 tumor-bearing NOD/SCID mice were treated with control Ab (LZ-1), 18R5, gemcitabine, or the combination of 18R5 and gemcitabine once a week for 6 weeks. The antibodies were administered at a concentration of 10 mg/kg. After they were harvested, the tumors from that experiment were analyzed for the expression of Wnt target genes at both the RNA and protein levels, using microarray and IHC, respectively.

Total RNA was extracted from the tumors, amplified, and subjected to microarray analysis. Total RNAs were amplified using the Ovation RNA Amplification System V2 (NuGEN, San Carlos, Calif.). Resulting amplified, antisense ss-cDNA was fragmented and biotinylated using the FL-Ovation cDNA Biotin Module V2 (NuGEN) for use on Affymetrix chips. Affymetrix HG-U133 plus 2 or MG 430 2.0 oligonucleotide microarrays were used in these experiments (performed at Almac Diagnostics, Durham, N.C.). After hybridization, Gene Chips were washed, stained, and scanned according to the manufacturer's instructions (Affymetrix, Santa Clara, Calif.). The quality of the cDNA and the fragmented cDNA were assessed by spectrophotometer and the Bioanalyzer before the array hybridization. The scanned raw chip data were quantified and scaled using the GCOS software package (Affymetrix) and subjected to a comprehensive assessment of Gene Chip Quality Control recommended by Affymetrix to detect any chips defects and outliers, which were excluded from the subsequent data analysis.

Array background adjustment and signal intensity normalization were performed with GCRMA algorithm in the open-source Bioconductor software (www.bioconductor.org). Genes differentially expressed between two groups or time points were identified with Bayesian t-test (Cyber-T), which combines student's t-test with a Bayesian estimate of the intra-group variance obtained from the observed variance of probe sets at a similar expression levels (Baldi P, Long AD. A Bayesian framework for the analysis of microarray expression data: regularized t-test and statistical inferences of gene changes. Bioinformatics. 2001; 17(6): 509-19).

For the human tumor gene chip analysis, samples were assayed on both human and mouse chips to assess treatment effects on bulk human tumor and on mouse stroma independently. Those Affymetrix probe sets that were not species-specific were omitted from the analysis.

In preparation for Smooth Muscle Actin alpha (SMAa) immunofluorescence, tumor tissue was frozen using OCT. 4 micron sections were obtained and stored frozen at −80° C. For SMAa staining, tissue was fixed using chilled acetone at −20° C. for 15 minutes and then allowed to dry and come to room temperature and then marked using a hydrophobic PAP pen. Slides were then washed using phosphate buffered saline (PBS). Tissue was blocked using normal horse serum R.T.U. (Vector Labs) for 2 hours at room temperature. Primary antibody staining was performed with 1:10,000 dilution of FITC-conjugated Smooth muscle actin alpha antibody (cline 1A4, #F3777, SIGMA) for 1 hour. Sections were washed 3 times using PBS containing 0.1% triton X-100. Slides were then air-dried and then mounted using Hard set mounting medium containing DAPI (vectashied H-500).

FIG. 51A shows the ACTA2 gene expression levels as detected by microarray. Tumors treated with the anti-FZD antibody 18R5 showed decreased levels of ACTA2 expression. FIG. 51B shows the results of the Smooth Muscle Actin alpha (SMAa) immunofluorescence on control mAb (upper panel) and 18R5 (lower panel)-treated OMP-PN4 tumors. Reduced amounts of SMAa was detected on the 18R5-treated tumors. The expression of ACTA2 and the amount of SMA were dramatically reduced in the tumor stroma in response to 18R5, suggesting that Wnt blockade (i) impacts this tumor compartment and (ii) does so by reducing a well established tumorgenicity marker. These results suggest that reduction of myofibroblast activation may be one of 18R5's anti-tumor mechanisms of action.

Example 22

Evaluation of the Tumorgenic Potential of Muc16-Positive OMP-PN13 Cells

As described above, 18R5 treatment induced gene expression and cell phenotype changes in pancreatic tumors, including increased mucin expression. In particular, IHC performed on treated PN-13 tumors revealed an increased number of Muc16-positive cells. Muc16 gene expression levels were also higher in treated tumors than in control tumors. The tumorigenicity of the 18R5-induced Muc16-positive cells was assessed to test the hypothesis that the 18R5-induced Muc16-positive cells are representative of a differentiated tumor cell sub-population.

OMP-PN13-bearing mice were treated with 18R5 according to the protocol described in Example 21. Mice were euthanized 12 days after initiation of the Ab treatment. Tumors were harvested and processed to obtain a single cell suspension using collagenase III to digest the tissues. Mouse stromal cells were stained with a biotinylated anti-H-2 Kd antibody and a biotinylated anti-CD45 antibody. They were then incubated with magnetic beads conjugated to streptavidin (Thermo MagnaBind) and depleted using a Dynal magnet. The resulting lin-depleted tumor cells were stained with an anti-Muc16 mAb detected with a PE-conjugated secondary Ab. Muc16-positive and Muc16-negative cells were sorted using an ARIA FACS machine ran by the DIVA software. See FIG. 52A. Cells were re-injected subcutaneously in the left flank of NOD/SCID mice for comparison of their tumorgenic potentials. Each cell type was injected into 10 mice. Each mouse received 75 cells. Representative pictures of tumors resulting from the injection of Muc16− (upper panel) and Muc16+ (lower panel) cells are shown in FIG. 52B. The growth curves for the Muc16− and Muc16+ tumors following injection into the mice are shown in FIG. 52C. No tumor grew after injection of the Muc16+ cells, while 7 of the 10 mice injected with the Muc16-cells developed tumors. The data suggest that 18R5-induced Muc16+ cells are non-tumorigenic, supporting induction of differentiation as an underlying mechanism of 18R5 anti-tumor activity.

Example 23

Additional In Vivo Studies with Anti-FZD Antibodies

PE13 breast tumor recurrence study with 18R5 mAb: PE13 breast tumor cells were injected into Nod-Scid mice and allowed to grow until the tumors had reached approximately 100 mm$^3$. The animals were randomized into two groups (n=10) and given taxol (15 mg/kg, twice per week)+ Control antibody (black squares) or the same dose of taxol+ Anti-FZD 18R5 (gray open circles). Antibodies were dosed at 20 mg/kg once per week. Taxol® treatments were stopped at day 70 and the antibody treatments continued. The results are shown in FIG. 53. 18R5 was observed to enhance the rate of tumor regression and to delay tumor recurrence after stopping taxol treatment.

PE13 breast tumor limiting dilution assay (LDA) study with 18R5 mAb; Animals bearing PE13 breast tumors were treated with either control antibody (gray circles). 18R5 (open triangles), taxol (black circles), or the combination of taxol and 18R5 (open squares). Taxol® was dosed at 15 mg/kg twice per week and the antibodies were dosed 20 mg/kg once per week. Tumors were harvested and the human tumor cells were purified by lin depletion. 50, 150, or 500 tumor cells were injected into a new cohort of mice (n=10 per cell dose). The results are shown in FIG. 54. Tumor growth frequency was monitored after 59 days and used to calculate the CSC frequency (L-calc).

PN4 pancreatic tumor recurrence study with 18R5 mAb: PN4 pancreatic tumor cells were injected into Nod-Scid mice and allowed to grow until the tumors had reached approximately 250 mm$^3$. The animals were given gemcitabine (75 mg/kg, once per week) for 5 weeks until tumors had regressed. The animals were randomized into two groups and given control antibody (black squares) or anti-FZD 18R5 (gray open circles). Antibodies were dosed at 10 mg/kg once per week. The results are shown in FIG. 55. 18R5 was observed to delay tumor recurrence after gemcitabine treatment.

PN4 pancreatic tumor growth study with 44R24 mAb: PN4 pancreatic tumors were injected into Nod-Scid mice. Tumors were allowed to grow until they had reached a volume of approximately 150 mm$^3$. Animals were randomized into 4 groups (n=10 per group) and given control antibody (black squares), anti-FZD5/8 44R24 (gray open triangles), gemcitabine (filled triangles), or combination of 44R24 plus gemcitabine (gray open circles). Gemcitabine was dosed at 15 mg/kg once per week and the antibodies were dosed at 20 mg/kg twice week. The results are shown in FIG. 56. 44R24 was observed to reduce tumor growth in combination with gemcitabine relative to gemcitabine alone.

Example 24

Epitope Mapping of Anti-FZD Antibody 44R24

Epitope mapping for the anti-FZD antibody 44R24 was performed in a manner similar to that described above in Example 5 for the antibodies 18R8 and 18R5. The ability of 44R24 to bind to a similar epitope as 18R8 was assessed by flow cytometry using a series of amino acid variants of FZD8 previously shown to disrupt binding of 18R8 (see Example 5 and FIGS. 6 and 7). Amino acids 126-127 of FZD8 were found to be required for binding 44R24 as indicated by reduced staining within the co-transfected (GFP positive) cell population. The results of the FACS experiments are shown in FIG. 57. These results show that 44R24 binds to an epitope that overlaps with the epitope of 18R8 and comprises shared amino acids 126-127.

Example 25

C28 Colon Tumor Growth Study with Anti-FZD Antibodies 18R5, 18R8 and 44R24

C28 tumor cells were injected sub-cutaneously in Nod-Scid mice. Tumors were allowed to grow until they had reached an average volume of 126 mm$^3$. Tumor bearing animals were groups were randomized into four groups (n=10 mice per group) and treated with either Control Ab (black squares), 18R8 (gray triangles), 44R24 (black open circles), or 18R5 (gray circles) (FIG. 58). Antibodies were dosed intraperitoneally at 15 mg/kg, twice per week. Tumor volumes are indicated. Treatment with antibodies 44R24 and 18R5 reduced growth relative to the control group, while 18R8 had no effect (FIG. 58).

Following treatment of the animals in the experiment shown in FIG. 58, tumors were harvested, fixed in formalin, embedded in paraffin, and cut in 5 micron sections. Tumor sections were analyzed for Cytokeratin 7 expression, a marker of colon cell differentiation, by immunohistochemistry (Vectastain kit, Vector Labs). Cytokeratin 7 expression was seen to be elevated after treatment with 44R24 or 18R5 (FIG. 59).

Example 26

Production and Purification of 18R5

A CHO-derived recombinant cell line expressing the 18R5 antibody was produced using standard methods known to one of skill in the art. For antibody production and purification, the cell line was cultured using a fed-batch bioreactor cell culture process and was grown in chemically-defined and serum-free media. The cell culture process was run for about 10-15 days and included a temperature shift from 37° C. to 34° C. at approximately 5 days post-inoculation.

The 18R5 antibody was purified in a multistep purification scheme. First, harvested cell culture fluid (HCCF) from the bioreactor(s) was purified by affinity chromatography using MabSelect SuRe™ (GE Healthcare Life Sciences). The HCCF was applied to the MabSelect SuRe™ column at 25-30 grams of protein per liter of resin and the column was subsequently washed three times. Bound 18R5 antibody was eluted from the column with 100 mM glycine-HCl (pH 3.2). The 18R5-containing eluate was held at low pH for 1 hour at room temperature for viral inactivation, followed by an adjustment of the pH to about 6.5 using 1M Bis-Tris buffer (pH 8.5). The eluate was then filtered through a 0.2 micron filter and stored at 2-8° C. until the next purification step.

Second, the 18R5-containing eluate was subjected to anion exchange chromatography using Capto Q resin (GE Healthcare Life Sciences). The 18R5 antibody flowed through the Capto Q column and was collected, while impurities bound to the column and were removed from the 18R5 pool. The flow-through pool containing the 18R5 antibody was filtered through a 0.2 micron filter and stored until the next purification step.

Third, the 18R5-containing flow-through pool was subjected to ceramic hydroxyapatite (CHT) chromatography on a packed CHT type I column (BioRad Laboratories). The 18R5 antibody and remaining impurities were bound to the CHT column. The column was washed two times with low salt buffers (0-100 mM NaCl) containing 5-10% polyethylene glycol (PEG). The 18R5 antibody was eluted from the column with a high salt buffer (400-1000 mM NaCl) containing 5-10% PEG and collected. Tangential flow ultrafiltration and diafiltration was used to exchange the high salt elution buffer with a buffer comprising histidine, NaCl and sucrose. The purified 18R5 antibody was filtered through a 0.2 micron filter and stored at 2-8° C. for future use.

Example 27

Residues within the OMP-18R5 Binding Site Impact Wnt Binding

As noted above, the 18R5 antibody binds to the Frizzled receptors by interaction via a discontinuous epitope. The surface of the FZD receptor within the 18R5 binding area contains a cleft, apparent in the crystal structure of FZD (FIG. 9 and FIG. 60A). The amino acid residues within the cleft of the BBS of each of the human FZD receptors are provided in Table 16. The residues that line the base of this cleft exhibit particularly high conservation between FZD family members suggesting functional importance. 18R5 binding to FZD blocks the interaction of Wnt to FZD demonstrating that the region is functionally relevant for Wnt signaling. To further explore the importance of residues within this binding region in FZD8, select residues that line the cleft were mutated to alternative residues (FIG. 60B). (In certain alternative embodiments, the analogous residues within another human FZD, as identified in Table 17 below, may instead be used in a screening method, as may other residues within the BBS). The ability of FZD receptors containing these substitutions to bind Wnt3A was then assessed (FIG. 60C). Each of the substitutions greatly decreased the ability of Wnt to bind to the FZD receptors confirming the importance of this region of the FZD receptor in mediating Wnt interaction.

TABLE 16

Amino acid residues in "cleft" of the Biological Binding Sites (BBS) of FZD Receptors

| Human Frizzled Receptor (aa sequence) | BBS Cleft Residues |
| --- | --- |
| FZD1 (SEQ ID NO: 26) | 153(F), 155-156(PL), 159(V), 173(Y), 201-202(LM), 209-212(WPDT) |
| FZD2 (SEQ ID NO: 30) | 76(F), 78-79(PL), 82(V), 96(Y), 124-125(LM), 132-135 (WPER) |
| FZD3 (SEQ ID NO: 34) | 65(F), 67-68(PM), 71(L), 85(Y), 113-114(LM), 121-124 (WPED) |
| FZD4 (SEQ ID NO: 38) | 85(F), 87-88(PL), 91(Y), 105(Y), 134-135(VL), 142-145(WPES) |
| FZD5 (SEQ ID NO: 42) | 70(F), 72-73(PL), 76(I) 90(Y), 119-120(LM), 127-130(WPER) |
| FZD6 (SEQ ID NO: 46) | 61(F), 63-64(PL), 67(L), 81(F), 109-110(LI), 117-120(WPEE) |
| FZD7 (SEQ ID NO: 50) | 86(F), 88-89(PL), 92(V), 106(Y), 134-135(LM), 142-145(WPER) |
| FZD8 (SEQ ID NO: 54) | 72(F), 74-75(PL), 78(I), 92(Y), 121-122(LM), and 129-132(WPDR) |
| FZD9 (SEQ ID NO: 58) | 76(F), 78-79(PL), 82(Y), 96(Y), 125-126(IM), 133-136(WPDS) |
| FZD10 (SEQ ID NO: 62) | 71(F), 73-74(PL), 77(Y), 91(Y), 120-121(IM), 128-131(WPDS) |

TABLE 17

Amino acid position of analogous residues of mutants in the ten human FZD receptors

| Frizzled | Mut1 | Mut2 | Mut3 | Mut4 |
| --- | --- | --- | --- | --- |
| FZD1 | 153 | 156 | 159 | 201 |
| FZD2 | 76 | 79 | 82 | 124 |
| FZD3 | 65 | 68 | 71 | 113 |
| FZD4 | 85 | 88 | 91 | 134 |
| FZD5 | 70 | 73 | 76 | 119 |
| FZD6 | 61 | 64 | 67 | 109 |
| FZD7 | 86 | 89 | 92 | 134 |
| FZD8 | 72 | 75 | 78 | 121 |
| FZD9 | 76 | 79 | 82 | 125 |
| FZD10 | 71 | 74 | 77 | 120 |

Example 28

Identification of Small Molecule Peptides that Bind the Wnt Binding Region of FZD To identify small molecule peptides that bind to FZD we screened peptide libraries (Ph.D. phage display peptide library system, New England Biolabs). The libraries were screened using the URSA method (Ultra Rapid Selection of Antibodies) using recombinant FZD8-Fc bound to protein A beads. After three rounds of enrichment, individual clones were tested for binding to FZD. As shown in FIG. 61, peptides were identified that bound to FZD but not to an irrelevant control protein (DLL4-Fc), demonstrating that they specifically interact with FZD. Representative positive clones are highlighted by arrows. The sequences of the FZD binding peptides were determined. Both linear peptides from a library of 12-mer peptides and cyclic peptides from a library comprised of seven random amino acids flanked by cysteine residues were isolated. As is shown in FIG. 62, the cyclic peptides displayed similar but distinct sequences suggesting that they adopt similar structure and demonstrated a clear consensus sequence.

To examine whether any of these FZD binding peptides interacted with FZD through the BBS, we examined the ability of the peptides to interact with FZD with amino acid substitutions that were shown in the experiments described above in Example 27 (FIG. 60C) to impact Wnt binding. As is shown in FIG. 63, FZD binding peptides were identified that specifically interact with FZD within the Wnt binding region. Several peptides displayed greatly reduced or eliminated binding to the FZD when an amino acid substitution was introduced within the cleft region, demonstrating the ability to identify small molecules that interact with this region.

Example 29

Inhibition of Wnt Signaling by Small Molecules that Bind the Wnt Binding Region of Frizzled To examine whether the peptides that bind the FZD extracellular domain and interacted with the BBS region were able to impact Wnt signaling, Wnt reporter assays were conducted. Two peptides were chemically synthesized containing the sequence of clones #2 and #24. The Wnt reporter assay utilized an 8×TCF luciferase reporter that is inducible by exogenous Wnt proteins that activate canonical Wnt signaling. As shown in FIG. 64, small peptides that bind to FZD protein were able to inhibit the ability of HEK293 cells to respond to Wnt3A.

Example 30

Identification of Non-Peptide Small Molecules that Bind to the FZD BBS Wnt Binding Region There are many ways in which one can identify small molecules that bind to the Wnt binding region of the FZD receptors. In one approach, one can make use of peptides that bind within the BBS, or more specifically, the cleft region of FZD to enable rapid and high throughput screens of small molecule chemical libraries. As one non-limiting example, the peptide can be labeled with a convenient reporter (e.g. radiolabel, fluorescent tag, or FRET tag). The labeled peptide can then be allowed to bind to FZD protein. The peptide-FZD complex can then be allowed to interact with a test compound from a small molecule library and the ability of the small molecule to displace the peptide from the FZD receptor or compete with the peptide for binding to the FZD protein can be measured. In such a manner one is able to identify small molecules that bind specifically to the FZD protein within the desired binding region.

Example 31

Treatment of Polycystic Kidney Disease with 18R5

The ability of 18R5 to treat polycystic kidney disease (PKD) can be demonstrated in murine models of PKD. There are several murine models of PKD which reflect the underlying mutations observed in human PKD and demonstrate pathology very comparable to the human disease (references below). Several of these models involve alteration in the levels of expression of either the PKD1 gene which encodes polycystin1 (PC1) or the PKD2 gene which encodes polycystin2 (PC2). These genes are mutated in almost all human cases of polycystic kidney disease. Utilizing one such model, one treats mice that possess altered expression of PKD1 or PKD2 (and are subsequently prone to develop PKD) by administration of 18R5 via IP injection at a dose of 15 mg/kg twice per week. After one month of treatment one can observe improvement in kidney function relative to control mice not treated with 18R5. This improved function is manifested by decreased size and abundance of kidney cysts, reduced proliferation of kidney epithelial cells as measurable by ki-67 IHC staining of tissue sections, and improved kidney function as measured by reduced blood urea concentrations. Relevant references include Happé et al. Hum Mol. Genet. 2009 Jul. 15; 18(14): 2532-42, Kim et al., J Am Soc Nephrol. 2009 December; 20(12):2556-69, and Kurbegovic et al., Hum Mol. Genet. 2010 Apr. 1; 19(7):1174-89, each of which is hereby incorporated by reference herein in its entirety.

Example 32

Additional Purification Scheme for Monoclonal Antibody 18R5

A CHO-derived recombinant cell line expressing the 18R5 antibody was produced using standard methods known to one of skill in the art. For antibody production and purification, the cell line was cultured using a fed-batch bioreactor cell culture process and was grown in chemically-defined and serum-free media. The cell culture process was run for about 10-15 days and included a temperature shift from 37° C. to 34° C. at approximately 5 days post-inoculation.

The 18R5 antibody was purified in a multistep purification scheme. First, harvested cell culture fluid (HCCF) from the bioreactor(s) was purified by affinity chromatography using MabSelect SuRe™ (GE Healthcare Life Sciences). The HCCF was applied to the MabSelect SuRe column at 25-30 grams of protein per liter of resin and the column was subsequently washed three times. Bound 18R5 antibody was eluted from the column with 100 mM glycine-HCl (pH 3.2). The 18R5-containing eluate was held at low pH for 1 hour at room temperature for viral inactivation, followed by an adjustment of the pH to about 6.75-6.85 using 0.5-1M Bis-Tris buffer (pH 8.5). The eluate was then filtered through a 0.2 micron filter and stored at 2-8° C. until the next purification step.

Second, the 18R5-containing eluate was subjected to anion exchange chromatography using Capto Q resin (GE Healthcare Life Sciences). The 18R5 antibody flowed through the Capto Q column and was collected, while impurities, such as aggregate, bound to the column and were removed from the 18R5 pool. The flow-through pool containing the 18R5 antibody was filtered through a 0.2 micron filter and stored until the next purification step.

Third, the 18R5-containing flow-through pool was subjected to ceramic hydroxyapatite (CHT) chromatography on a packed CHT type I column (BioRad Laboratories). The 18R5 antibody and remaining impurities, such as aggregates, were bound to the CHT column. The column was washed two times with low salt buffers (0-100 mM NaCl) containing 0-10% polyethylene glycol (PEG). The 18R5 antibody was eluted from the column with a high salt buffer (400-1000 mM NaCl, such as, for example, 546 mM) containing 10-13% PEG (such as, for example, 12.5% PEG) and collected. Tangential flow ultrafiltration and diafiltration were used to exchange the high salt elution buffer with a buffer comprising histidine and NaCl. After diafiltration, the 18R5-containing solution was diluted with an excipient buffer comprising histidine, NaCl, sucrose and polysorbate-20. The purified 18R5 antibody was filtered through a 0.2 micron filter and stored at 2-8° C., or frozen at −65° C. or below, for future use.

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference In addition, U.S. patent application Ser. No. 12/568,534, filed on Sep. 28, 2009, which published as U.S. Patent Publication No. 2010/0104574, is hereby incorporated by reference herein in its entirety.

What I claim is:

1. An isolated polypeptide comprising an amino acid sequence selected from the group consisting of SEQ ID NOs:98-116, wherein the amino acid sequence specifically binds a human Frizzled (FZD) receptor.

2. The polypeptide of claim 1,
   (a) which is less than 100 amino acids in length;
   (b) which is less than 20 amino acids in length;
   (c) which has a molecular weight of less than 2000 Daltons;
   (d) which is a modified polypeptide;
   (e) which is detectably labeled;
   (f) which is a cyclic polypeptide comprising an amino acid sequence selected from the group consisting of SEQ ID NO:98-112;
   (g) which is a linear polypeptide comprising an amino acid sequence selected from the group consisting of SEQ ID Nos:113-116; and/or
   (h) which is an inhibitor of Wnt signaling.

3. The polypeptide of claim 1, which consists of an amino acid sequence selected from the group consisting of SEQ ID NO:98-116.

4. The polypeptide of claim 1, which comprises the amino acid sequence of SEQ ID NO:112.

5. The polypeptide of claim 1, which comprises the amino acid sequence of SEQ ID NO:108.

6. The polypeptide of claim 1, wherein the human FZD receptor is FZD8.

7. The polypeptide of claim 1, wherein
   (a) the polypeptide inhibits the binding of a Wnt to a human FZD receptor; or
   (b) the polypeptide inhibits the binding of Wnt3A to the human FZD8 receptor.

8. The polypeptide of claim 1, wherein the polypeptide inhibits Wnt signaling.

9. A pharmaceutical composition comprising the polypeptide of claim 1.

10. An inhibitor of Wnt signaling which comprises the polypeptide of claim 1.

11. A method of inhibiting Wnt signaling in a cell, comprising contacting the cell with an effective amount of the polypeptide of claim 1.

12. The method of claim 11, wherein the cell is a tumor cell.

13. A method of inducing differentiation of a cell, comprising contacting the cell with an effective amount of the polypeptide of claim 1.

14. The method of claim 13, wherein the cell is a tumor cell.

15. A method of inhibiting growth of a tumor, comprising contacting the tumor with an effective amount of the polypeptide of claim 1.

* * * * *

SEQUENCE LISTING

```
<160> NUMBER OF SEQ ID NOS: 136

<210> SEQ ID NO 1
<211> LENGTH: 10
<212> TYPE: PRT
<213> ORGANISM: Artificial Sequence
<220> FEATURE:
<223> OTHER INFORMATION: heavy chain CDR1

<400> SEQUENCE: 1

Gly Phe Thr Phe Ser His Tyr Thr Leu Ser
1               5                   10
```

```
<210> SEQ ID NO 2
<211> LENGTH: 17
<212> TYPE: PRT
<213> ORGANISM: Artificial Sequence
<220> FEATURE:
<223> OTHER INFORMATION: heavy chain CDR2

<400> SEQUENCE: 2

Val Ile Ser Gly Asp Gly Ser Tyr Thr Tyr Tyr Ala Asp Ser Val Lys
1               5                   10                  15
Gly

<210> SEQ ID NO 3
<211> LENGTH: 9
<212> TYPE: PRT
<213> ORGANISM: Artificial Sequence
<220> FEATURE:
<223> OTHER INFORMATION: heavy chain CDR3

<400> SEQUENCE: 3

Asn Phe Ile Lys Tyr Val Phe Ala Asn
1               5

<210> SEQ ID NO 4
<211> LENGTH: 11
<212> TYPE: PRT
<213> ORGANISM: Artificial Sequence
<220> FEATURE:
<223> OTHER INFORMATION: light chain CDR1

<400> SEQUENCE: 4

Ser Gly Asp Lys Leu Gly Lys Lys Tyr Ala Ser
1               5                   10

<210> SEQ ID NO 5
<211> LENGTH: 8
<212> TYPE: PRT
<213> ORGANISM: Artificial Sequence
<220> FEATURE:
<223> OTHER INFORMATION: light chain CDR2

<400> SEQUENCE: 5

Glu Lys Asp Asn Arg Pro Ser Gly
1               5

<210> SEQ ID NO 6
<211> LENGTH: 9
<212> TYPE: PRT
<213> ORGANISM: Artificial Sequence
<220> FEATURE:
<223> OTHER INFORMATION: light chain CDR3

<400> SEQUENCE: 6

Ser Ser Phe Ala Gly Asn Ser Leu Glu
1               5

<210> SEQ ID NO 7
<211> LENGTH: 11
<212> TYPE: PRT
<213> ORGANISM: Artificial Sequence
<220> FEATURE:
<223> OTHER INFORMATION: light chain CDR1

<400> SEQUENCE: 7

Ser Gly Asp Asn Ile Gly Ser Phe Tyr Val His
1               5                   10
```

<210> SEQ ID NO 8
<211> LENGTH: 8
<212> TYPE: PRT
<213> ORGANISM: Artificial Sequence
<220> FEATURE:
<223> OTHER INFORMATION: light chain CDR2

<400> SEQUENCE: 8

Asp Lys Ser Asn Arg Pro Ser Gly
1               5

<210> SEQ ID NO 9
<211> LENGTH: 9
<212> TYPE: PRT
<213> ORGANISM: Artificial Sequence
<220> FEATURE:
<223> OTHER INFORMATION: light chain  CDR3

<400> SEQUENCE: 9

Gln Ser Tyr Ala Asn Thr Leu Ser Leu
1               5

<210> SEQ ID NO 10
<211> LENGTH: 118
<212> TYPE: PRT
<213> ORGANISM: Artificial Sequence
<220> FEATURE:
<223> OTHER INFORMATION: 18R5/18R8 heavy chain variable region (VH)

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Thr Leu Ser Trp Val Arg Gln Ala Pro Gly Lys Gly Leu Glu Trp Val
        35                  40                  45

Ser Val Ile Ser Gly Asp Gly Ser Tyr Thr Tyr Tyr Ala Asp Ser Val
    50                  55                  60

Lys Gly Arg Phe Thr Ile Ser Ser Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Phe Ile Lys Tyr Val Phe Ala Asn Trp Gly Gln Gly Thr
            100                 105                 110

Leu Val Thr Val Ser Ser
        115

<210> SEQ ID NO 11
<211> LENGTH: 463
<212> TYPE: PRT
<213> ORGANISM: Artificial Sequence
<220> FEATURE:
<223> OTHER INFORMATION: Full-length 18R5/18R8 heavy chain (IgG2)
<220> FEATURE:
<221> NAME/KEY: MISC_FEATURE
<222> LOCATION: (20)..(137)
<223> OTHER INFORMATION: variable region (VH)

<400> SEQUENCE: 11

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

-continued

Pro Gly Gly Ser Leu Arg Leu Ser Cys Ala Ala Ser Gly Phe Thr Phe
            35                  40                  45

Ser His Tyr Thr Leu Ser Trp Val Arg Gln Ala Pro Gly Lys Gly Leu
    50                  55                  60

Glu Trp Val Ser Val Ile Ser Gly Asp Gly Ser Tyr Thr Tyr Tyr Ala
65                  70                  75                  80

Asp Ser Val Lys Gly Arg Phe Thr Ile Ser Ser Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asn Phe Ile Lys Tyr Val Phe Ala Asn Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 12
<211> LENGTH: 108
<212> TYPE: PRT
<213> ORGANISM: Artificial Sequence
<220> FEATURE:
<223> OTHER INFORMATION: 18R8 light chain variable region (VL)

<400> SEQUENCE: 12

Asp Ile Glu Leu Thr Gln Pro Pro Ser Val Ser Val Ala Pro Gly Gln
1               5                   10                  15

Thr Ala Arg Ile Ser Cys Ser Gly Asp Lys Leu Gly Lys Lys Tyr Ala
            20                  25                  30

Ser Trp Tyr Gln Gln Lys Pro Gly Gln Ala Pro Val Leu Val Ile Tyr
        35                  40                  45

Glu Lys Asp Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Phe Ala Gly Asn Ser Leu Glu
                85                  90                  95

Val Phe Gly Gly Gly Thr Lys Leu Thr Val Leu Gly
            100                 105

<210> SEQ ID NO 13
<211> LENGTH: 232
<212> TYPE: PRT
<213> ORGANISM: Artificial Sequence
<220> FEATURE:
<223> OTHER INFORMATION: Full-length 18R8 light chain (lambda)
<220> FEATURE:
<221> NAME/KEY: MISC_FEATURE
<222> LOCATION: (20)..(127)
<223> OTHER INFORMATION: variable region (VL)

<400> SEQUENCE: 13

Met Ala Trp Ala Leu Leu Leu Thr Leu Leu Thr Gln Gly Thr Gly
1               5                   10                  15

Ser Trp Ala Asp Ile Glu Leu Thr Gln Pro Pro Ser Val Ser Val Ala
            20                  25                  30

Pro Gly Gln Thr Ala Arg Ile Ser Cys Ser Gly Asp Lys Leu Gly Lys
        35                  40                  45

Lys Tyr Ala Ser Trp Tyr Gln Gln Lys Pro Gly Gln Ala Pro Val Leu
    50                  55                  60

Val Ile Tyr Glu Lys Asp Asn Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Glu Asp Glu Ala Asp Tyr Tyr Cys Ser Ser Phe Ala Gly Asn
            100                 105                 110

Ser Leu Glu Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys

```
                165                 170                 175
Ala Gly Val Glu Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
            195                 200                 205

Arg Ser Tyr Ser Cys Gln Val Thr His Glu Gly Ser Thr Val Glu Lys
        210                 215                 220

Thr Val Ala Pro Thr Glu Cys Ser
225                 230

<210> SEQ ID NO 14
<211> LENGTH: 108
<212> TYPE: PRT
<213> ORGANISM: Artificial Sequence
<220> FEATURE:
<223> OTHER INFORMATION: 18R5 light chain variable region (VL)

<400> SEQUENCE: 14

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Phe Tyr Val
            20                  25                  30

His Trp Tyr Gln Gln Lys Pro Gly Gln Ala Pro Val Leu Val Ile Tyr
        35                  40                  45

Asp Lys Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Ala Asn Thr Leu Ser Leu
                85                  90                  95

Val Phe Gly Gly Gly Thr Lys Leu Thr Val Leu Gly
            100                 105

<210> SEQ ID NO 15
<211> LENGTH: 232
<212> TYPE: PRT
<213> ORGANISM: Artificial Sequence
<220> FEATURE:
<223> OTHER INFORMATION: Full-length 18R5 light chain (lambda)
<220> FEATURE:
<221> NAME/KEY: MISC_FEATURE
<222> LOCATION: (20)..(232)
<223> OTHER INFORMATION: variable region (VL)

<400> SEQUENCE: 15

Met Ala Trp Ala Leu Leu Leu Thr Leu Leu Thr Gln Gly Thr Gly
1               5                   10                  15

Ser Trp Ala Asp Ile Glu Leu Thr Gln Pro Pro Ser Val Ser Val Ala
            20                  25                  30

Pro Gly Gln Thr Ala Arg Ile Ser Cys Ser Gly Asp Asn Ile Gly Ser
        35                  40                  45

Phe Tyr Val His Trp Tyr Gln Gln Lys Pro Gly Gln Ala Pro Val Leu
    50                  55                  60

Val Ile Tyr Asp Lys Ser Asn Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Glu Asp Glu Ala Asp Tyr Tyr Cys Gln Ser Tyr Ala Asn Thr
            100                 105                 110
```

```
Leu Ser Leu Val Phe Gly Gly Thr Lys Leu Thr Val Leu Gly Gln
            115                 120                 125

Pro Lys Ala Ala Pro Ser Val Thr Leu Phe Pro Pro Ser Ser Glu Glu
        130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
            195                 200                 205

Arg Ser Tyr Ser Cys Gln Val Thr His Glu Gly Ser Thr Val Glu Lys
        210                 215                 220

Thr Val Ala Pro Thr Glu Cys Ser
225                 230

<210> SEQ ID NO 16
<211> LENGTH: 485
<212> TYPE: PRT
<213> ORGANISM: Artificial Sequence
<220> FEATURE:
<223> OTHER INFORMATION: Fzd7 ECD Fc fusion protein

<400> SEQUENCE: 16

Met Arg Asp Pro Gly Ala Ala Pro Leu Ser Ser Leu Gly Leu Cys
1               5                   10                  15

Ala Leu Val Leu Ala Leu Leu Gly Ala Leu Ser Ala Gly Ala Gly Ala
                20                  25                  30

Gln Pro Tyr His Gly Glu Lys Gly Ile Ser Val Pro Asp His Gly Phe
            35                  40                  45

Cys Gln Pro Ile Ser Ile Pro Leu Cys Thr Asp Ile Ala Tyr Asn Gln
        50                  55                  60

Thr Ile Leu Pro Asn Leu Leu Gly His Thr Asn Gln Glu Asp Ala Gly
65                  70                  75                  80

Leu Glu Val His Gln Phe Tyr Pro Leu Val Lys Val Gln Cys Ser Pro
                85                  90                  95

Glu Leu Arg Phe Phe Leu Cys Ser Met Tyr Ala Pro Val Cys Thr Val
            100                 105                 110

Leu Asp Gln Ala Ile Pro Pro Cys Arg Ser Leu Cys Glu Arg Ala Arg
        115                 120                 125

Gln Gly Cys Glu Ala Leu Met Asn Lys Phe Gly Phe Gln Trp Pro Glu
    130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Gly Pro Gly Gly Gly Pro
                165                 170                 175

Thr Ala Tyr Pro Thr Ala Pro Tyr Leu Pro Asp Leu Pro Phe Thr Ala
            180                 185                 190

Leu Pro Pro Gly Ala Ser Asp Gly Arg Gly Arg Pro Ala Phe Pro Phe
        195                 200                 205

Ser Cys Pro Arg Gln Leu Lys Val Pro Pro Tyr Leu Gly Tyr Arg Phe
    210                 215                 220

Leu Gly Glu Arg Asp Cys Gly Ala Pro Cys Glu Pro Gly Arg Ala Asn
225                 230                 235                 240
```

Gly Leu Met Tyr Phe Lys Glu Glu Arg Arg Phe Ala Arg Leu Gly
              245                 250                 255

Arg Ala Asp Lys Thr His Thr Cys Pro Pro Cys Pro Ala Pro Glu Leu
          260                 265                 270

Leu Gly Gly Pro Ser Val Phe Leu Phe Pro Pro Lys Pro Lys Asp Thr
              275                 280                 285

Leu Met Ile Ser Arg Thr Pro Glu Val Thr Cys Val Val Val Asp Val
          290                 295                 300

Ser His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
              325                 330                 335

Thr Tyr Arg Val Val Ser Val Leu Thr Val Leu His Gln Asp Trp Leu
          340                 345                 350

Asn Gly Lys Glu Tyr Lys Cys Lys Val Ser Asn Lys Ala Leu Pro Ala
              355                 360                 365

Pro Ile Glu Lys Thr Ile Ser Lys Ala Lys Gly Gln Pro Arg Glu Pro
          370                 375                 380

Gln Val Tyr Thr Leu Pro Pro Ser Arg Asp Glu Leu Thr Lys Asn Gln
385                 390                 395                 400

Val Ser Leu Thr Cys Leu Val Lys Gly Phe Tyr Pro Ser Asp Ile Ala
              405                 410                 415

Val Glu Trp Glu Ser Asn Gly Gln Pro Glu Asn Asn Tyr Lys Thr Thr
          420                 425                 430

Pro Pro Val Leu Asp Ser Asp Gly Ser Phe Phe Leu Tyr Ser Lys Leu
              435                 440                 445

Thr Val Asp Lys Ser Arg Trp Gln Gln Gly Asn Val Phe Ser Cys Ser
          450                 455                 460

Val Met His Glu Ala Leu His Asn His Tyr Thr Gln Lys Ser Leu Ser
465                 470                 475                 480

Leu Ser Pro Gly Lys
              485

<210> SEQ ID NO 17
<211> LENGTH: 354
<212> TYPE: DNA
<213> ORGANISM: Artificial Sequence
<220> FEATURE:
<223> OTHER INFORMATION: Nucleotide sequence encoding 18R5/18R8 heavy
      chain variable region (VH)

<400> SEQUENCE: 17
gaagtgcaac tggtggaaag cggcggcggc ctggtgcaac tggcggcag cctgagactg      60 agctgcgctg cctccggatt tacctttct cattatactc tgtcttgggt gcgccaagcc     120
cctgggaagg gtctcgagtg ggtgagcgtt atctctggtg atggtagcta taccatt      180 gctgatagcg tgaaaggcag atttaccatt tcaagtgata attccaaaaa cacctgtat      240 ctgcaaatga acagcctgag agctgaagat acagccgtgt attattgcgc tagaaatttt     300
attaagtatg tttttgctaa ttggggccaa ggcacctgg tgacagttag ctca           354

<210> SEQ ID NO 18
<211> LENGTH: 1389
<212> TYPE: DNA
<213> ORGANISM: Artificial Sequence
<220> FEATURE:
<223> OTHER INFORMATION: Nucleotide sequence encoding full-length 18R5/18R8 heavy chain (IgG2)
<220> FEATURE:
<221> NAME/KEY: misc_feature
<222> LOCATION: (58)..(411)
<223> OTHER INFORMATION: variable region (VH)

<400> SEQUENCE: 18

```
atgaaacacc tgtggttctt cctcctgctg gtggcagctc ccagatgggt cctgtccgaa      60
gtgcaactgg tggaaagcgg cggcggcctg gtgcaacctg gcggcagcct gagactgagc     120
tgcgctgcct ccggatttac cttttctcat tatactctgt cttgggtgcg ccaagcccct     180
gggaagggtc tcgagtgggt gagcgttatc tctggtgatg gtagctatac ctattatgct     240
gatagcgtga aaggcagatt taccatttca agtgataatt ccaaaaacac cctgtatctg     300
caaatgaaca gcctgagagc tgaagataca gccgtgtatt attgcgctag aaattttatt     360
aagtatgttt ttgctaattg gggccaaggc accctggtga cagttagctc agccagcaca     420
aagggcccta gcgtcttccc tctggctccc tgcagcagga gcaccagcga gagcacagcc     480
gccctgggct gcctggtcaa ggactacttc cccgaaccgg tgacggtgtc gtggaactca     540
ggcgctctga ccagcggcgt gcacaccttc ccagctgtcc tacagtcctc aggactctac     600
tccctcagca gcgtggtgac cgtgccctcc agcaacttcg gcacccagac ctacacctgc     660
aacgtagatc acaagcccag caacaccaag gtggacaaga cagttgagcg caaatgttgt     720
gtcgagtgcc caccgtgccc agcaccacct gtggcaggac cgtcagtctt cctcttcccc     780
ccaaaaccca aggacaccct catgatctcc cggacccctg aggtcacgtg cgtggtggtg     840
gacgtgagcc acgaagaccc cgaggtccag ttcaactggt acgtggacgg cgtggaggtg     900
cataatgcca agacaaagcc acgggaggag cagttcaaca gcacgttccg tgtggtcagc     960
gtcctcaccg ttgtgcacca ggactggctg aacggcaagg agtacaagtg caaggtctcc    1020
aacaaaggcc tcccagcccc catcgagaaa accatctcca aaaccaaagg gcagcccga    1080
gaaccacagg tgtacaccct gcccccatcc cgggaggaga tgaccaagaa ccaggtcagc    1140
ctgacctgcc tggtcaaagg cttctacccc agcgacatcg ccgtggagtg ggagagcaat    1200
gggcagccgg agaacaacta caagaccaca cctcccatgc tggactccga cggctccttc    1260
ttcctctaca gcaagctcac cgtggacaag agcaggtggc agcaggggaa cgtcttctca    1320
tgctccgtga tgcatgaggc tctgcacaac cactacacgc agaagagcct ctccctgtct    1380
ccgggtaaa                                                             1389
```

<210> SEQ ID NO 19
<211> LENGTH: 324
<212> TYPE: DNA
<213> ORGANISM: Artificial Sequence
<220> FEATURE:
<223> OTHER INFORMATION: 18R8 light chain variable region (VL)

<400> SEQUENCE: 19

```
gatatcgaac tgacccagcc tccttcagtg agcgttgcac aggtcagac cgctagaatc       60
tcttgtagcg gcgataagct gggtaagaag tatgcttctt ggtaccagca gaaacccggg     120
caggctccag ttctggtgat ttatgagaag gataatagac cctcaggcat ccctgaacgc     180
tttagcggat ccaacagcgg caacaccgct accctgacca ttagcggcac tcaggctgaa     240
gacgaagccg attattattg ctcttctttt gctggtaatt ctctggaggt gtttggcggc     300
ggcaccaagt taaccgtcct gggt                                            324
```

<210> SEQ ID NO 20
<211> LENGTH: 696
<212> TYPE: DNA
<213> ORGANISM: Artificial Sequence
<220> FEATURE:
<223> OTHER INFORMATION: full-length 18R8 light chain (lambda)
<220> FEATURE:
<221> NAME/KEY: misc_feature
<222> LOCATION: (58)..(381)
<223> OTHER INFORMATION: variable region (VL)

<400> SEQUENCE: 20

```
atggcctggg ctctgctgct cctcaccctc ctcactcagg gcacaggatc ctgggctgat    60
atcgaactga cccagcctcc ttcagtgagc gttgcaccag gtcagaccgc tagaatctct   120
tgtagcggcg ataagctggg taagaagtat gcttcttggt accagcagaa acccgggcag   180
gctccagttc tggtgattta tgagaaggat aatagaccct caggcatccc tgaacgcttt   240
agcggatcca acagcggcaa caccgctacc ctgaccatta gcggcactca ggctgaagac   300
gaagccgatt attattgctc ttcttttgct ggtaattctc tggaggtgtt tggcggcggc   360
accaagttaa ccgtcctggg tcagcccaag gctgccccca gcgtcactct gttccctccc   420
tcctctgagg agctgcaagc caacaaggcc acactggtgt gtctcataag tgacttctac   480
cctggagccg tgacagtggc ctggaaggca gatagcagcc ccgtcaaggc tggagtggag   540
accaccacac cctccaaaca aagcaacaac aagtacgctg ccagcagcta tctgagcctg   600
acacctgagc agtggaagtc cacagaagc tacagctgcc aggtcacaca tgaagggagc   660
accgtggaga agacagtggc ccctacagaa tgttca                             696
```

<210> SEQ ID NO 21
<211> LENGTH: 324
<212> TYPE: DNA
<213> ORGANISM: Artificial Sequence
<220> FEATURE:
<223> OTHER INFORMATION: 18R5 light chain variable region (VL)

<400> SEQUENCE: 21

```
gatatcgagc tgactcagcc tccatccgtg agtgtggccc ctggtcagac agcacgcatc    60
agctgctccg gggacaatat cggatctttc tacgtgcact ggtatcagca gaagcctggt   120
caggctccag ttctcgttat ctatgataag agtaatcgcc cctctgggat tccagagcgc   180
ttcagcggaa gcaacagcgg aaatactgca actctcacaa tttccggtac tcaggctgag   240
gacgaagccg actattactg ccaaagctac gcaaacaccc tgtccctcgt cttcggaggc   300
ggaaccaagt taaccgtcct gggt                                           324
```

<210> SEQ ID NO 22
<211> LENGTH: 696
<212> TYPE: DNA
<213> ORGANISM: Artificial Sequence
<220> FEATURE:
<223> OTHER INFORMATION: full-length 18R5 light chain (lambda)
<220> FEATURE:
<221> NAME/KEY: misc_feature
<222> LOCATION: (58)..(381)
<223> OTHER INFORMATION: variable region (VL)

<400> SEQUENCE: 22

```
atggcatggg cactgctgct gctcactctg ctgacacaag gtactggctc ttgggccgat    60
atcgagctga ctcagcctcc atccgtgagt gtggcccctg gtcagacagc acgcatcagc   120
tgctccgggg acaatatcgg atctttctac gtgcactggt atcagcagaa gcctggtcag   180
```

```
gctccagttc tcgttatcta tgataagagt aatcgcccct ctgggattcc agagcgcttc    240
agcggaagca acagcggaaa tactgcaact ctcacaattt ccggtactca ggctgaggac    300
gaagccgact attactgcca aagctacgca acaccctgt  ccctcgtctt cggaggcgga    360
accaagttaa ccgtcctggg tcagcccaag gctgccccca gcgtcactct gttccctccc    420
tcctctgagg agctgcaagc caacaaggcc acactggtgt gtctcataag tgacttctac    480
cctggagccg tgacagtggc ctggaaggca gatagcagcc ccgtcaaggc tggagtggag    540
accaccacac cctccaaaca agcaacaac  aagtacgctg ccagcagcta tctgagcctg    600
acacctgagc agtggaagtc ccacagaagc tacagctgcc aggtcacaca tgaagggagc    660
accgtggaga agacagtggc ccctacagaa tgttca                              696

<210> SEQ ID NO 23
<211> LENGTH: 1455
<212> TYPE: DNA
<213> ORGANISM: Artificial Sequence
<220> FEATURE:
<223> OTHER INFORMATION: Fzd7 ECD Fc fusion protein

<400> SEQUENCE: 23
atgcgggacc ccggcgcggc cgctccgctt tcgtccctgg gcctctgtgc cctggtgctg     60
gcgctgctgg gcgcactgtc cgcgggcgcc ggggcgcagc cgtaccacgg agagaagggc    120
atctccgtgc cggaccacgg cttctgccag cccatctcca tccgctgtg  cacggacatc    180 gcctacaacc agaccatcct gcccaacctg ctgggccaca cgaaccaaga ggacgcgggc    240
ctcgaggtgc accagttcta cccgctggtg aaggtgcagt gttctcccga actccgcttt    300
ttcttatgct ccatgtatgc gcccgtgtgc accgtgctcg atcaggccat cccgccgtgt    360
cgttctctgt gcgagcgcgc ccgccagggc tgcgaggcgc tcatgaacaa gttcggcttc    420
cagtggcccg agcggctgcg ctgcgagaac ttcccggtgc acggtgcggg cgagatctgc    480
gtgggccaga acacgtcgga cggctccggg ggcccaggcg gcggcccac  tgcctaccct    540 accgcgccct acctgccgga cctgcccttc accgcgctgc cccggggggc ctcagatggc    600 aggggggcgtc ccgccttccc cttctcatgc cccgtcagc tcaaggtgcc cccgtacctg    660
ggctaccgct tcctgggtga gcgcgattgt ggcgcccgt  gcgaaccggg ccgtgccaac    720
ggcctgatgt actttaagga ggaggagagg gcttcgccc  gctcgggcg cgccgacaaa    780 actcacacat gcccaccgtg cccagcacct gaactcctgg ggggaccgtc agtcttcctc    840
ttccccccaa aacccaagga caccctcatg atctcccgga cccctgaggt cacatgcgtg    900
gtggtggacg tgagccacga agaccctgag gtcaagttca actggtacgt ggacggcgtg    960
gaggtgcata atgccaagac aaagccgcgg gaggagcagt acaacagcac gtaccgtgtg   1020
gtcagcgtcc tcaccgtcct gcaccaggac tggctgaatg gcaaggagta caagtgcaag   1080
gtctccaaca aagccctccc agcccccatc gagaaaacca tctccaaagc caaagggcag   1140
ccccgagaac cacaggtgta caccctgccc ccatcccggg atgagctgac caagaaccag   1200
gtcagcctga cctgcctggt caaaggcttc tatcccagcg acatcgccgt ggagtgggag   1260
agcaatgggc agccggagaa caactacaag accacgcctc ccgtgctgga ctccgacggc   1320
tccttcttcc tctacagcaa gctcaccgtg gacaagagca ggtggcagca ggggaacgtc   1380
ttctcatgct ccgtgatgca tgaggctctg cacaaccact acacacagaa gagcctctcc   1440
ctgtctccgg gtaaa                                                   1455
```

```
<210> SEQ ID NO 24
<211> LENGTH: 14
<212> TYPE: PRT
<213> ORGANISM: Artificial Sequence
<220> FEATURE:
<223> OTHER INFORMATION: fragment of Human frizzled receptor
<220> FEATURE:
<221> NAME/KEY: MISC_FEATURE
<222> LOCATION: (2)..(2)
<223> OTHER INFORMATION: Is aspartic acid/glutamic acid
<220> FEATURE:
<221> NAME/KEY: MISC_FEATURE
<222> LOCATION: (3)..(3)
<223> OTHER INFORMATION: Is glutamic acid/aspartic acid
<220> FEATURE:
<221> NAME/KEY: MISC_FEATURE
<222> LOCATION: (12)..(12)
<223> OTHER INFORMATION: Is tyrosine/tryptophan

<400> SEQUENCE: 24

Gln Xaa Xaa Ala Gly Leu Glu Val His Gln Phe Xaa Pro Leu
1               5                   10

<210> SEQ ID NO 25
<211> LENGTH: 6
<212> TYPE: PRT
<213> ORGANISM: Artificial Sequence
<220> FEATURE:
<223> OTHER INFORMATION: 'top edge' of the Biological Binding Site (BBS)

<400> SEQUENCE: 25

Gly Leu Glu Val His Gln
1               5

<210> SEQ ID NO 26
<211> LENGTH: 647
<212> TYPE: PRT
<213> ORGANISM: Artificial Sequence
<220> FEATURE:
<223> OTHER INFORMATION: Human FZD1

<400> SEQUENCE: 26

Met Ala Glu Glu Glu Ala Pro Lys Lys Ser Arg Ala Ala Gly Gly Gly
1               5                   10                  15

Ala Ser Trp Glu Leu Cys Ala Gly Ala Leu Ser Ala Arg Leu Ala Glu
                20                  25                  30

Glu Gly Ser Gly Asp Ala Gly Gly Arg Arg Arg Pro Pro Val Asp Pro
            35                  40                  45

Arg Arg Leu Ala Arg Gln Leu Leu Leu Leu Trp Leu Leu Glu Ala
    50                  55                  60

Pro Leu Leu Leu Gly Val Arg Ala Gln Ala Ala Gly Gln Gly Pro Gly
65                  70                  75                  80

Gln Gly Pro Gly Pro Gly Gln Gln Pro Pro Pro Pro Gln Gln Gln
                85                  90                  95

Gln Ser Gly Gln Gln Tyr Asn Gly Glu Arg Gly Ile Ser Val Pro Asp
            100                 105                 110

His Gly Tyr Cys Gln Pro Ile Ser Ile Pro Leu Cys Thr Asp Ile Ala
        115                 120                 125

Tyr Asn Gln Thr Ile Met Pro Asn Leu Leu Gly His Thr Asn Gln Glu
    130                 135                 140

Asp Ala Gly Leu Glu Val His Gln Phe Tyr Pro Leu Val Lys Val Gln
145                 150                 155                 160

Cys Ser Ala Glu Leu Lys Phe Phe Leu Cys Ser Met Tyr Ala Pro Val
                165                 170                 175
```

```
Cys Thr Val Leu Glu Gln Ala Leu Pro Pro Cys Arg Ser Leu Cys Glu
            180                 185                 190

Arg Ala Arg Gln Gly Cys Glu Ala Leu Met Asn Lys Phe Gly Phe Gln
        195                 200                 205

Trp Pro Asp Thr Leu Lys Cys Glu Lys Phe Pro Val His Gly Ala Gly
210                 215                 220

Glu Leu Cys Val Gly Gln Asn Thr Ser Asp Lys Gly Thr Pro Thr Pro
225                 230                 235                 240

Ser Leu Leu Pro Glu Phe Trp Thr Ser Asn Pro Gln His Gly Gly Gly
            245                 250                 255

Gly His Arg Gly Gly Phe Pro Gly Gly Ala Gly Ala Ser Glu Arg Gly
        260                 265                 270

Lys Phe Ser Cys Pro Arg Ala Leu Lys Val Pro Ser Tyr Leu Asn Tyr
        275                 280                 285

His Phe Leu Gly Glu Lys Asp Cys Gly Ala Pro Cys Glu Pro Thr Lys
        290                 295                 300

Val Tyr Gly Leu Met Tyr Phe Gly Pro Glu Glu Leu Arg Phe Ser Arg
305                 310                 315                 320

Thr Trp Ile Gly Ile Trp Ser Val Leu Cys Cys Ala Ser Thr Leu Phe
            325                 330                 335

Thr Val Leu Thr Tyr Leu Val Asp Met Arg Arg Phe Ser Tyr Pro Glu
            340                 345                 350

Arg Pro Ile Ile Phe Leu Ser Gly Cys Tyr Thr Ala Val Ala Val Ala
        355                 360                 365

Tyr Ile Ala Gly Phe Leu Leu Glu Asp Arg Val Val Cys Asn Asp Lys
        370                 375                 380

Phe Ala Glu Asp Gly Ala Arg Thr Val Ala Gln Gly Thr Lys Lys Glu
385                 390                 395                 400

Gly Cys Thr Ile Leu Phe Met Met Leu Tyr Phe Phe Ser Met Ala Ser
            405                 410                 415

Ser Ile Trp Trp Val Ile Leu Ser Leu Thr Trp Phe Leu Ala Ala Gly
            420                 425                 430

Met Lys Trp Gly His Glu Ala Ile Glu Ala Asn Ser Gln Tyr Phe His
        435                 440                 445

Leu Ala Ala Trp Ala Val Pro Ala Ile Lys Thr Ile Thr Ile Leu Ala
450                 455                 460

Leu Gly Gln Val Asp Gly Asp Val Leu Ser Gly Val Cys Phe Val Gly
465                 470                 475                 480

Leu Asn Asn Val Asp Ala Leu Arg Gly Phe Val Leu Ala Pro Leu Phe
            485                 490                 495

Val Tyr Leu Phe Ile Gly Thr Ser Phe Leu Leu Ala Gly Phe Val Ser
            500                 505                 510

Leu Phe Arg Ile Arg Thr Ile Met Lys His Asp Gly Thr Lys Thr Glu
        515                 520                 525

Lys Leu Glu Lys Leu Met Val Arg Ile Gly Val Phe Ser Val Leu Tyr
        530                 535                 540

Thr Val Pro Ala Thr Ile Val Ile Ala Cys Tyr Phe Tyr Glu Gln Ala
545                 550                 555                 560

Phe Arg Asp Gln Trp Glu Arg Ser Trp Val Ala Gln Ser Cys Lys Ser
            565                 570                 575

Tyr Ala Ile Pro Cys Pro His Leu Gln Ala Gly Gly Gly Ala Pro Pro
            580                 585                 590
```

His Pro Pro Met Ser Pro Asp Phe Thr Val Phe Met Ile Lys Tyr Leu
        595                 600                 605

Met Thr Leu Ile Val Gly Ile Thr Ser Gly Phe Trp Ile Trp Ser Gly
610                 615                 620

Lys Thr Leu Asn Ser Trp Arg Lys Phe Tyr Thr Arg Leu Thr Asn Ser
625                 630                 635                 640

Lys Gln Gly Glu Thr Thr Val
                645

<210> SEQ ID NO 27
<211> LENGTH: 321
<212> TYPE: PRT
<213> ORGANISM: Artificial Sequence
<220> FEATURE:
<223> OTHER INFORMATION: extracellular domain (ECD)

<400> SEQUENCE: 27

Met Ala Glu Glu Ala Pro Lys Lys Ser Arg Ala Ala Gly Gly Gly
1               5                   10                  15

Ala Ser Trp Glu Leu Cys Ala Gly Ala Leu Ser Ala Arg Leu Ala Glu
                20                  25                  30

Glu Gly Ser Gly Asp Ala Gly Gly Arg Arg Arg Pro Pro Val Asp Pro
            35                  40                  45

Arg Arg Leu Ala Arg Gln Leu Leu Leu Leu Trp Leu Leu Glu Ala
50                  55                  60

Pro Leu Leu Leu Gly Val Arg Ala Gln Ala Ala Gly Gln Gly Pro Gly
65                  70                  75                  80

Gln Gly Pro Gly Pro Gly Gln Gln Pro Pro Pro Pro Gln Gln Gln
                85                  90                  95

Gln Ser Gly Gln Gln Tyr Asn Gly Glu Arg Gly Ile Ser Val Pro Asp
            100                 105                 110

His Gly Tyr Cys Gln Pro Ile Ser Ile Pro Leu Cys Thr Asp Ile Ala
        115                 120                 125

Tyr Asn Gln Thr Ile Met Pro Asn Leu Leu Gly His Thr Asn Gln Glu
    130                 135                 140

Asp Ala Gly Leu Glu Val His Gln Phe Tyr Pro Leu Val Lys Val Gln
145                 150                 155                 160

Cys Ser Ala Glu Leu Lys Phe Phe Leu Cys Ser Met Tyr Ala Pro Val
                165                 170                 175

Cys Thr Val Leu Glu Gln Ala Leu Pro Pro Cys Arg Ser Leu Cys Glu
            180                 185                 190

Arg Ala Arg Gln Gly Cys Glu Ala Leu Met Asn Lys Phe Gly Phe Gln
        195                 200                 205

Trp Pro Asp Thr Leu Lys Cys Glu Lys Phe Pro Val His Gly Ala Gly
    210                 215                 220

Glu Leu Cys Val Gly Gln Asn Thr Ser Asp Lys Gly Thr Pro Thr Pro
225                 230                 235                 240

Ser Leu Leu Pro Glu Phe Trp Thr Ser Asn Pro Gln His Gly Gly Gly
                245                 250                 255

Gly His Arg Gly Gly Phe Pro Gly Gly Ala Gly Ala Ser Glu Arg Gly
            260                 265                 270

Lys Phe Ser Cys Pro Arg Ala Leu Lys Val Pro Ser Tyr Leu Asn Tyr
        275                 280                 285

His Phe Leu Gly Glu Lys Asp Cys Gly Ala Pro Cys Glu Pro Thr Lys
    290                 295                 300

Val Tyr Gly Leu Met Tyr Phe Gly Pro Glu Glu Leu Arg Phe Ser Arg
305                 310                 315                 320

Thr

<210> SEQ ID NO 28
<211> LENGTH: 151
<212> TYPE: PRT
<213> ORGANISM: Artificial Sequence
<220> FEATURE:
<223> OTHER INFORMATION: Human FZD1 Fri domain

<400> SEQUENCE: 28

Gln Gln Pro Pro Pro Pro Gln Gln Gln Ser Gly Gln Gln Tyr
1               5                   10                  15

Asn Gly Glu Arg Gly Ile Ser Val Pro Asp His Gly Tyr Cys Gln Pro
                20                  25                  30

Ile Ser Ile Pro Leu Cys Thr Asp Ile Ala Tyr Asn Gln Thr Ile Met
            35                  40                  45

Pro Asn Leu Leu Gly His Thr Asn Gln Glu Asp Ala Gly Leu Glu Val
        50                  55                  60

His Gln Phe Tyr Pro Leu Val Lys Val Gln Cys Ser Ala Glu Leu Lys
65                  70                  75                  80

Phe Phe Leu Cys Ser Met Tyr Ala Pro Val Cys Thr Val Leu Glu Gln
                85                  90                  95

Ala Leu Pro Pro Cys Arg Ser Leu Cys Glu Arg Ala Arg Gln Gly Cys
            100                 105                 110

Glu Ala Leu Met Asn Lys Phe Gly Phe Gln Trp Pro Asp Thr Leu Lys
        115                 120                 125

Cys Glu Lys Phe Pro Val His Gly Ala Gly Glu Leu Cys Val Gly Gln
130                 135                 140

Asn Thr Ser Asp Lys Gly Thr
145                 150

<210> SEQ ID NO 29
<211> LENGTH: 1944
<212> TYPE: DNA
<213> ORGANISM: Homo sapiens

<400> SEQUENCE: 29
atggctgagg aggaggcgcc taagaagtcc cgggccgccg gcggtggcgc gagctgggaa      60
ctttgtgccg ggcgctctc ggcccggctg gcggaggagg gcagcgggga cgccggtggc     120
cgccgccgcc cgccagttga ccccggcga ttggcgcgcc agctgctgct gctgctttgg     180
ctgctggagg ctccgctgct gctgggggtc cgggcccagg cggcgggcca ggggccaggc     240
caggggcccg gccgggggca gcaaccgccg ccgccgcctc agcagcaaca gagcgggcag     300
cagtacaacg gcgagcgggg catctccgtc ccggaccacg gctattgcca gcccatctcc     360
atcccgctgt gcacggacat cgcgtacaac cagaccatca tgcccaacct gctgggccac     420
acgaaccagg aggacgcggg cctggaggtg caccagttct accctctagt gaaagtgcag     480
tgttccgctg agctcaagtt cttcctgtgc tccatgtacg cgcccgtgtg caccgtgcta     540
gagcaggcgc tgccgccctg ccgctccctg tgcgagcgcg cgcgccaggg ctgcgaggcg     600
ctcatgaaca agttcggctt ccagtggcca gacacgctca gtgtgagaa gttcccggtg     660 cacggcgccg gcgagctgtg cgtgggccag aacacgtccg acaagggcac ccgcgacgcc     720
tcgctgcttc cagagttctg gaccagcaac cctcagcacg gcggcggagg caccgtggcc     780

-continued

```
ggcttcccgg ggggcgccgg cgcgtcggag cgaggcaagt tctcctgccc gcgcgccctc    840
aaggtgccct cctacctcaa ctaccacttc ctggggagag aggactgcgg cgcaccttgt    900
gagccgacca aggtgtatgg gctcatgtac ttcgggcccg aggagctgcg cttctcgcgc    960
acctggattg gcatttggtc agtgctgtgc tgcgcctcca cgctcttcac ggtgcttacg   1020
tacctggtgg acatgcggcg cttcagctac ccggagcggc ccatcatctt cttgtccggc   1080
tgttacacgg ccgtggccgt ggcctacatc gccggcttcc tcctggaaga ccgagtggtg   1140
tgtaatgaca agttcgccga ggacggggca cgcactgtgg cgcagggcac caagaaggag   1200
ggctgcacca tcctcttcat gatgctctac ttcttcagca tggccagctc catctggtgg   1260
gtgatcctgt cgctcacctg gttcctggcg gctggcatga agtggggcca cgaggccatc   1320
gaagccaact cacagtattt tcacctggcc gcctgggctg tgccggccat caagaccatc   1380
accatcctgg cgctgggcca ggtggacggc gatgtgctga gcggagtgtg cttcgtgggg   1440
cttaacaacg tggacgcgct gcgtggcttc gtgctggcgc ccctcttcgt gtacctgttt   1500
atcggcacgt cctttctgct ggccggcttt gtgtcgctct ccgcatccg caccatcatg   1560 aagcacgatg caccaagac cgagaagctg gagaagctca tggtgcgcat tggcgtcttc   1620
agcgtgctgt acactgtgcc agccaccatc gtcatcgcct gctacttcta cgagcaggcc   1680
ttccgggacc agtgggaacg cagctgggtg gcccagagct gcaagagcta cgctatcccc   1740
tgccctcacc tccaggcggg cggaggcgcc ccgccgcacc cgcccatgag cccggacttc   1800
acggtcttca tgattaagta ccttatgacg ctgatcgtgg gcatcacgtc gggcttctgg   1860
atctggtccg gcaagaccct caactcctgg aggaagttct acacgaggct caccaacagc   1920
aaacaagggg agactacagt ctga                                          1944
```

<210> SEQ ID NO 30
<211> LENGTH: 565
<212> TYPE: PRT
<213> ORGANISM: Artificial Sequence
<220> FEATURE:
<223> OTHER INFORMATION: Human FZD2
<220> FEATURE:
<221> NAME/KEY: MISC_FEATURE
<222> LOCATION: (1)..(250)
<223> OTHER INFORMATION: extracellular domain (ECD) of FZD2

<400> SEQUENCE: 30

```
Met Arg Pro Arg Ser Ala Leu Pro Arg Leu Leu Pro Leu Leu Leu
1               5                   10                  15

Leu Pro Ala Ala Gly Pro Ala Gln Phe His Gly Glu Lys Gly Ile Ser
            20                  25                  30

Ile Pro Asp His Gly Phe Cys Gln Pro Ile Ser Ile Pro Leu Cys Thr
        35                  40                  45

Asp Ile Ala Tyr Asn Gln Thr Ile Met Pro Asn Leu Leu Gly His Thr
    50                  55                  60

Asn Gln Glu Asp Ala Gly Leu Glu Val His Gln Phe Tyr Pro Leu Val
65                  70                  75                  80

Lys Val Gln Cys Ser Pro Glu Leu Arg Phe Phe Leu Cys Ser Met Tyr
                85                  90                  95

Ala Pro Val Cys Thr Val Leu Glu Gln Ala Ile Pro Pro Cys Arg Ser
            100                 105                 110

Ile Cys Glu Arg Ala Arg Gln Gly Cys Glu Ala Leu Met Asn Lys Phe
        115                 120                 125

Gly Phe Gln Trp Pro Glu Arg Leu Arg Cys Glu His Phe Pro Arg His
```

```
                130                 135                 140
Gly Ala Glu Gln Ile Cys Val Gly Gln Asn His Ser Glu Asp Gly Ala
145                 150                 155                 160

Pro Ala Leu Leu Thr Thr Ala Pro Pro Gly Leu Gln Pro Gly Ala
            165                 170                 175

Gly Gly Thr Pro Gly Gly Pro Gly Gly Gly Ala Pro Pro Arg Tyr
            180                 185                 190

Ala Thr Leu Glu His Pro Phe His Cys Pro Arg Val Leu Lys Val Pro
            195                 200                 205

Ser Tyr Leu Ser Tyr Lys Phe Leu Gly Glu Arg Asp Cys Ala Ala Pro
            210                 215                 220

Cys Glu Pro Ala Arg Pro Asp Gly Ser Met Phe Ser Gln Glu Glu
225                 230                 235                 240

Thr Arg Phe Ala Arg Leu Trp Ile Leu Thr Trp Ser Val Leu Cys Cys
            245                 250                 255

Ala Ser Thr Phe Phe Thr Val Thr Thr Tyr Leu Val Asp Met Gln Arg
            260                 265                 270

Phe Arg Tyr Pro Glu Arg Pro Ile Ile Phe Leu Ser Gly Cys Tyr Thr
            275                 280                 285

Met Val Ser Val Ala Tyr Ile Ala Gly Phe Val Leu Gln Glu Arg Val
            290                 295                 300

Val Cys Asn Glu Arg Phe Ser Glu Asp Gly Tyr Arg Thr Val Val Gln
305                 310                 315                 320

Gly Thr Lys Lys Glu Gly Cys Thr Ile Leu Phe Met Met Leu Tyr Phe
            325                 330                 335

Phe Ser Met Ala Ser Ser Ile Trp Trp Val Ile Leu Ser Leu Thr Trp
            340                 345                 350

Phe Leu Ala Ala Gly Met Lys Trp Gly His Glu Ala Ile Glu Ala Asn
            355                 360                 365

Ser Gln Tyr Phe His Leu Ala Ala Trp Ala Val Pro Ala Val Lys Thr
            370                 375                 380

Ile Thr Ile Leu Ala Met Gly Gln Ile Asp Gly Asp Leu Leu Ser Gly
385                 390                 395                 400

Val Cys Phe Val Gly Leu Asn Ser Leu Asp Pro Leu Arg Gly Phe Val
            405                 410                 415

Leu Ala Pro Leu Phe Val Tyr Leu Phe Ile Gly Thr Ser Phe Leu Leu
            420                 425                 430

Ala Gly Phe Val Ser Leu Phe Arg Ile Arg Thr Ile Met Lys His Asp
            435                 440                 445

Gly Thr Lys Thr Glu Lys Leu Glu Arg Leu Met Val Arg Ile Gly Val
            450                 455                 460

Phe Ser Val Leu Tyr Thr Val Pro Ala Thr Ile Val Ile Ala Cys Tyr
465                 470                 475                 480

Phe Tyr Glu Gln Ala Phe Arg Glu His Trp Glu Arg Ser Trp Val Ser
            485                 490                 495

Gln His Cys Lys Ser Leu Ala Ile Pro Cys Pro Ala His Tyr Thr Pro
            500                 505                 510

Arg Met Ser Pro Asp Phe Thr Val Tyr Met Ile Lys Tyr Leu Met Thr
            515                 520                 525

Leu Ile Val Gly Ile Thr Ser Gly Phe Trp Ile Trp Ser Gly Lys Thr
            530                 535                 540

Leu His Ser Trp Arg Lys Phe Tyr Thr Arg Leu Thr Asn Ser Arg His
545                 550                 555                 560
```

```
Gly Glu Thr Thr Val
            565

<210> SEQ ID NO 31
<211> LENGTH: 250
<212> TYPE: PRT
<213> ORGANISM: Artificial Sequence
<220> FEATURE:
<223> OTHER INFORMATION: extracellular domain (ECD) of FZD2

<400> SEQUENCE: 31

Met Arg Pro Arg Ser Ala Leu Pro Arg Leu Leu Leu Pro Leu Leu Leu
1               5                   10                  15

Leu Pro Ala Ala Gly Pro Ala Gln Phe His Gly Glu Lys Gly Ile Ser
            20                  25                  30

Ile Pro Asp His Gly Phe Cys Gln Pro Ile Ser Ile Pro Leu Cys Thr
        35                  40                  45

Asp Ile Ala Tyr Asn Gln Thr Ile Met Pro Asn Leu Leu Gly His Thr
    50                  55                  60

Asn Gln Glu Asp Ala Gly Leu Glu Val His Gln Phe Tyr Pro Leu Val
65                  70                  75                  80

Lys Val Gln Cys Ser Pro Glu Leu Arg Phe Phe Leu Cys Ser Met Tyr
                85                  90                  95

Ala Pro Val Cys Thr Val Leu Glu Gln Ala Ile Pro Pro Cys Arg Ser
            100                 105                 110

Ile Cys Glu Arg Ala Arg Gln Gly Cys Glu Ala Leu Met Asn Lys Phe
        115                 120                 125

Gly Phe Gln Trp Pro Glu Arg Leu Arg Cys Glu His Phe Pro Arg His
    130                 135                 140

Gly Ala Glu Gln Ile Cys Val Gly Gln Asn His Ser Glu Asp Gly Ala
145                 150                 155                 160

Pro Ala Leu Leu Thr Thr Ala Pro Pro Gly Leu Gln Pro Gly Ala
                165                 170                 175

Gly Gly Thr Pro Gly Gly Pro Gly Gly Gly Ala Pro Pro Arg Tyr
            180                 185                 190

Ala Thr Leu Glu His Pro Phe His Cys Pro Arg Val Leu Lys Val Pro
        195                 200                 205

Ser Tyr Leu Ser Tyr Lys Phe Leu Gly Glu Arg Asp Cys Ala Ala Pro
    210                 215                 220

Cys Glu Pro Ala Arg Pro Asp Gly Ser Met Phe Phe Ser Gln Glu Glu
225                 230                 235                 240

Thr Arg Phe Ala Arg Leu Trp Ile Leu Thr
                245                 250

<210> SEQ ID NO 32
<211> LENGTH: 136
<212> TYPE: PRT
<213> ORGANISM: Artificial Sequence
<220> FEATURE:
<223> OTHER INFORMATION: Human FZD2 Fri domain

<400> SEQUENCE: 32

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
```

```
        35                  40                  45
Glu Val His Gln Phe Tyr Pro Leu Val Lys Val Gln Cys Ser Pro Glu
        50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly
        130                 135

<210> SEQ ID NO 33
<211> LENGTH: 1698
<212> TYPE: DNA
<213> ORGANISM: Artificial Sequence
<220> FEATURE:
<223> OTHER INFORMATION: Human FZD2

<400> SEQUENCE: 33
atgcggcccc gcagcgccct gccccgcctg ctgctgccgc tgctgctgct gcccgccgcc      60
gggccggccc agttccacgg ggagaagggc atctccatcc ggaccacgg cttctgccag     120 cccatctcca tcccgctgtg cacggacatc gcctacaacc agaccatcat gcccaacctt     180
ctgggccaca cgaaccagga ggacgcaggc ctagaggtgc accagttcta tccgctggtg     240
aaggtgcagt gctcgcccga actgcgcttc ttcctgtgct ccatgtacgc cccgtgtgc      300 accgtgctgg aacaggccat cccgccgtgc cgctctatct gtgagcgcgc cgccagggc      360 tgcgaagccc tcatgaacaa gttcggtttt cagtggcccg agcgcctgcg ctgcgagcac     420
ttcccgcgcc acggcgccga gcagatctgc gtcggccaga accactccga ggacggagct     480
cccgcgctac tcaccaccgc gccgccgccg ggactgcagc cgggtgccgg gggcacccc     540 ggtggcccgg gcgcggcgg cgctccccg cgctacgcca cgctggagca cccccttcca      600
tgcccgcgcg tcctcaaggt gccatcctat ctcagctaca gtttctgggg cgagcgtgat     660
tgtgctgcgc cctgcgaacc tgcgcggccc gatggttcca tgttcttctc acaggaggag     720
acgcgtttcg cgcgcctctg gatcctcacc tggtcggtgc tgtgctgcgc ttccaccttc     780
ttcactgtca ccacgtactt ggtagacatg cagcgcttcc gctacccaga gcggcctatc     840
atttttctgt cgggctgcta caccatggtg tcggtggcct acatcgcggg cttcgtgctc     900
caggagcgcg tggtgtgcaa cgagcgcttc tccgaggacg ttaccgcac ggtggtgcag      960 ggcaccaaga aggagggctg caccatcctc ttcatgatgc tctacttctt cagcatggcc    1020
agctccatct ggtgggtcat cctgtcgctc acctggttcc tggcagccgg catgaagtgg    1080
ggccacgagg ccatcgaggc caactctcag tacttccacc tggccgcctg gccgtgccg     1140 gccgtcaaga ccatcaccat cctggccatg ggccagatcg acggcgacct gctgagcggc    1200
gtgtgcttcg taggcctcaa cagcctggac ccgctgcggg gcttcgtgct agcgccgctc    1260
ttcgtgtacc tgttcatcgg cacgtccttc ctcctggccg gcttcgtgtc gctcttccgc    1320
atccgcacca tcatgaagca cgacggcacc aagaccgaaa agctggagcg gctcatggtg    1380
cgcatcggcg tcttctccgt gctctacaca gtgcccgcca ccatcgtcat cgcttgctac    1440
ttctacgagc aggccttccg cgagcactgg gagcgctcgt gggtgagcca gcactgcaag    1500
```

-continued

```
agcctggcca tcccgtgccc ggcgcactac acgccgcgca tgtcgcccga cttcacggtc   1560
tacatgatca aatacctcat gacgctcatc gtgggcatca cgtcgggctt ctggatctgg   1620
tcgggcaaga cgctgcactc gtggaggaag ttctacactc gcctcaccaa cagccgacac   1680
ggtgagacca ccgtgtga                                                 1698
```

<210> SEQ ID NO 34
<211> LENGTH: 666
<212> TYPE: PRT
<213> ORGANISM: Artificial Sequence
<220> FEATURE:
<223> OTHER INFORMATION: Human FZD3 full length

<400> SEQUENCE: 34

```
Met Ala Met Thr Trp Ile Val Phe Ser Leu Trp Pro Leu Thr Val Phe
1               5                   10                  15

Met Gly His Ile Gly Gly His Ser Leu Phe Ser Cys Glu Pro Ile Thr
            20                  25                  30

Leu Arg Met Cys Gln Asp Leu Pro Tyr Asn Thr Thr Phe Met Pro Asn
        35                  40                  45

Leu Leu Asn His Tyr Asp Gln Gln Thr Ala Ala Leu Ala Met Glu Pro
    50                  55                  60

Phe His Pro Met Val Asn Leu Asp Cys Ser Arg Asp Phe Arg Pro Phe
65                  70                  75                  80

Leu Cys Ala Leu Tyr Ala Pro Ile Cys Met Glu Tyr Gly Arg Val Thr
                85                  90                  95

Leu Pro Cys Arg Arg Leu Cys Gln Arg Ala Tyr Ser Glu Cys Ser Lys
            100                 105                 110

Leu Met Glu Met Phe Gly Val Pro Trp Pro Glu Asp Met Glu Cys Ser
        115                 120                 125

Arg Phe Pro Asp Cys Asp Glu Pro Tyr Pro Arg Leu Val Asp Leu Asn
    130                 135                 140

Leu Ala Gly Glu Pro Thr Glu Gly Ala Pro Val Ala Val Gln Arg Asp
145                 150                 155                 160

Tyr Gly Phe Trp Cys Pro Arg Glu Leu Lys Ile Asp Pro Asp Leu Gly
                165                 170                 175

Tyr Ser Phe Leu His Val Arg Asp Cys Ser Pro Pro Cys Pro Asn Met
            180                 185                 190

Tyr Phe Arg Arg Glu Glu Leu Ser Phe Ala Arg Tyr Phe Ile Gly Leu
        195                 200                 205

Ile Ser Ile Ile Cys Leu Ser Ala Thr Leu Phe Thr Phe Leu Thr Phe
    210                 215                 220

Leu Ile Asp Val Thr Arg Phe Arg Tyr Pro Glu Arg Pro Ile Ile Phe
225                 230                 235                 240

Tyr Ala Val Cys Tyr Met Met Val Ser Leu Ile Phe Phe Ile Gly Phe
                245                 250                 255

Leu Leu Glu Asp Arg Val Ala Cys Asn Ala Ser Ile Pro Ala Gln Tyr
            260                 265                 270

Lys Ala Ser Thr Val Thr Gln Gly Ser His Asn Lys Ala Cys Thr Met
        275                 280                 285

Leu Phe Met Ile Leu Tyr Phe Phe Thr Met Ala Gly Ser Val Trp Trp
    290                 295                 300

Val Ile Leu Thr Ile Thr Trp Phe Leu Ala Ala Val Pro Lys Trp Gly
305                 310                 315                 320
```

```
Ser Glu Ala Ile Glu Lys Lys Ala Leu Leu Phe His Ala Ser Ala Trp
            325                 330                 335

Gly Ile Pro Gly Thr Leu Thr Ile Ile Leu Leu Ala Met Asn Lys Ile
            340                 345                 350

Glu Gly Asp Asn Ile Ser Gly Val Cys Phe Val Gly Leu Tyr Asp Val
            355                 360                 365

Asp Ala Leu Arg Tyr Phe Val Leu Ala Pro Leu Cys Leu Tyr Val Val
            370                 375                 380

Val Gly Val Ser Leu Leu Leu Ala Gly Ile Ile Ser Leu Asn Arg Val
385                 390                 395                 400

Arg Ile Glu Ile Pro Leu Glu Lys Glu Asn Gln Asp Lys Leu Val Lys
            405                 410                 415

Phe Met Ile Arg Ile Gly Val Phe Ser Ile Leu Tyr Leu Val Pro Leu
            420                 425                 430

Leu Val Val Ile Gly Cys Tyr Phe Tyr Glu Gln Ala Tyr Arg Gly Ile
            435                 440                 445

Trp Glu Thr Thr Trp Ile Gln Glu Arg Cys Arg Glu Tyr His Ile Pro
            450                 455                 460

Cys Pro Tyr Gln Val Thr Gln Met Ser Arg Pro Asp Leu Ile Leu Phe
465                 470                 475                 480

Leu Met Lys Tyr Leu Met Ala Leu Ile Val Gly Ile Pro Ser Val Phe
            485                 490                 495

Trp Val Gly Ser Lys Lys Thr Cys Phe Glu Trp Ala Ser Phe Phe His
            500                 505                 510

Gly Arg Arg Lys Lys Glu Ile Val Asn Glu Ser Arg Gln Val Leu Gln
            515                 520                 525

Glu Pro Asp Phe Ala Gln Ser Leu Leu Arg Asp Pro Asn Thr Pro Ile
            530                 535                 540

Ile Arg Lys Ser Arg Gly Thr Ser Thr Gln Gly Thr Ser Thr His Ala
545                 550                 555                 560

Ser Ser Thr Gln Leu Ala Met Val Asp Asp Gln Arg Ser Lys Ala Gly
            565                 570                 575

Ser Ile His Ser Lys Val Ser Ser Tyr His Gly Ser Leu His Arg Ser
            580                 585                 590

Arg Asp Gly Arg Tyr Thr Pro Cys Ser Tyr Arg Gly Met Glu Glu Arg
            595                 600                 605

Leu Pro His Gly Ser Met Ser Arg Leu Thr Asp His Ser Arg His Ser
            610                 615                 620

Ser Ser His Arg Leu Asn Glu Gln Ser Arg His Ser Ser Ile Arg Asp
625                 630                 635                 640

Leu Ser Asn Asn Pro Met Thr His Ile Thr His Gly Thr Ser Met Asn
            645                 650                 655

Arg Val Ile Glu Glu Asp Gly Thr Ser Ala
            660                 665

<210> SEQ ID NO 35
<211> LENGTH: 204
<212> TYPE: PRT
<213> ORGANISM: Artificial Sequence
<220> FEATURE:
<223> OTHER INFORMATION: extracellular domain (ECD) of FZD3

<400> SEQUENCE: 35

Met Ala Met Thr Trp Ile Val Phe Ser Leu Trp Pro Leu Thr Val Phe
1               5                   10                  15
```

```
Met Gly His Ile Gly Gly His Ser Leu Phe Ser Cys Glu Pro Ile Thr
                20                  25                  30

Leu Arg Met Cys Gln Asp Leu Pro Tyr Asn Thr Thr Phe Met Pro Asn
            35                  40                  45

Leu Leu Asn His Tyr Asp Gln Gln Thr Ala Ala Leu Ala Met Glu Pro
        50                  55                  60

Phe His Pro Met Val Asn Leu Asp Cys Ser Arg Asp Phe Arg Pro Phe
65                  70                  75                  80

Leu Cys Ala Leu Tyr Ala Pro Ile Cys Met Glu Tyr Gly Arg Val Thr
                85                  90                  95

Leu Pro Cys Arg Arg Leu Cys Gln Arg Ala Tyr Ser Glu Cys Ser Lys
            100                 105                 110

Leu Met Glu Met Phe Gly Val Pro Trp Pro Glu Asp Met Glu Cys Ser
        115                 120                 125

Arg Phe Pro Asp Cys Asp Glu Pro Tyr Pro Arg Leu Val Asp Leu Asn
    130                 135                 140

Leu Ala Gly Glu Pro Thr Glu Gly Ala Pro Val Ala Val Gln Arg Asp
145                 150                 155                 160

Tyr Gly Phe Trp Cys Pro Arg Glu Leu Lys Ile Asp Pro Asp Leu Gly
                165                 170                 175

Tyr Ser Phe Leu His Val Arg Asp Cys Ser Pro Pro Cys Pro Asn Met
            180                 185                 190

Tyr Phe Arg Arg Glu Glu Leu Ser Phe Ala Arg Tyr
        195                 200

<210> SEQ ID NO 36
<211> LENGTH: 126
<212> TYPE: PRT
<213> ORGANISM: Artificial Sequence
<220> FEATURE:
<223> OTHER INFORMATION: Human FZD3 Fri domain

<400> SEQUENCE: 36

Gly His Ile Gly Gly His Ser Leu Phe Ser Cys Glu Pro Ile Thr Leu
1               5                   10                  15

Arg Met Cys Gln Asp Leu Pro Tyr Asn Thr Thr Phe Met Pro Asn Leu
            20                  25                  30

Leu Asn His Tyr Asp Gln Gln Thr Ala Ala Leu Ala Met Glu Pro Phe
        35                  40                  45

His Pro Met Val Asn Leu Asp Cys Ser Arg Asp Phe Arg Pro Phe Leu
    50                  55                  60

Cys Ala Leu Tyr Ala Pro Ile Cys Met Glu Tyr Gly Arg Val Thr Leu
65                  70                  75                  80

Pro Cys Arg Arg Leu Cys Gln Arg Ala Tyr Ser Glu Cys Ser Lys Leu
                85                  90                  95

Met Glu Met Phe Gly Val Pro Trp Pro Glu Asp Met Glu Cys Ser Arg
            100                 105                 110

Phe Pro Asp Cys Asp Glu Pro Tyr Pro Arg Leu Val Asp Leu
        115                 120                 125

<210> SEQ ID NO 37
<211> LENGTH: 2001
<212> TYPE: DNA
<213> ORGANISM: Artificial Sequence
<220> FEATURE:
<223> OTHER INFORMATION: Human FZD3 full length

<400> SEQUENCE: 37
```

```
atggctatga cttggattgt cttctctctt tggcccttga ctgtgttcat ggggcatata    60
ggtgggcaca gtttgttttc ttgtgaacct attaccttga ggatgtgcca agatttgcct   120
tataatacta ccttcatgcc taatcttctg aatcattatg accaacagac agcagctttg   180
gcaatggagc cattccaccc tatggtgaat ctggattgtt ctcgggattt ccggcctttt   240
ctttgtgcac tctacgctcc tatttgtatg gaatatggac gtgtcacact tccctgtcgt   300
aggctgtgtc agcgggctta cagtgagtgt tcgaagctca tggagatgtt tggtgttcct   360
tggcctgaag atatggaatg cagtaggttc ccagattgtg atgagccata tcctcgactt   420
gtggatctga atttagctgg agaaccaact gaaggagccc cagtggcagt gcagagagac   480
tatggttttt ggtgtccccg agagttaaaa attgatcctg atctgggtta ttcttttctg   540
catgtgcgtg attgttcacc tccttgtcca aatatgtact tcagaagaga agaactgtca   600
tttgctcgct atttcatagg attgatttca atcatttgcc tctcggccac attgtttact   660
tttttaactt ttttgattga tgtcacaaga ttccgttatc ctgaaaggcc tattatattt   720
tatgcagtct gctacatgat ggtatcctta attttcttca ttggattttt gcttgaagat   780
cgagtagcct gcaatgcatc catccctgca caatataagg cttccacagt gacacaagga   840
tctcataata aagcctgtac catgcttttt atgatactct attttttttac tatggctggc   900
agtgtatggt gggtaattct taccatcaca tggttttag cagctgtgcc aaagtggggt   960
agtgaagcta ttgagaagaa agcattgctg tttcacgcca gtgcatgggg catccccgga  1020
actctaacca tcatccttttt agcgatgaat aaaattgaag gtgacaatat tagtggcgtg  1080
tgttttgttg gcctctacga tgttgatgca ttgagatatt ttgttcttgc tcccctctgc  1140
ctgtatgtgg tagttggggt ttctctcctc ttagctggca ttatatccct aaacagagtt  1200
cgaattgaga ttccattaga aaaggagaac caagataaat tagtgaagtt tatgatccgg  1260
atcggtgttt tcagcattct ttatctcgta ccactcttgg ttgtaattgg atgctacttt  1320
tatgagcaag cttaccgggg catctgggaa acaacgtgga tacaagaacg ctgcagagaa  1380
tatcacattc catgtccata tcaggttact caaatgagtc gtccagactt gattctcttt  1440
ctgatgaaat acctgatggc tctcatagtt ggcattccct ctgtattttg ggttggaagc  1500
aaaaagacat gctttgaatg ggccagtttt tttcatggtc gtaggaaaaa agagatagtg  1560
aatgagagcc gacaggtact ccaggaacct gattttgctc agtctctcct gagggatcca  1620
aatactccta tcataagaaa gtcaagggga acttccactc aaggaacatc cacccatgct  1680
tcttcaactc agctggctat ggtggatgat caaagaagca agcaggaag catccacagc  1740
aaagtgagca gctaccacgg cagcctccac agatcacgtg atggcaggta cacgccctgc  1800
agttacagag gaatggagga gagactacct catggcagca tgtcacgact aacagatcac  1860
tccaggcata gtagttctca tcggctcaat gaacagtcac gacatagcag catcagagat  1920
ctcagtaata atcccatgac tcatatcaca catggcacca gcatgaatcg ggttattgaa  1980
gaagatggaa ccagtgctta a                                            2001
```

<210> SEQ ID NO 38
<211> LENGTH: 540
<212> TYPE: PRT
<213> ORGANISM: Artificial Sequence
<220> FEATURE:
<223> OTHER INFORMATION: Human FZD4 full length
<220> FEATURE:
<221> NAME/KEY: MISC_FEATURE
<222> LOCATION: (1)..(224)

<223> OTHER INFORMATION: the extracellular domain (ECD) of FZD4

<400> SEQUENCE: 38

```
Met Leu Ala Met Ala Trp Arg Gly Ala Gly Pro Ser Val Pro Gly Ala
 1               5                  10                  15

Pro Gly Gly Val Gly Leu Ser Leu Gly Leu Leu Leu Gln Leu Leu Leu
            20                  25                  30

Leu Leu Gly Pro Ala Arg Gly Phe Gly Asp Glu Glu Glu Arg Arg Cys
        35                  40                  45

Asp Pro Ile Arg Ile Ser Met Cys Gln Asn Leu Gly Tyr Asn Val Thr
    50                  55                  60

Lys Met Pro Asn Leu Val Gly His Glu Leu Gln Thr Asp Ala Glu Leu
 65                  70                  75                  80

Gln Leu Thr Thr Phe Thr Pro Leu Ile Gln Tyr Gly Cys Ser Ser Gln
                85                  90                  95

Leu Gln Phe Phe Leu Cys Ser Val Tyr Val Pro Met Cys Thr Glu Lys
            100                 105                 110

Ile Asn Ile Pro Ile Gly Pro Cys Gly Gly Met Cys Leu Ser Val Lys
        115                 120                 125

Arg Arg Cys Glu Pro Val Leu Lys Glu Phe Gly Phe Ala Trp Pro Glu
130                 135                 140

Ser Leu Asn Cys Ser Lys Phe Pro Pro Gln Asn Asp His Asn His Met
145                 150                 155                 160

Cys Met Glu Gly Pro Gly Asp Glu Glu Val Pro Leu Pro His Lys Thr
                165                 170                 175

Pro Ile Gln Pro Gly Glu Glu Cys His Ser Val Gly Thr Asn Ser Asp
            180                 185                 190

Gln Tyr Ile Trp Val Lys Arg Ser Leu Asn Cys Val Leu Lys Cys Gly
        195                 200                 205

Tyr Asp Ala Gly Leu Tyr Ser Arg Ser Ala Lys Glu Phe Thr Asp Ile
    210                 215                 220

Trp Met Ala Val Trp Ala Ser Leu Cys Phe Ile Ser Thr Ala Phe Thr
225                 230                 235                 240

Val Leu Thr Phe Leu Ile Asp Ser Ser Arg Phe Ser Tyr Pro Glu Arg
                245                 250                 255

Pro Ile Ile Phe Leu Ser Met Cys Tyr Asn Ile Tyr Ser Ile Ala Tyr
            260                 265                 270

Ile Val Arg Leu Thr Val Gly Arg Glu Arg Ile Ser Cys Asp Phe Glu
        275                 280                 285

Glu Ala Ala Glu Pro Val Leu Ile Gln Glu Gly Leu Lys Asn Thr Gly
    290                 295                 300

Cys Ala Ile Ile Phe Leu Leu Met Tyr Phe Phe Gly Met Ala Ser Ser
305                 310                 315                 320

Ile Trp Trp Val Ile Leu Thr Leu Thr Trp Phe Leu Ala Ala Gly Leu
                325                 330                 335

Lys Trp Gly His Glu Ala Ile Glu Met His Ser Ser Tyr Phe His Ile
            340                 345                 350

Ala Ala Trp Ala Ile Pro Ala Val Lys Thr Ile Val Ile Leu Ile Met
        355                 360                 365

Arg Leu Val Asp Ala Asp Glu Leu Thr Gly Leu Cys Tyr Val Gly Asn
    370                 375                 380

Gln Asn Leu Asp Ala Leu Thr Gly Phe Val Val Ala Pro Leu Phe Thr
385                 390                 395                 400
```

Tyr Leu Val Ile Gly Thr Leu Phe Ile Ala Ala Gly Leu Val Ala Leu
                405                 410                 415

Phe Lys Ile Arg Ser Asn Leu Gln Lys Asp Gly Thr Lys Thr Asp Lys
            420                 425                 430

Leu Glu Arg Leu Met Val Lys Ile Gly Val Phe Ser Val Leu Tyr Thr
        435                 440                 445

Val Pro Ala Thr Cys Val Ile Ala Cys Tyr Phe Tyr Glu Ile Ser Asn
    450                 455                 460

Trp Ala Leu Phe Arg Tyr Ser Ala Asp Asp Ser Asn Met Ala Val Glu
465                 470                 475                 480

Met Leu Lys Ile Phe Met Ser Leu Leu Val Gly Ile Thr Ser Gly Met
                485                 490                 495

Trp Ile Trp Ser Ala Lys Thr Leu His Thr Trp Gln Lys Cys Ser Asn
            500                 505                 510

Arg Leu Val Asn Ser Gly Lys Val Lys Arg Glu Lys Arg Gly Asn Gly
        515                 520                 525

Trp Val Lys Pro Gly Lys Gly Ser Glu Thr Val Val
    530                 535                 540

<210> SEQ ID NO 39
<211> LENGTH: 224
<212> TYPE: PRT
<213> ORGANISM: Artificial Sequence
<220> FEATURE:
<223> OTHER INFORMATION: extracellular domain (ECD) of FZD4

<400> SEQUENCE: 39

Met Leu Ala Met Ala Trp Arg Gly Ala Gly Pro Ser Val Pro Gly Ala
1               5                   10                  15

Pro Gly Gly Val Gly Leu Ser Leu Gly Leu Leu Leu Gln Leu Leu Leu
                20                  25                  30

Leu Leu Gly Pro Ala Arg Gly Phe Gly Asp Glu Glu Glu Arg Arg Cys
            35                  40                  45

Asp Pro Ile Arg Ile Ser Met Cys Gln Asn Leu Gly Tyr Asn Val Thr
        50                  55                  60

Lys Met Pro Asn Leu Val Gly His Glu Leu Gln Thr Asp Ala Glu Leu
65                  70                  75                  80

Gln Leu Thr Thr Phe Thr Pro Leu Ile Gln Tyr Gly Cys Ser Ser Gln
                85                  90                  95

Leu Gln Phe Phe Leu Cys Ser Val Tyr Val Pro Met Cys Thr Glu Lys
            100                 105                 110

Ile Asn Ile Pro Ile Gly Pro Cys Gly Gly Met Cys Leu Ser Val Lys
        115                 120                 125

Arg Arg Cys Glu Pro Val Leu Lys Glu Phe Gly Phe Ala Trp Pro Glu
130                 135                 140

Ser Leu Asn Cys Ser Lys Phe Pro Pro Gln Asn Asp His Asn His Met
145                 150                 155                 160

Cys Met Glu Gly Pro Gly Asp Glu Glu Val Pro Leu Pro His Lys Thr
                165                 170                 175

Pro Ile Gln Pro Gly Glu Glu Cys His Ser Val Gly Thr Asn Ser Asp
            180                 185                 190

Gln Tyr Ile Trp Val Lys Arg Ser Leu Asn Cys Val Leu Lys Cys Gly
        195                 200                 205

Tyr Asp Ala Gly Leu Tyr Ser Arg Ser Ala Lys Glu Phe Thr Asp Ile
210                 215                 220

```
<210> SEQ ID NO 40
<211> LENGTH: 131
<212> TYPE: PRT
<213> ORGANISM: Artificial Sequence
<220> FEATURE:
<223> OTHER INFORMATION: Human FZD4 Fri domain

<400> SEQUENCE: 40

Phe Gly Asp Glu Glu Arg Arg Cys Asp Pro Ile Arg Ile Ser Met
1               5                   10                  15

Cys Gln Asn Leu Gly Tyr Asn Val Thr Lys Met Pro Asn Leu Val Gly
            20                  25                  30

His Glu Leu Gln Thr Asp Ala Glu Leu Gln Leu Thr Thr Phe Thr Pro
        35                  40                  45

Leu Ile Gln Tyr Gly Cys Ser Ser Gln Leu Gln Phe Phe Leu Cys Ser
    50                  55                  60

Val Tyr Val Pro Met Cys Thr Glu Lys Ile Asn Ile Pro Ile Gly Pro
65                  70                  75                  80

Cys Gly Gly Met Cys Leu Ser Val Lys Arg Arg Cys Glu Pro Val Leu
                85                  90                  95

Lys Glu Phe Gly Phe Ala Trp Pro Glu Ser Leu Asn Cys Ser Lys Phe
            100                 105                 110

Pro Pro Gln Asn Asp His Asn His Met Cys Met Glu Gly Pro Gly Asp
        115                 120                 125

Glu Glu Val
    130

<210> SEQ ID NO 41
<211> LENGTH: 1623
<212> TYPE: DNA
<213> ORGANISM: Artificial Sequence
<220> FEATURE:
<223> OTHER INFORMATION: Human FZD4 full length

<400> SEQUENCE: 41
atgctggcca tggcctggcg gggcgcaggg ccgagcgtcc cggggggcgcc cggggggcgtc      60 ggtctcagtc tggggttgct cctgcagttg ctgctgctcc tggggccggc gcgggggcttc     120 ggggacgagg aagagcggcg ctgcgacccc atccgcatct ccatgtgcca gaacctcggc     180
tacaacgtga ccaagatgcc aaacctggtt gggcacgagc tgcagacgga cgccgagctg     240
cagctgacaa ctttcacacc gctcatccag tacggctgct ccagccagct gcagttcttc     300
ctttgttctg tttatgtgcc aatgtgcaca gagaagatca acatccccat tggcccatgc     360
ggcggcatgt gtctttcagt caagagacgc tgtgaacccg tcctgaagga atttggattt     420
gcctggccag agagtctgaa ctgcagcaaa ttcccaccac agaacgacca caaccacatg     480
tgcatggaag ggccaggtga tgaagaggtg cccttacctc acaaaacccc catccagcct     540
ggggaagagt gtcactctgt gggaaccaat tctgatcagt acatctgggt gaaaaggagc     600
ctgaactgtg tgctcaagtg tggctatgat gctggcttat acagccgctc agccaaggag     660
ttcactgata tctggatggc tgtgtgggcc agcctgtgtt tcatctccac tgccttcaca     720
gtactgacct cctgatcga ttcttctagg ttttcctacc ctgagcgccc catcatattt     780
ctcagtatgt gctataatat ttatagcatt gcttatattg tcaggctgac tgtaggccgg     840
gaaaggatat cctgtgattt tgaagaggca gcagaacctg ttctcatcca agaaggactt     900
aagaacacag gatgtgcaat aattttcttg ctgatgtact tttttggaat ggccagctcc     960
```

```
atttggtggg ttattctgac actcacttgg tttttggcag caggactcaa atggggtcat    1020
gaagccattg aaatgcacag ctcttatttc cacattgcag cctgggccat ccccgcagtg    1080
aaaaccattg tcatcttgat tatgagactg gtggatgcag atgaactgac tggcttgtgc    1140
tatgttggaa accaaaatct cgatgccctc accgggttcg tggtggctcc cctctttact    1200
tatttggtca ttggaacttt gttcattgct gcaggtttgg tggccttgtt caaaattcgg    1260
tcaaatcttc aaaaggatgg gacaaagaca gacaagttag aaagactgat ggtcaagatt    1320
ggggtgttct cagtactgta cacagttcct gcaacgtgtg tgattgcctg ttatttttat    1380
gaaatctcca actgggcact ttttcggtat tctgcagatg attccaacat ggctgttgaa    1440
atgttgaaaa tttttatgtc tttgttggtg ggcatcactt caggcatgtg gatttggtct    1500
gccaaaactc ttcacacgtg gcagaagtgt tccaacagat tggtgaattc tggaaaggta    1560
aagagagaga agagaggaaa tggttgggtg aagcctggaa aaggcagtga gactgtggta    1620
taa                                                                 1623
```

<210> SEQ ID NO 42
<211> LENGTH: 585
<212> TYPE: PRT
<213> ORGANISM: Artificial Sequence
<220> FEATURE:
<223> OTHER INFORMATION: Human FZD5 full length
<220> FEATURE:
<221> NAME/KEY: MISC_FEATURE
<222> LOCATION: (1)..(233)
<223> OTHER INFORMATION: extracellular domain (ECD) of FZD5

<400> SEQUENCE: 42

```
Met Ala Arg Pro Asp Pro Ser Ala Pro Pro Ser Leu Leu Leu Leu Leu
1               5                   10                  15

Leu Ala Gln Leu Val Gly Arg Ala Ala Ala Ala Ser Lys Ala Pro Val
            20                  25                  30

Cys Gln Glu Ile Thr Val Pro Met Cys Arg Gly Ile Gly Tyr Asn Leu
        35                  40                  45

Thr His Met Pro Asn Gln Phe Asn His Asp Thr Gln Asp Glu Ala Gly
    50                  55                  60

Leu Glu Val His Gln Phe Trp Pro Leu Val Glu Ile Gln Cys Ser Pro
65                  70                  75                  80

Asp Leu Arg Phe Phe Leu Cys Ser Met Tyr Thr Pro Ile Cys Leu Pro
                85                  90                  95

Asp Tyr His Lys Pro Leu Pro Pro Cys Arg Ser Val Cys Glu Arg Ala
            100                 105                 110

Lys Ala Gly Cys Ser Pro Leu Met Arg Gln Tyr Gly Phe Ala Trp Pro
        115                 120                 125

Glu Arg Met Ser Cys Asp Arg Leu Pro Val Leu Gly Arg Asp Ala Glu
    130                 135                 140

Val Leu Cys Met Asp Tyr Asn Arg Ser Glu Ala Thr Thr Ala Pro Pro
145                 150                 155                 160

Arg Pro Phe Pro Ala Lys Pro Thr Leu Pro Gly Pro Pro Gly Ala Pro
                165                 170                 175

Ala Ser Gly Gly Glu Cys Pro Ala Gly Gly Pro Phe Val Cys Lys Cys
            180                 185                 190

Arg Glu Pro Phe Val Pro Ile Leu Lys Glu Ser His Pro Leu Tyr Asn
        195                 200                 205

Lys Val Arg Thr Gly Gln Val Pro Asn Cys Ala Val Pro Cys Tyr Gln
    210                 215                 220
```

```
Pro Ser Phe Ser Ala Asp Glu Arg Thr Phe Ala Thr Phe Trp Ile Gly
225                 230                 235                 240

Leu Trp Ser Val Leu Cys Phe Ile Ser Thr Ser Thr Val Ala Thr
            245                 250                 255

Phe Leu Ile Asp Met Glu Arg Phe Arg Tyr Pro Glu Arg Pro Ile Ile
            260                 265                 270

Phe Leu Ser Ala Cys Tyr Leu Cys Val Ser Leu Gly Phe Leu Val Arg
            275                 280                 285

Leu Val Val Gly His Ala Ser Val Ala Cys Ser Arg Glu His Asn His
            290                 295                 300

Ile His Tyr Glu Thr Thr Gly Pro Ala Leu Cys Thr Ile Val Phe Leu
305                 310                 315                 320

Leu Val Tyr Phe Phe Gly Met Ala Ser Ser Ile Trp Trp Val Ile Leu
            325                 330                 335

Ser Leu Thr Trp Phe Leu Ala Ala Gly Met Lys Trp Gly Asn Glu Ala
            340                 345                 350

Ile Ala Gly Tyr Ala Gln Tyr Phe His Leu Ala Ala Trp Leu Ile Pro
            355                 360                 365

Ser Val Lys Ser Ile Thr Ala Leu Ala Leu Ser Ser Val Asp Gly Asp
            370                 375                 380

Pro Val Ala Gly Ile Cys Tyr Val Gly Asn Gln Asn Leu Asn Ser Leu
385                 390                 395                 400

Arg Gly Phe Val Leu Gly Pro Leu Val Leu Tyr Leu Val Gly Thr
            405                 410                 415

Leu Phe Leu Leu Ala Gly Phe Val Ser Leu Phe Arg Ile Arg Ser Val
            420                 425                 430

Ile Lys Gln Gly Gly Thr Lys Thr Asp Lys Leu Glu Lys Leu Met Ile
            435                 440                 445

Arg Ile Gly Ile Phe Thr Leu Leu Tyr Thr Val Pro Ala Ser Ile Val
450                 455                 460

Val Ala Cys Tyr Leu Tyr Glu Gln His Tyr Arg Glu Ser Trp Glu Ala
465                 470                 475                 480

Ala Leu Thr Cys Ala Cys Pro Gly His Asp Thr Gly Gln Pro Arg Ala
            485                 490                 495

Lys Pro Glu Tyr Trp Val Leu Met Leu Lys Tyr Phe Met Cys Leu Val
            500                 505                 510

Val Gly Ile Thr Ser Gly Val Trp Ile Trp Ser Gly Lys Thr Val Glu
            515                 520                 525

Ser Trp Arg Arg Phe Thr Ser Arg Cys Cys Cys Arg Pro Arg Arg Gly
            530                 535                 540

His Lys Ser Gly Gly Ala Met Ala Ala Gly Asp Tyr Pro Glu Ala Ser
545                 550                 555                 560

Ala Ala Leu Thr Gly Arg Thr Gly Pro Pro Gly Pro Ala Ala Thr Tyr
            565                 570                 575

His Lys Gln Val Ser Leu Ser His Val
            580                 585

<210> SEQ ID NO 43
<211> LENGTH: 233
<212> TYPE: PRT
<213> ORGANISM: Artificial Sequence
<220> FEATURE:
<223> OTHER INFORMATION: extracellular domain (ECD) of FZD5

<400> SEQUENCE: 43
```

```
Met Ala Arg Pro Asp Pro Ser Ala Pro Pro Ser Leu Leu Leu Leu
1               5                   10                  15

Leu Ala Gln Leu Val Gly Arg Ala Ala Ala Ser Lys Ala Pro Val
            20                  25                  30

Cys Gln Glu Ile Thr Val Pro Met Cys Arg Gly Ile Gly Tyr Asn Leu
            35                  40                  45

Thr His Met Pro Asn Gln Phe Asn His Asp Thr Gln Asp Glu Ala Gly
        50                  55                  60

Leu Glu Val His Gln Phe Trp Pro Leu Val Glu Ile Gln Cys Ser Pro
65                  70                  75                  80

Asp Leu Arg Phe Phe Leu Cys Ser Met Tyr Thr Pro Ile Cys Leu Pro
                85                  90                  95

Asp Tyr His Lys Pro Leu Pro Pro Cys Arg Ser Val Cys Glu Arg Ala
                100                 105                 110

Lys Ala Gly Cys Ser Pro Leu Met Arg Gln Tyr Gly Phe Ala Trp Pro
            115                 120                 125

Glu Arg Met Ser Cys Asp Arg Leu Pro Val Leu Gly Arg Asp Ala Glu
130                 135                 140

Val Leu Cys Met Asp Tyr Asn Arg Ser Glu Ala Thr Thr Ala Pro Pro
145                 150                 155                 160

Arg Pro Phe Pro Ala Lys Pro Thr Leu Pro Gly Pro Pro Gly Ala Pro
                165                 170                 175

Ala Ser Gly Gly Glu Cys Pro Ala Gly Gly Pro Phe Val Cys Lys Cys
            180                 185                 190

Arg Glu Pro Phe Val Pro Ile Leu Lys Glu Ser His Pro Leu Tyr Asn
            195                 200                 205

Lys Val Arg Thr Gly Gln Val Pro Asn Cys Ala Val Pro Cys Tyr Gln
210                 215                 220

Pro Ser Phe Ser Ala Asp Glu Arg Thr
225                 230

<210> SEQ ID NO 44
<211> LENGTH: 131
<212> TYPE: PRT
<213> ORGANISM: Artificial Sequence
<220> FEATURE:
<223> OTHER INFORMATION: Human FZD5 Fri domain

<400> SEQUENCE: 44

Ala Ser Lys Ala Pro Val Cys Gln Glu Ile Thr Val Pro Met Cys Arg
1               5                   10                  15

Gly Ile Gly Tyr Asn Leu Thr His Met Pro Asn Gln Phe Asn His Asp
            20                  25                  30

Thr Gln Asp Glu Ala Gly Leu Glu Val His Gln Phe Trp Pro Leu Val
        35                  40                  45

Glu Ile Gln Cys Ser Pro Asp Leu Arg Phe Phe Leu Cys Ser Met Tyr
    50                  55                  60

Thr Pro Ile Cys Leu Pro Asp Tyr His Lys Pro Leu Pro Pro Cys Arg
65                  70                  75                  80

Ser Val Cys Glu Arg Ala Lys Ala Gly Cys Ser Pro Leu Met Arg Gln
                85                  90                  95

Tyr Gly Phe Ala Trp Pro Glu Arg Met Ser Cys Asp Arg Leu Pro Val
                100                 105                 110

Leu Gly Arg Asp Ala Glu Val Leu Cys Met Asp Tyr Asn Arg Ser Glu
            115                 120                 125
```

Ala Thr Thr
    130

<210> SEQ ID NO 45
<211> LENGTH: 1758
<212> TYPE: DNA
<213> ORGANISM: Artificial Sequence
<220> FEATURE:
<223> OTHER INFORMATION: Human FZD5 full length

<400> SEQUENCE: 45

| | | | | | |
|---|---|---|---|---|---|
| atggctcggc | ctgacccatc | cgcgccgccc | tcgctgttgc | tgctgctcct | ggcgcagctg | 60 |
| gtgggccggg | cggccgccgc | gtccaaggcc | ccggtgtgcc | aggaaatcac | ggtgcccatg | 120 |
| tgccgcggca | tcggctacaa | cctgacgcac | atgcccaacc | agttcaacca | cgacacgcag | 180 |
| gacgaggcgg | gcctggaggt | gcaccagttc | tggccgctgg | tggagatcca | atgctcgccg | 240 |
| gacctgcgct | tcttcctatg | ctctatgtac | acgcccatct | gtctgcccga | ctaccacaag | 300 |
| ccgctgccgc | cctgccgctc | ggtgtgcgag | cgcgccaagg | ccggctgctc | gccgctgatg | 360 |
| cgccagtacg | gcttcgcctg | gcccgagcgc | atgagctgcg | accgcctccc | ggtgctgggc | 420 |
| cgcgacgccg | aggtcctctg | catggattac | aaccgcagcg | aggccaccac | ggcgcccccc | 480 |
| aggcctttcc | cagccaagcc | cacccttcca | ggcccgccag | gggcgccggc | ctcggggggc | 540 |
| gaatgccccg | ctgggggccc | gttcgtgtgc | aagtgtcgcg | agcccttcgt | gcccattctg | 600 |
| aaggagtcac | acccgctcta | caacaaggtg | cggacgggcc | aggtgcccaa | ctgcgcggta | 660 |
| ccctgctacc | agccgtcctt | cagtgccgac | gagcgcacgt | tcgccacctt | ctggataggc | 720 |
| ctgtggtcgg | tgctgtgctt | catctccacg | tccaccacag | tggccacctt | cctcatcgac | 780 |
| atggaacgct | tccgctatcc | tgagcgcccc | atcatcttcc | tgtcagcctg | ctacctgtgc | 840 |
| gtgtcgctgg | gcttcctggt | gcgtctggtc | gtgggccatg | ccagcgtggc | ctgcagccgc | 900 |
| gagcacaacc | acatccacta | cgagaccacg | ggccctgcac | tgtgcaccat | cgtcttcctc | 960 |
| ctggtctact | tcttcggcat | ggccagctcc | atctggtggg | tcatcctgtc | gctcacctgg | 1020 |
| ttcctggccg | ccggcatgaa | gtggggcaac | gaggccatcg | cgggctacgc | gcagtacttc | 1080 |
| cacctggctg | cgtggctcat | cccagcgtc | aagtccatca | cggcactggc | gctgagctcc | 1140 |
| gtggacgggg | acccagtggc | cggcatctgc | tacgtgggca | accagaacct | gaactcgctg | 1200 |
| cgcggcttcg | tgctgggccc | gctggtgctc | tacctgctgg | tgggcacgct | cttcctgctg | 1260 |
| gcgggcttcg | tgtcgctctt | ccgcatccgc | agcgtcatca | agcagggcgg | caccaagacg | 1320 |
| gacaagctgg | agaagctcat | gatccgcatc | ggcatcttca | cgctgctcta | cacggtcccc | 1380 |
| gccagcattg | tggtggcctg | ctacctgtac | gagcagcact | accgcgagag | ctgggaggcg | 1440 |
| gcgctcacct | gcgcctgccc | gggccacgac | accggccagc | cgcgcgccaa | gcccgagtac | 1500 |
| tgggtgctca | tgctcaagta | cttcatgtgc | ctggtggtgg | gcatcacgtc | gggcgtctgg | 1560 |
| atctggtcgg | gcaagacggt | ggagtcgtgg | cggcgtttca | ccagccgctg | ctgctgccgc | 1620 |
| ccgcggcgcg | gccacaagag | cggggcgcc | atggccgcag | gggactaccc | cgaggcgagc | 1680 |
| gccgcgctca | caggcaggac | cgggccgccg | ggccccgccg | ccacctacca | caagcaggtg | 1740 |
| tccctgtcgc | acgtgtag | | | | | 1758 |

<210> SEQ ID NO 46
<211> LENGTH: 706
<212> TYPE: PRT
<213> ORGANISM: Artificial Sequence
<220> FEATURE:
<223> OTHER INFORMATION: Human FZD6 full length
<220> FEATURE:
<221> NAME/KEY: MISC_FEATURE
<222> LOCATION: (1)..(207)
<223> OTHER INFORMATION: extracellular domain (ECD) of FZD6

<400> SEQUENCE: 46

```
Met Glu Met Phe Thr Phe Leu Leu Thr Cys Ile Phe Leu Pro Leu Leu
1               5                   10                  15

Arg Gly His Ser Leu Phe Thr Cys Glu Pro Ile Thr Val Pro Arg Cys
            20                  25                  30

Met Lys Met Ala Tyr Asn Met Thr Phe Phe Pro Asn Leu Met Gly His
        35                  40                  45

Tyr Asp Gln Ser Ile Ala Ala Val Glu Met Glu His Phe Leu Pro Leu
    50                  55                  60

Ala Asn Leu Glu Cys Ser Pro Asn Ile Glu Thr Phe Leu Cys Lys Ala
65                  70                  75                  80

Phe Val Pro Thr Cys Ile Glu Gln Ile His Val Val Pro Pro Cys Arg
                85                  90                  95

Lys Leu Cys Glu Lys Val Tyr Ser Asp Cys Lys Lys Leu Ile Asp Thr
            100                 105                 110

Phe Gly Ile Arg Trp Pro Glu Glu Leu Glu Cys Asp Arg Leu Gln Tyr
        115                 120                 125

Cys Asp Glu Thr Val Pro Val Thr Phe Asp Pro His Thr Glu Phe Leu
    130                 135                 140

Gly Pro Gln Lys Lys Thr Glu Gln Val Gln Arg Asp Ile Gly Phe Trp
145                 150                 155                 160

Cys Pro Arg His Leu Lys Thr Ser Gly Gly Gln Gly Tyr Lys Phe Leu
                165                 170                 175

Gly Ile Asp Gln Cys Ala Pro Pro Cys Pro Asn Met Tyr Phe Lys Ser
            180                 185                 190

Asp Glu Leu Glu Phe Ala Lys Ser Phe Ile Gly Thr Val Ser Ile Phe
        195                 200                 205

Cys Leu Cys Ala Thr Leu Phe Thr Phe Leu Thr Phe Leu Ile Asp Val
    210                 215                 220

Arg Arg Phe Arg Tyr Pro Glu Arg Pro Ile Ile Tyr Tyr Ser Val Cys
225                 230                 235                 240

Tyr Ser Ile Val Ser Leu Met Tyr Phe Ile Gly Phe Leu Leu Gly Asp
                245                 250                 255

Ser Thr Ala Cys Asn Lys Ala Asp Glu Lys Leu Glu Leu Gly Asp Thr
            260                 265                 270

Val Val Leu Gly Ser Gln Asn Lys Ala Cys Thr Val Leu Phe Met Leu
        275                 280                 285

Leu Tyr Phe Phe Thr Met Ala Gly Thr Val Trp Trp Val Ile Leu Thr
    290                 295                 300

Ile Thr Trp Phe Leu Ala Ala Gly Arg Lys Trp Ser Cys Glu Ala Ile
305                 310                 315                 320

Glu Gln Lys Ala Val Trp Phe His Ala Val Ala Trp Gly Thr Pro Gly
                325                 330                 335

Phe Leu Thr Val Met Leu Leu Ala Met Asn Lys Val Glu Gly Asp Asn
            340                 345                 350

Ile Ser Gly Val Cys Phe Val Gly Leu Tyr Asp Leu Asp Ala Ser Arg
        355                 360                 365

Tyr Phe Val Leu Leu Pro Leu Cys Leu Cys Val Phe Val Gly Leu Ser
```

```
              370                 375                 380
Leu Leu Leu Ala Gly Ile Ile Ser Leu Asn His Val Arg Gln Val Ile
385                 390                 395                 400

Gln His Asp Gly Arg Asn Gln Glu Lys Leu Lys Lys Phe Met Ile Arg
                405                 410                 415

Ile Gly Val Phe Ser Gly Leu Tyr Leu Val Pro Leu Val Thr Leu Leu
            420                 425                 430

Gly Cys Tyr Val Tyr Glu Gln Val Asn Arg Ile Thr Trp Glu Ile Thr
            435                 440                 445

Trp Val Ser Asp His Cys Arg Gln Tyr His Ile Pro Cys Pro Tyr Gln
            450                 455                 460

Ala Lys Ala Lys Ala Arg Pro Glu Leu Ala Leu Phe Met Ile Lys Tyr
465                 470                 475                 480

Leu Met Thr Leu Ile Val Gly Ile Ser Ala Val Phe Trp Val Gly Ser
                485                 490                 495

Lys Lys Thr Cys Thr Glu Trp Ala Gly Phe Phe Lys Arg Asn Arg Lys
            500                 505                 510

Arg Asp Pro Ile Ser Glu Ser Arg Arg Val Leu Gln Glu Ser Cys Glu
            515                 520                 525

Phe Phe Leu Lys His Asn Ser Lys Val Lys His Lys Lys His Tyr
            530                 535                 540

Lys Pro Ser Ser His Lys Leu Lys Val Ile Ser Lys Ser Met Gly Thr
545                 550                 555                 560

Ser Thr Gly Ala Thr Ala Asn His Gly Thr Ser Ala Val Ala Ile Thr
                565                 570                 575

Ser His Asp Tyr Leu Gly Gln Glu Thr Leu Thr Glu Ile Gln Thr Ser
            580                 585                 590

Pro Glu Thr Ser Met Arg Glu Val Lys Ala Asp Gly Ala Ser Thr Pro
            595                 600                 605

Arg Leu Arg Glu Gln Asp Cys Gly Glu Pro Ala Ser Pro Ala Ala Ser
            610                 615                 620

Ile Ser Arg Leu Ser Gly Glu Gln Val Asp Gly Lys Gly Gln Ala Gly
625                 630                 635                 640

Ser Val Ser Glu Ser Ala Arg Ser Glu Gly Arg Ile Ser Pro Lys Ser
                645                 650                 655

Asp Ile Thr Asp Thr Gly Leu Ala Gln Ser Asn Asn Leu Gln Val Pro
            660                 665                 670

Ser Ser Ser Glu Pro Ser Ser Leu Lys Gly Ser Thr Ser Leu Leu Val
            675                 680                 685

His Pro Val Ser Gly Val Arg Lys Glu Gln Gly Gly Cys His Ser
            690                 695                 700

Asp Thr
705

<210> SEQ ID NO 47
<211> LENGTH: 207
<212> TYPE: PRT
<213> ORGANISM: Artificial Sequence
<220> FEATURE:
<223> OTHER INFORMATION: extracellular domain (ECD) of FZD6

<400> SEQUENCE: 47

Met Glu Met Phe Thr Phe Leu Leu Thr Cys Ile Phe Leu Pro Leu Leu
1               5                   10                  15

Arg Gly His Ser Leu Phe Thr Cys Glu Pro Ile Thr Val Pro Arg Cys
```

```
                    20                  25                  30
Met Lys Met Ala Tyr Asn Met Thr Phe Phe Pro Asn Leu Met Gly His
            35                  40                  45

Tyr Asp Gln Ser Ile Ala Ala Val Glu Met Glu His Phe Leu Pro Leu
    50                  55                  60

Ala Asn Leu Glu Cys Ser Pro Asn Ile Glu Thr Phe Leu Cys Lys Ala
65                  70                  75                  80

Phe Val Pro Thr Cys Ile Glu Gln Ile His Val Val Pro Pro Cys Arg
                85                  90                  95

Lys Leu Cys Glu Lys Val Tyr Ser Asp Cys Lys Lys Leu Ile Asp Thr
            100                 105                 110

Phe Gly Ile Arg Trp Pro Glu Leu Glu Cys Asp Arg Leu Gln Tyr
        115                 120                 125

Cys Asp Glu Thr Val Pro Val Thr Phe Asp Pro His Thr Glu Phe Leu
    130                 135                 140

Gly Pro Gln Lys Lys Thr Glu Gln Val Gln Arg Asp Ile Gly Phe Trp
145                 150                 155                 160

Cys Pro Arg His Leu Lys Thr Ser Gly Gln Gly Tyr Lys Phe Leu
                165                 170                 175

Gly Ile Asp Gln Cys Ala Pro Pro Cys Pro Asn Met Tyr Phe Lys Ser
            180                 185                 190

Asp Glu Leu Glu Phe Ala Lys Ser Phe Ile Gly Thr Val Ser Ile
        195                 200                 205

<210> SEQ ID NO 48
<211> LENGTH: 127
<212> TYPE: PRT
<213> ORGANISM: Artificial Sequence
<220> FEATURE:
<223> OTHER INFORMATION: Human FZD6 Fri domain

<400> SEQUENCE: 48

His Ser Leu Phe Thr Cys Glu Pro Ile Thr Val Pro Arg Cys Met Lys
1               5                   10                  15

Met Ala Tyr Asn Met Thr Phe Phe Pro Asn Leu Met Gly His Tyr Asp
            20                  25                  30

Gln Ser Ile Ala Ala Val Glu Met Glu His Phe Leu Pro Leu Ala Asn
        35                  40                  45

Leu Glu Cys Ser Pro Asn Ile Glu Thr Phe Leu Cys Lys Ala Phe Val
    50                  55                  60

Pro Thr Cys Ile Glu Gln Ile His Val Val Pro Pro Cys Arg Lys Leu
65                  70                  75                  80

Cys Glu Lys Val Tyr Ser Asp Cys Lys Lys Leu Ile Asp Thr Phe Gly
                85                  90                  95

Ile Arg Trp Pro Glu Glu Leu Glu Cys Asp Arg Leu Gln Tyr Cys Asp
            100                 105                 110

Glu Thr Val Pro Val Thr Phe Asp Pro His Thr Glu Phe Leu Gly
        115                 120                 125

<210> SEQ ID NO 49
<211> LENGTH: 2121
<212> TYPE: DNA
<213> ORGANISM: Artificial Sequence
<220> FEATURE:
<223> OTHER INFORMATION: Human FZD6 full length

<400> SEQUENCE: 49
```

```
atggaaatgt ttacattttt gttgacgtgt attttctac ccctcctaag agggcacagt    60
ctcttcacct gtgaaccaat tactgttccc agatgtatga aaatggccta caacatgacg   120
tttttcccta atctgatggg tcattatgac cagagtattg ccgcggtgga aatggagcat   180
tttcttcctc tcgcaaatct ggaatgttca ccaaacattg aaactttcct ctgcaaagca   240
tttgtaccaa cctgcataga acaaattcat gtggttccac cttgtcgtaa actttgtgag   300
aaagtatatt ctgattgcaa aaaattaatt gacacttttg ggatccgatg gcctgaggag   360
cttgaatgtg acagattaca atactgtgat gagactgttc ctgtaacttt tgatccacac   420
acagaatttc ttggtcctca gaagaaaaca gaacaagtcc aaagagacat tggattttgg   480
tgtccaaggc atcttaagac ttctgggggga caaggatata agtttctggg aattgaccag   540
tgtgcgcctc catgccccaa catgtatttt aaaagtgatg agctagagtt tgcaaaaagt   600
tttattggaa cagtttcaat attttgtctt tgtgcaactc tgttcacatt ccttactttt   660
ttaattgatg ttagaagatt cagataccca gagagaccaa ttatatatta ctctgtctgt   720
tacagcattg tatctcttat gtacttcatt ggatttttgc taggcgatag cacagcctgc   780
aataaggcag atgagaagct agaacttggt gacactgttg tcctaggctc tcaaaataag   840
gcttgcaccg ttttgttcat gcttttgtat tttttcacaa tggctggcac tgtgtggtgg   900
gtgattctta ccattacttg gttcttagct gcaggaagaa aatggagttg gaagccatc    960
gagcaaaaag cagtgtggtt tcatgctgtt gcatggggaa caccaggttt cctgactgtt  1020
atgcttcttg ctatgaacaa agttgaagga gacaacatta gtggagtttg ctttgttggc  1080
ctttatgacc tggatgcttc tcgctacttt gtactcttgc cactgtgcct ttgtgtgttt  1140
gttgggctct ctcttctttt agctggcatt atttccttaa atcatgttcg acaagtcata  1200
caacatgatg gccggaacca agaaaaacta agaaatttta tgattcgaat tggagtcttc  1260
agcggcttgt atcttgtgcc attagtgaca cttctcggat gttacgtcta tgagcaagtg  1320
aacaggatta cctgggagat aacttgggtc tctgatcatt gtcgtcagta ccatatccca  1380
tgtccttatc aggcaaaagc aaaagctcga ccagaattgg ctttatttat gataaaatac  1440
ctgatgacat taattgttgg catctctgct gtcttctggg ttggaagcaa aaagacatgc  1500
acagaatggg ctgggttttt taacgaaat cgcaagagag atccaatcag tgaaagtcga  1560
agagtactac aggaatcatg tgagtttttc ttaaagcaca attctaaagt taaacacaaa  1620
aagaagcact ataaaccaag ttcacacaag ctgaaggtca tttccaaatc catgggaacc  1680
agcacaggag ctacagcaaa tcatggcact tctgcagtag caattactag ccatgattac  1740
ctaggacaag aaactttgac agaaatccaa acctcaccag aaacatcaat gagagaggtg  1800
aaagcggacg gagctagcac ccccaggtta agagaacagg actgtggtga acctgcctcg  1860
ccagcagcat ccatctccag actctctggg gaacaggtcg acgggaaggg ccaggcaggc  1920
agtgtatctg aaagtgcgcg gagtgaagga aggattagtc aaagagtga tattactgac  1980
actggcctgg cacagagcaa caatttgcag gtccccagtt cttcagaacc aagcagcctc  2040
aaaggttcca catctctgct tgttcacccg gtttcaggag tgagaaaaga gcagggaggt  2100
ggttgtcatt cagatacttg a                                           2121
```

<210> SEQ ID NO 50
<211> LENGTH: 574
<212> TYPE: PRT
<213> ORGANISM: Artificial Sequence
<220> FEATURE:
<223> OTHER INFORMATION: Human FZD7 full length

```
<220> FEATURE:
<221> NAME/KEY: MISC_FEATURE
<222> LOCATION: (1)..(255)
<223> OTHER INFORMATION: extracellular domain (ECD) of FZD7

<400> SEQUENCE: 50

Met Arg Asp Pro Gly Ala Ala Ala Pro Leu Ser Ser Leu Gly Leu Cys
1               5                   10                  15

Ala Leu Val Leu Ala Leu Leu Gly Ala Leu Ser Ala Gly Ala Gly Ala
            20                  25                  30

Gln Pro Tyr His Gly Glu Lys Gly Ile Ser Val Pro Asp His Gly Phe
        35                  40                  45

Cys Gln Pro Ile Ser Ile Pro Leu Cys Thr Asp Ile Ala Tyr Asn Gln
    50                  55                  60

Thr Ile Leu Pro Asn Leu Leu Gly His Thr Asn Gln Glu Asp Ala Gly
65                  70                  75                  80

Leu Glu Val His Gln Phe Tyr Pro Leu Val Lys Val Gln Cys Ser Pro
                85                  90                  95

Glu Leu Arg Phe Phe Leu Cys Ser Met Tyr Ala Pro Val Cys Thr Val
            100                 105                 110

Leu Asp Gln Ala Ile Pro Pro Cys Arg Ser Leu Cys Glu Arg Ala Arg
        115                 120                 125

Gln Gly Cys Glu Ala Leu Met Asn Lys Phe Gly Phe Gln Trp Pro Glu
    130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Pro Gly Gly Gly Pro
                165                 170                 175

Thr Ala Tyr Pro Thr Ala Pro Tyr Leu Pro Asp Leu Pro Phe Thr Ala
            180                 185                 190

Leu Pro Pro Gly Ala Ser Asp Gly Arg Gly Arg Pro Ala Phe Pro Phe
        195                 200                 205

Ser Cys Pro Arg Gln Leu Lys Val Pro Pro Tyr Leu Gly Tyr Arg Phe
    210                 215                 220

Leu Gly Glu Arg Asp Cys Gly Ala Pro Cys Glu Pro Gly Arg Ala Asn
225                 230                 235                 240

Gly Leu Met Tyr Phe Lys Glu Glu Arg Arg Phe Ala Arg Leu Trp
                245                 250                 255

Val Gly Val Trp Ser Val Leu Cys Cys Ala Ser Thr Leu Phe Thr Val
            260                 265                 270

Leu Thr Tyr Leu Val Asp Met Arg Arg Phe Ser Tyr Pro Glu Arg Pro
        275                 280                 285

Ile Ile Phe Leu Ser Gly Cys Tyr Phe Met Val Ala Val Ala His Val
    290                 295                 300

Ala Gly Phe Leu Leu Glu Asp Arg Ala Val Cys Val Glu Arg Phe Ser
305                 310                 315                 320

Asp Asp Gly Tyr Arg Thr Val Ala Gln Gly Thr Lys Lys Glu Gly Cys
                325                 330                 335

Thr Ile Leu Phe Met Val Leu Tyr Phe Phe Gly Met Ala Ser Ser Ile
            340                 345                 350

Trp Trp Val Ile Leu Ser Leu Thr Trp Phe Leu Ala Ala Gly Met Lys
        355                 360                 365

Trp Gly His Glu Ala Ile Glu Ala Asn Ser Gln Tyr Phe His Leu Ala
    370                 375                 380
```

```
Ala Trp Ala Val Pro Ala Val Lys Thr Ile Thr Ile Leu Ala Met Gly
385                 390                 395                 400

Gln Val Asp Gly Asp Leu Leu Ser Gly Val Cys Tyr Val Gly Leu Ser
            405                 410                 415

Ser Val Asp Ala Leu Arg Gly Phe Val Leu Ala Pro Leu Phe Val Tyr
            420                 425                 430

Leu Phe Ile Gly Thr Ser Phe Leu Leu Ala Gly Phe Val Ser Leu Phe
            435                 440                 445

Arg Ile Arg Thr Ile Met Lys His Asp Gly Thr Lys Thr Glu Lys Leu
            450                 455                 460

Glu Lys Leu Met Val Arg Ile Gly Val Phe Ser Val Leu Tyr Thr Val
465                 470                 475                 480

Pro Ala Thr Ile Val Leu Ala Cys Tyr Phe Tyr Glu Gln Ala Phe Arg
                485                 490                 495

Glu His Trp Glu Arg Thr Trp Leu Leu Gln Thr Cys Lys Ser Tyr Ala
            500                 505                 510

Val Pro Cys Pro Pro Gly His Phe Pro Pro Met Ser Pro Asp Phe Thr
            515                 520                 525

Val Phe Met Ile Lys Tyr Leu Met Thr Met Ile Val Gly Ile Thr Thr
            530                 535                 540

Gly Phe Trp Ile Trp Ser Gly Lys Thr Leu Gln Ser Trp Arg Arg Phe
545                 550                 555                 560

Tyr His Arg Leu Ser His Ser Ser Lys Gly Glu Thr Ala Val
            565                 570

<210> SEQ ID NO 51
<211> LENGTH: 255
<212> TYPE: PRT
<213> ORGANISM: Artificial Sequence
<220> FEATURE:
<223> OTHER INFORMATION: extracellular domain (ECD) of FZD7

<400> SEQUENCE: 51

Met Arg Asp Pro Gly Ala Ala Pro Leu Ser Ser Leu Gly Leu Cys
1               5                   10                  15

Ala Leu Val Leu Ala Leu Leu Gly Ala Leu Ser Ala Gly Ala Gly Ala
            20                  25                  30

Gln Pro Tyr His Gly Glu Lys Gly Ile Ser Val Pro Asp His Gly Phe
            35                  40                  45

Cys Gln Pro Ile Ser Ile Pro Leu Cys Thr Asp Ile Ala Tyr Asn Gln
            50                  55                  60

Thr Ile Leu Pro Asn Leu Leu Gly His Thr Asn Gln Glu Asp Ala Gly
65                  70                  75                  80

Leu Glu Val His Gln Phe Tyr Pro Leu Val Lys Val Gln Cys Ser Pro
                85                  90                  95

Glu Leu Arg Phe Phe Leu Cys Ser Met Tyr Ala Pro Val Cys Thr Val
            100                 105                 110

Leu Asp Gln Ala Ile Pro Pro Cys Arg Ser Leu Cys Glu Arg Ala Arg
            115                 120                 125

Gln Gly Cys Glu Ala Leu Met Asn Lys Phe Gly Phe Gln Trp Pro Glu
            130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Pro Gly Gly Pro
            165                 170                 175
```

```
Thr Ala Tyr Pro Thr Ala Pro Tyr Leu Pro Asp Leu Pro Phe Thr Ala
            180                 185                 190

Leu Pro Pro Gly Ala Ser Asp Gly Arg Gly Arg Pro Ala Phe Pro Phe
        195                 200                 205

Ser Cys Pro Arg Gln Leu Lys Val Pro Pro Tyr Leu Gly Tyr Arg Phe
    210                 215                 220

Leu Gly Glu Arg Asp Cys Gly Ala Pro Cys Glu Pro Gly Arg Ala Asn
225                 230                 235                 240

Gly Leu Met Tyr Phe Lys Glu Glu Arg Arg Phe Ala Arg Leu
                245                 250                 255

<210> SEQ ID NO 52
<211> LENGTH: 139
<212> TYPE: PRT
<213> ORGANISM: Artificial Sequence
<220> FEATURE:
<223> OTHER INFORMATION: Human FZD7 Fri domain

<400> SEQUENCE: 52

Ala Gln Pro Tyr His Gly Glu Lys Gly Ile Ser Val Pro Asp His Gly
1               5                   10                  15

Phe Cys Gln Pro Ile Ser Ile Pro Leu Cys Thr Asp Ile Ala Tyr Asn
            20                  25                  30

Gln Thr Ile Leu Pro Asn Leu Leu Gly His Thr Asn Gln Glu Asp Ala
        35                  40                  45

Gly Leu Glu Val His Gln Phe Tyr Pro Leu Val Lys Val Gln Cys Ser
    50                  55                  60

Pro Glu Leu Arg Phe Phe Leu Cys Ser Met Tyr Ala Pro Val Cys Thr
65                  70                  75                  80

Val Leu Asp Gln Ala Ile Pro Pro Cys Arg Ser Leu Cys Glu Arg Ala
                85                  90                  95

Arg Gln Gly Cys Glu Ala Leu Met Asn Lys Phe Gly Phe Gln Trp Pro
            100                 105                 110

Glu Arg Leu Arg Cys Glu Asn Phe Pro Val His Gly Ala Gly Glu Ile
        115                 120                 125

Cys Val Gly Gln Asn Thr Ser Asp Gly Ser Gly
    130                 135

<210> SEQ ID NO 53
<211> LENGTH: 1725
<212> TYPE: DNA
<213> ORGANISM: Artificial Sequence
<220> FEATURE:
<223> OTHER INFORMATION: Human FZD7 full length

<400> SEQUENCE: 53
atgcgggacc ccggcgcggc cgctccgctt cgtccctgg gcctctgtgc cctggtgctg        60
gcgctgctgg gcgcactgtc cgcgggcgcc ggggcgcagc cgtaccacgg agagaagggc      120
atctccgtgc cggaccacgg cttctgccag cccatctcca tcccgctgtg cacggacatc      180
gcctacaacc agaccatcct gcccaacctg ctgggccaca cgaaccaaga ggacgcgggc      240
ctcgaggtgc accagttcta cccgctggtg aaggtgcagt gttctcccga actccgcttt      300
ttcttatgct ccatgtatgc gcccgtgtgc accgtgctcg atcaggccat cccgccgtgt      360
cgttctctgt gcgagcgcgc ccgccagggc tgcgaggcgc tcatgaacaa gttcggcttc      420
cagtggcccg agcggctgcg ctgcgagaac ttccgggtgc acggtgcggg cgagatctgc      480
gtgggccaga acacgtcgga cggctccggg ggcccaggcg gcggcccac tgcctaccct      540
```

-continued

```
accgcgccct aacctgccgga cctgcccttc accgcgctgc ccccgggggc ctcagatggc    600 aggggggcgtc ccgccttccc cttctcatgc ccccgtcagc tcaaggtgcc cccgtacctg    660
ggctaccgct tcctgggtga gcgcgattgt ggcgccccgt gcgaaccggg ccgtgccaac    720
ggcctgatgt actttaagga ggaggagagg cgcttcgccc gcctctgggt gggcgtgtgg    780
tccgtgctgt gctgcgcctc gacgctcttt accgttctca cctacctggt ggacatgcgg    840
cgcttcagct acccagagcg gcccatcatc ttcctgtcgg gctgctactt catggtggcc    900
gtggcgcacg tggccggctt ccttctagag gaccgcgccg tgtgcgtgga gcgcttctcg    960
gacgatggct accgcacggt ggcgcagggc accaagaagg agggctgcac catcctcttc    1020
atggtgctct acttcttcgg catggccagc tccatctggt gggtcattct gtctctcact    1080
tggttcctgg cggccggcat gaagtggggc acgcgaggcca tcgaggccaa ctcgcagtac    1140
ttccacctgg ccgcgtgggc cgtgcccgcc gtcaagacca tcactatcct ggccatgggc    1200
caggtagacg gggacctgct gagcggggtg tgctacgttg gcctctccag tgtggacgcg    1260
ctgcggggct tcgtgctggc gcctctgttc gtctacctct tcataggcac gtccttcttg    1320
ctggccggct tcgtgtccct cttccgtatc cgcaccatca tgaaacacga cggcaccaag    1380
accgagaagc tggagaagct catggtgcgc atcggcgtct tcagcgtgct ctacacagtg    1440
cccgccacca tcgtcctggc ctgctacttc tacgagcagg ccttccgcga gcactgggag    1500
cgcacctggc tcctgcagac gtgcaagagc tatgccgtgc cctgcccgcc cggccacttc    1560
ccgcccatga gccccgactt caccgtcttc atgatcaagt acctgatgac catgatcgtc    1620
ggcatcacca ctggcttctg gatctggtcg ggcaagaccc tgcagtcgtg gcgccgcttc    1680
taccacagac ttagccacag cagcaagggg gagactgcgg tatga                    1725
```

<210> SEQ ID NO 54
<211> LENGTH: 694
<212> TYPE: PRT
<213> ORGANISM: Artificial Sequence
<220> FEATURE:
<223> OTHER INFORMATION: Human FZD8 full length
<220> FEATURE:
<221> NAME/KEY: MISC_FEATURE
<222> LOCATION: (1)..(277)
<223> OTHER INFORMATION: extracellular domain (ECD) of FZD8

<400> SEQUENCE: 54

```
Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125
```

```
Trp Pro Asp Arg Met Arg Cys Asp Arg Leu Pro Glu Gln Gly Asn Pro
130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Gly Glu Gln Pro
        165                 170                 175

Pro Ser Gly Ser Gly His Gly Arg Pro Pro Gly Ala Arg Pro Pro His
        180                 185                 190

Arg Gly Gly Gly Arg Gly Gly Gly Gly Asp Ala Ala Ala Pro Pro
        195                 200                 205

Ala Arg Gly Gly Gly Gly Gly Lys Ala Arg Pro Pro Gly Gly Gly
210                 215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255

Ile Ala Asn Cys Ala Leu Pro Cys His Asn Pro Phe Phe Ser Gln Asp
                260                 265                 270

Glu Arg Ala Phe Thr Val Phe Trp Ile Gly Leu Trp Ser Val Leu Cys
        275                 280                 285

Phe Val Ser Thr Phe Ala Thr Val Ser Thr Phe Leu Ile Asp Met Glu
        290                 295                 300

Arg Phe Lys Tyr Pro Glu Arg Pro Ile Ile Phe Leu Ser Ala Cys Tyr
305                 310                 315                 320

Leu Phe Val Ser Val Gly Tyr Leu Val Arg Leu Val Ala Gly His Glu
                325                 330                 335

Lys Val Ala Cys Ser Gly Gly Ala Pro Gly Ala Gly Gly Ala Gly Gly
                340                 345                 350

Ala Gly Gly Ala Ala Ala Gly Ala Ala Gly Ala Gly Ala Gly Ala Gly
        355                 360                 365

Gly Pro Gly Gly Arg Gly Glu Tyr Glu Glu Leu Gly Ala Val Glu Gln
        370                 375                 380

His Val Arg Tyr Glu Thr Thr Gly Pro Ala Leu Cys Thr Val Val Phe
385                 390                 395                 400

Leu Leu Val Tyr Phe Phe Gly Met Ala Ser Ser Ile Trp Trp Val Ile
                405                 410                 415

Leu Ser Leu Thr Trp Phe Leu Ala Ala Gly Met Lys Trp Gly Asn Glu
                420                 425                 430

Ala Ile Ala Gly Tyr Ser Gln Tyr Phe His Leu Ala Ala Trp Leu Val
        435                 440                 445

Pro Ser Val Lys Ser Ile Ala Val Leu Ala Leu Ser Ser Val Asp Gly
450                 455                 460

Asp Pro Val Ala Gly Ile Cys Tyr Val Gly Asn Gln Ser Leu Asp Asn
465                 470                 475                 480

Leu Arg Gly Phe Val Leu Ala Pro Leu Val Ile Tyr Leu Phe Ile Gly
                485                 490                 495

Thr Met Phe Leu Leu Ala Gly Phe Val Ser Leu Phe Arg Ile Arg Ser
                500                 505                 510

Val Ile Lys Gln Gln Asp Gly Pro Thr Lys Thr His Lys Leu Glu Lys
                515                 520                 525

Leu Met Ile Arg Leu Gly Leu Phe Thr Val Leu Tyr Thr Val Pro Ala
        530                 535                 540

Ala Val Val Val Ala Cys Leu Phe Tyr Glu Gln His Asn Arg Pro Arg
```

```
                545                 550                 555                 560
Trp Glu Ala Thr His Asn Cys Pro Cys Leu Arg Asp Leu Gln Pro Asp
                    565                 570                 575

Gln Ala Arg Arg Pro Asp Tyr Ala Val Phe Met Leu Lys Tyr Phe Met
                580                 585                 590

Cys Leu Val Val Gly Ile Thr Ser Gly Val Trp Val Trp Ser Gly Lys
                595                 600                 605

Thr Leu Glu Ser Trp Arg Ser Leu Cys Thr Arg Cys Cys Trp Ala Ser
                610                 615                 620

Lys Gly Ala Ala Val Gly Gly Ala Gly Thr Ala Ala Gly Gly
625                 630                 635                 640

Gly Gly Gly Pro Gly Gly Gly Gly Gly Pro Gly Gly Gly
                    645                 650                 655

Gly Pro Gly Gly Gly Gly Ser Leu Tyr Ser Asp Val Ser Thr Gly
                660                 665                 670

Leu Thr Trp Arg Ser Gly Thr Ala Ser Ser Val Ser Tyr Pro Lys Gln
                675                 680                 685

Met Pro Leu Ser Gln Val
        690

<210> SEQ ID NO 55
<211> LENGTH: 277
<212> TYPE: PRT
<213> ORGANISM: Artificial Sequence
<220> FEATURE:
<223> OTHER INFORMATION: extracellular domain (ECD) of FZD8

<400> SEQUENCE: 55

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Gly Glu Gln Pro
                165                 170                 175

Pro Ser Gly Ser Gly His Gly Arg Pro Pro Gly Ala Arg Pro Pro His
            180                 185                 190

Arg Gly Gly Gly Arg Gly Gly Gly Gly Asp Ala Ala Ala Pro Pro
        195                 200                 205

Ala Arg Gly Gly Gly Gly Gly Gly Lys Ala Arg Pro Pro Gly Gly Gly
```

```
                    210                 215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255

Ile Ala Asn Cys Ala Leu Pro Cys His Asn Pro Phe Phe Ser Gln Asp
            260                 265                 270

Glu Arg Ala Phe Thr
        275

<210> SEQ ID NO 56
<211> LENGTH: 131
<212> TYPE: PRT
<213> ORGANISM: Artificial Sequence
<220> FEATURE:
<223> OTHER INFORMATION: Human FZD8 Fri domain

<400> SEQUENCE: 56

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr
    130

<210> SEQ ID NO 57
<211> LENGTH: 2085
<212> TYPE: DNA
<213> ORGANISM: Artificial Sequence
<220> FEATURE:
<223> OTHER INFORMATION: Human FZD8 full length

<400> SEQUENCE: 57
atggagtggg gttacctgtt ggaagtgacc tcgctgctgg ccgccttggc gctgctgcag      60
cgctctagcg gcgctgcggc cgcctcggcc aaggagctgg catgccaaga gatcaccgtg     120
ccgctgtgta agggcatcgg ctacaactac acctacatgc ccaatcagtt caaccacgac     180
acgcaagacg aggcgggcct ggaggtgcac cagttctggc cgctggtgga gatccagtgc     240
tcgcccgatc tcaagttctt cctgtgcagc atgtacacgc ccatctgcct agaggactac     300
aagaagccgc tgccgccctg ccgctcggtg tgcgagcgcg ccaaggccgg ctgcgcgccg     360
ctcatgcgcc agtacggctt cgcctggccc gaccgcatgc gctgcgaccg gctgcccgag     420
caaggcaacc tgacacgct gtgcatggac tacaaccgca ccgacctaac caccgccgcg     480
cccagcccgc cgcgccgcct gccgccgccg ccgcccggcg agcagccgcc ttcgggcagc     540
```

```
ggccacggcc gcccgccggg ggccaggccc ccgcaccgcg gaggcggcag gggcggtggc    600
ggcggggacg cggcggcgcc cccagctcgc ggcggcggcg gtggcgggaa ggcgcggccc    660
cctggcggcg gcgcggctcc ctgcgagccc gggtgccagt gccgcgcgcc tatggtgagc    720
gtgtccagcg agcgccaccc gctctacaac cgcgtcaaga caggccagat cgctaactgc    780
gcgctgccct gccacaaccc cttttttcagc caggacgagc gcgccttcac cgtcttctgg    840
atcggcctgt ggtcggtgct ctgcttcgtg tccaccttcg ccaccgtctc caccttcctt    900
atcgacatgg agcgcttcaa gtacccggag cggcccatta tcttcctctc ggcctgctac    960
ctcttcgtgt cggtgggcta cctagtgcgc ctggtggcgg ccacgagaa ggtggcgtgc    1020
agcggtggcg cgccgggcgc ggggggcgct ggggcgcgg cggcgcggc ggcgggcgcg    1080
ggcgcggcgg gcgcgggcgc gggcggcccg ggcgggcgcg gcgagtacga ggagctgggc    1140
gcggtggagc agcacgtgcg ctacgagacc accggccccg cgctgtgcac cgtggtcttc    1200
ttgctggtct acttcttcgg catggccagc tccatctggt gggtgatctt gtcgctcaca    1260
tggttcctgg cggccggtat gaagtggggc aacgaagcca tcgccggcta ctcgcagtac    1320
ttccacctgg ccgcgtggct tgtgcccagc gtcaagtcca tcgcggtgct ggcgctcagc    1380
tcggtggacg cgacccggt ggcgggcatc tgctacgtgg caaccagag cctggacaac    1440
ctgcgcggct tcgtgctggc gccgctggtc atctacctct tcatcggcac catgttcctg    1500
ctggccggct tcgtgtccct gttccgcatc cgctcggtca tcaagcaaca ggacggcccc    1560
accaagacgc acaagctgga gaagctgatg atccgcctgg gcctgttcac cgtgctctac    1620
accgtgcccg ccgcggtggt ggtcgcctgc ctcttctacg agcagcacaa ccgcccgcgc    1680
tgggaggcca cgcacaactg cccgtgcctg cgggacctgc agcccgacca ggcacgcagg    1740
cccgactacg ccgtcttcat gctcaagtac ttcatgtgcc tagtggtggg catcaccctcg    1800
ggcgtgtggg tctggtccgg caagacgctg gagtcctggc gctccctgtg cacccgctgc    1860
tgctgggcca gcaagggcgc gcggtggc gggggcgcgg gcgccacggc cgcgggggt    1920
ggcggcgggc cggggggcgg cggcggcggg ggacccggcg gcggcggggg gccgggcggc    1980
ggcggggct ccctctacag cgacgtcagc actggcctga cgtggcggtc gggcacggcg    2040
agctccgtgt cttatccaaa gcagatgcca ttgtcccagg tctga                   2085
```

<210> SEQ ID NO 58
<211> LENGTH: 591
<212> TYPE: PRT
<213> ORGANISM: Artificial Sequence
<220> FEATURE:
<223> OTHER INFORMATION: Human FZD9 full length
<220> FEATURE:
<221> NAME/KEY: MISC_FEATURE
<222> LOCATION: (1)..(230)
<223> OTHER INFORMATION: extracellular domain (ECD) of FZD9

<400> SEQUENCE: 58

Met Ala Val Ala Pro Leu Arg Gly Ala Leu Leu Leu Trp Gln Leu Leu
1               5                   10                  15

Ala Ala Gly Gly Ala Ala Leu Glu Ile Gly Arg Phe Asp Pro Glu Arg
            20                  25                  30

Gly Arg Gly Ala Ala Pro Cys Gln Ala Val Glu Ile Pro Met Cys Arg
        35                  40                  45

Gly Ile Gly Tyr Asn Leu Thr Arg Met Pro Asn Leu Leu Gly His Thr
    50                  55                  60

Ser Gln Gly Glu Ala Ala Ala Glu Leu Ala Glu Phe Ala Pro Leu Val

```
            65                  70                  75                  80
        Gln Tyr Gly Cys His Ser His Leu Arg Phe Phe Leu Cys Ser Leu Tyr
                        85                  90                  95
        Ala Pro Met Cys Thr Asp Gln Val Ser Thr Pro Ile Pro Ala Cys Arg
                        100                 105                 110
        Pro Met Cys Glu Gln Ala Arg Leu Arg Cys Ala Pro Ile Met Glu Gln
                        115                 120                 125
        Phe Asn Phe Gly Trp Pro Asp Ser Leu Asp Cys Ala Arg Leu Pro Thr
                        130                 135                 140
        Arg Asn Asp Pro His Ala Leu Cys Met Glu Ala Pro Glu Asn Ala Thr
        145                 150                 155                 160
        Ala Gly Pro Ala Glu Pro His Lys Gly Leu Gly Met Leu Pro Val Ala
                        165                 170                 175
        Pro Arg Pro Ala Arg Pro Gly Asp Leu Gly Pro Gly Ala Gly Gly
                        180                 185                 190
        Ser Gly Thr Cys Glu Asn Pro Glu Lys Phe Gln Tyr Val Glu Lys Ser
                        195                 200                 205
        Arg Ser Cys Ala Pro Arg Cys Gly Pro Gly Val Glu Val Phe Trp Ser
        210                 215                 220
        Arg Arg Asp Lys Asp Phe Ala Leu Val Trp Met Ala Val Trp Ser Ala
        225                 230                 235                 240
        Leu Cys Phe Phe Ser Thr Ala Phe Thr Val Leu Thr Phe Leu Leu Glu
                        245                 250                 255
        Pro His Arg Phe Gln Tyr Pro Glu Arg Pro Ile Ile Phe Leu Ser Met
                        260                 265                 270
        Cys Tyr Asn Val Tyr Ser Leu Ala Phe Leu Ile Arg Ala Val Ala Gly
                        275                 280                 285
        Ala Gln Ser Val Ala Cys Asp Gln Glu Ala Gly Ala Leu Tyr Val Ile
                        290                 295                 300
        Gln Glu Gly Leu Glu Asn Thr Gly Cys Thr Leu Val Phe Leu Leu Leu
        305                 310                 315                 320
        Tyr Tyr Phe Gly Met Ala Ser Ser Leu Trp Trp Val Leu Thr Leu
                        325                 330                 335
        Thr Trp Phe Leu Ala Ala Gly Lys Lys Trp Gly His Glu Ala Ile Glu
                        340                 345                 350
        Ala His Gly Ser Tyr Phe His Met Ala Ala Trp Gly Leu Pro Ala Leu
                        355                 360                 365
        Lys Thr Ile Val Ile Leu Thr Leu Arg Lys Val Ala Gly Asp Glu Leu
        370                 375                 380
        Thr Gly Leu Cys Tyr Val Ala Ser Thr Asp Ala Ala Leu Thr Gly
        385                 390                 395                 400
        Phe Val Leu Val Pro Leu Ser Gly Tyr Leu Val Leu Gly Ser Ser Phe
                        405                 410                 415
        Leu Leu Thr Gly Phe Val Ala Leu Phe His Ile Arg Lys Ile Met Lys
                        420                 425                 430
        Thr Gly Gly Thr Asn Thr Glu Lys Leu Glu Lys Leu Met Val Lys Ile
                        435                 440                 445
        Gly Val Phe Ser Ile Leu Tyr Thr Val Pro Ala Thr Cys Val Ile Val
                        450                 455                 460
        Cys Tyr Val Tyr Glu Arg Leu Asn Met Asp Phe Trp Arg Leu Arg Ala
        465                 470                 475                 480
        Thr Glu Gln Pro Cys Ala Ala Ala Gly Pro Gly Gly Arg Arg Asp
                        485                 490                 495
```

```
Cys Ser Leu Pro Gly Gly Ser Val Pro Thr Val Ala Val Phe Met Leu
            500                 505                 510
Lys Ile Phe Met Ser Leu Val Val Gly Ile Thr Ser Gly Val Trp Val
        515                 520                 525
Trp Ser Ser Lys Thr Phe Gln Thr Trp Gln Ser Leu Cys Tyr Arg Lys
    530                 535                 540
Ile Ala Ala Gly Arg Ala Arg Ala Lys Ala Cys Arg Ala Pro Gly Ser
545                 550                 555                 560
Tyr Gly Arg Gly Thr His Cys His Tyr Lys Ala Pro Thr Val Val Leu
                565                 570                 575
His Met Thr Lys Thr Asp Pro Ser Leu Glu Asn Pro Thr His Leu
            580                 585                 590

<210> SEQ ID NO 59
<211> LENGTH: 230
<212> TYPE: PRT
<213> ORGANISM: Artificial Sequence
<220> FEATURE:
<223> OTHER INFORMATION: extracellular domain (ECD) of FZD9

<400> SEQUENCE: 59

Met Ala Val Ala Pro Leu Arg Gly Ala Leu Leu Leu Trp Gln Leu Leu
1               5                   10                  15
Ala Ala Gly Gly Ala Ala Leu Glu Ile Gly Arg Phe Asp Pro Glu Arg
            20                  25                  30
Gly Arg Gly Ala Ala Pro Cys Gln Ala Val Glu Ile Pro Met Cys Arg
        35                  40                  45
Gly Ile Gly Tyr Asn Leu Thr Arg Met Pro Asn Leu Leu Gly His Thr
    50                  55                  60
Ser Gln Gly Glu Ala Ala Ala Glu Leu Ala Glu Phe Ala Pro Leu Val
65                  70                  75                  80
Gln Tyr Gly Cys His Ser His Leu Arg Phe Phe Leu Cys Ser Leu Tyr
                85                  90                  95
Ala Pro Met Cys Thr Asp Gln Val Ser Thr Pro Ile Pro Ala Cys Arg
            100                 105                 110
Pro Met Cys Glu Gln Ala Arg Leu Arg Cys Ala Pro Ile Met Glu Gln
        115                 120                 125
Phe Asn Phe Gly Trp Pro Asp Ser Leu Asp Cys Ala Arg Leu Pro Thr
    130                 135                 140
Arg Asn Asp Pro His Ala Leu Cys Met Glu Ala Pro Glu Asn Ala Thr
145                 150                 155                 160
Ala Gly Pro Ala Glu Pro His Lys Gly Leu Gly Met Leu Pro Val Ala
                165                 170                 175
Pro Arg Pro Ala Arg Pro Gly Asp Leu Gly Pro Gly Ala Gly Gly
            180                 185                 190
Ser Gly Thr Cys Glu Asn Pro Glu Lys Phe Gln Tyr Val Glu Lys Ser
        195                 200                 205
Arg Ser Cys Ala Pro Arg Cys Gly Pro Gly Val Glu Val Phe Trp Ser
    210                 215                 220
Arg Arg Asp Lys Asp Phe
225                 230

<210> SEQ ID NO 60
<211> LENGTH: 137
<212> TYPE: PRT
<213> ORGANISM: Artificial Sequence
```

```
<220> FEATURE:
<223> OTHER INFORMATION: Human FZD9 fri domain

<400> SEQUENCE: 60

Leu Glu Ile Gly Arg Phe Asp Pro Glu Arg Gly Arg Gly Ala Ala Pro
1               5                   10                  15

Cys Gln Ala Val Glu Ile Pro Met Cys Arg Gly Ile Gly Tyr Asn Leu
            20                  25                  30

Thr Arg Met Pro Asn Leu Leu Gly His Thr Ser Gln Gly Glu Ala Ala
        35                  40                  45

Ala Glu Leu Ala Glu Phe Ala Pro Leu Val Gln Tyr Gly Cys His Ser
    50                  55                  60

His Leu Arg Phe Phe Leu Cys Ser Leu Tyr Ala Pro Met Cys Thr Asp
65                  70                  75                  80

Gln Val Ser Thr Pro Ile Pro Ala Cys Arg Pro Met Cys Glu Gln Ala
                85                  90                  95

Arg Leu Arg Cys Ala Pro Ile Met Glu Gln Phe Asn Phe Gly Trp Pro
            100                 105                 110

Asp Ser Leu Asp Cys Ala Arg Leu Pro Thr Arg Asn Asp Pro His Ala
        115                 120                 125

Leu Cys Met Glu Ala Pro Glu Asn Ala
    130                 135

<210> SEQ ID NO 61
<211> LENGTH: 1776
<212> TYPE: DNA
<213> ORGANISM: Artificial Sequence
<220> FEATURE:
<223> OTHER INFORMATION: Human FZD9 full length

<400> SEQUENCE: 61
```

| | | |
|---|---|---|
| atggccgtgg cgcctctgcg gggggcgctg ctgctgtggc agctgctggc ggcgggcggc | 60 |
| gcggcactgg agatcggccg cttcgacccg gagcgcgggc gcggggctgc gccgtgccag | 120 |
| gcggtggaga tccccatgtg ccgcggcatc ggctacaacc tgacccgcat gcccaacctg | 180 |
| ctgggccaca cgtcgcaggg cgaggcggct gccgagctag cggagttcgc gccgctggtg | 240 |
| cagtacggct gccacagcca cctgcgcttc ttcctgtgct cgctctacgc gcccatgtgc | 300 |
| accgaccagg tctcgacgcc cattcccgcc tgccggccca tgtgcgagca ggcgcgcctg | 360 |
| cgctgcgcgc ccatcatgga gcagttcaac ttcggctggc cggactcgct cgactgcgcc | 420 |
| cggctgccca cgcgcaacga cccgcacgcg ctgtgcatgg aggcgcccga gaacgccacg | 480 |
| gccggccccg cggagcccca aagggcctg gcatgctgc ccgtggcgcc gcggcccgcg | 540 |
| cgccctcccg agacctgggc ccggggcgcg gcggcagtg gcacctgcga gaaccccgag | 600 |
| aagttccagt acgtggagaa gagccgctcg tgcgcaccgc gctgcgggcc cggcgtcgag | 660 |
| gtgttctggt cccggcgcga caaggacttc gcgctggtct ggatggccgt gtggtcggcg | 720 |
| ctgtgcttct tctccaccgc cttcactgtg ctcaccttct gctggagcc ccaccgcttc | 780 |
| cagtaccccg agcgccccat catcttcctc tccatgtgct acaacgtcta ctcgctggcc | 840 |
| ttcctgatcc gtgcggtggc cggagcgcag agcgtggcct gtgaccagga ggcgggcgcg | 900 |
| ctctacgtga tccaggaggg cctggagaac acgggctgca cgctggtctt cctactgctc | 960 |
| tactacttcg gcatggccag ctcgctctgg tgggtggtcc tgacgctcac ctggttcctg | 1020 |
| gctgccggga gaaatggggg ccacgaggcc atcgaggccc acggcagcta tttccacatg | 1080 |
| gctgcctggg gcctgcccgc gctcaagacc atcgtcatcc tgaccctgcg caaggtggcg | 1140 |

```
ggtgatgagc tgactgggct ttgctacgtg ccagcacgg atgcagcagc gctcacgggc    1200
ttcgtgctgg tgcccctctc tggctacctg gtgctgggca gtagtttcct cctgaccggc    1260
ttcgtggccc tcttccacat ccgcaagatc atgaagacgg gcggcaccaa cacagagaag    1320
ctggagaagc tcatggtcaa gatcggggtc ttctccatcc tctacacggt gcccgccacc    1380
tgcgtcatcg tttgctatgt ctacgaacgc ctcaacatgg acttctggcg ccttcgggcc    1440
acagagcagc catgcgcagc ggccgcgggg cccggaggcc ggagggactg ctcgctgcca    1500
gggggctcgg tgcccaccgt ggcggtcttc atgctcaaaa ttttcatgtc actggtggtg    1560
gggatcacca gcggcgtctg ggtgtggagc tccaagactt ccagacctg gcagagcctg    1620 tgctaccgca agatagcagc tggccgggcc cgggccaagg cctgccgcgc ccccgggagc    1680 tacgacgtg gcacgcactg ccactataag gctcccaccg tggtcttgca catgactaag    1740
acggacccct ctttggagaa ccccacacac ctctag                             1776
```

<210> SEQ ID NO 62
<211> LENGTH: 581
<212> TYPE: PRT
<213> ORGANISM: Artificial Sequence
<220> FEATURE:
<223> OTHER INFORMATION: Human FZD10 full length
<220> FEATURE:
<221> NAME/KEY: MISC_FEATURE
<222> LOCATION: (1)..(227)
<223> OTHER INFORMATION: extracellular domain (ECD) of FZD10

<400> SEQUENCE: 62

```
Met Gln Arg Pro Gly Pro Arg Leu Trp Leu Val Leu Gln Val Met Gly
1               5                   10                  15

Ser Cys Ala Ala Ile Ser Ser Met Asp Met Glu Arg Pro Gly Asp Gly
            20                  25                  30

Lys Cys Gln Pro Ile Glu Ile Pro Met Cys Lys Asp Ile Gly Tyr Asn
        35                  40                  45

Met Thr Arg Met Pro Asn Leu Met Gly His Glu Asn Gln Arg Glu Ala
    50                  55                  60

Ala Ile Gln Leu His Glu Phe Ala Pro Leu Val Glu Tyr Gly Cys His
65                  70                  75                  80

Gly His Leu Arg Phe Phe Leu Cys Ser Leu Tyr Ala Pro Met Cys Thr
                85                  90                  95

Glu Gln Val Ser Thr Pro Ile Pro Ala Cys Arg Val Met Cys Glu Gln
            100                 105                 110

Ala Arg Leu Lys Cys Ser Pro Ile Met Glu Gln Phe Asn Phe Lys Trp
        115                 120                 125

Pro Asp Ser Leu Asp Cys Arg Lys Leu Pro Asn Lys Asn Asp Pro Asn
    130                 135                 140

Tyr Leu Cys Met Glu Ala Pro Asn Asn Gly Ser Asp Glu Pro Thr Arg
145                 150                 155                 160

Gly Ser Gly Leu Phe Pro Pro Leu Phe Arg Pro Gln Arg Pro His Ser
                165                 170                 175

Ala Gln Glu His Pro Leu Lys Asp Gly Gly Pro Gly Arg Gly Gly Cys
            180                 185                 190

Asp Asn Pro Gly Lys Phe His His Val Glu Lys Ser Ala Ser Cys Ala
        195                 200                 205

Pro Leu Cys Thr Pro Gly Val Asp Val Tyr Trp Ser Arg Glu Asp Lys
    210                 215                 220
```

```
Arg Phe Ala Val Val Trp Leu Ala Ile Trp Ala Val Leu Cys Phe Phe
225                 230                 235                 240

Ser Ser Ala Phe Thr Val Leu Thr Phe Leu Ile Asp Pro Ala Arg Phe
                245                 250                 255

Arg Tyr Pro Glu Arg Pro Ile Ile Phe Leu Ser Met Cys Tyr Cys Val
            260                 265                 270

Tyr Ser Val Gly Tyr Leu Ile Arg Leu Phe Ala Gly Ala Glu Ser Ile
        275                 280                 285

Ala Cys Asp Arg Asp Ser Gly Gln Leu Tyr Val Ile Gln Glu Gly Leu
    290                 295                 300

Glu Ser Thr Gly Cys Thr Leu Val Phe Leu Val Leu Tyr Tyr Phe Gly
305                 310                 315                 320

Met Ala Ser Ser Leu Trp Trp Val Val Leu Thr Leu Thr Trp Phe Leu
                325                 330                 335

Ala Ala Gly Lys Lys Trp Gly His Glu Ala Ile Glu Ala Asn Ser Ser
            340                 345                 350

Tyr Phe His Leu Ala Ala Trp Ala Ile Pro Ala Val Lys Thr Ile Leu
        355                 360                 365

Ile Leu Val Met Arg Arg Val Ala Gly Asp Glu Leu Thr Gly Val Cys
    370                 375                 380

Tyr Val Gly Ser Met Asp Val Asn Ala Leu Thr Gly Phe Val Leu Ile
385                 390                 395                 400

Pro Leu Ala Cys Tyr Leu Val Ile Gly Thr Ser Phe Ile Leu Ser Gly
                405                 410                 415

Phe Val Ala Leu Phe His Ile Arg Arg Val Met Lys Thr Gly Gly Glu
            420                 425                 430

Asn Thr Asp Lys Leu Glu Lys Leu Met Val Arg Ile Gly Leu Phe Ser
        435                 440                 445

Val Leu Tyr Thr Val Pro Ala Thr Cys Val Ile Ala Cys Tyr Phe Tyr
    450                 455                 460

Glu Arg Leu Asn Met Asp Tyr Trp Lys Ile Leu Ala Ala Gln His Lys
465                 470                 475                 480

Cys Lys Met Asn Asn Gln Thr Lys Thr Leu Asp Cys Leu Met Ala Ala
                485                 490                 495

Ser Ile Pro Ala Val Glu Ile Phe Met Val Lys Ile Phe Met Leu Leu
            500                 505                 510

Val Val Gly Ile Thr Ser Gly Met Trp Ile Trp Thr Ser Lys Thr Leu
        515                 520                 525

Gln Ser Trp Gln Gln Val Cys Ser Arg Arg Leu Lys Lys Lys Ser Arg
    530                 535                 540

Arg Lys Pro Ala Ser Val Ile Thr Ser Gly Gly Ile Tyr Lys Lys Ala
545                 550                 555                 560

Gln His Pro Gln Lys Thr His Gly Lys Tyr Glu Ile Pro Ala Gln
                565                 570                 575

Ser Pro Thr Cys Val
            580

<210> SEQ ID NO 63
<211> LENGTH: 227
<212> TYPE: PRT
<213> ORGANISM: Artificial Sequence
<220> FEATURE:
<223> OTHER INFORMATION: extracellular domain (ECD) of FZD10

<400> SEQUENCE: 63
```

Met Gln Arg Pro Gly Pro Arg Leu Trp Leu Val Leu Gln Val Met Gly
1               5                   10                  15

Ser Cys Ala Ala Ile Ser Ser Met Asp Met Glu Arg Pro Gly Asp Gly
            20                  25                  30

Lys Cys Gln Pro Ile Glu Ile Pro Met Cys Lys Asp Ile Gly Tyr Asn
        35                  40                  45

Met Thr Arg Met Pro Asn Leu Met Gly His Glu Asn Gln Arg Glu Ala
    50                  55                  60

Ala Ile Gln Leu His Glu Phe Ala Pro Leu Val Glu Tyr Gly Cys His
65                  70                  75                  80

Gly His Leu Arg Phe Phe Leu Cys Ser Leu Tyr Ala Pro Met Cys Thr
                85                  90                  95

Glu Gln Val Ser Thr Pro Ile Pro Ala Cys Arg Val Met Cys Glu Gln
                100                 105                 110

Ala Arg Leu Lys Cys Ser Pro Ile Met Glu Gln Phe Asn Phe Lys Trp
            115                 120                 125

Pro Asp Ser Leu Asp Cys Arg Lys Leu Pro Asn Lys Asn Asp Pro Asn
        130                 135                 140

Tyr Leu Cys Met Glu Ala Pro Asn Asn Gly Ser Asp Glu Pro Thr Arg
145                 150                 155                 160

Gly Ser Gly Leu Phe Pro Pro Leu Phe Arg Pro Gln Arg Pro His Ser
                165                 170                 175

Ala Gln Glu His Pro Leu Lys Asp Gly Gly Pro Gly Arg Gly Gly Cys
                180                 185                 190

Asp Asn Pro Gly Lys Phe His His Val Glu Lys Ser Ala Ser Cys Ala
        195                 200                 205

Pro Leu Cys Thr Pro Gly Val Asp Val Tyr Trp Ser Arg Glu Asp Lys
        210                 215                 220

Arg Phe Ala
225

<210> SEQ ID NO 64
<211> LENGTH: 134
<212> TYPE: PRT
<213> ORGANISM: Artificial Sequence
<220> FEATURE:
<223> OTHER INFORMATION: Human FZD10 fri domain

<400> SEQUENCE: 64

Ile Ser Ser Met Asp Met Glu Arg Pro Gly Asp Gly Lys Cys Gln Pro
1               5                   10                  15

Ile Glu Ile Pro Met Cys Lys Asp Ile Gly Tyr Asn Met Thr Arg Met
            20                  25                  30

Pro Asn Leu Met Gly His Glu Asn Gln Arg Glu Ala Ala Ile Gln Leu
        35                  40                  45

His Glu Phe Ala Pro Leu Val Glu Tyr Gly Cys His Gly His Leu Arg
    50                  55                  60

Phe Phe Leu Cys Ser Leu Tyr Ala Pro Met Cys Thr Glu Gln Val Ser
65                  70                  75                  80

Thr Pro Ile Pro Ala Cys Arg Val Met Cys Glu Gln Ala Arg Leu Lys
                85                  90                  95

Cys Ser Pro Ile Met Glu Gln Phe Asn Phe Lys Trp Pro Asp Ser Leu
                100                 105                 110

Asp Cys Arg Lys Leu Pro Asn Lys Asn Asp Pro Asn Tyr Leu Cys Met
            115                 120                 125

Glu Ala Pro Asn Asn Gly
    130

<210> SEQ ID NO 65
<211> LENGTH: 1746
<212> TYPE: DNA
<213> ORGANISM: Artificial Sequence
<220> FEATURE:
<223> OTHER INFORMATION: Human FZD10 full length

<400> SEQUENCE: 65

| | | |
|---|---|---|
| atgcagcgcc cgggcccccg cctgtggctg gtcctgcagg tgatgggctc gtgcgccgcc | 60 |
| atcagctcca tggacatgga gcgcccgggc gacggcaaat gccagcccat cgagatcccg | 120 |
| atgtgcaagg acatcggcta caacatgact cgtatgccca acctgatggg ccacgagaac | 180 |
| cagcgcgagg cagccatcca gttgcacgag ttcgcgccgc tggtggagta cggctgccac | 240 |
| ggccacctcc gcttcttcct gtgctcgctg tacgcgccga tgtgcaccga gcaggtctct | 300 |
| accccatcc ccgcctgccg ggtcatgtgc gagcaggccc ggctcaagtg ctccccgatt | 360 |
| atggagcagt tcaacttcaa gtggcccgac tccctggact gccgaaaact ccccaacaag | 420 |
| aacgacccca actacctgtg catggaggcg cccaacaacg gctcggacga gcccaccccg | 480 |
| ggctcgggcc tgttcccgcc gctgttccgg ccgcagcggc cccacagcgc gcaggagcac | 540 |
| ccgctgaagg acgggggccc cgggcgcggc ggctgcgaca cccgggcaa gttccaccac | 600 |
| gtggagaaga gcgcgtcgtg cgcgccgctc tgcacgcccg gcgtggacgt gtactggagc | 660 |
| cgcgaggaca gcgcttcgc agtggtctgg ctggccatct gggcggtgct gtgcttcttc | 720 |
| tccagcgcct tcaccgtgct caccttcctc atcgacccgg cccgcttccg ctaccccgag | 780 |
| cgccccatca tcttcctctc catgtgctac tgcgtctact ccgtgggcta cctcatccgc | 840 |
| ctcttcgccg gcgccgagag catcgcctgc gaccgggaca gcggccagct ctatgtcatc | 900 |
| caggagggac tggagagcac cggctgcacg ctggtcttcc tggtcctcta ctacttcggc | 960 |
| atggccagct cgctgtggtg ggtggtcctc acgctcacct ggttcctggc cgccggcaag | 1020 |
| aagtggggcc acgaggccat cgaagccaac agcagctact ccacctggc agcctgggcc | 1080 |
| atcccggcgg tgaagaccat cctgatcctg gtcatgcgca gggtggcggg ggacgagctc | 1140 |
| accggggtct gctacgtggg cagcatggac gtcaacgcgc tcaccggctt cgtgctcatt | 1200 |
| cccctggcct gctacctggt catcggcacg tccttcatcc tctcgggctt cgtggccctg | 1260 |
| ttccacatcc ggagggtgat gaagacgggc ggcgagaaca cggacaagct ggagaagctc | 1320 |
| atggtgcgta tcgggctctt ctctgtgctg tacaccgtgc cggccacctg tgtgatcgcc | 1380 |
| tgctactttt acgaacgcct caacatggat tactggaaga tcctggcggc gcagcacaag | 1440 |
| tgcaaaatga acaaccagac taaaacgctg gactgcctga tggccgcctc catccccgcc | 1500 |
| gtggagatct tcatggtgaa gatctttatg ctgctggtgg tggggatcac cagcgggatg | 1560 |
| tggatttgga cctccaagac tctgcagtcc tggcagcagg tgtgcagccg taggttaaag | 1620 |
| aagaagagcc ggagaaaacc ggccagcgtg atcaccagcg tgggatttta caaaaaagcc | 1680 |
| cagcatcccc agaaaactca ccacgggaaa tatgagatcc ctgcccagtc gcccacctgc | 1740 |
| gtgtga | 1746 |

<210> SEQ ID NO 66
<211> LENGTH: 5
<212> TYPE: PRT
<213> ORGANISM: Artificial Sequence
<220> FEATURE:

```
<223> OTHER INFORMATION: a region of FZD8

<400> SEQUENCE: 66

Gln Tyr Gly Phe Ala
1               5

<210> SEQ ID NO 67
<211> LENGTH: 14
<212> TYPE: PRT
<213> ORGANISM: Artificial Sequence
<220> FEATURE:
<223> OTHER INFORMATION: a region of FZD8

<400> SEQUENCE: 67

Gln Asp Glu Ala Gly Leu Glu Val His Gln Phe Trp Pro Leu
1               5                   10

<210> SEQ ID NO 68
<211> LENGTH: 8
<212> TYPE: PRT
<213> ORGANISM: Artificial Sequence
<220> FEATURE:
<223> OTHER INFORMATION: region within the human frizzled receptor(s)
      FZD1, FZD2, FZD5, FZD7, and/or FZD8

<400> SEQUENCE: 68

Ala Gly Leu Glu Val His Gln Phe
1               5

<210> SEQ ID NO 69
<211> LENGTH: 5
<212> TYPE: PRT
<213> ORGANISM: Artificial Sequence
<220> FEATURE:
<223> OTHER INFORMATION: synthetic fragment of human frizzled receptor
<220> FEATURE:
<221> NAME/KEY: MISC_FEATURE
<222> LOCATION: (1)..(1)
<223> OTHER INFORMATION: Is lysine/glutamine
<220> FEATURE:
<221> NAME/KEY: MISC_FEATURE
<222> LOCATION: (2)..(2)
<223> OTHER INFORMATION: Is phenylalanine/tyrosine
<220> FEATURE:
<221> NAME/KEY: MISC_FEATURE
<222> LOCATION: (5)..(5)
<223> OTHER INFORMATION: Is glutamine/alanine

<400> SEQUENCE: 69

Xaa Xaa Gly Phe Xaa
1               5

<210> SEQ ID NO 70
<211> LENGTH: 4
<212> TYPE: PRT
<213> ORGANISM: Artificial
<220> FEATURE:
<223> OTHER INFORMATION: Cleft of the BBS

<400> SEQUENCE: 70

Trp Pro Asp Arg
1

<210> SEQ ID NO 71
<211> LENGTH: 11
<212> TYPE: PRT
<213> ORGANISM: Artificial Sequence
<220> FEATURE:
<223> OTHER INFORMATION: light chain CDR1
```

-continued

```
<220> FEATURE:
<221> NAME/KEY: MISC_FEATURE
<222> LOCATION: (4)..(4)
<223> OTHER INFORMATION: Is lysine/asparagine
<220> FEATURE:
<221> NAME/KEY: MISC_FEATURE
<222> LOCATION: (5)..(5)
<223> OTHER INFORMATION: Is leucine/isoleucine
<220> FEATURE:
<221> NAME/KEY: MISC_FEATURE
<222> LOCATION: (7)..(7)
<223> OTHER INFORMATION: Is lysine/serine
<220> FEATURE:
<221> NAME/KEY: MISC_FEATURE
<222> LOCATION: (8)..(8)
<223> OTHER INFORMATION: Is lysine/phenylalanine
<220> FEATURE:
<221> NAME/KEY: MISC_FEATURE
<222> LOCATION: (10)..(10)
<223> OTHER INFORMATION: Is alanine/valine
<220> FEATURE:
<221> NAME/KEY: MISC_FEATURE
<222> LOCATION: (11)..(11)
<223> OTHER INFORMATION: Is serine/histidine

<400> SEQUENCE: 71

Ser Gly Asp Xaa Xaa Gly Xaa Xaa Tyr Xaa Xaa
1               5                   10

<210> SEQ ID NO 72
<211> LENGTH: 8
<212> TYPE: PRT
<213> ORGANISM: Artificial Sequence
<220> FEATURE:
<223> OTHER INFORMATION: light chain CDR2
<220> FEATURE:
<221> NAME/KEY: MISC_FEATURE
<222> LOCATION: (1)..(1)
<223> OTHER INFORMATION: Is glutamic acid/aspartic acid
<220> FEATURE:
<221> NAME/KEY: MISC_FEATURE
<222> LOCATION: (3)..(3)
<223> OTHER INFORMATION: Is aspartic acid/serine

<400> SEQUENCE: 72

Xaa Lys Xaa Asn Arg Pro Ser Gly
1               5

<210> SEQ ID NO 73
<211> LENGTH: 10
<212> TYPE: PRT
<213> ORGANISM: Artificial Sequence
<220> FEATURE:
<223> OTHER INFORMATION: light chain CDR3
<220> FEATURE:
<221> NAME/KEY: MISC_FEATURE
<222> LOCATION: (1)..(1)
<223> OTHER INFORMATION: Is serine/glutamine
<220> FEATURE:
<221> NAME/KEY: MISC_FEATURE
<222> LOCATION: (3)..(3)
<223> OTHER INFORMATION: Is phenylalanine/tyrosine
<220> FEATURE:
<221> NAME/KEY: MISC_FEATURE
<222> LOCATION: (5)..(5)
<223> OTHER INFORMATION: Is glycine/asparagine
<220> FEATURE:
<221> NAME/KEY: MISC_FEATURE
<222> LOCATION: (6)..(6)
<223> OTHER INFORMATION: Is asparagine/threonine
<220> FEATURE:
<221> NAME/KEY: MISC_FEATURE
<222> LOCATION: (7)..(7)
<223> OTHER INFORMATION: Is no amino acid/leucine
<220> FEATURE:
```

```
<221> NAME/KEY: MISC_FEATURE
<222> LOCATION: (10)..(10)
<223> OTHER INFORMATION: Is glutamic acid/no amino acid

<400> SEQUENCE: 73

Xaa Ser Xaa Ala Xaa Xaa Xaa Ser Leu Xaa
 1               5                  10

<210> SEQ ID NO 74
<211> LENGTH: 4
<212> TYPE: PRT
<213> ORGANISM: Artificial Sequence
<220> FEATURE:
<223> OTHER INFORMATION: antibody

<400> SEQUENCE: 74

Tyr Gly Phe Ala
 1

<210> SEQ ID NO 75
<211> LENGTH: 25
<212> TYPE: DNA
<213> ORGANISM: Artificial Sequence
<220> FEATURE:
<223> OTHER INFORMATION: primer

<400> SEQUENCE: 75
cgctctccaa ggcgccaagg agagg                                            25

<210> SEQ ID NO 76
<211> LENGTH: 696
<212> TYPE: DNA
<213> ORGANISM: Artificial Sequence
<220> FEATURE:
<223> OTHER INFORMATION: 18R5  LC coding (codon-optimized)

<400> SEQUENCE: 76
atggcctggg ccctgctgct gctgaccctg ctgacacagg gcaccggctc ttgggccgac     60
atcgagctga cccagcctcc ctccgtgtcc gtggcccctg gccagaccgc ccggatctcc    120
tgctccggcg acaacatcgg cagcttctac gtgcactggt atcagcagaa acctggacag    180
gcccctgtgc tggtgatcta cgacaagtcc aaccggcctt ccggcatccc tgagcggttc    240
tccggctcca actccggcaa caccgccacc ctgaccatct ccggcaccca ggccgaggac    300
gaggccgact actactgcca gtcctacgcc aacaccctgt ccctggtgtt tggcggcgga    360
acaaagctga ccgtgctggg ccagcctaag gccgctcctt ccgtgaccct gttccctcct    420
tcctccgagg agctgcaggc caacaaggcc accctggtgt gcctgatctc cgacttctac    480
cctggcgctg tgactgtggc ttggaaggcc gactcctccc ctgtgaaggc cggcgtggag    540
acaaccaccc cttccaagca gtccaacaac aagtacgccg cctcctccta cctgtccctg    600 accccctgagc agtggaagtc ccaccggtcc tactcttgcc aggtgaccca cgagggctcc    660
accgtggaaa agacagtggc acccaccgag tgctcc                              696

<210> SEQ ID NO 77
<211> LENGTH: 10
<212> TYPE: PRT
<213> ORGANISM: Artificial Sequence
<220> FEATURE:
<223> OTHER INFORMATION: heavy chain CDR1

<400> SEQUENCE: 77

Gly Phe Thr Phe Ser Ser Tyr Tyr Ile Thr
```

<210> SEQ ID NO 78
<211> LENGTH: 17
<212> TYPE: PRT
<213> ORGANISM: Artificial Sequence
<220> FEATURE:
<223> OTHER INFORMATION: heavy chain CDR2

<400> SEQUENCE: 78

Thr Ile Ser Tyr Ser Ser Ser Asn Thr Tyr Tyr Ala Asp Ser Val Lys
1               5                   10                  15
Gly

<210> SEQ ID NO 79
<211> LENGTH: 6
<212> TYPE: PRT
<213> ORGANISM: Artificial Sequence
<220> FEATURE:
<223> OTHER INFORMATION: heavy chain CDR3

<400> SEQUENCE: 79

Ser Ile Val Phe Asp Tyr
1               5

<210> SEQ ID NO 80
<211> LENGTH: 11
<212> TYPE: PRT
<213> ORGANISM: Artificial Sequence
<220> FEATURE:
<223> OTHER INFORMATION: light chain CDR1

<400> SEQUENCE: 80

Ser Gly Asp Ala Leu Gly Asn Arg Tyr Val Tyr
1               5                   10

<210> SEQ ID NO 81
<211> LENGTH: 2
<212> TYPE: PRT
<213> ORGANISM: Artificial Sequence
<220> FEATURE:
<223> OTHER INFORMATION: light chain CDR2

<400> SEQUENCE: 81

Ser Gly
1

<210> SEQ ID NO 82
<211> LENGTH: 11
<212> TYPE: PRT
<213> ORGANISM: Artificial Sequence
<220> FEATURE:
<223> OTHER INFORMATION: light chain CDR3

<400> SEQUENCE: 82

Gly Ser Trp Asp Thr Arg Pro Tyr Pro Lys Tyr
1               5                   10

<210> SEQ ID NO 83
<211> LENGTH: 696
<212> TYPE: DNA
<213> ORGANISM: Artificial Sequence
<220> FEATURE:
<223> OTHER INFORMATION: 18R4605 LC coding

<400> SEQUENCE: 83

```
atggcatggg cattattgct acttactcta ttgacgcaag gaacgggttc atgggcagac      60
atagaactaa ctcagccacc ctctgttagc gttgcaccgg gacagacggc acgtatatcg     120
tgctcgggag acaatatagg aagtttctat gtacattggt atcaacagaa acctggtcaa     180
gcacctgtat tagtaatcta tgacaaaagt aaccgacctt ccggaatacc tgagcgtttc     240
agtggttcga actccggcaa cactgcaact ttaactatat ctggaactca ggcggaggat     300
gaggctgact actactgcca gagttacgca aacactctgt ccctggtgtt tggcggcgga     360
acaaagttaa ccgtgctggg ccagcctaag gccgcacctt cggtgaccct attccctcct     420
tcatccgagg agctacaggc caacaaggcc accttagtgt gcctaatctc gacttctat      480
cctggtgctg taacggtagc gtggaaggcc gactcatcgc cggtgaaggc cggtgtggag     540
acaacgactc cttccaagca gtccaacaac aaatacgccg cgtcctccta cctgtcccta     600
accctgagc agtggaagtc ccaccgttca tactcgtgcc aggtgacgca cgagggttca     660
acggtcgaaa agacagtagc acctactgaa tgctca                              696
```

`<210>` SEQ ID NO 84
`<211>` LENGTH: 696
`<212>` TYPE: DNA
`<213>` ORGANISM: Artificial Sequence
`<220>` FEATURE:
`<223>` OTHER INFORMATION: 18R4805 LC coding

`<400>` SEQUENCE: 84

```
atggcatggg cattattact acttactcta cttacgcaag gaacgggttc atgggcagac      60
atagaactaa ctcagccgcc gtctgttagc gttgcaccgg gacagacggc acgtatatcg     120
tgctcgggag acaatattgg ttctttctat gtacattggt atcaacagaa acctggtcaa     180
gcacctgtat tagtaatata tgacaaaagt aaccgtcctt cgggaatacc tgagcgtttc     240
agtggttcga actcgggcaa cactgcaact ttaactatat ctggaacgca ggcggaggat     300
gaggcggact actattgcca aagttacgca aacactctat ccttagtgtt tggtggagga     360
acaaagttaa ccgtgctagg ccagcctaag gccgcacctt cggtgaccct attccctcct     420
tcatccgagg agctacaggc gaacaaagcc accttagtgt gcctaatctc agactttat     480
cctggtgctg taacggtagc gtggaaggcg gactcatcgc cggtgaaggc cggtgtggag     540
acaacgactc cttccaagca gtccaacaac aaatacgcag cgagtagtta cctgtcccta     600
accctgagc agtggaagtc gcaccgttca tactcgtgcc aggttacgca cgagggttca     660
acggtcgaaa agacagtagc acctacggaa tgctca                              696
```

`<210>` SEQ ID NO 85
`<211>` LENGTH: 115
`<212>` TYPE: PRT
`<213>` ORGANISM: Artificial Sequence
`<220>` FEATURE:
`<223>` OTHER INFORMATION: 44R24 VH

`<400>` SEQUENCE: 85

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Ile Thr Trp Val Arg Gln Ala Pro Gly Lys Gly Leu Glu Trp Val
        35                  40                  45

Ser Thr Ile Ser Tyr Ser Ser Asn Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Ile Val Phe Asp Tyr Trp Gly Gln Gly Thr Leu Val Thr
            100                 105                 110

Val Ser Ser
        115

<210> SEQ ID NO 86
<211> LENGTH: 104
<212> TYPE: PRT
<213> ORGANISM: Artificial Sequence
<220> FEATURE:
<223> OTHER INFORMATION: 44R24 VL

<400> SEQUENCE: 86

Asp Ile Glu Leu Thr Gln Pro Pro Ser Val Ser Val Ala Pro Gly Gln
 1               5                  10                  15

Thr Ala Arg Ile Ser Cys Ser Gly Asp Ala Leu Gly Asn Arg Tyr Val
             20                  25                  30

Tyr Trp Tyr Gln Gln Lys Pro Gly Gln Ala Pro Val Leu Val Ile Pro
         35                  40                  45

Ser Gly Ile Pro Glu Arg Phe Ser Gly Ser Asn Ser Gly Asn Thr Ala
 50                  55                  60

Thr Leu Thr Ile Ser Gly Thr Gln Ala Glu Asp Glu Ala Asp Tyr Tyr
 65                  70                  75                  80

Cys Gly Ser Trp Asp Thr Arg Pro Tyr Pro Lys Tyr Val Phe Gly Gly
                 85                  90                  95

Gly Thr Lys Leu Thr Val Leu Gly
            100

<210> SEQ ID NO 87
<211> LENGTH: 354
<212> TYPE: DNA
<213> ORGANISM: Artificial Sequence
<220> FEATURE:
<223> OTHER INFORMATION: 18R5/18R8 VH coding (codon-optimized)

<400> SEQUENCE: 87
gaggtgcagc tggtcgagtc tggcggcgga ctggtgcagc ctggcggctc cctgagactg      60
tcctgcgccg cctccggctt caccttctcc cactacaccc tgtcctgggt gcgccaggca     120
ccagggaagg gactggagtg ggtctccgtg atctccggcg acggtcctca cactactac      180 gccgactccg tgaagggccg gttcaccatc tcctccgaca actccaagaa caccctgtac     240
ctgcagatga actctctgag agccgaggac accgccgtgt actactgcgc ccggaacttc     300
atcaagtacg tgttcgccaa ctggggccag ggcaccctgg tgaccgtgtc ctcc           354

<210> SEQ ID NO 88
<211> LENGTH: 324
<212> TYPE: DNA
<213> ORGANISM: Artificial
<220> FEATURE:
<223> OTHER INFORMATION: 18R8 VL codon-optimized coding sequence

<400> SEQUENCE: 88
gacatcgagc tgacccagcc tcccteegtg tctgtggctc ctggccagac cgcccggatc      60
tcctgctccg gcgacaagct gggcaagaag tacgcctcct ggtatcagca gaagcctgga     120
```

| | |
|---|---|
| caggcccctg tgctggtcat ctacgagaag gacaaccggc ctagcggcat ccctgagcgg | 180 |
| ttctccggct ccaactccgg caacaccgcc accctgacca tctccggcac ccaggccgag | 240 |
| gacgaggccg actactactg ctcctccttc gccggcaact ccctggaagt gttcggcgga | 300 |
| ggcaccaagc tgaccgtgct gggc | 324 |

<210> SEQ ID NO 89
<211> LENGTH: 324
<212> TYPE: DNA
<213> ORGANISM: Artificial Sequence
<220> FEATURE:
<223> OTHER INFORMATION: 18R5 VL coding (codon-optimized)

<400> SEQUENCE: 89

| | |
|---|---|
| gacatcgagc tgacccagcc tcctccgtg tccgtggccc ctggccagac cgcccggatc | 60 |
| tcctgctccg gcgacaacat cggcagcttc tacgtgcact ggtatcagca gaaacctgga | 120 |
| caggcccctg tgctggtgat ctacgacaag tccaaccggc cttccggcat ccctgagcgg | 180 |
| ttctccggct ccaactccgg caacaccgcc accctgacca tctccggcac ccaggccgag | 240 |
| gacgaggccg actactactg ccagtcctac gccaacaccc tgtccctggt gtttggcggc | 300 |
| ggaacaaagc tgaccgtgct gggc | 324 |

<210> SEQ ID NO 90
<211> LENGTH: 324
<212> TYPE: DNA
<213> ORGANISM: Artificial Sequence
<220> FEATURE:
<223> OTHER INFORMATION: 18R4605 VL coding

<400> SEQUENCE: 90

| | |
|---|---|
| gacatagaac taactcagcc accctctgtt agcgttgcac cgggacagac ggcacgtata | 60 |
| tcgtgctcgg gagacaatat aggaagtttc tatgtacatt ggtatcaaca gaaacctggt | 120 |
| caagcacctg tattagtaat ctatgacaaa agtaaccgac cttccggaat acctgagcgt | 180 |
| ttcagtggtt cgaactccgg caacactgca actttaacta tatctggaac tcaggcggag | 240 |
| gatgaggctg actactactg ccagagttac gcaaacactc tgtccctggt gtttggcggc | 300 |
| ggaacaaagt taaccgtgct gggc | 324 |

<210> SEQ ID NO 91
<211> LENGTH: 1365
<212> TYPE: DNA
<213> ORGANISM: Artificial Sequence
<220> FEATURE:
<223> OTHER INFORMATION: 44R24 HC coding

<400> SEQUENCE: 91

| | |
|---|---|
| atgaagcacc tgtggttctt tctgctgctg gtggccgctc ctagatgggt gctgtccgag | 60 |
| gtgcagctgg tggagtctgg cggaggactg gtgcagcctg gcggctccct gagactgtct | 120 |
| tgcgccgcct ccggcttcac cttctcctct tactacatca cctgggtgcg ccaggctcct | 180 |
| ggcaagggac tggaatgggt gtccaccatc tcctactcct ccagcaacac ctactacgcc | 240 |
| gactccgtga agggccggtt caccatctcc cgggacaact ccaagaacac cctgtacctg | 300 |
| cagatgaact ccctgagggc cgaggacacc gccgtgtact actgcgcccg gtccatcgtg | 360 |
| ttcgactact ggggccaggg caccctggtg accgtgtcct cttccgtgtt ccctctggcc | 420 |
| ccttgctccc ggtccacctc tgagtctacc gccgctctgg gctgcctggt gaaggactac | 480 |

```
ttccctgagc ctgtgaccgt gtcctggaac tctggcgccc tgacctctgg cgtgcacacc     540
ttccctgccg tgctgcagtc ctccggcctg tactccctgt cctccgtggt gaccgtgcct     600
tcctccaact tcggcaccca gacctacacc tgcaacgtgg accacaagcc ttccaacacc     660
aaggtggaca agaccgtgga gcggaagtgc tgcgtggagt gccctccttg tcctgctcct     720
cctgtggctg gcccttctgt gttcctgttc cctcctaagc ctaaggacac cctgatgatc     780
tcccggaccc ctgaagtgac ctgcgtggtg gtggacgtgt cccacgagga ccctgaggtg     840
cagttcaatt ggtacgtgga cggcgtggag gtgcacaacg ccaagaccaa gcctcgggag     900
gaacagttca actccacctt ccgggtggtg tctgtgctga ccgtggtgca ccaggactgg     960
ctgaacggca agaatacaa gtgcaaggtg tccaacaagg cctgcctgc ccctatcgaa    1020 aagaccatct ctaagaccaa gggccagcct cgcgagcctc aggtctacac cctgcctcct    1080
agccgggagg aaatgaccaa gaaccaggtg tccctgacct gtctggtgaa gggcttctac    1140
ccttccgata cgccgtgga gtgggagtct aacggccagc tgagaacaa ctacaagacc    1200 accctcctta tgctggactc cgacggctcc ttcttcctgt actccaagct gacagtggac    1260
aagtcccggt ggcagcaggg caacgtgttc tcctgctccg tgatgcacga ggccctgcac    1320
aaccactaca cccagaagtc cctgtccctg tctcctggca agtga                    1365

<210> SEQ ID NO 92
<211> LENGTH: 324
<212> TYPE: DNA
<213> ORGANISM: Artificial Sequence
<220> FEATURE:
<223> OTHER INFORMATION: 18R4805 VL coding

<400> SEQUENCE: 92
gacatagaac taactcagcc gccgtctgtt agcgttgcac cgggacagac ggcacgtata      60
tcgtgctcgg gagacaatat tggttctttc tatgtacatt ggtatcaaca gaaacctggt     120
caagcacctg tattagtaat atatgacaaa agtaaccgtc cttcgggaat acctgagcgt     180
ttcagtggtt cgaactcggg caacactgca actttaacta tatctggaac gcaggcggag     240
gatgaggcgg actactattg ccaaagttac gcaaacactc tatccttagt gtttggtgga     300
ggaacaaagt taaccgtgct aggc                                            324

<210> SEQ ID NO 93
<211> LENGTH: 672
<212> TYPE: DNA
<213> ORGANISM: Artificial Sequence
<220> FEATURE:
<223> OTHER INFORMATION: 44R24 LC coding

<400> SEQUENCE: 93
atggcttggg ctctgctgct gctgacctg ctgacacagg gcaccggctc ttgggccgac      60
atcgagctga cccagcctcc ctctgtgtct gtggcccctg gccagaccgc caggatctct     120
tgctctggcg acgccctggg caacagatac gtgtactgg atcagcagaa gccaggccag     180
gcccctgtgc tggtgatccc ttccggcatc cctgagcggt tctccggctc caactccggc     240
aacaccgcca ccctgaccat ctctggcacc caggccgagg acgaggccga ctactactgc     300
ggctcctggg acacccggcc ttaccctaag tacgtgttcg gcggaggcac caagctgacc     360 gtgctggcc cttccgtgac cctgttccct ccatcctccg aggaactgca ggccaacaag     420
gccaccctgt gtgctgat ctccgacttc taccctggcg ccgtgaccgt ggcttggaag     480
gccgactcta gccctgtgaa ggccggcgtg gagacaacca cccttccaa gcagtccaac     540
```

```
aacaagtacg ccgcctcctc ctacctgtcc ctgaccctg agcagtggaa gtcccaccgg    600
tcctactctt gccaggtgac ccacgagggc tccaccgtgg aaaagaccgt ggcccctacc    660
gagtgctcct ag                                                        672
```

<210> SEQ ID NO 94
<211> LENGTH: 345
<212> TYPE: DNA
<213> ORGANISM: Artificial Sequence
<220> FEATURE:
<223> OTHER INFORMATION: 44R24 VH coding

<400> SEQUENCE: 94

```
gaggtgcagc tggtggagtc tggcggagga ctggtgcagc ctggcggctc cctgagactg    60
tcttgcgccg cctccggctt caccttctcc tcttactaca tcacctgggt gcgccaggct    120
cctggcaagg gactggaatg ggtgtccacc atctcctact cctccagcaa cacctactac    180
gccgactccg tgaagggccg gttcaccatc tcccggaca actccaagaa caccctgtac    240
ctgcagatga actccctgag gccgaggac accgccgtgt actactgcgc ccggtccatc    300
gtgttcgact actggggcca gggcaccctg gtgaccgtgt cctct                    345
```

<210> SEQ ID NO 95
<211> LENGTH: 312
<212> TYPE: DNA
<213> ORGANISM: Artificial Sequence
<220> FEATURE:
<223> OTHER INFORMATION: 44R24 VL coding

<400> SEQUENCE: 95

```
gacatcgagc tgacccagcc tccctctgtg tctgtggccc ctggccagac cgccaggatc    60
tcttgctctg gcgacgccct gggcaacaga tacgtgtact ggtatcagca aaagccaggc    120
caggcccctg tgctggtgat cccttccggc atccctgagc ggttctccgg ctccaactcc    180
ggcaacaccg ccaccctgac catctctggc acccaggccg aggacgaggc cgactactac    240
tgcggctcct gggacacccg gccttaccct aagtacgtgt tcggcggagg caccaagctg    300
accgtgctgg gc                                                        312
```

<210> SEQ ID NO 96
<211> LENGTH: 1389
<212> TYPE: DNA
<213> ORGANISM: Artificial Sequence
<220> FEATURE:
<223> OTHER INFORMATION: 18R5/18R8/18R4605/18R4805 IgG2 HC coding
        (codon-optimized)

<400> SEQUENCE: 96

```
atgaagcacc tgtggttctt tctgctgctg gtcgccgctc ctagatgggt gctgtccgag    60
gtgcagctgg tcgagtctgg cggcggactg gtgcagcctg gcggctccct gagactgtcc    120
tgcgccgcct ccggcttcac cttctcccac tacaccctgt cctgggtgcg ccaggcacca    180
gggaagggac tggagtgggt ctccgtgatc tccggcgacg gctcctacac ctactacgcc    240
gactccgtga agggccggtt caccatctcc tccgacaact ccaagaacac cctgtacctg    300
cagatgaact ctctgagagc cgaggacacc gccgtgtact actgcgcccg gaacttcatc    360
aagtacgtgt tcgccaactg ggggcagggc accctggtga ccgtgtcctc cgcctccacc    420
aagggccctt ccgtgttccc tctggcccct gctcccggt ccacctccga gtccaccgcc    480
gctctgggct gcctggtgaa ggactacttc cctgagcctg tgacagtgtc ctggaactct    540
```

```
ggcgccctga cctccggcgt gcacaccttc cctgccgtgc tgcagtcctc cggcctgtac    600
tccctgtcct ccgtggtgac agtgccttcc tccaacttcg gcacccagac ctacacctgc    660
aacgtggacc acaagccttc caacaccaag gtggacaaga ccgtggagcg aagtgctgc     720 gtggagtgcc ctccttgccc tgcccctcct gtggctggtc ctagcgtgtt cctgttccct    780
cctaagccta aggacaccct gatgatctcc cggacccctg aggtgacctg cgtggtggtg    840
gacgtgtccc acgaggatcc tgaagtccag ttcaattggt acgtggacgg cgtggaggtg    900
cacaacgcca agaccaagcc tcgggaggag cagttcaact ccaccttccg ggtggtgtcc    960
gtgctgaccg tggtgcacca ggactggctg aacggcaaag aatacaagtg caaagtctcc    1020
aacaagggcc tgcctgcccc tatcgaaaag accatcagca agaccaaggg ccagcctcgc    1080
gagcctcagg tgtacaccct gcctccctct cgcgaagaga tgaccaagaa ccaggtgtcc    1140
ctgacctgtc tggtgaaggg cttctaccct tccgatatcg ccgtggagtg ggagtccaac    1200
ggccagcctg agaacaacta caagaccacc ctcctatgc tggactccga cggctctttc     1260
ttcctgtact ccaagctgac agtggacaag tcccggtggc agcagggcaa cgtgttctcc    1320
tgctccgtga tgcacgaggc cctgcacaat cactacaccc agaagtccct gtccctgtct    1380
cctggcaag                                                            1389

<210> SEQ ID NO 97
<211> LENGTH: 696
<212> TYPE: DNA
<213> ORGANISM: Artificial Sequence
<220> FEATURE:
<223> OTHER INFORMATION: 18R8 lambda LC coding (codon-optimized)

<400> SEQUENCE: 97
atggcctggg ccctgctgct gctgaccctg ctgacacagg gcaccggctc ttgggccgac    60
atcgagctga cccagcctcc ctccgtgtct gtggctcctg gccagaccgc ccggatctcc    120
tgctccggcg acaagctggg caagaagtac gcctcctggt atcagcagaa gcctggacag    180
gcccctgtgc tggtcatcta cgagaaggac aaccggccta gcggcatccc tgagcggttc    240
tccggctcca actccggcaa caccgccacc ctgaccatct ccggcaccca ggccgaggac    300
gaggccgact actactgctc ctccttcgcc ggcaactccc tggaagtgtt cggcggaggc    360
accaagctga ccgtgctggg ccagcctaag gccgctcctt ccgtgaccct gttccctcct    420
tcctccgagg aactgcaggc caacaaggcc accctggtct gcctgatctc cgacttctac    480
cctggcgccg tgaccgtggc ctggaaggcc gactcctccc ctgtgaaggc cggcgtggag    540
acaaccaccc cttccaagca gtccaacaac aagtacgccg cctcctccta cctgtccctg    600 accctgagc agtggaagtc caccggtcc tactcttgcc aggtcaccca cgagggctcc      660
accgtggaaa agacagtggc ccccaccgag tgctcc                              696

<210> SEQ ID NO 98
<211> LENGTH: 9
<212> TYPE: PRT
<213> ORGANISM: Artificial Sequence
<220> FEATURE:
<223> OTHER INFORMATION: Cyclic peptide

<400> SEQUENCE: 98

Cys Pro Leu Tyr Phe Pro Leu Tyr Cys
1               5
```

```
<210> SEQ ID NO 99
<211> LENGTH: 9
<212> TYPE: PRT
<213> ORGANISM: Artificial Sequence
<220> FEATURE:
<223> OTHER INFORMATION: Cyclic peptide

<400> SEQUENCE: 99

Cys Pro Leu Val Trp Pro Leu Ile Cys
1               5

<210> SEQ ID NO 100
<211> LENGTH: 9
<212> TYPE: PRT
<213> ORGANISM: Artificial Sequence
<220> FEATURE:
<223> OTHER INFORMATION: Cyclic peptide

<400> SEQUENCE: 100

Cys Pro Leu Ala Trp Pro Leu Ile Cys
1               5

<210> SEQ ID NO 101
<211> LENGTH: 9
<212> TYPE: PRT
<213> ORGANISM: Artificial Sequence
<220> FEATURE:
<223> OTHER INFORMATION: Cyclic peptide

<400> SEQUENCE: 101

Cys Pro Val Lys Tyr Pro Leu Val Cys
1               5

<210> SEQ ID NO 102
<211> LENGTH: 9
<212> TYPE: PRT
<213> ORGANISM: Artificial Sequence
<220> FEATURE:
<223> OTHER INFORMATION: Cyclic peptide

<400> SEQUENCE: 102

Cys Pro Leu Arg Phe Pro Leu Phe Cys
1               5

<210> SEQ ID NO 103
<211> LENGTH: 9
<212> TYPE: PRT
<213> ORGANISM: Artificial Sequence
<220> FEATURE:
<223> OTHER INFORMATION: Cyclic peptide

<400> SEQUENCE: 103

Cys Pro Leu Ala Trp Pro Leu Ile Cys
1               5

<210> SEQ ID NO 104
<211> LENGTH: 9
<212> TYPE: PRT
<213> ORGANISM: Artificial Sequence
<220> FEATURE:
<223> OTHER INFORMATION: Cyclic peptide

<400> SEQUENCE: 104

Cys Pro Val Ala Phe Pro Leu Tyr Cys
1               5

<210> SEQ ID NO 105
```

```
<211> LENGTH: 9
<212> TYPE: PRT
<213> ORGANISM: Artificial Sequence
<220> FEATURE:
<223> OTHER INFORMATION: Cyclic peptide

<400> SEQUENCE: 105

Cys Pro Val Asn Tyr Pro Leu Tyr Cys
1               5

<210> SEQ ID NO 106
<211> LENGTH: 9
<212> TYPE: PRT
<213> ORGANISM: Artificial Sequence
<220> FEATURE:
<223> OTHER INFORMATION: Cyclic peptide

<400> SEQUENCE: 106

Cys Pro Val Lys Phe Pro Leu Tyr Cys
1               5

<210> SEQ ID NO 107
<211> LENGTH: 9
<212> TYPE: PRT
<213> ORGANISM: Artificial Sequence
<220> FEATURE:
<223> OTHER INFORMATION: Cyclic peptide

<400> SEQUENCE: 107

Cys Pro Leu Thr Tyr Pro Leu Tyr Cys
1               5

<210> SEQ ID NO 108
<211> LENGTH: 9
<212> TYPE: PRT
<213> ORGANISM: Artificial Sequence
<220> FEATURE:
<223> OTHER INFORMATION: Cyclic peptide

<400> SEQUENCE: 108

Cys Pro Leu Arg Trp Pro Leu Met Cys
1               5

<210> SEQ ID NO 109
<211> LENGTH: 9
<212> TYPE: PRT
<213> ORGANISM: Artificial Sequence
<220> FEATURE:
<223> OTHER INFORMATION: Cyclic peptide

<400> SEQUENCE: 109

Cys Pro Leu Gln Tyr Pro Leu Met Cys
1               5

<210> SEQ ID NO 110
<211> LENGTH: 9
<212> TYPE: PRT
<213> ORGANISM: Artificial Sequence
<220> FEATURE:
<223> OTHER INFORMATION: Cyclic peptide

<400> SEQUENCE: 110

Cys Pro Leu Ser Phe Pro Leu Tyr Cys
1               5

<210> SEQ ID NO 111
<211> LENGTH: 9
```

```
<212> TYPE: PRT
<213> ORGANISM: Artificial Sequence
<220> FEATURE:
<223> OTHER INFORMATION: Cyclic peptide

<400> SEQUENCE: 111

Cys Pro Leu Asn Trp Pro Leu Met Cys
1               5

<210> SEQ ID NO 112
<211> LENGTH: 9
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (3)..(3)
<223> OTHER INFORMATION: Xaa is Leu or Val
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa is Tyr, Phe, or Trp
<220> FEATURE:
<221> NAME/KEY: MISC_FEATURE
<222> LOCATION: (8)..(8)
<223> OTHER INFORMATION: Xaa is Tyr, Phe, Ile, Val, or Met

<400> SEQUENCE: 112

Cys Pro Xaa Xaa Xaa Pro Leu Xaa Cys
1               5

<210> SEQ ID NO 113
<211> LENGTH: 12
<212> TYPE: PRT
<213> ORGANISM: Artificial Sequence
<220> FEATURE:
<223> OTHER INFORMATION: Peptide

<400> SEQUENCE: 113

Asp Thr Leu Ser Ala Leu Ile Glu Arg Gly Leu Met
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Peptide

<400> SEQUENCE: 114

Asp Val Trp Trp Leu Gly Ser Thr Trp Leu Lys Arg
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Peptide

<400> SEQUENCE: 115

Phe Gly Asn Tyr Leu Asn Asp Val Arg Phe Leu Ile
1               5                   10
```

<210> SEQ ID NO 116
<211> LENGTH: 12
<212> TYPE: PRT
<213> ORGANISM: Artificial Sequence
<220> FEATURE:
<223> OTHER INFORMATION: Peptide

<400> SEQUENCE: 116

Thr Asn Leu Ala Asp Ile Ala His Trp Ile Ser Gly
1               5                   10

<210> SEQ ID NO 117
<211> LENGTH: 112
<212> TYPE: PRT
<213> ORGANISM: Artificial Sequence
<220> FEATURE:
<223> OTHER INFORMATION: h-FZD1

<400> SEQUENCE: 117

Cys Gln Pro Ile Ser Ile Pro Leu Cys Thr Asp Ile Ala Tyr Asn Gln
1               5                   10                  15

Thr Ile Met Pro Asn Leu Leu Gly His Thr Asn Gln Glu Asp Ala Gly
            20                  25                  30

Leu Glu Val His Gln Phe Tyr Pro Leu Val Lys Val Gln Cys Ser Ala
        35                  40                  45

Glu Leu Lys Phe Phe Leu Cys Ser Met Tyr Ala Pro Val Cys Thr Val
    50                  55                  60

Leu Glu Gln Ala Leu Pro Pro Cys Arg Ser Leu Cys Glu Arg Ala Arg
65                  70                  75                  80

Gln Gly Cys Glu Ala Leu Met Asn Lys Phe Gly Phe Gln Trp Pro Asp
                85                  90                  95

Thr Leu Lys Cys Glu Lys Phe Pro Val His Gly Ala Gly Glu Leu Cys
            100                 105                 110

<210> SEQ ID NO 118
<211> LENGTH: 112
<212> TYPE: PRT
<213> ORGANISM: Artificial Sequence
<220> FEATURE:
<223> OTHER INFORMATION: h-FZD2

<400> SEQUENCE: 118

Cys Gln Pro Ile Ser Ile Pro Leu Cys Thr Asp Ile Ala Tyr Asn Gln
1               5                   10                  15

Thr Ile Met Pro Asn Leu Leu Gly His Thr Asn Gln Glu Asp Ala Gly
            20                  25                  30

Leu Glu Val His Gln Phe Tyr Pro Leu Val Lys Val Gln Cys Ser Pro
        35                  40                  45

Glu Leu Arg Phe Phe Leu Cys Ser Met Tyr Ala Pro Val Cys Thr Val
    50                  55                  60

Leu Glu Gln Ala Ile Pro Pro Cys Arg Ser Ile Cys Glu Arg Ala Arg
65                  70                  75                  80

Gln Gly Cys Glu Ala Leu Met Asn Lys Phe Gly Phe Gln Trp Pro Glu
                85                  90                  95

Arg Leu Arg Cys Glu His Phe Pro Arg His Gly Ala Glu Gln Ile Cys
            100                 105                 110

<210> SEQ ID NO 119
<211> LENGTH: 106
<212> TYPE: PRT
<213> ORGANISM: Artificial Sequence
<220> FEATURE:
<223> OTHER INFORMATION: h-FZD3

<400> SEQUENCE: 119

Cys Glu Pro Ile Thr Leu Arg Met Cys Gln Asp Leu Pro Tyr Asn Thr
1               5                   10                  15

Thr Phe Met Pro Asn Leu Leu Asn His Tyr Asp Gln Gln Thr Ala Ala
            20                  25                  30

Leu Ala Met Glu Pro Phe His Pro Met Val Asn Leu Asp Cys Ser Arg
        35                  40                  45

Asp Phe Arg Pro Phe Leu Cys Ala Leu Tyr Ala Pro Ile Cys Met Glu
    50                  55                  60

Tyr Gly Arg Val Thr Leu Pro Cys Arg Arg Leu Cys Gln Arg Ala Tyr
65                  70                  75                  80

Ser Glu Cys Ser Lys Leu Met Glu Met Phe Gly Val Pro Trp Pro Glu
                85                  90                  95

Asp Met Glu Cys Ser Arg Phe Pro Asp Cys
            100                 105

<210> SEQ ID NO 120
<211> LENGTH: 114
<212> TYPE: PRT
<213> ORGANISM: Artificial Sequence
<220> FEATURE:
<223> OTHER INFORMATION: h-FZD4

<400> SEQUENCE: 120

Cys Asp Pro Ile Arg Ile Ser Met Cys Gln Asn Leu Gly Tyr Asn Val
1               5                   10                  15

Thr Lys Met Pro Asn Leu Val Gly His Glu Leu Gln Thr Asp Ala Glu
            20                  25                  30

Leu Gln Leu Thr Thr Phe Thr Pro Leu Ile Gln Tyr Gly Cys Ser Ser
        35                  40                  45

Gln Leu Gln Phe Phe Leu Cys Ser Val Tyr Val Pro Met Cys Thr Glu
    50                  55                  60

Lys Ile Asn Ile Pro Ile Gly Pro Cys Gly Gly Met Cys Leu Ser Val
65                  70                  75                  80

Lys Arg Arg Cys Glu Pro Val Leu Lys Glu Phe Gly Phe Ala Trp Pro
                85                  90                  95

Glu Ser Leu Asn Cys Ser Lys Phe Pro Pro Gln Asn Asp His Asn His
            100                 105                 110

Met Cys

<210> SEQ ID NO 121
<211> LENGTH: 115
<212> TYPE: PRT
<213> ORGANISM: Artificial Sequence
<220> FEATURE:
<223> OTHER INFORMATION: h-FZD5

<400> SEQUENCE: 121

Cys Gln Glu Ile Thr Val Pro Met Cys Arg Gly Ile Gly Tyr Asn Leu
1               5                   10                  15

Thr His Met Pro Asn Gln Phe Asn His Asp Thr Gln Asp Glu Ala Gly
            20                  25                  30

Leu Glu Val His Gln Phe Trp Pro Leu Val Glu Ile Gln Cys Ser Pro
        35                  40                  45

Asp Leu Arg Phe Phe Leu Cys Ser Met Tyr Thr Pro Ile Cys Leu Pro

Asp Tyr His Lys Pro Leu Pro Pro Cys Arg Ser Val Cys Glu Arg Ala
65                  70                  75                  80

Lys Ala Gly Cys Ser Pro Leu Met Arg Gln Tyr Gly Phe Ala Trp Pro
                85                  90                  95

Glu Arg Met Ser Cys Asp Arg Leu Pro Val Leu Gly Arg Asp Ala Glu
            100                 105                 110

Val Leu Cys
        115

<210> SEQ ID NO 122
<211> LENGTH: 106
<212> TYPE: PRT
<213> ORGANISM: Artificial Sequence
<220> FEATURE:
<223> OTHER INFORMATION: h-FZD6

<400> SEQUENCE: 122

Cys Glu Pro Ile Thr Val Pro Arg Cys Met Lys Met Ala Tyr Asn Met
1               5                   10                  15

Thr Phe Phe Pro Asn Leu Met Gly His Tyr Asp Gln Ser Ile Ala Ala
            20                  25                  30

Val Glu Met Glu His Phe Leu Pro Leu Ala Asn Leu Glu Cys Ser Pro
        35                  40                  45

Asn Ile Glu Thr Phe Leu Cys Lys Ala Phe Val Pro Thr Cys Ile Glu
    50                  55                  60

Gln Ile His Val Pro Pro Cys Arg Lys Leu Cys Glu Lys Val Tyr
65                  70                  75                  80

Ser Asp Cys Lys Lys Leu Ile Asp Thr Phe Gly Ile Arg Trp Pro Glu
                85                  90                  95

Glu Leu Glu Cys Asp Arg Leu Gln Tyr Cys
            100                 105

<210> SEQ ID NO 123
<211> LENGTH: 112
<212> TYPE: PRT
<213> ORGANISM: Artificial Sequence
<220> FEATURE:
<223> OTHER INFORMATION: h-FZD7

<400> SEQUENCE: 123

Cys Gln Pro Ile Ser Ile Pro Leu Cys Thr Asp Ile Ala Tyr Asn Gln
1               5                   10                  15

Thr Ile Leu Pro Asn Leu Leu Gly His Thr Asn Gln Glu Asp Ala Gly
            20                  25                  30

Leu Glu Val His Gln Phe Tyr Pro Leu Val Lys Val Gln Cys Ser Pro
        35                  40                  45

Glu Leu Arg Phe Phe Leu Cys Ser Met Tyr Ala Pro Val Cys Thr Val
    50                  55                  60

Leu Asp Gln Ala Ile Pro Pro Cys Arg Ser Leu Cys Glu Arg Ala Arg
65                  70                  75                  80

Gln Gly Cys Glu Ala Leu Met Asn Lys Phe Gly Phe Gln Trp Pro Glu
                85                  90                  95

Arg Leu Arg Cys Glu Asn Phe Pro Val His Gly Ala Gly Glu Ile Cys
            100                 105                 110

<210> SEQ ID NO 124
<211> LENGTH: 114

```
<212> TYPE: PRT
<213> ORGANISM: Artificial Sequence
<220> FEATURE:
<223> OTHER INFORMATION: h-FZD8

<400> SEQUENCE: 124

Cys Gln Glu Ile Thr Val Pro Leu Cys Lys Gly Ile Gly Tyr Asn Tyr
1               5                   10                  15

Thr Tyr Met Pro Asn Gln Phe Asn His Asp Thr Gln Asp Glu Ala Gly
            20                  25                  30

Leu Glu Val His Gln Phe Trp Pro Leu Val Glu Ile Gln Cys Ser Pro
        35                  40                  45

Asp Leu Lys Phe Phe Leu Cys Ser Met Tyr Thr Pro Ile Cys Leu Glu
    50                  55                  60

Asp Tyr Lys Lys Pro Leu Pro Pro Cys Arg Ser Val Cys Glu Arg Ala
65                  70                  75                  80

Lys Ala Gly Cys Ala Pro Leu Met Arg Gln Tyr Gly Phe Ala Trp Pro
                85                  90                  95

Asp Arg Met Arg Cys Asp Arg Leu Pro Glu Gln Gly Asn Pro Asp Thr
            100                 105                 110

Leu Cys

<210> SEQ ID NO 125
<211> LENGTH: 114
<212> TYPE: PRT
<213> ORGANISM: Artificial Sequence
<220> FEATURE:
<223> OTHER INFORMATION: h-FZD9

<400> SEQUENCE: 125

Cys Gln Ala Val Glu Ile Pro Met Cys Arg Gly Ile Gly Tyr Asn Leu
1               5                   10                  15

Thr Arg Met Pro Asn Leu Leu Gly His Thr Ser Gln Gly Glu Ala Ala
            20                  25                  30

Ala Glu Leu Ala Glu Phe Ala Pro Leu Val Gln Tyr Gly Cys His Ser
        35                  40                  45

His Leu Arg Phe Phe Leu Cys Ser Leu Tyr Ala Pro Met Cys Thr Asp
    50                  55                  60

Gln Val Ser Thr Pro Ile Pro Ala Cys Arg Pro Met Cys Glu Gln Ala
65                  70                  75                  80

Arg Leu Arg Cys Ala Pro Ile Met Glu Gln Phe Asn Phe Gly Trp Pro
                85                  90                  95

Asp Ser Leu Asp Cys Ala Arg Leu Pro Thr Arg Asn Asp Pro His Ala
            100                 105                 110

Leu Cys

<210> SEQ ID NO 126
<211> LENGTH: 114
<212> TYPE: PRT
<213> ORGANISM: Artificial Sequence
<220> FEATURE:
<223> OTHER INFORMATION: h-FZD10

<400> SEQUENCE: 126

Cys Gln Pro Ile Glu Ile Pro Met Cys Lys Asp Ile Gly Tyr Asn Met
1               5                   10                  15

Thr Arg Met Pro Asn Leu Met Gly His Glu Asn Gln Arg Glu Ala Ala
            20                  25                  30
```

Ile Gln Leu His Glu Phe Ala Pro Leu Val Glu Tyr Gly Cys His Gly
                35                  40                  45

His Leu Arg Phe Phe Leu Cys Ser Leu Tyr Ala Pro Met Cys Thr Glu
 50                      55                  60

Gln Val Ser Thr Pro Ile Pro Ala Cys Arg Val Met Cys Glu Gln Ala
 65                  70                  75                  80

Arg Leu Lys Cys Ser Pro Ile Met Glu Gln Phe Asn Phe Lys Trp Pro
                 85                  90                  95

Asp Ser Leu Asp Cys Arg Lys Leu Pro Asn Lys Asn Asp Pro Asn Tyr
            100                 105                 110

Leu Cys

<210> SEQ ID NO 127
<211> LENGTH: 117
<212> TYPE: PRT
<213> ORGANISM: Artificial Sequence
<220> FEATURE:
<223> OTHER INFORMATION: "h-Fz2"

<400> SEQUENCE: 127

Phe Cys Gln Pro Ile Ser Ile Pro Leu Cys Thr Asp Ile Ala Tyr Asn
1               5                  10                  15

Gln Thr Ile Met Pro Asn Leu Leu Gly His Thr Asn Gln Glu Asp Ala
                20                  25                  30

Gly Leu Glu Val His Gln Phe Tyr Pro Leu Val Lys Val Gln Cys Ser
                35                  40                  45

Pro Glu Leu Arg Phe Phe Leu Cys Ser Met Tyr Ala Pro Val Cys Thr
 50                      55                  60

Val Leu Glu Gln Ala Ile Pro Pro Cys Arg Ser Ile Cys Glu Arg Ala
 65                  70                  75                  80

Arg Gln Gly Cys Glu Ala Leu Met Asn Lys Phe Gly Phe Gln Trp Pro
                 85                  90                  95

Glu Arg Leu Arg Cys Glu His Phe Pro Arg His Gly Ala Glu Gln Ile
            100                 105                 110

Cys Val Gly Gln Asn
        115

<210> SEQ ID NO 128
<211> LENGTH: 117
<212> TYPE: PRT
<213> ORGANISM: Artificial Sequence
<220> FEATURE:
<223> OTHER INFORMATION: "h-Fz7"

<400> SEQUENCE: 128

Phe Cys Gln Pro Ile Ser Ile Pro Leu Cys Thr Asp Ile Ala Tyr Asn
1               5                  10                  15

Gln Thr Ile Leu Pro Asn Leu Leu Gly His Thr Asn Gln Glu Asp Ala
                20                  25                  30

Gly Leu Glu Val His Gln Phe Tyr Pro Leu Val Lys Val Gln Cys Ser
                35                  40                  45

Pro Glu Leu Arg Phe Phe Leu Cys Ser Met Tyr Ala Pro Val Cys Thr
 50                      55                  60

Val Leu Asp Gln Ala Ile Pro Pro Cys Arg Ser Leu Cys Glu Arg Ala
 65                  70                  75                  80

Arg Gln Gly Cys Glu Ala Leu Met Asn Lys Phe Gly Phe Gln Trp Pro
                 85                  90                  95

Glu Arg Leu Arg Cys Glu Asn Phe Pro Val His Gly Ala Gly Glu Ile
            100                 105                 110

Cys Val Gly Gln Asn
        115

<210> SEQ ID NO 129
<211> LENGTH: 117
<212> TYPE: PRT
<213> ORGANISM: Artificial Sequence
<220> FEATURE:
<223> OTHER INFORMATION: "h-Fz1"

<400> SEQUENCE: 129

Tyr Cys Gln Pro Ile Ser Ile Pro Leu Cys Thr Asp Ile Ala Tyr Asn
1               5                   10                  15

Gln Thr Ile Met Pro Asn Leu Leu Gly His Thr Asn Gln Glu Asp Ala
            20                  25                  30

Gly Leu Glu Val His Gln Phe Tyr Pro Leu Val Lys Val Gln Cys Ser
        35                  40                  45

Ala Glu Leu Lys Phe Phe Leu Cys Ser Met Tyr Ala Pro Val Cys Thr
    50                  55                  60

Val Leu Glu Gln Ala Leu Pro Pro Cys Arg Ser Leu Cys Glu Arg Ala
65                  70                  75                  80

Arg Gln Gly Cys Glu Ala Leu Met Asn Lys Phe Gly Phe Gln Trp Pro
                85                  90                  95

Asp Thr Leu Lys Cys Glu Lys Phe Pro Val His Gly Ala Gly Glu Leu
            100                 105                 110

Cys Val Gly Gln Asn
        115

<210> SEQ ID NO 130
<211> LENGTH: 120
<212> TYPE: PRT
<213> ORGANISM: Artificial Sequence
<220> FEATURE:
<223> OTHER INFORMATION: "h-Fz5"

<400> SEQUENCE: 130

Val Cys Gln Glu Ile Thr Val Pro Met Cys Arg Gly Ile Gly Tyr Asn
1               5                   10                  15

Leu Thr His Met Pro Asn Gln Phe Asn His Asp Thr Gln Asp Glu Ala
            20                  25                  30

Gly Leu Glu Val His Gln Phe Trp Pro Leu Val Glu Ile Gln Cys Ser
        35                  40                  45

Pro Asp Leu Arg Phe Phe Leu Cys Ser Met Tyr Thr Pro Ile Cys Leu
    50                  55                  60

Pro Asp Tyr His Lys Pro Leu Pro Pro Cys Arg Ser Val Cys Glu Arg
65                  70                  75                  80

Ala Lys Ala Gly Cys Ser Pro Leu Met Arg Gln Tyr Gly Phe Ala Trp
                85                  90                  95

Pro Glu Arg Met Ser Cys Asp Arg Leu Pro Val Leu Gly Arg Asp Ala
            100                 105                 110

Glu Val Leu Cys Met Asp Tyr Asn
        115                 120

<210> SEQ ID NO 131
<211> LENGTH: 119
<212> TYPE: PRT
<213> ORGANISM: Artificial Sequence
<220> FEATURE:
<223> OTHER INFORMATION: "h-Fz8"

<400> SEQUENCE: 131

Ala Cys Gln Glu Ile Thr Val Pro Leu Cys Lys Gly Ile Gly Tyr Asn
1               5                   10                  15

Tyr Thr Tyr Met Pro Asn Gln Phe Asn His Asp Thr Gln Asp Glu Ala
            20                  25                  30

Gly Leu Glu Val His Gln Phe Trp Pro Leu Val Glu Ile Gln Cys Ser
        35                  40                  45

Pro Asp Leu Lys Phe Phe Leu Cys Ser Met Tyr Thr Pro Ile Cys Leu
    50                  55                  60

Glu Asp Tyr Lys Lys Pro Leu Pro Pro Cys Arg Ser Val Cys Glu Arg
65                  70                  75                  80

Ala Lys Ala Gly Cys Ala Pro Leu Met Arg Gln Tyr Gly Phe Ala Trp
                85                  90                  95

Pro Asp Arg Met Arg Cys Asp Arg Leu Pro Glu Gln Gly Asn Pro Asp
            100                 105                 110

Thr Leu Cys Met Asp Tyr Asn
        115

<210> SEQ ID NO 132
<211> LENGTH: 119
<212> TYPE: PRT
<213> ORGANISM: Artificial Sequence
<220> FEATURE:
<223> OTHER INFORMATION: "h-Fz9"

<400> SEQUENCE: 132

Pro Cys Gln Ala Val Glu Ile Pro Met Cys Arg Gly Ile Gly Tyr Asn
1               5                   10                  15

Leu Thr Arg Met Pro Asn Leu Leu Gly His Thr Ser Gln Gly Glu Ala
            20                  25                  30

Ala Ala Glu Leu Ala Glu Phe Ala Pro Leu Val Gln Tyr Gly Cys His
        35                  40                  45

Ser His Leu Arg Phe Phe Leu Cys Ser Leu Tyr Ala Pro Met Cys Thr
    50                  55                  60

Asp Gln Val Ser Thr Pro Ile Pro Ala Cys Arg Pro Met Cys Glu Gln
65                  70                  75                  80

Ala Arg Leu Arg Cys Ala Pro Ile Met Glu Gln Phe Asn Phe Gly Trp
                85                  90                  95

Pro Asp Ser Leu Asp Cys Ala Arg Leu Pro Thr Arg Asn Asp Pro His
            100                 105                 110

Ala Leu Cys Met Glu Ala Pro
        115

<210> SEQ ID NO 133
<211> LENGTH: 119
<212> TYPE: PRT
<213> ORGANISM: Artificial Sequence
<220> FEATURE:
<223> OTHER INFORMATION: "h-Fz10"

<400> SEQUENCE: 133

Lys Cys Gln Pro Ile Glu Ile Pro Met Cys Lys Asp Ile Gly Tyr Asn
1               5                   10                  15

Met Thr Arg Met Pro Asn Leu Met Gly His Glu Asn Gln Arg Glu Ala
            20                  25                  30

```
Ala Ile Gln Leu His Glu Phe Ala Pro Leu Val Glu Tyr Gly Cys His
        35                  40                  45

Gly His Leu Arg Phe Phe Leu Cys Ser Leu Tyr Ala Pro Met Cys Thr
 50                  55                  60

Glu Gln Val Ser Thr Pro Ile Pro Ala Cys Arg Val Met Cys Glu Gln
65                  70                  75                  80

Ala Arg Leu Lys Cys Ser Pro Ile Met Glu Gln Phe Asn Phe Lys Trp
                85                  90                  95

Pro Asp Ser Leu Asp Cys Arg Lys Leu Pro Asn Lys Asn Asp Pro Asn
               100                 105                 110

Tyr Leu Cys Met Glu Ala Pro
          115

<210> SEQ ID NO 134
<211> LENGTH: 119
<212> TYPE: PRT
<213> ORGANISM: Artificial Sequence
<220> FEATURE:
<223> OTHER INFORMATION: "h-Fz4"

<400> SEQUENCE: 134

Arg Cys Asp Pro Ile Arg Ile Ser Met Cys Gln Asn Leu Gly Tyr Asn
1               5                   10                  15

Val Thr Lys Met Pro Asn Leu Val Gly His Glu Leu Gln Thr Asp Ala
                20                  25                  30

Glu Leu Gln Leu Thr Thr Phe Thr Pro Leu Ile Gln Tyr Cys Cys Ser
        35                  40                  45

Ser Gln Leu Gln Phe Phe Leu Cys Ser Val Tyr Val Pro Met Cys Thr
 50                  55                  60

Glu Lys Ile Asn Ile Pro Ile Gly Pro Cys Gly Gly Met Cys Leu Ser
65                  70                  75                  80

Val Lys Arg Arg Cys Glu Pro Val Leu Lys Glu Phe Gly Phe Ala Trp
                85                  90                  95

Pro Glu Ser Leu Asn Cys Ser Lys Phe Pro Pro Gln Asn Asp His Asn
               100                 105                 110

His Met Cys Met Glu Gly Pro
          115

<210> SEQ ID NO 135
<211> LENGTH: 112
<212> TYPE: PRT
<213> ORGANISM: Artificial Sequence
<220> FEATURE:
<223> OTHER INFORMATION: "h-Fz3"

<400> SEQUENCE: 135

Ser Cys Glu Pro Ile Thr Leu Arg Met Cys Gln Asp Leu Pro Tyr Asn
1               5                   10                  15

Thr Thr Phe Met Pro Asn Leu Leu Asn His Tyr Asp Gln Gln Thr Ala
                20                  25                  30

Ala Leu Ala Met Glu Pro Phe His Pro Met Val Asn Leu Asp Cys Ser
        35                  40                  45

Arg Asp Phe Arg Pro Phe Leu Cys Ala Leu Tyr Ala Pro Ile Cys Met
 50                  55                  60

Glu Tyr Gly Arg Val Thr Leu Pro Cys Arg Arg Leu Cys Gln Arg Ala
65                  70                  75                  80
```

```
Tyr Ser Glu Cys Ser Lys Leu Met Glu Met Phe Gly Val Pro Trp Pro
                85                  90                  95

Glu Asp Met Glu Cys Ser Arg Phe Pro Asp Cys Asp Glu Pro Tyr Pro
            100                 105                 110

<210> SEQ ID NO 136
<211> LENGTH: 112
<212> TYPE: PRT
<213> ORGANISM: Artificial Sequence
<220> FEATURE:
<223> OTHER INFORMATION: "h-Fz6"

<400> SEQUENCE: 136

Thr Cys Glu Pro Ile Thr Val Pro Arg Cys Met Lys Met Ala Tyr Asn
1               5                   10                  15

Met Thr Phe Phe Pro Asn Leu Met Gly His Tyr Asp Gln Ser Ile Ala
            20                  25                  30

Ala Val Glu Met Glu His Phe Leu Pro Leu Ala Asn Leu Glu Cys Ser
            35                  40                  45

Pro Asn Ile Glu Thr Phe Leu Cys Lys Ala Phe Val Pro Thr Cys Ile
        50                  55                  60

Glu Gln Ile His Val Val Pro Pro Cys Arg Lys Leu Cys Glu Lys Val
65                  70                  75                  80

Tyr Ser Asp Cys Lys Lys Leu Ile Asp Thr Phe Gly Ile Arg Trp Pro
                85                  90                  95

Glu Glu Leu Glu Cys Asp Arg Leu Gln Tyr Cys Asp Glu Thr Val Pro
            100                 105                 110
```